US012741017B2

(12) United States Patent
Savelyeva et al.

(10) Patent No.: US 12,741,017 B2
(45) Date of Patent: Sep. 22, 2026

(54) CANCER VACCINE

(71) Applicants: University of Southampton, Southampton (GB); Cancer Research Malaysia, Subang Jaya (MY)

(72) Inventors: Natalia Savelyeva, Southampton (GB); Gareth Thomas, Southampton (GB); Christian Ottensmeier, Southampton (GB); Chuan Wang, Southampton (GB); Sok Ching Cheong, Subang Jaya (MY); Kue Peng Lim, Subang Jaya (MY)

(73) Assignees: UNIVERSITY OF SOUTHAMPTON, Hampshire (GB); CANCER RESEARCH MALAYSIA, Selangor (MY)

( * ) Notice: Subject to any disclaimer, the term of this patent is extended or adjusted under 35 U.S.C. 154(b) by 47 days.

(21) Appl. No.: 17/264,469

(22) PCT Filed: Oct. 19, 2020

(86) PCT No.: PCT/GB2020/052631
§ 371 (c)(1),
(2) Date: Jan. 29, 2021

(87) PCT Pub. No.: WO2021/074655
PCT Pub. Date: Apr. 22, 2021

(65) Prior Publication Data

US 2022/0233666 A1 Jul. 28, 2022

(30) Foreign Application Priority Data

Oct. 18, 2019 (GB) ..................................... 1915163

(51) Int. Cl.
*A61K 39/00* (2006.01)
*A61P 35/00* (2006.01)

(52) U.S. Cl.
CPC ...... *A61K 39/001186* (2018.08); *A61P 35/00* (2018.01); *A61K 2039/53* (2013.01); *A61K 2039/80* (2018.08)

(58) Field of Classification Search
CPC ........ A61K 39/001186; A61K 2039/53; A61K 2039/80; A61P 35/00
See application file for complete search history.

(56) References Cited

U.S. PATENT DOCUMENTS 6,287,569 B1 * 9/2001 Kipps ........... A61K 39/001184 435/235.1
11,260,118 B2 * 3/2022 Chai .................. A61K 39/0011
2007/0253969 A1 * 11/2007 Stevenson .............. A61K 39/12 424/184.1
2018/0271964 A1 9/2018 Thess et al.
2023/0158131 A1 5/2023 Fotin-Mieczek et al.

FOREIGN PATENT DOCUMENTS

JP 2016-514097 A 5/2016
WO WO-0012127 A2 * 3/2000 ......... A61K 39/0011
WO WO-2009018500 A1 * 2/2009 .............. A61P 35/00
WO WO 2010/037539 A1 4/2010
WO WO 2013/009165 A1 1/2013
WO WO-2018169385 A1 * 9/2018 ......... A61K 39/3955

OTHER PUBLICATIONS

Nelson et al., Ann. Intern Med. 2009; 151:727-737 (Year: 2009).*
Kataja et al., Ann Oncol 2009; 20(sup 4): iv10-14 (Year: 2009).*
Balmana et al. Ann Oncol 2009; 20(supp 4):iv19-20 (Year: 2009).*
Deutscher, Guide to Protein Purification p. 738 (1990). (Year: 1990).*
Chomez (Cancer Research, 2001, 61:5544-5551).*
Japanese Office Action for Japanese Application No. 2022-522840, dated Sep. 17, 2024, with English translation.
Chai et al., "In vitro evaluation of dual-antigenic PV1 peptide vaccine in head and neck cancer patients," Human Vaccines and Immunotherapeutics (2019), vol. 15, No. 1, pp. 167-178.
International Search Report issued Feb. 23, 2021, in PCT/GB2020/052631.
Lim et al., "Abstract 1573: MAGED4B drives oral carcinogenesis and is a promising peptide vaccine target for the treatment of oral squamous cell carcinoma," AACR 103rd Annual Meeting 2012, Mar. 31-Apr. 4, 2012, Chicago, IL.
Lim et al., "Identification of immunogenic MAGED4B peptides for vaccine development in oral cancer immunotherapy," Human Vaccines and Immunotherapeutics (2014), vol. 10, No. 11, pp. 3214-3223.
Riccione et al., "CD27 stimulation unveils the efficacy of linked class I/II peptide vaccines in poorly immunogenic tumors by orchestring a coordinated CD4/CD8 T cell response," Oncoimmunology (2018), vol. 7, No. 12, e1502904 (14 pages).
Smahel et al., "The effect of helper epitopes and cellular localization of an antigen on the outcome of gene gun DNA immunization," Gene Therapy (2014), vol. 21, pp. 225-232.
UK IPO Search Report dated Mar. 31, 2020, in GB1915163.8.

* cited by examiner

*Primary Examiner* — Julie Wu
(74) *Attorney, Agent, or Firm* — Birch, Stewart, Kolasch & Birch, LLP

(57) ABSTRACT

The present invention relates to nucleic acid vaccines which encode at least a MAGED4B protein, for use in the treatment of cancer in particular. Synergistic combinations with other anti-cancer agents are described, particularly immune checkpoint inhibitors. The cancer vaccine may further comprise an immunologically active fragment to enhance the immune response, and an additional cancer antigen, such as FJX1. Particular combination therapies of interest include immunotherapies, radiotherapy, targeted therapies and chemotherapies.

25 Claims, 29 Drawing Sheets

Specification includes a Sequence Listing.

Figure 2

Target validation example 2: expression

Testis FEP Dysplasia SCC NPC

MAGED4B

FJX1

D4B/HLA-A2 tetramer
Negative control (FMO)
D4B tetramer+
0
Comp-PE-A
FSC-A
Comp-PE-A
HD1
D4B tetramer+
0
FSC-A
HN290
D4B tetramer+
0.093
Comp-PE-A
FSC-A
HN296
D4B tetramer+
0.097
Comp-PE-A
FSC-A
HN323
D4B tetramer+
0.037
Comp-PE-A
FSC-A
HN331
D4B tetramer+
0.058
Comp-PE-A
FSC-A

Figure 4:
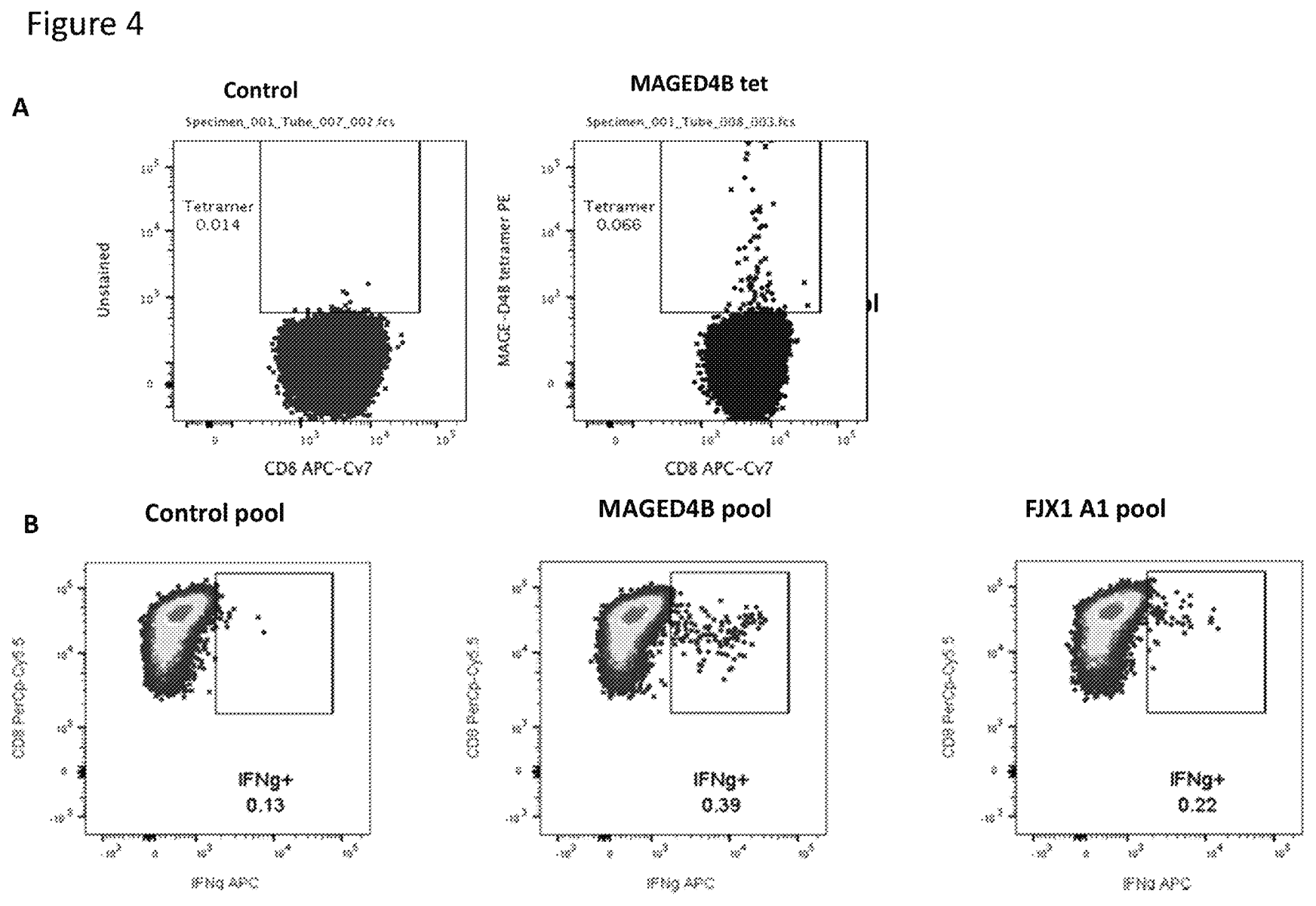

Control

Tetramer
0.014

Unstained

CD8 APC-Cy7

MAGED4B tet

Tetramer
0.066

MAGE-D4B tetramer PE

CD8 APC-Cy7

B

Control pool

IFNg+
0.13

CD8 PerCp-Cy5.5

IFNg APC

MAGED4B pool

IFNg+
0.39

CD8 PerCp-Cy5.5

IFNg APC

FJX1 A1 pool

IFNg+
0.22

CD8 PerCp-Cy5.5

IFNg APC

| | CD3 Count | % CD8+ | % CD4+ | % PD1+ | % D4B+ | % D4B+PD1+ |
|---|---|---|---|---|---|---|
| HN364 | 46290 | 34.3 | 59.5 | 1.07 | 0.076 | 0.015 |
| HN366 | 23938 | 9.57 | 83.4 | 6.21 | 0.042 | 0 |

A
B16/AAD model positive for MAGED4B/FJX1 antigens
Treatment strategy
D 1
D 3
D 5
DNA vaccines
D 6
αPD-1 mAb start from d 3, with 3 d intervals until termination
D 26
DNA vaccines
D 35
efficacy graph, TIL/ ELISpot
B
Tumour Volume (mm³)
1000
800
600
400
200
0
0
10
20
30
40
Days post tumour cells inoculation
Control
DNA vaccine
α-PD-1
α-PD1+ DNA vaccine
n.s.
*
*
*

C MAGED4B pool

Spots/ 5E5 splenocytes 0 20 40 60 80

IgG+pDOM α-PD1 DV α-PD1+DV

* * n.s.

Treatment strategy
B16/AAD model positive for MAGED4B/FJX1 antigens
D 1
D 5
DNA vaccines
D 12
DNA vaccines
D 26
efficacy graph, TIL/ ELISPOT
A.
Tumour volume (mm3)
3000
2000
1000
0
1 4 7 10 13 16 19 22
Treatment (Day)
pDom
DV
*
B.
Control
Tumour
Tumour
DV
Tumour
T cells
C.
CD4+ cells (%)
20
15
10
5
0
**
pDOM
DV
CD8+ cells (%)
10
8
6
4
2
0
pDOM
DV
CD4+/PD1+ cells (%)
30
20
10
0
**
pDOM
DV
CD8+/PD1+ cells (%)
10
8
6
4
2
0
*
pDOM
DV C57BL/6
DNA vaccines
DNA vaccines
ELISPOT
D 1
D 8
D 22
A Dom/ no Dom
SFU /10^6 splenocytes
0
200
400
600
800
*
p30
Irr peptide
D4B pool
FJX1 pool
p30
Irr peptide
D4B pool
FJX1 pool
pSPDOM-D4B-FJX1
pSP-D4B-FJX1
B Leader (SP)/ no Leader (no SP)
SFU /10^6 splenocytes
0
100
200
300
400
500
*
*
p30
Irr peptide
D4B pool
FJX1 pool
p30
Irr peptide
D4B pool
FJX1 pool
pSPDOM-FJX1
pnoSPDOM-FJX1

Fig 13 pDOM: CMV promoter, T7, leader, DOM1, BGH poly A pMAGED4B or pFJX1: CMV promoter, T7, leader, MAGED4B/FJX1, BGH poly A pFJX1-MITD: CMV promoter, T7, leader, FJX1, Linker, MITD, BGH poly A pPVXCP-MAGED4B: CMV promoter, T7, leader, PVXCP, Linker, MAGED4B, BGH poly A pMIP3a-MAGED4B: CMV promoter, T7, leader, MIP3a, Linker, MAGED4B, BGH poly A C57BL/6
day 1
day14
day21
day35
i.m.
EP
Bleeding
Terminate
FJX1 1uM in vitro stim
pDOM
DB-FJX1-CO
DB-FJX1-CO BASIC1
DB-FJX1-CO SV40
DB-FJX1-CO CpG
pDOM-FJX1 plasmid
% CD4 or CD8 T cells
0
5
10
15
20
p=0.0186
p=0.0093
p=0.0366
CD107a/b
PD-1
4-1BB
PD-1
CD4 T cells
CD107a/b
PD-1
4-1BB
PD-1
CD8 T cells
Kruskal-Wallis test

SEQUENCE LISTING

<160> NUMBER OF SEQ ID NOS: 43

<210> SEQ ID NO 1
<211> LENGTH: 19
<212> TYPE: PRT
<213> ORGANISM: Homo sapiens

<400> SEQUENCE: 1

```
Met Gly Trp Ser Cys Ile Ile Phe Phe Leu Val Ala Thr Ala Thr Gly
1               5                   10                  15

Val His Ser
```

<210> SEQ ID NO 2
<211> LENGTH: 256
<212> TYPE: PRT
<213> ORGANISM: Homo sapiens

<400> SEQUENCE: 2

```
Lys Asn Leu Asp Cys Trp Val Asp Asn Glu Glu Asp Ile Asp Val Ile
1               5                   10                  15

Leu Lys Lys Ser Thr Ile Leu Asn Leu Asp Ile Asn Asn Asp Ile Ile
            20                  25                  30

Ser Asp Ile Ser Gly Phe Asn Ser Ser Val Ile Thr Tyr Pro Asp Ala
        35                  40                  45

Gln Leu Val Pro Gly Ile Asn Gly Lys Ala Ile His Leu Val Asn Asn
    50                  55                  60

Glu Ser Ser Glu Val Ile Val His Lys Ala Met Asp Ile Glu Tyr Asn
65                  70                  75                  80

Asp Met Phe Asn Asn Phe Thr Val Ser Phe Trp Leu Arg Val Pro Lys
                85                  90                  95

Val Ser Ala Ser His Leu Glu Gln Tyr Gly Thr Asn Glu Tyr Ser Ile
            100                 105                 110

Ile Ser Ser Met Lys Lys His Ser Leu Ser Ile Gly Ser Gly Trp Ser
        115                 120                 125

Val Ser Leu Lys Gly Asn Asn Leu Ile Trp Thr Leu Lys Asp Ser Ala
    130                 135                 140

Gly Glu Val Arg Gln Ile Thr Phe Arg Asp Leu Pro Asp Lys Phe Asn
145                 150                 155                 160

Ala Tyr Leu Ala Asn Lys Trp Val Phe Ile Thr Ile Thr Asn Asp Arg
                165                 170                 175

Leu Ser Ser Ala Asn Leu Tyr Ile Asn Gly Val Leu Met Gly Ser Ala
            180                 185                 190

Glu Ile Thr Gly Leu Gly Ala Ile Arg Glu Asp Asn Asn Ile Thr Leu
        195                 200                 205

Lys Leu Asp Arg Cys Asn Asn Asn Asn Gln Tyr Val Ser Ile Asp Lys
    210                 215                 220

Phe Arg Ile Phe Cys Lys Ala Leu Asn Pro Lys Glu Ile Glu Lys Leu
225                 230                 235                 240

Tyr Thr Ser Tyr Leu Ser Ile Thr Phe Leu Arg Asp Phe Trp Gly Asn
                245                 250                 255
```

<210> SEQ ID NO 3
<211> LENGTH: 741
<212> TYPE: PRT
<213> ORGANISM: Homo sapiens

<400> SEQUENCE: 3

```
Met Ala Glu Gly Ser Phe Ser Val Gln Ser Glu Ser Tyr Ser Val Glu
1               5                   10                  15

Asp Met Asp Glu Gly Ser Asp Glu Val Gly Glu Glu Glu Met Val Glu
            20                  25                  30

Gly Asn Asp Tyr Glu Glu Phe Gly Ala Phe Gly Gly Tyr Gly Thr Leu
        35                  40                  45

Thr Ser Phe Asp Ile His Ile Leu Arg Ala Phe Gly Ser Leu Gly Pro
    50                  55                  60

Gly Leu Arg Ile Leu Ser Asn Glu Pro Trp Glu Leu Glu Asn Pro Val
65                  70                  75                  80

Leu Ala Gln Thr Leu Val Glu Ala Leu Gln Leu Asp Pro Glu Thr Leu
                85                  90                  95

Ala Asn Glu Thr Ala Ala Arg Ala Ala Asn Val Ala Arg Ala Ala Ala
            100                 105                 110

Ser Asn Arg Ala Ala Arg Ala Ala Ala Ala Ala Ala Arg Thr Ala Phe
        115                 120                 125

Ser Gln Val Val Ala Ser His Arg Val Ala Thr Pro Gln Val Ser Gly
    130                 135                 140

Glu Asp Thr Gln Pro Thr Thr Tyr Ala Ala Glu Ala Gln Gly Pro Thr
145                 150                 155                 160

Pro Glu Pro Pro Leu Ala Ser Pro Gln Thr Ser Gln Met Leu Val Thr
                165                 170                 175

Ser Lys Met Ala Ala Pro Glu Ala Pro Ala Thr Ser Ala Gln Ser Gln
            180                 185                 190

Thr Gly Ser Pro Ala Gln Glu Ala Ala Thr Glu Gly Pro Ser Ser Ala
        195                 200                 205

Cys Ala Phe Ser Gln Ala Pro Cys Ala Arg Glu Val Asp Ala Asn Arg
    210                 215                 220

Pro Ser Thr Ala Phe Leu Gly Gln Asn Asp Val Phe Asp Phe Thr Gln
225                 230                 235                 240

Pro Ala Gly Val Ser Gly Met Ala Phe Pro Arg Pro Lys Arg Pro Ala
                245                 250                 255

Pro Ala Gln Glu Ala Ala Thr Glu Gly Pro Ser Ala Ala Ser Gly Val
            260                 265                 270

Pro Gln Thr Gly Pro Gly Arg Glu Val Ala Ala Thr Arg Pro Lys Thr
        275                 280                 285

Thr Lys Ser Gly Lys Ala Leu Ala Lys Thr Arg Trp Val Glu Pro Gln
    290                 295                 300

Asn Val Val Ala Ala Ala Ala Ala Lys Ala Lys Met Ala Thr Ser Ile
305                 310                 315                 320

Pro Glu Pro Glu Gly Ala Ala Ala Ala Thr Ala Gln His Ser Ala Glu
                325                 330                 335

Pro Trp Ala Arg Met Gly Gly Lys Arg Thr Lys Lys Ser Lys His Leu
            340                 345                 350

Asp Asp Glu Tyr Glu Ser Ser Glu Glu Glu Arg Glu Thr Pro Ala Val
        355                 360                 365

Pro Pro Thr Trp Arg Ala Ser Gln Pro Ser Leu Thr Val Arg Ala Gln
    370                 375                 380

Leu Ala Pro Arg Pro Pro Met Ala Pro Arg Ser Gln Ile Pro Ser Arg
385                 390                 395                 400

His Val Leu Cys Leu Pro Pro Arg Asn Val Thr Leu Leu Gln Glu Arg
                405                 410                 415

Ala Asn Lys Leu Val Lys Tyr Leu Met Ile Lys Asp Tyr Lys Lys Ile
```

-continued

```
            420                 425                 430

Pro Ile Lys Arg Ala Asp Met Leu Lys Asp Val Ile Arg Glu Tyr Asp
        435                 440                 445

Glu His Phe Pro Glu Ile Ile Glu Arg Ala Thr Tyr Thr Leu Glu Lys
    450                 455                 460

Lys Phe Gly Ile His Leu Lys Glu Ile Asp Lys Glu Glu His Leu Tyr
465                 470                 475                 480

Ile Leu Val Cys Thr Arg Asp Ser Ser Ala Arg Leu Leu Gly Lys Thr
                485                 490                 495

Lys Asp Thr Pro Arg Leu Ser Leu Leu Leu Val Ile Leu Gly Val Ile
            500                 505                 510

Phe Met Asn Gly Asn Arg Ala Ser Glu Ala Val Leu Trp Glu Ala Leu
        515                 520                 525

Arg Lys Met Gly Leu Arg Pro Gly Val Arg His Pro Phe Leu Gly Asp
    530                 535                 540

Leu Arg Lys Leu Ile Thr Asp Asp Phe Val Lys Gln Lys Tyr Leu Glu
545                 550                 555                 560

Tyr Lys Lys Ile Pro Asn Ser Asn Pro Pro Glu Tyr Glu Phe Leu Trp
                565                 570                 575

Gly Leu Arg Ala Arg His Glu Thr Ser Lys Met Arg Val Leu Arg Phe
            580                 585                 590

Ile Ala Gln Asn Gln Asn Arg Asp Pro Arg Glu Trp Lys Ala His Phe
        595                 600                 605

Leu Glu Ala Val Asp Asp Ala Phe Lys Thr Met Asp Val Asp Met Ala
    610                 615                 620

Glu Glu His Ala Arg Ala Gln Met Arg Ala Gln Met Asn Ile Gly Asp
625                 630                 635                 640

Glu Ala Leu Ile Gly Arg Trp Ser Trp Asp Asp Ile Gln Val Glu Leu
                645                 650                 655

Leu Thr Trp Asp Glu Asp Gly Asp Phe Gly Asp Ala Trp Ala Arg Ile
            660                 665                 670

Pro Phe Ala Phe Trp Ala Arg Tyr His Gln Tyr Ile Leu Asn Ser Asn
        675                 680                 685

Arg Ala Asn Arg Arg Ala Thr Trp Arg Ala Gly Val Ser Ser Gly Thr
    690                 695                 700

Asn Gly Gly Ala Ser Thr Ser Val Leu Asp Gly Pro Ser Thr Ser Ser
705                 710                 715                 720

Thr Ile Arg Thr Arg Asn Ala Ala Arg Ala Gly Ala Ser Phe Phe Ser
                725                 730                 735

Trp Ile Gln His Arg
            740


<210> SEQ ID NO 4
<211> LENGTH: 437
<212> TYPE: PRT
<213> ORGANISM: Homo sapiens

<400> SEQUENCE: 4

Met Gly Arg Arg Met Arg Gly Ala Ala Ala Thr Ala Gly Leu Trp Leu
1               5                   10                  15

Leu Ala Leu Gly Ser Leu Leu Ala Leu Trp Gly Gly Leu Leu Pro Pro
            20                  25                  30

Arg Thr Glu Leu Pro Ala Ser Arg Pro Pro Glu Asp Arg Leu Pro Arg
        35                  40                  45
```

```
Arg Pro Ala Arg Ser Gly Gly Pro Ala Pro Ala Pro Arg Phe Pro Leu
    50                  55                  60

Pro Pro Pro Leu Ala Trp Asp Ala Arg Gly Gly Ser Leu Lys Thr Phe
65                  70                  75                  80

Arg Ala Leu Leu Thr Leu Ala Ala Gly Ala Asp Gly Pro Pro Arg Gln
                85                  90                  95

Ser Arg Ser Glu Pro Arg Trp His Val Ser Ala Arg Gln Pro Arg Pro
            100                 105                 110

Glu Glu Ser Ala Ala Val His Gly Gly Val Phe Trp Ser Arg Gly Leu
        115                 120                 125

Glu Glu Gln Val Pro Pro Gly Phe Ser Glu Ala Gln Ala Ala Ala Trp
    130                 135                 140

Leu Glu Ala Ala Arg Gly Ala Arg Met Val Ala Leu Glu Arg Gly Gly
145                 150                 155                 160

Cys Gly Arg Ser Ser Asn Arg Leu Ala Arg Phe Ala Asp Gly Thr Arg
                165                 170                 175

Ala Cys Val Arg Tyr Gly Ile Asn Pro Glu Gln Ile Gln Gly Glu Ala
            180                 185                 190

Leu Ser Tyr Tyr Leu Ala Arg Leu Leu Gly Leu Gln Arg His Val Pro
        195                 200                 205

Pro Leu Ala Leu Ala Arg Val Glu Ala Arg Gly Ala Gln Trp Ala Gln
    210                 215                 220

Val Gln Glu Glu Leu Arg Ala Ala His Trp Thr Glu Gly Ser Val Val
225                 230                 235                 240

Ser Leu Thr Arg Trp Leu Pro Asn Leu Thr Asp Val Val Val Pro Ala
                245                 250                 255

Pro Trp Arg Ser Glu Asp Gly Arg Leu Arg Pro Leu Arg Asp Ala Gly
            260                 265                 270

Gly Glu Leu Ala Asn Leu Ser Gln Ala Glu Leu Val Asp Leu Val Gln
        275                 280                 285

Trp Thr Asp Leu Ile Leu Phe Asp Tyr Leu Thr Ala Asn Phe Asp Arg
    290                 295                 300

Leu Val Ser Asn Leu Phe Ser Leu Gln Trp Asp Pro Arg Val Met Gln
305                 310                 315                 320

Arg Ala Thr Ser Asn Leu His Arg Gly Pro Gly Gly Ala Leu Val Phe
                325                 330                 335

Leu Asp Asn Glu Ala Gly Leu Val His Gly Tyr Arg Val Ala Gly Met
            340                 345                 350

Trp Asp Lys Tyr Asn Glu Pro Leu Leu Gln Ser Val Cys Val Phe Arg
        355                 360                 365

Glu Arg Thr Ala Arg Arg Val Leu Glu Leu His Arg Gly Gln Asp Ala
    370                 375                 380

Ala Ala Arg Leu Leu Arg Leu Tyr Arg Arg His Glu Pro Arg Phe Pro
385                 390                 395                 400

Glu Leu Ala Ala Leu Ala Asp Pro His Ala Gln Leu Leu Gln Arg Arg
                405                 410                 415

Leu Asp Phe Leu Ala Lys His Ile Leu His Cys Lys Ala Lys Tyr Gly
            420                 425                 430

Arg Arg Ser Gly Thr
        435
```

<210> SEQ ID NO 5
<211> LENGTH: 7
<212> TYPE: PRT

<213> ORGANISM: Homo sapiens

<400> SEQUENCE: 5

Ala Ala Ala Gly Pro Gly Pro
1 5

<210> SEQ ID NO 6
<211> LENGTH: 5
<212> TYPE: PRT
<213> ORGANISM: Homo sapiens

<400> SEQUENCE: 6

Gly Ser Gly Ser Gly
1 5

<210> SEQ ID NO 7
<211> LENGTH: 7446
<212> TYPE: DNA
<213> ORGANISM: Homo sapiens

<400> SEQUENCE: 7
gcatgcgcag gctacccagc cgcggggggt gcacggagaa aaggggcggg gtggtccggg 60
ctgctgtgct ggcagcagta ggcgagggcg cggctgcggg gttcctggtg ctgaggacgg 120
acgccattgg agttcccgag aaggtaagga tccagcccca gacaggaccg ggagagggcg 180
agtggaaccc gacacgctgc gccctccctc cgcctccgga tctgaacaaa gcccaagcac 240
tcagaaccgg aaccccatta gacccaaggt ctagatagga gcccccatca ccatcagacc 300
caggcgcccc gatctgagcc ctactgaaac cggagcccag gatcctcacc cctttagcag 360
acccgtgtgc tccgagctga gctcccttgg acctgaggcc ccacccccac cccaaccact 420
cctagattac tcgaaccgag ctgaccgctt gccccccttcc tggagtgccc agtcctcgcg 480
tttgagatct gcagcgctcc gattggagcc tcacctaggt ctgaggcccc cactccatcc 540
gcctctagtg ctcgagtctg agccccacct aggccccccg cccggaccta gccaaaggtc 600
cctggggttc tgtttcgcag agcttgcggc ttgccactgt ccctgttgtc tgagctctcc 660
catctgctcc cccttcatcc cggtcccctt ctctggcccg taaatccaaa ccctttgttt 720
ctctcttccc caatgcattc cctttgggac tcttcggacc ccagccctcc agaacacccc 780
ctcgtcaaat ctagccgctg ggatggcgag cctgcccatc ctaaactccg ctttcagtgc 840
ggcgcctcct gcgacctcct ctgtcccttt ccttgggctc tgtccctgac caggtctacc 900
ccatcagaaa gccaaaccgt ctcccccccg ctcctcctcc cccccccgc cccctactgc 960 ctaatattgc ctagtaacct gatgattgtc gcccctcacc tcccgggaga tcccgcctcc 1020
cattggatcc cgccccctcc ccctgcagct gcttcaccct ccctctcagg ctgagctctc 1080
atctccctgg gacccgcagc atggctgagg gaagcttcag cgtgcaatcg gaaagctaca 1140
gtgttgaaga catggatgag ggtagcgacg aagtcgggga ggaagagatg gttgaaggca 1200
acgactatga agaattcggt gcgtttggtg gctatggcac cctcaccagc tttgacatcc 1260
atatcctcag agccttcgga agcttgggtc caggccttcg catcttatcg gtgaggcccc 1320
ttcctggaca cctgctggcc tgggcctttc ccctgtgaat gggggaggga ggagggggga 1380
gccaggaggg ttgtgtggga aaggactgcc cagcttccca agccttccct cccctgctcg 1440
gaagaagaag atttgggaag gtcttggggt gttcagggct gactgctggg aagaggctgg 1500
ccagcacagg gaagctaaca caagtatgtc gtcgagtggc ctgccttccc caacccctct 1560
ctctggcctt gcagaatgag ccctgggaac tggaaaaccc tgtgctggcc cagaccctgg 1620

```
tggaggcatt gcagctggat ccggaaacac ttgccaatga gacggccgcc cgtgctgcca   1680
acgtagcccg cgccgccgcc tccaaccgtg cggctcgggc cgctgccgcc gctgcccgta   1740
ccgccttcag tcaggtggtc gctagccacc gggtggccac gccgcaggtc tcaggagagg   1800
atacccagcc cacgacctac gccgccgagg ctcaggggcc cacccctgag ccaccccttg   1860
cttctccgca gacctcccag atgttagtca ccagtaagat ggctgccccc gaggctccgg   1920
caacctccgc acagtcccag acaggctccc cggcccagga ggctgctact gagggcccta   1980
gtagcgcctg tgctttctct caggctccgt gtgccaggga ggtggacgcc aaccggccca   2040
gcacagcctt cctgggccag aatgatgtct tcgatttcac tcagccggca ggtgtcagtg   2100
gcatggcctt cccgcgcccc aagagacctg ccccagccca agaggctgcc acagagggcc   2160
ccagtgctgc ctctggtgtg ccccagacgg gacctggcag ggaggtggca gccacccggc   2220
ccaagaccac caagtcgggg aaggcgctgg ccaagactcg gtgggtggag cctcagaatg   2280
ttgtggcagc agctgctgcc aaggccaaga tggccacgag catccctgag ccggagggtg   2340
cagctgctgc cactgctcag cacagtgctg agccctgggc caggatggga ggcaagagga   2400
ccaagaaggt gagatccccc tgccccctgc cacctccaca ccccccttgct cctgtccttt   2460
ccttctcctc cctttcctgc tcctctcctc cctctcctct ccccttctt cctctcttct   2520
cctctttccc ctccttctct cctcacctcc cctctcctcc cctcctctcc tctcagctag   2580
tccatgtttc tccaacacaa gtttgctgag catgttttca ctccacgtag tccctaccct   2640
caggactggt gggagaagag gctggctcag tgcctggcac ttagtaagca cgcagcacat   2700
gccagccgct gctggtactg ctctcatttc caagagcctg ctacgggtga ggtgcgtgcc   2760
gggtgctttg gcacggggag cctggtagcc ctgggtctct cctctctcaa atgatacagt   2820
ccaagcacct ggatgatgag tatgagagca gcgaggagga gagagagact cccgcggtcc   2880
cacccacctg gagagcatca cagccctcat tgacggtgcg ggctcagttg gcccctcggc   2940
ccccgatggc cccgaggtcc cagataccct caaggcacgt actgtgcctg cccccccgca   3000
acgtgaccct tctgcaggag agggtaagaa gcccaccctc ccccatctcc ttcctctcct   3060
cccttgtggg ccacgtctct gctgtcaccc atgccttgac ctccccgcat gttcctcctt   3120
ctccaggcaa ataagttggt gaaatacctg atgattaagg actacaagaa gatccccatc   3180
aagcgcgcag gtaggcagcc tgtgccccct tcaccatccc ctagtctgtg ggcatccctt   3240
tgcttgcgtg ccacggctgg tccctccata gccacaggac ggggtcctgg ctgcgtcacc   3300
ctcggcagag ctgaccaagg ggctacagct ctatgacccc tgctcagccc aggtgctttc   3360
tccaactctt ccccctcctg cagacatgct gaaggatgtc atcagagaat atgatgaaca   3420
tttccctgag atcattgaac gagcaacgta caccctggaa aaggtgggtg caggatggga   3480
gcagctctgt gggggaagag cgggcatggg ggtgcggtga ccctgcagcc cctcaaggcc   3540
cagtctctgg agccatctct cacctctccg actctgagct tccactgcac tggcagtttg   3600
actcgtgctt cctgccctcg gcttctctct ctcatgctct ctgagtgtct cgccgtctgg   3660
ccaggtgggt ctcatcgcct ctgccagcgt cagctcccac agcgaaggtc ttccgtgtgc   3720
tgtcttcttc tgccctcgct cacgagtttg gattccttgc tgaggagcag ttctaacccg   3780
gaatcactgt ctgccggcag gatgcccagc atggggtttg gatctcacac tctgttttct   3840
cccccacgta gaagtttggg atccacctga aggagatcga caaggaagaa cacctgtata   3900
ttcttgtctg cacacgggac tcctcagctc gcctccttgg aaagtaagaa agggaaagcg   3960
```

```
ggtcgtggcc ttcctcggtg gtgtcccttc cctgcccaca ccccttcagt gaagcaggaa   4020
gacggggctt gagtgcggcg caccgctccc acacacagcg agggctgcct ggtgactgct   4080
ggatgaaagg aatgatagcc tggggtgagg ccttgctgcc atcagttctc cccaagctgc   4140
tgccgggctt tatccccaaa gcttcggagg aaagtgcctc ttcctcctgc ctgcctggcc   4200
tgggcctggc agagctggcc taggggagag ctgcctcttc agtgtaggtg ctgatgtgga   4260
aggggcagga aaggtctgga gccatctctg ggcacacgtt tgccatttgc agagcttcgg   4320
ctccctgcct cgccctgtcc tctgcagaac cctgtcaggg aagtgttagt acccatgttt   4380
tatagaggag gcgattaagt ctcaggcgga ggtgcgaatg gtctgtcagc agctagtgaa   4440
ctgtgcctgt cctgggaaga gttcccctca agctgggaaa cctgagagag gctagttggg   4500
agagcctggt ggtgtctctc aggcaaatag ctgctaaaca ggatttctct ttccacacct   4560
ttagaaccaa ggacactccc aggctgagtc tcctcttggt gattctgggc gtcatcttca   4620
tgaatggcaa ccgtgccagc gagggtgagt ggctggacct gcaactgggg ggctgcccat   4680
agtctcatct tctgggtgcc aaactctcgt acctcctctc ccctcgcagc tgtcctctgg   4740
gaggcactac gcaagatggg actgcgccct gggtatgatt ggcctctcca gctcctcccc   4800
tcggtgctat cctctggcca aagaggtcct gggattgcaa tagcctggtg gtctggcgca   4860
agggcgtggg gtgccctggg ctcggtagag agcaaaggat ctcaccaggg cggatgggga   4920
agcggtgctg gacgctgctc agccctctct ctgctctgtg gccccagatg acatctaaga   4980
gagacagtca gagtcaggga ttccatcaaa tccctacctg gggcgtccct gaccaacagt   5040
cctctggcct ctgctgcatg cccaggcctc cacagcgact ccccgggggc tgggaagtca   5100
tagtcatgct agggagggcc cctgccaccg tctctgctca tggattcctt tccttgccct   5160
cagggtgagg cacccattcc tcggcgatct gaggaagctc atcacagatg actttgtgaa   5220
gcagaagtaa gtatcacctg agctaactgc ggctctcact cgagcatcct ttgtgtgctg   5280
gtctggctga gaaagcagtt ccctatccca aatcttcaac tggagggatg ggtgcctctg   5340
acctgggagt gagtggcagt ggggggtatg cgagtgtgtg gggagccgaa ggccagggcg   5400
gtcttgggaa aagggagctc acgtcacctg agaacacggt gtggggtgtg aaaacggccg   5460
ccatcacctt gagcacctgc cctgtagact gacacaagag ttccccctgg tttacaccta   5520
aggaacccgg agctcagaga ggagacgcct ctgagcatgg ctcccagctg gtaagggcct   5580
cagcccaact ctcctgattt tcaggccagg ggccaccctc tccccgtccc tggaggactt   5640
gccaacgcac aggcgcgcat gcacaccaac aaagggtcag gacttgagga ggatgcctgg   5700
agcacgcttc tcctggctga ctgtttcttc ctctccagtc gtttcctctg gtgggcctct   5760
ccagggctcc gccggggtgt ggccaagacc ctcgaggtgg ggtgtgctca gagcaggggg   5820
cctgaagaat ggctcctctg tttacaacac acccaacagg aagctggggt catcgtgatg   5880
aggggcacaa acttgtggcc tccctacaga caaatgccct acatgtggac cccctgcacc   5940
tccgcatggc ttccggggag gaccaatggc aaaaggcttt gaaggcctca cttttgcagg   6000
cagaagtcct gggagtgggt ttgggaatga gtgaagggct ggaggggcag gacagtcctc   6060
ttccaggagc tgagctgcgg catcgggttg aggaggggcc ccctggaacc catccgttca   6120
gcaacaggtc tgcttggcta gcagcaaagt ttactttcct ctcatgccaa ggtacctgga   6180
atacaagaag atccccaaca gcaacccacc tgagtatgaa ttcctctggg gcctgcgagc   6240
ccgccatgag accagcaaga tgagggtcct gagattcatc gcccaggtaa gggagcgcct   6300
ctgttgggtg cccggcaccg gggtggtgc tctccacacc ttgcttgttt cttggtcgag   6360
```

gcctccttcc cattaccccg tattccagtg agggtaccaa acactcacag aggcacctga 6420
gcaccctaca caaggtcaca gatggggcaa aatcccaggt ctggcacagg agagtaggag 6480
cccccaatcc ctgtggtcct gatttttgcc atcattgcac aaagcacacg ggagggggtg 6540
aggcgggccg cgggtgctca gccagtgtgg ggtagctctg tgtctatgcc tgccctttc 6600 ctcctcagaa tcagaaccga gacccccggg aatggaaggc tcatttcttg gaggctgtgg 6660
atgatgcttt caagacaatg gatgtggata tggccgagga acatgccagg gcccagatga 6720
gggcccagat gaatatcggg gatgaagcgc tgattggacg gtggagctgg gatgacatac 6780
aagtcgagct cctgacctgg gatgaggacg gagattttgg cgatgcctgg gccaggatcc 6840
cctttgcttt ctgggccaga taccatcagt acattctgaa tagcaaccgt gccaacagga 6900
gggccacgtg gagagctggc gtcagcagtg gcaccaatgg aggggccagc accagcgtcc 6960
tagatggccc cagcaccagc tccaccatcc ggaccagaaa tgctgccaga gctggcgcca 7020
gcttcttctc ctggatccag taagagtttc ggtagagaaa tgagactctg caggagggct 7080
gcggaggggg gtgagatgtc agagggaggg ccagggtggg ggcgctgggg gcaacggcaa 7140
cagcatggac ggacacttat tttgttacgt acacccctcc ctggttcgcg tgtgtccacg 7200
gatgttgtca ctttggtttc ttgtgctttt ataggcaccg ttgacgaact gcagcgatct 7260
tactggccaa gccagagcgc ctcctctcag attccttctc gacacagcac cctaggcggc 7320
ttcttcctgt cagtcggagg tggcatgcaa gatgaagctc tctttgctct tcctgctttc 7380
attttgtgct tttccttgtg ttttcatgtt ttgggtatca gtgttacatt aaagttgcaa 7440
aattaa 7446

<210> SEQ ID NO 8
<211> LENGTH: 2406
<212> TYPE: DNA
<213> ORGANISM: Homo sapiens

<400> SEQUENCE: 8
agttcccagc gccgggcgga gcgccggaca gagccccgca gcgccccgcg gccgcgatgg 60
ggccgaagcg cccgaagccc cggagcccac aaactgccgg gcccgcctcg ccgccgggac 120
ccgggtgcct gggctcggct tgaagcggcg gcggcgcacc ggcacagccg cgggagcatg 180
ggcaggagga tgcggggcgc cgccgccacc gcggggctct ggctgctggc gctgggctcg 240
ctgctggcgc tgtggggagg gctcctgccg ccgcggaccg agctgcccgc ctcccggccg 300
cccgaagacc gactcccacg gcgcccggcc cggagcggcg gccccgcgcc cgcgcctcgc 360
ttccctctgc ccccgcccct ggcgtgggac gcccgcggcg gctccctgaa aactttccgg 420
gcgctgctca ccctggcggc cggcgcggac ggcccgcccc ggcagtcccg gagcgagccc 480
aggtggcacg tgtcagccag gcagccccgg ccggaggaga gcgccgcggt gcacgggggc 540
gtcttctgga gccgcggcct ggaggagcag gtgccccggg gcttttcgga ggcccaggcg 600
gcggcgtggc tggaggcggc tcgcggcgcc cggatggtgg ccctggagcg cgggggttgc 660
gggcgcagct ccaaccgact ggcccgtttt gccgacggca cccgcgcctg cgtgcgctac 720
ggcatcaacc cggagcagat tcagggcgag gccctgtctt actatctggc gcgcctgctg 780
ggcctccagc gccacgtgcc gccgctggca ctggctcggg tggaggctcg gggcgcgcag 840
tgggcgcagg tgcaggagga gctgcgcgct gcgcactgga ccgagggcag cgtggtgagc 900
ctgacacgct ggctgcccaa cctcacggac gtggtggtgc ccgcgccctg gcgctcggag 960

-continued

```
gacggccgtc tgcgcccccct ccgggatgcc gggggtgagc tggccaacct cagccaggcg   1020

gagctggtgg acctagtaca atggaccgac ttaatccttt tcgactacct gacggccaac   1080

ttcgaccggc tcgtaagcaa cctcttcagc ctgcagtggg acccgcgcgt catgcagcgt   1140

gccaccagca acctgcaccg cggtccgggc ggggcgctgg tctttctgga caatgaggcg   1200

ggcttggtgc acggctaccg ggtagcaggc atgtgggaca agtataacga gccgctgttg   1260

cagtcagtgt gcgtgttccg cgagcggacc gcgcggcgcg tcctggagct gcaccgcgga   1320

caggacgccg cggcccggct gctgcgcctc taccggcgcc acgagcctcg cttccccgag   1380

ctggccgccc ttgcagaccc ccacgctcag ctgctacagc gccgcctcga cttcctcgcc   1440

aagcacattt tgcactgtaa ggccaagtac ggccgccggt ctgggactta gtgtcaccgg   1500

gaggaaaaga gagagatctg ggctggggt atggatgatg gggggaaggg cggtcgcctc   1560

tgccactgtc agggaccagc cggccaacgc ccacccgcaa aggtgtctaa aaacttcagc   1620

ttttcaccca cctgcccctt tctttcaatc ccacgctgtt tcctttcaaa gttctgggag   1680

gacgaactca ccgaggcgag aagtgtaaca ttctctccac ccagcttata aaaggattct   1740

ttactgtgcc agcacgggga ttggatccga agaaactggc tactggggtt tggcccccga   1800

gtggccgtcc ctgtgggaga tgcaccccat tcttgggccc cccctcattc cctttccgaa   1860

aaaggaaaac ttgcgtttga gccgttgagc taattctgca attttctacc aaacagagcg   1920

ctggtggccc cggagcaggg ctgtgacatt ggctggtgga gccccccttcc tgtgttctcc   1980

ctttgttcca gcgccgcgat ggtgagatca ctgttccaag caggggggacg gctcgcgata   2040

ggacaaagag agcaggacct ccagactctg gggagccctg cagaccttga caatttgcct   2100

gactcattcc tgacctcttg tcattttggc ctgaaggcta caaattcagg gtcagctgta   2160

tgcactaagt caaataatga atttcttcct ccctctcgca accgaccaaa attttgacaa   2220

cgatgatgtt caccagaagg aaaaaaaaaa atcagtttta tgcactttat tttgttttga   2280

ttttcatttt ttattaagaa aaaattttat tttacagaat ttaccttctc tgtatatatg   2340

tgcataaagt gtggtgtaaa tatactaaac aaacttatat ttcaataaaa gggagtttaa   2400

aattta                                                               2406
```

<210> SEQ ID NO 9
<211> LENGTH: 646
<212> TYPE: DNA
<213> ORGANISM: Homo sapiens

<400> SEQUENCE: 9

```
acattgatta ttgactagtt attaatagta atcaattacg gggtcattag ttcatagccc     60

atatatggag ttccgcgtta cataacttac ggtaaatggc ccgcctggct gaccgcccaa    120

cgacccccgc ccattgacgt caataatgac gtatgttccc atagtaacgc caatagggac    180

tttccattga cgtcaatggg tggagtattt acggtaaact gcccacttgg cagtacatca    240

agtgtatcat atgccaagta cgccccctat tgacgtcaat gacggtaaat ggcccgcctg    300

gcattatgcc cagtacatga ccttatggga ctttcctact tggcagtaca tctacgtatt    360

agtcatcgct attaccatgg tgatgcggtt ttggcagtac atcaatgggc gtggatagcg    420

gtttgactca cggggatttc caagtctcca ccccattgac gtcaatggga gtttgttttg    480

gcaccaaaat caacgggact ttccaaaatg tcgtaacaac tccgccccat tgacgcaaat    540

gggcggtagg cgtgtacggt gggaggtcta tataagcaga gctctctggc taactagaga    600

acccactgct tactggctta tcgaaattaa tacgactcac tatagg                   646
```

<210> SEQ ID NO 10
<211> LENGTH: 5
<212> TYPE: PRT
<213> ORGANISM: Homo sapiens

<400> SEQUENCE: 10

Gly Gly Gly Gly Gly
1 5

<210> SEQ ID NO 11
<211> LENGTH: 5
<212> TYPE: PRT
<213> ORGANISM: Homo sapiens

<400> SEQUENCE: 11

Ser Ser Ser Ser Ser
1 5

<210> SEQ ID NO 12
<211> LENGTH: 9743
<212> TYPE: DNA
<213> ORGANISM: Homo sapiens

<400> SEQUENCE: 12
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gcttgccgcc 900
accatgggtt ggagctgtat catcttcttt ctggtagcaa cagctacagg tgtgcactcc 960
aaaaaccttg attgttgggt cgacaacgaa gaagacatcg atgttatcct gaaaaagtct 1020
accattctga acttggacat caacaacgat attatctccg acatctctgg tttcaactcc 1080
tctgttatca catatccaga tgctcaattg gtgccgggca tcaacggcaa agctatccac 1140
ctggttaaca acgaatcttc tgaagttatc gtgcacaagg ccatggacat cgaatacaac 1200
gacatgttca acaacttcac cgttagcttc tggctgcgcg ttccgaaagt ttctgcttcc 1260
cacctggaac agtacggcac taacgagtac tccatcatca gctctatgaa gaaacactcc 1320
ctgtccatcg gctctggttg gtctgtttcc ctgaagggta acaacctgat ctggactctg 1380
aaagactccg cgggcgaagt tcgtcagatc actttccgcg acctgccgga caagttcaac 1440

-continued

```
gcgtacctgg ctaacaaatg ggttttcatc actatcacta acgatcgtct gtcttctgct   1500
aacctgtaca tcaacggcgt tctgatgggc tccgctgaaa tcactggtct gggcgctatc   1560
cgtgaggaca acaacatcac tcttaagctg gaccgttgca acaacaacaa ccagtacgta   1620
tccatcgaca agttccgtat cttctgcaaa gcactgaacc cgaaagagat cgaaaaactg   1680
tataccagct acctgtctat caccttcctg cgtgacttct ggggtaacgc ggccgctgga   1740
cccggaccta tggctgaggg aagcttcagc gtgcaatcgg aaagctacag tgttgaagac   1800
atggatgagg gtagcgacga agtcggggag gaagagatgg ttgaaggcaa cgactatgaa   1860
gaattcggtg cgtttggtgg ctatggcacc ctcaccagct ttgacatcca tatcctcaga   1920
gccttcggaa gcttgggtcc aggccttcgc atcttatcga atgagccctg ggaactggaa   1980
aaccctgtgc tggcccagac cctggtggag gcattgcagc tggatccgga aacacttgcc   2040
aatgagacgg ccgcccgtgc tgccaacgta gcccgcgccg ccgcctccaa ccgtgcggct   2100
cgggccgctg ccgccgctgc ccgtaccgcc ttcagtcagg tggtcgctag ccaccgggtg   2160
gccacgccgc aggtctcagg agaggatacc cagcccacga cctacgccgc cgaggctcag   2220
gggcccaccc ctgagccacc ccttgcttct ccgcagacct cccagatgtt agtcaccagt   2280
aagatggctg cccccgaggc tccggcaacc tccgcacagt cccagacagg ctccccggcc   2340
caggaggctg ctactgaggg ccctagtagc gcctgtgctt tctctcaggc tccgtgtgcc   2400
agggaggtgg acgccaaccg gcccagcaca gccttcctgg gccagaatga tgtcttcgat   2460
ttcactcagc cggcaggtgt cagtggcatg gccttcccgc gccccaagag acctgcccca   2520
gcccaagagg ctgccacaga gggccccagt gctgcctctg gtgtgcccca gacgggacct   2580
ggcagggagg tggcagccac ccggcccaag accaccaagt cggggaaggc gctggccaag   2640
actcggtggg tggagcctca gaatgttgtg gcagcagctg ctgccaaggc caagatggcc   2700
acgagcatcc ctgagccgga gggtgcagct gctgccactg ctcagcacag tgctgagccc   2760
tgggccagga tgggaggcaa gaggaccaag aagtccaagc acctggatga tgagtatgag   2820
agcagcgagg aggagagaga gactcccgcg gtcccaccca cctggagagc atcacagccc   2880
tcattgacgg tgcgggctca gttggcccct cggcccccga tggccccgag gtcccagata   2940
ccctcaaggc acgtactgtg cctgcccccc cgcaacgtga cccttctgca ggagagggca   3000
aataagttgg tgaaatacct gatgattaag gactacaaga agatccccat caagcgcgca   3060
gacatgctga aggatgtcat cagagaatat gatgaacatt tccctgagat cattgaacga   3120
gcaacgtaca ccctggaaaa gaagtttggg atccacctga aggagatcga caaggaagaa   3180
cacctgtata ttcttgtctg cacacgggac tcctcagctc gcctccttgg aaaaaccaag   3240
gacactccca ggctgagtct cctcttggtg attctgggcg tcatcttcat gaatggcaac   3300
cgtgccagcg aggctgtcct ctgggaggca ctacgcaaga tgggactgcg ccctggggtg   3360
aggcacccat tcctcggcga tctgaggaag ctcatcacag atgactttgt gaagcagaag   3420
tacctggaat acaagaagat ccccaacagc aacccacctg agtatgaatt cctctggggc   3480
ctgcgagccc gccatgagac cagcaagatg agggtcctga gattcatcgc ccagaatcag   3540
aaccgagacc cccgggaatg gaaggctcat ttcttggagg ctgtggatga tgctttcaag   3600
acaatggatg tggatatggc cgaggaacat gccagggccc agatgagggc ccagatgaat   3660
atcggggatg aagcgctgat tggacggtgg agctgggatg acatacaagt cgagctcctg   3720
acctgggatg aggacggaga ttttggcgat gcctgggcca ggatcccctt tgctttctgg   3780
gccagatacc atcagtacat tctgaatagc aaccgtgcca acaggagggc cacgtggaga   3840
```

```
gctggcgtca gcagtggcac caatggaggg gccagcacca gcgtcctaga tggccccagc   3900
accagctcca ccatccggac cagaaatgct gccagagctg gcgccagctt cttctcctgg   3960
atccagcacc gtggttctgg ctctggcatg ggcaggagga tgcggggcgc cgccgccacc   4020
gcggggctct ggctgctggc gctgggctcg ctgctggcgc tgtggggagg gctcctgccg   4080
ccgcggaccg agctgcccgc ctcccggccg cccgaagacc gactcccacg gcgcccggcc   4140
cggagcggcg gccccgcgcc cgcgcctcgc ttccctctgc ccccgcccct ggcgtgggac   4200
gcccgcggcg gctccctgaa aactttccgg gcgctgctca ccctggcggc cggcgcggac   4260
ggcccgcccc ggcagtcccg gagcgagccc aggtggcacg tgtcagccag gcagccccgg   4320
ccggaggaga gcgccgcggt gcacgggggc gtcttctgga gccgcggcct ggaggagcag   4380
gtgcccccgg gcttttcgga ggcccaggcg gcggcgtggc tggaggcggc tcgcggcgcc   4440
cggatggtgg ccctggagcg cgggggttgc gggcgcagct ccaaccgact ggcccgtttt   4500
gccgacggca cccgcgcctg cgtgcgctac ggcatcaacc cggagcagat tcagggcgag   4560
gccctgtctt actatctggc gcgcctgctg ggcctccagc gccacgtgcc gccgctggca   4620
ctggctcggg tggaggctcg ggcgcgcag tgggcgcagg tgcaggagga gctgcgcgct   4680
gcgcactgga ccgagggcag cgtggtgagc ctgacacgct ggctgcccaa cctcacggac   4740
gtggtggtgc ccgcgccctg gcgctcggag gacggccgtc tgcgccccct ccgggatgcc   4800
gggggtgagc tggccaacct cagccaggcg gagctggtgg acctagtaca atggaccgac   4860
ttaatccttt tcgactacct gacggccaac ttcgaccggc tcgtaagcaa cctcttcagc   4920
ctgcagtggg acccgcgcgt catgcagcgt gccaccagca acctgcaccg cggtccgggc   4980
ggggcgctgg tctttctgga caatgaggcg ggcttggtgc acggctaccg ggtagcaggc   5040
atgtgggaca agtataacga gccgctgttg cagtcagtgt gcgtgttccg cgagcggacc   5100
gcgcggcgcg tcctggagct gcaccgcgga caggacgccg cggcccggct gctgcgcctc   5160
taccggcgcc acgagcctcg cttccccgag ctggccgccc ttgcagaccc ccacgctcag   5220
ctgctacagc gccgcctcga cttcctcgcc aagcacattt tgcactgtaa ggccaagtac   5280
ggccgccggt ctgggactta gactcgagga cgggcccgtt taaacccgct gatcagcctc   5340
gactgtgcct tctagttgcc agccatctgt tgtttgcccc tcccccgtgc cttccttgac   5400
cctggaaggt gccactccca ctgtcctttc ctaataaaat gaggaaattg catcgcattg   5460
tctgagtagg tgtcattcta ttctgggggg tggggtgggg caggacagca agggggagga   5520
ttgggaagac aatagcaggc atgctgggga tgcggtgggc tctatggctt ctgaggcgga   5580
aagaaccagc tggggctcta gggggtatcc ccacgcgccc tgtagcggcg cattaagcgc   5640
ggcgggtgtg gtggttacgc gcagcgtgac cgctacactt gccagcgccc tagcgcccgc   5700
tcctttcgct ttcttccctt cctttctcgc cacgttcgcc ggctttcccc gtcaagctct   5760
aaatcggggg ctccctttag ggttccgatt tagtgcttta cggcacctcg accccaaaaa   5820
acttgattag ggtgatggtt cacgtagtgg gccatcgccc tgatagacgg tttttcgccc   5880
tttgacgttg gagtccacgt tctttaatag tggactcttg ttccaaactg gaacaacact   5940
caaccctatc tcggtctatt cttttgattt ataagggatt ttgccgattt cggcctattg   6000
gttaaaaaat gagctgattt aacaaaaatt taacgcgaat taattctgtg gaatgtgtgt   6060
cagttagggt gtggaaagtc cccaggctcc ccagcaggca gaagtatgca aagcatgcat   6120
ctcaattagt cagcaaccag gtgtggaaag tccccaggct ccccagcagg cagaagtatg   6180
```

-continued

```
caaagcatgc atctcaatta gtcagcaacc atagtcccgc ccctaactcc gcccatcccg   6240
cccctaactc cgcccagttc cgcccattct ccgccccatg gctgactaat tttttttatt   6300
tatgcagagg ccgaggccgc ctctgcctct gagctattcc agaagtagtg aggaggcttt   6360
tttggaggcc taggcttttg caaaaagctc ccgggagctt gtatatccat tttcggatct   6420
gatcaagaga caggatgagg atcgtttcgc atgattgaac aagatggatt gcacgcaggt   6480
tctccggccg cttgggtgga gaggctattc ggctatgact gggcacaaca gacaatcggc   6540
tgctctgatg ccgccgtgtt ccggctgtca gcgcaggggc gcccggttct ttttgtcaag   6600
accgacctgt ccggtgccct gaatgaactg caggacgagg cagcgcggct atcgtggctg   6660
gccacgacgg gcgttccttg cgcagctgtg ctcgacgttg tcactgaagc gggaagggac   6720
tggctgctat tgggcgaagt gccggggcag gatctcctgt catctcacct tgctcctgcc   6780
gagaaagtat ccatcatggc tgatgcaatg cggcggctgc atacgcttga tccggctacc   6840
tgcccattcg accaccaagc gaaacatcgc atcgagcgag cacgtactcg gatggaagcc   6900
ggtcttgtcg atcaggatga tctggacgaa gagcatcagg ggctcgcgcc agccgaactg   6960
ttcgccaggc tcaaggcgcg catgcccgac ggcgaggatc tcgtcgtgac ccatggcgat   7020
gcctgcttgc cgaatatcat ggtggaaaat ggccgctttt ctggattcat cgactgtggc   7080
cggctgggtg tggcggaccg ctatcaggac atagcgttgg ctacccgtga tattgctgaa   7140
gagcttggcg gcgaatgggc tgaccgcttc ctcgtgcttt acggtatcgc cgctcccgat   7200
tcgcagcgca tcgccttcta tcgccttctt gacgagttct tctgagcggg actctggggt   7260
tcgaaatgac cgaccaagcg acgcccaacc tgccatcacg agatttcgat tccaccgccg   7320
ccttctatga aaggttgggc ttcggaatcg ttttccggga cgccggctgg atgatcctcc   7380
agcgcgggga tctcatgctg gagttcttcg cccaccccaa cttgtttatt gcagcttata   7440
atggttacaa ataaagcaat agcatcacaa atttcacaaa taaagcattt ttttcactgc   7500
attctagttg tggtttgtcc aaactcatca atgtatctta tcatgtctgt ataccgtcga   7560
cctctagcta gagcttggcg taatcatggt catagctgtt tcctgtgtga aattgttatc   7620
cgctcacaat tccacacaac atacgagccg gaagcataaa gtgtaaagcc tggggtgcct   7680
aatgagtgag ctaactcaca ttaattgcgt tgcgctcact gcccgctttc cagtcgggaa   7740
acctgtcgtg ccagctgcat taatgaatcg gccaacgcgc ggggagaggc ggtttgcgta   7800
ttgggcgctc ttccgcttcc tcgctcactg actcgctgcg ctcggtcgtt cggctgcggc   7860
gagcggtatc agctcactca aaggcggtaa tacggttatc cacagaatca ggggataacg   7920
caggaaagaa catgtgagca aaaggccagc aaaaggccag gaaccgtaaa aaggccgcgt   7980
tgctggcgtt tttccatagg ctccgccccc ctgacgagca tcacaaaaat cgacgctcaa   8040
gtcagaggtg gcgaaacccg acaggactat aaagatacca ggcgtttccc cctggaagct   8100
ccctcgtgcg ctctcctgtt ccgaccctgc cgcttaccgg atacctgtcc gcctttctcc   8160
cttcgggaag cgtggcgctt tctcatagct cacgctgtag gtatctcagt tcggtgtagg   8220
tcgttcgctc caagctgggc tgtgtgcacg aaccccccgt tcagcccgac cgctgcgcct   8280
tatccggtaa ctatcgtctt gagtccaacc cggtaagaca cgacttatcg ccactggcag   8340
cagccactgg taacaggatt agcagagcga ggtatgtagg cggtgctaca gagttcttga   8400
agtggtggcc taactacggc tacactagaa gaacagtatt tggtatctgc gctctgctga   8460
agccagttac cttcggaaaa agagttggta gctcttgatc cggcaaacaa accaccgctg   8520
gtagcggttt ttttgtttgc aagcagcaga ttacgcgcag aaaaaaagga tctcaagaag   8580
```

```
atcctttgat cttttctacg gggtctgacg ctcagtggaa cgaaaactca cgttaaggga   8640

ttttggtcat gagattatca aaaaggatct tcacctagat ccttttaaat taaaaatgaa   8700

gttttaaatc aatctaaagt atatatgagt aaacttggtc tgacagttac caatgcttaa   8760

tcagtgaggc acctatctca gcgatctgtc tatttcgttc atccatagtt gcctgactcc   8820

ccgtcgtgta gataactacg atacgggagg gcttaccatc tggccccagt gctgcaatga   8880

taccgcgaga cccacgctca ccggctccag atttatcagc aataaaccag ccagccggaa   8940

gggccgagcg cagaagtggt cctgcaactt tatccgcctc catccagtct attaattgtt   9000

gccgggaagc tagagtaagt agttcgccag ttaatagttt gcgcaacgtt gttgccattg   9060

ctacaggcat cgtggtgtca cgctcgtcgt ttggtatggc ttcattcagc tccggttccc   9120

aacgatcaag gcgagttaca tgatccccca tgttgtgcaa aaaagcggtt agctccttcg   9180

gtcctccgat cgttgtcaga agtaagttgg ccgcagtgtt atcactcatg gttatggcag   9240

cactgcataa ttctcttact gtcatgccat ccgtaagatg cttttctgtg actggtgagt   9300

actcaaccaa gtcattctga gaatagtgta tgcggcgacc gagttgctct tgcccggcgt   9360

caatacggga taataccgcg ccacatagca gaactttaaa agtgctcatc attggaaaac   9420

gttcttcggg gcgaaaactc tcaaggatct taccgctgtt gagatccagt tcgatgtaac   9480

ccactcgtgc acccaactga tcttcagcat cttttacttt caccagcgtt tctgggtgag   9540

caaaaacagg aaggcaaaat gccgcaaaaa agggaataag ggcgacacgg aaatgttgaa   9600

tactcatact cttccttttt caatattatt gaagcattta tcagggttat tgtctcatga   9660

gcggatacat atttgaatgt atttagaaaa ataaacaaat aggggttccg cgcacatttc   9720

cccgaaaagt gccacctgac gtc                                           9743
```

<210> SEQ ID NO 13
<211> LENGTH: 8417
<212> TYPE: DNA
<213> ORGANISM: Homo sapiens

<400> SEQUENCE: 13

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttgccgcc    900
```

-continued

```
accatgggtt ggagctgtat catcttcttt ctggtagcaa cagctacagg tgtgcactcc    960
aaaaaccttg attgttgggt cgacaacgaa gaagacatcg atgttatcct gaaaaagtct   1020
accattctga acttggacat caacaacgat attatctccg acatctctgg tttcaactcc   1080
tctgttatca catatccaga tgctcaattg gtgccgggca tcaacggcaa agctatccac   1140
ctggttaaca acgaatcttc tgaagttatc gtgcacaagg ccatggacat cgaatacaac   1200
gacatgttca acaacttcac cgttagcttc tggctgcgcg ttccgaaagt ttctgcttcc   1260
cacctggaac agtacggcac taacgagtac tccatcatca gctctatgaa gaaacactcc   1320
ctgtccatcg gctctggttg gtctgtttcc ctgaagggta acaacctgat ctggactctg   1380
aaagactccg cgggcgaagt tcgtcagatc actttccgcg acctgccgga caagttcaac   1440
gcgtacctgg ctaacaaatg ggttttcatc actatcacta acgatcgtct gtcttctgct   1500
aacctgtaca tcaacggcgt tctgatgggc tccgctgaaa tcactggtct gggcgctatc   1560
cgtgaggaca acaacatcac tcttaagctg gaccgttgca acaacaacaa ccagtacgta   1620
tccatcgaca agttccgtat cttctgcaaa gcactgaacc cgaaagagat cgaaaaactg   1680
tataccagct acctgtctat caccttcctg cgtgacttct ggggtaacgc ggccgctgga   1740
cccggaccta tggctgaggg aagcttcagc gtgcaatcgg aaagctacag tgttgaagac   1800
atggatgagg gtagcgacga agtcggggag gaagagatgg ttgaaggcaa cgactatgaa   1860
gaattcggtg cgtttggtgg ctatggcacc ctcaccagct ttgacatcca tatcctcaga   1920
gccttcggaa gcttgggtcc aggccttcgc atcttatcga atgagccctg ggaactggaa   1980
aaccctgtgc tggcccagac cctggtggag gcattgcagc tggatccgga aacacttgcc   2040
aatgagacgg ccgcccgtgc tgccaacgta gcccgcgccg ccgcctccaa ccgtgcggct   2100
cgggccgctg ccgccgctgc ccgtaccgcc ttcagtcagg tggtcgctag ccaccgggtg   2160
gccacgccgc aggtctcagg agaggatacc cagcccacga cctacgccgc cgaggctcag   2220
gggcccaccc ctgagccacc ccttgcttct ccgcagacct cccagatgtt agtcaccagt   2280
aagatggctg cccccgaggc tccggcaacc tccgcacagt cccagacagg ctccccggcc   2340
caggaggctg ctactgaggg ccctagtagc gcctgtgctt tctctcaggc tccgtgtgcc   2400
agggaggtgg acgccaaccg gcccagcaca gccttcctgg gccagaatga tgtcttcgat   2460
ttcactcagc cggcaggtgt cagtggcatg gccttcccgc gccccaagag acctgcccca   2520
gcccaagagg ctgccacaga gggccccagt gctgcctctg gtgtgcccca gacgggacct   2580
ggcagggagg tggcagccac ccggcccaag accaccaagt cggggaaggc gctggccaag   2640
actcggtggg tggagcctca gaatgttgtg gcagcagctg ctgccaaggc caagatggcc   2700
acgagcatcc ctgagccgga gggtgcagct gctgccactg ctcagcacag tgctgagccc   2760
tgggccagga tgggaggcaa gaggaccaag aagtccaagc acctggatga tgagtatgag   2820
agcagcgagg aggagagaga gactcccgcg gtcccaccca cctggagagc atcacagccc   2880
tcattgacgg tgcgggctca gttggcccct cggcccccga tggccccgag gtcccagata   2940
ccctcaaggc acgtactgtg cctgcccccc cgcaacgtga cccttctgca ggagagggca   3000
aataagttgg tgaaatacct gatgattaag gactacaaga agatccccat caagcgcgca   3060
gacatgctga aggatgtcat cagagaatat gatgaacatt tccctgagat cattgaacga   3120
gcaacgtaca ccctggaaaa gaagtttggg atccacctga aggagatcga caaggaagaa   3180
cacctgtata ttcttgtctg cacacgggac tcctcagctc gcctccttgg aaaaaccaag   3240
gacactccca ggctgagtct cctcttggtg attctgggcg tcatcttcat gaatggcaac   3300
```

```
cgtgccagcg aggctgtcct ctgggaggca ctacgcaaga tgggactgcg ccctggggtg   3360
aggcacccat tcctcggcga tctgaggaag ctcatcacag atgactttgt gaagcagaag   3420
tacctggaat acaagaagat ccccaacagc aacccacctg agtatgaatt cctctggggc   3480
ctgcgagccc gccatgagac cagcaagatg agggtcctga gattcatcgc ccagaatcag   3540
aaccgagacc cccgggaatg gaaggctcat ttcttggagg ctgtggatga tgctttcaag   3600
acaatggatg tggatatggc cgaggaacat gccagggccc agatgagggc ccagatgaat   3660
atcggggatg aagcgctgat tggacggtgg agctgggatg acatacaagt cgagctcctg   3720
acctgggatg aggacggaga ttttggcgat gcctgggcca ggatcccctt tgctttctgg   3780
gccagatacc atcagtacat tctgaatagc aaccgtgcca acaggagggc cacgtggaga   3840
gctggcgtca gcagtggcac caatggaggg gccagcacca gcgtcctaga tggccccagc   3900
accagctcca ccatccggac cagaaatgct gccagagctg gcgccagctt cttctcctgg   3960
atccagcacc gttgaactcg aggacgggcc cgtttaaacc cgctgatcag cctcgactgt   4020
gccttctagt tgccagccat ctgttgtttg cccctccccc gtgccttcct tgaccctgga   4080
aggtgccact cccactgtcc tttcctaata aaatgaggaa attgcatcgc attgtctgag   4140
taggtgtcat tctattctgg ggggtggggt ggggcaggac agcaaggggg aggattggga   4200
agacaatagc aggcatgctg gggatgcggt gggctctatg gcttctgagg cggaaagaac   4260
cagctggggc tctagggggt atccccacgc gccctgtagc ggcgcattaa gcgcggcggg   4320
tgtggtggtt acgcgcagcg tgaccgctac acttgccagc gccctagcgc ccgctccttt   4380
cgctttcttc ccttcctttc tcgccacgtt cgccggcttt ccccgtcaag ctctaaatcg   4440
ggggctccct ttagggttcc gatttagtgc tttacggcac ctcgacccca aaaaacttga   4500
ttagggtgat ggttcacgta gtgggccatc gccctgatag acggtttttc gccctttgac   4560
gttggagtcc acgttcttta atagtggact cttgttccaa actggaacaa cactcaaccc   4620
tatctcggtc tattcttttg atttataagg gattttgccg atttcggcct attggttaaa   4680
aaatgagctg atttaacaaa aatttaacgc gaattaattc tgtggaatgt gtgtcagtta   4740
gggtgtggaa agtccccagg ctccccagca ggcagaagta tgcaaagcat gcatctcaat   4800
tagtcagcaa ccaggtgtgg aaagtcccca ggctccccag caggcagaag tatgcaaagc   4860
atgcatctca attagtcagc aaccatagtc ccgcccctaa ctccgcccat cccgccccta   4920
actccgccca gttccgccca ttctccgccc catggctgac taattttttt tatttatgca   4980
gaggccgagg ccgcctctgc ctctgagcta ttccagaagt agtgaggagg cttttttgga   5040
ggcctaggct tttgcaaaaa gctcccggga gcttgtatat ccattttcgg atctgatcaa   5100
gagacaggat gaggatcgtt tcgcatgatt gaacaagatg gattgcacgc aggttctccg   5160
gccgcttggg tggagaggct attcggctat gactgggcac aacagacaat cggctgctct   5220
gatgccgccg tgttccggct gtcagcgcag gggcgcccgg ttctttttgt caagaccgac   5280
ctgtccggtg ccctgaatga actgcaggac gaggcagcgc ggctatcgtg gctggccacg   5340
acgggcgttc cttgcgcagc tgtgctcgac gttgtcactg aagcgggaag ggactggctg   5400
ctattgggcg aagtgccggg gcaggatctc ctgtcatctc accttgctcc tgccgagaaa   5460
gtatccatca tggctgatgc aatgcggcgg ctgcatacgc ttgatccggc tacctgccca   5520
ttcgaccacc aagcgaaaca tcgcatcgag cgagcacgta ctcggatgga agccggtctt   5580
gtcgatcagg atgatctgga cgaagagcat caggggctcg cgccagccga actgttcgcc   5640
```

```
aggctcaagg cgcgcatgcc cgacggcgag gatctcgtcg tgacccatgg cgatgcctgc   5700
ttgccgaata tcatggtgga aaatggccgc ttttctggat tcatcgactg tggccggctg   5760
ggtgtggcgg accgctatca ggacatagcg ttggctaccc gtgatattgc tgaagagctt   5820
ggcggcgaat gggctgaccg cttcctcgtg ctttacggta tcgccgctcc cgattcgcag   5880
cgcatcgcct tctatcgcct tcttgacgag ttcttctgag cgggactctg gggttcgaaa   5940
tgaccgacca agcgacgccc aacctgccat cacgagattt cgattccacc gccgccttct   6000
atgaaaggtt gggcttcgga atcgttttcc gggacgccgg ctggatgatc ctccagcgcg   6060
gggatctcat gctggagttc ttcgcccacc ccaacttgtt tattgcagct tataatggtt   6120
acaaataaag caatagcatc acaaatttca caaataaagc atttttttca ctgcattcta   6180
gttgtggttt gtccaaactc atcaatgtat cttatcatgt ctgtataccg tcgacctcta   6240
gctagagctt ggcgtaatca tggtcatagc tgtttcctgt gtgaaattgt tatccgctca   6300
caattccaca caacatacga gccggaagca taaagtgtaa agcctggggt gcctaatgag   6360
tgagctaact cacattaatt gcgttgcgct cactgcccgc tttccagtcg ggaaacctgt   6420
cgtgccagct gcattaatga atcggccaac gcgcggggag aggcggtttg cgtattgggc   6480
gctcttccgc ttcctcgctc actgactcgc tgcgctcggt cgttcggctg cggcgagcgg   6540
tatcagctca ctcaaaggcg gtaatacggt tatccacaga atcaggggat aacgcaggaa   6600
agaacatgtg agcaaaaggc cagcaaaagg ccaggaaccg taaaaaggcc gcgttgctgg   6660
cgtttttcca taggctccgc ccccctgacg agcatcacaa aaatcgacgc tcaagtcaga   6720
ggtggcgaaa cccgacagga ctataaagat accaggcgtt tccccctgga agctccctcg   6780
tgcgctctcc tgttccgacc ctgccgctta ccggatacct gtccgccttt ctcccttcgg   6840
gaagcgtggc gctttctcat agctcacgct gtaggtatct cagttcggtg taggtcgttc   6900
gctccaagct gggctgtgtg cacgaacccc ccgttcagcc cgaccgctgc gccttatccg   6960
gtaactatcg tcttgagtcc aacccggtaa gacacgactt atcgccactg gcagcagcca   7020
ctggtaacag gattagcaga gcgaggtatg taggcggtgc tacagagttc ttgaagtggt   7080
ggcctaacta cggctacact agaagaacag tatttggtat ctgcgctctg ctgaagccag   7140
ttaccttcgg aaaaagagtt ggtagctctt gatccggcaa acaaaccacc gctggtagcg   7200
gtttttttgt ttgcaagcag cagattacgc gcagaaaaaa aggatctcaa gaagatcctt   7260
tgatcttttc tacggggtct gacgctcagt ggaacgaaaa ctcacgttaa gggattttgg   7320
tcatgagatt atcaaaaagg atcttcacct agatcctttt aaattaaaaa tgaagtttta   7380
aatcaatcta aagtatatat gagtaaactt ggtctgacag ttaccaatgc ttaatcagtg   7440
aggcacctat ctcagcgatc tgtctatttc gttcatccat agttgcctga ctccccgtcg   7500
tgtagataac tacgatacgg gagggcttac catctggccc cagtgctgca atgataccgc   7560
gagacccacg ctcaccggct ccagatttat cagcaataaa ccagccagcc ggaagggccg   7620
agcgcagaag tggtcctgca actttatccg cctccatcca gtctattaat tgttgccggg   7680
aagctagagt aagtagttcg ccagttaata gtttgcgcaa cgttgttgcc attgctacag   7740
gcatcgtggt gtcacgctcg tcgtttggta tggcttcatt cagctccggt tcccaacgat   7800
caaggcgagt tacatgatcc cccatgttgt gcaaaaaagc ggttagctcc ttcggtcctc   7860
cgatcgttgt cagaagtaag ttggccgcag tgttatcact catggttatg gcagcactgc   7920
ataattctct tactgtcatg ccatccgtaa gatgcttttc tgtgactggt gagtactcaa   7980
ccaagtcatt ctgagaatag tgtatgcggc gaccgagttg ctcttgcccg gcgtcaatac   8040
```

```
gggataatac cgcgccacat agcagaactt taaaagtgct catcattgga aaacgttctt   8100

cggggcgaaa actctcaagg atcttaccgc tgttgagatc cagttcgatg taacccactc   8160

gtgcacccaa ctgatcttca gcatctttta ctttcaccag cgtttctggg tgagcaaaaa   8220

caggaaggca aaatgccgca aaaaagggaa taagggcgac acggaaatgt tgaatactca   8280

tactcttcct ttttcaatat tattgaagca tttatcaggg ttattgtctc atgagcggat   8340

acatatttga atgtatttag aaaaataaac aaataggggt tccgcgcaca tttccccgaa   8400

aagtgccacc tgacgtc                                                  8417
```

<210> SEQ ID NO 14
<211> LENGTH: 7505
<212> TYPE: DNA
<213> ORGANISM: Homo sapiens

<400> SEQUENCE: 14

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gcttgccgcc    900

accatgggtt ggagctgtat catcttcttt ctggtagcaa cagctacagg tgtgcactcc    960

aaaaaccttg attgttgggt cgacaacgaa gaagacatcg atgttatcct gaaaaagtct   1020

accattctga acttggacat caacaacgat attatctccg acatctctgg tttcaactcc   1080

tctgttatca catatccaga tgctcaattg gtgccgggca tcaacggcaa agctatccac   1140

ctggttaaca acgaatcttc tgaagttatc gtgcacaagg ccatggacat cgaatacaac   1200

gacatgttca acaacttcac cgttagcttc tggctgcgcg ttccgaaagt ttctgcttcc   1260

cacctggaac agtacggcac taacgagtac tccatcatca gctctatgaa gaaacactcc   1320

ctgtccatcg gctctggttg gtctgtttcc ctgaagggta acaacctgat ctggactctg   1380

aaagactccg cgggcgaagt tcgtcagatc actttccgcg acctgccgga caagttcaac   1440

gcgtacctgg ctaacaaatg ggttttcatc actatcacta acgatcgtct gtcttctgct   1500

aacctgtaca tcaacggcgt tctgatgggc tccgctgaaa tcactggtct gggcgctatc   1560

cgtgaggaca acaacatcac tcttaagctg gaccgttgca acaacaacaa ccagtacgta   1620

tccatcgaca agttccgtat cttctgcaaa gcactgaacc cgaaagagat cgaaaaactg   1680
```

```
tataccagct acctgtctat caccttcctg cgtgacttct ggggtaacgc ggccgctgga   1740
cccggaccta tgggcaggag gatgcggggc gccgccgcca ccgcggggct ctggctgctg   1800
gcgctgggct cgctgctggc gctgtgggga gggctcctgc cgccgcggac cgagctgccc   1860
gcctcccggc cgcccgaaga ccgactccca cggcgcccgg cccggagcgg cggccccgcg   1920
cccgcgcctc gcttccctct gcccccgccc ctggcgtggg acgcccgcgg cggctccctg   1980
aaaactttcc gggcgctgct caccctggcg gccggcgcgg acggcccgcc ccggcagtcc   2040
cggagcgagc ccaggtggca cgtgtcagcc aggcagcccc ggccggagga gagcgccgcg   2100
gtgcacgggg gcgtcttctg gagccgcggc ctggaggagc aggtgccccc gggcttttcg   2160
gaggcccagg cggcggcgtg gctggaggcg gctcgcggcg cccggatggt ggccctggag   2220
cgcgggggtt gcgggcgcag ctccaaccga ctggcccgtt ttgccgacgg cacccgcgcc   2280
tgcgtgcgct acggcatcaa cccggagcag attcagggcg aggccctgtc ttactatctg   2340
gcgcgcctgc tgggcctcca gcgccacgtg ccgccgctgg cactggctcg ggtggaggct   2400
cggggcgcgc agtgggcgca ggtgcaggag gagctgcgcg ctgcgcactg gaccgagggc   2460
agcgtggtga gcctgacacg ctggctgccc aacctcacgg acgtggtggt gcccgcgccc   2520
tggcgctcgg aggacggccg tctgcgcccc ctccgggatg ccgggggtga gctggccaac   2580
ctcagccagg cggagctggt ggacctagta caatggaccg acttaatcct tttcgactac   2640
ctgacggcca acttcgaccg gctcgtaagc aacctcttca gcctgcagtg ggacccgcgc   2700
gtcatgcagc gtgccaccag caacctgcac cgcggtccgg gcggggcgct ggtctttctg   2760
gacaatgagg cgggcttggt gcacggctac cgggtagcag gcatgtggga caagtataac   2820
gagccgctgt tgcagtcagt gtgcgtgttc cgcgagcgga ccgcgcggcg cgtcctggag   2880
ctgcaccgcg gacaggacgc cgcggcccgg ctgctgcgcc tctaccggcg ccacgagcct   2940
cgcttccccg agctggccgc ccttgcagac ccccacgctc agctgctaca gcgccgcctc   3000
gacttcctcg ccaagcacat tttgcactgt aaggccaagt acggccgccg gtctgggact   3060
tagactcgag gacgggcccg tttaaacccg ctgatcagcc tcgactgtgc cttctagttg   3120
ccagccatct gttgtttgcc cctcccccgt gccttccttg accctggaag gtgccactcc   3180
cactgtcctt tcctaataaa atgaggaaat tgcatcgcat tgtctgagta ggtgtcattc   3240
tattctgggg ggtggggtgg ggcaggacag caagggggag gattgggaag acaatagcag   3300
gcatgctggg gatgcggtgg gctctatggc ttctgaggcg gaaagaacca gctggggctc   3360
taggggtat ccccacgcgc cctgtagcgg cgcattaagc gcggcgggtg tggtggttac   3420
gcgcagcgtg accgctacac ttgccagcgc cctagcgccc gctcctttcg ctttcttccc   3480
ttcctttctc gccacgttcg ccggctttcc ccgtcaagct ctaaatcggg ggctcccttt   3540
agggttccga tttagtgctt tacggcacct cgaccccaaa aaacttgatt agggtgatgg   3600
ttcacgtagt gggccatcgc cctgatagac ggtttttcgc cctttgacgt tggagtccac   3660
gttctttaat agtggactct tgttccaaac tggaacaaca ctcaacccta tctcggtcta   3720
ttcttttgat ttataaggga ttttgccgat ttcggcctat tggttaaaaa atgagctgat   3780
ttaacaaaaa tttaacgcga attaattctg tggaatgtgt gtcagttagg gtgtggaaag   3840
tccccaggct ccccagcagg cagaagtatg caaagcatgc atctcaatta gtcagcaacc   3900
aggtgtggaa agtccccagg ctccccagca ggcagaagta tgcaaagcat gcatctcaat   3960
tagtcagcaa ccatagtccc gcccctaact ccgcccatcc cgcccctaac tccgcccagt   4020
tccgcccatt ctccgcccca tggctgacta atttttttta tttatgcaga ggccgaggcc   4080
```

```
gcctctgcct ctgagctatt ccagaagtag tgaggaggct tttttggagg cctaggcttt   4140
tgcaaaaagc tcccgggagc ttgtatatcc attttcggat ctgatcaaga gacaggatga   4200
ggatcgtttc gcatgattga acaagatgga ttgcacgcag gttctccggc cgcttgggtg   4260
gagaggctat tcggctatga ctgggcacaa cagacaatcg gctgctctga tgccgccgtg   4320
ttccggctgt cagcgcaggg gcgcccggtt ctttttgtca agaccgacct gtccggtgcc   4380
ctgaatgaac tgcaggacga ggcagcgcgg ctatcgtggc tggccacgac gggcgttcct   4440
tgcgcagctg tgctcgacgt tgtcactgaa gcgggaaggg actggctgct attgggcgaa   4500
gtgccggggc aggatctcct gtcatctcac cttgctcctg ccgagaaagt atccatcatg   4560
gctgatgcaa tgcggcggct gcatacgctt gatccggcta cctgcccatt cgaccaccaa   4620
gcgaaacatc gcatcgagcg agcacgtact cggatggaag ccggtcttgt cgatcaggat   4680
gatctggacg aagagcatca ggggctcgcg ccagccgaac tgttcgccag gctcaaggcg   4740
cgcatgcccg acggcgagga tctcgtcgtg acccatggcg atgcctgctt gccgaatatc   4800
atggtggaaa atggccgctt ttctggattc atcgactgtg gccggctggg tgtggcggac   4860
cgctatcagg acatagcgtt ggctacccgt gatattgctg aagagcttgg cggcgaatgg   4920
gctgaccgct tcctcgtgct ttacggtatc gccgctcccg attcgcagcg catcgccttc   4980
tatcgccttc ttgacgagtt cttctgagcg ggactctggg gttcgaaatg accgaccaag   5040
cgacgcccaa cctgccatca cgagatttcg attccaccgc cgccttctat gaaaggttgg   5100
gcttcggaat cgttttccgg gacgccggct ggatgatcct ccagcgcggg gatctcatgc   5160
tggagttctt cgcccacccc aacttgttta ttgcagctta taatggttac aaataaagca   5220
atagcatcac aaatttcaca aataaagcat ttttttcact gcattctagt tgtggtttgt   5280
ccaaactcat caatgtatct tatcatgtct gtataccgtc gacctctagc tagagcttgg   5340
cgtaatcatg gtcatagctg tttcctgtgt gaaattgtta tccgctcaca attccacaca   5400
acatacgagc cggaagcata aagtgtaaag cctggggtgc ctaatgagtg agctaactca   5460
cattaattgc gttgcgctca ctgcccgctt tccagtcggg aaacctgtcg tgccagctgc   5520
attaatgaat cggccaacgc gcggggagag gcggtttgcg tattgggcgc tcttccgctt   5580
cctcgctcac tgactcgctg cgctcggtcg ttcggctgcg gcgagcggta tcagctcact   5640
caaaggcggt aatacggtta tccacagaat caggggataa cgcaggaaag aacatgtgag   5700
caaaaggcca gcaaaaggcc aggaaccgta aaaaggccgc gttgctggcg tttttccata   5760
ggctccgccc ccctgacgag catcacaaaa atcgacgctc aagtcagagg tggcgaaacc   5820
cgacaggact ataaagatac caggcgtttc cccctggaag ctccctcgtg cgctctcctg   5880
ttccgaccct gccgcttacc ggatacctgt ccgcctttct cccttcggga agcgtggcgc   5940
tttctcatag ctcacgctgt aggtatctca gttcggtgta ggtcgttcgc tccaagctgg   6000
gctgtgtgca cgaacccccc gttcagcccg accgctgcgc cttatccggt aactatcgtc   6060
ttgagtccaa cccggtaaga cacgacttat cgccactggc agcagccact ggtaacagga   6120
ttagcagagc gaggtatgta ggcggtgcta cagagttctt gaagtggtgg cctaactacg   6180
gctacactag aagaacagta tttggtatct gcgctctgct gaagccagtt accttcggaa   6240
aaagagttgg tagctcttga tccggcaaac aaaccaccgc tggtagcggt ttttttgttt   6300
gcaagcagca gattacgcgc agaaaaaaag gatctcaaga agatcctttg atcttttcta   6360
cggggtctga cgctcagtgg aacgaaaact cacgttaagg gattttggtc atgagattat   6420
```

caaaaaggat cttcacctag atccttttaa attaaaaatg aagttttaaa tcaatctaaa 6480
gtatatatga gtaaacttgg tctgacagtt accaatgctt aatcagtgag gcacctatct 6540
cagcgatctg tctatttcgt tcatccatag ttgcctgact ccccgtcgtg tagataacta 6600
cgatacggga gggcttacca tctggcccca gtgctgcaat gataccgcga gacccacgct 6660
caccggctcc agatttatca gcaataaacc agccagccgg aagggccgag cgcagaagtg 6720
gtcctgcaac tttatccgcc tccatccagt ctattaattg ttgccgggaa gctagagtaa 6780
gtagttcgcc agttaatagt ttgcgcaacg ttgttgccat tgctacaggc atcgtggtgt 6840
cacgctcgtc gtttggtatg gcttcattca gctccggttc ccaacgatca aggcgagtta 6900
catgatcccc catgttgtgc aaaaaagcgg ttagctcctt cggtcctccg atcgttgtca 6960
gaagtaagtt ggccgcagtg ttatcactca tggttatggc agcactgcat aattctctta 7020
ctgtcatgcc atccgtaaga tgcttttctg tgactggtga gtactcaacc aagtcattct 7080
gagaatagtg tatgcggcga ccgagttgct cttgcccggc gtcaatacgg gataataccg 7140
cgccacatag cagaacttta aaagtgctca tcattggaaa acgttcttcg gggcgaaaac 7200
tctcaaggat cttaccgctg ttgagatcca gttcgatgta acccactcgt gcacccaact 7260
gatcttcagc atcttttact ttcaccagcg tttctgggtg agcaaaaaca ggaaggcaaa 7320
atgccgcaaa aaagggaata agggcgacac ggaaatgttg aatactcata ctcttccttt 7380
ttcaatatta ttgaagcatt tatcagggtt attgtctcat gagcggatac atatttgaat 7440
gtatttagaa aaataaacaa ataggggttc cgcgcacatt tccccgaaaa gtgccacctg 7500
acgtc 7505

<210> SEQ ID NO 15
<211> LENGTH: 576
<212> TYPE: DNA
<213> ORGANISM: Homo sapiens

<400> SEQUENCE: 15
tagtaatcaa ttacggggtc attagttcat agcccatata tggagttccg cgttacataa 60
cttacggtaa atggcccgcc tggctgaccg cccaacgacc cccgcccatt gacgtcaata 120
atgacgtatg ttcccatagt aacgccaata gggactttcc attgacgtca atgggtggag 180
tatttacggt aaactgccca cttggcagta catcaagtgt atcatatgcc aagtacgccc 240
cctattgacg tcaatgacgg taaatggccc gcctggcatt atgcccagta catgacctta 300
tgggactttc ctacttggca gtacatctac gtattagtca tcgctattac catggtgatg 360
cggttttggc agtacatcaa tgggcgtgga tagcggtttg actcacgggg atttccaagt 420
ctccacccca ttgacgtcaa tgggagtttg ttttggcacc aaaatcaacg ggactttcca 480
aaatgtcgta acaactccgc cccattgacg caaatgggcg gtaggcgtgt acggtgggag 540
gtctatataa gcagagctgg tttagtgaac cgtcag 576

<210> SEQ ID NO 16
<211> LENGTH: 2226
<212> TYPE: DNA
<213> ORGANISM: Homo sapiens

<400> SEQUENCE: 16
atggctgagg gaagcttcag cgtgcaatcg gaaagctaca gtgttgaaga catggatgag 60
ggtagcgacg aagtcgggga ggaagagatg gttgaaggca acgactatga agaattcggt 120
gcgtttggtg gctatggcac cctcaccagc tttgacatcc atatcctcag agccttcgga 180

```
agcttgggtc caggccttcg catcttatcg aatgagccct gggaactgga aaaccctgtg    240
ctggcccaga ccctggtgga ggcattgcag ctggatccgg aaacacttgc caatgagacg    300
gccgcccgtg ctgccaacgt agcccgcgcc gccgcctcca accgtgcggc tcgggccgct    360
gccgccgctg cccgtaccgc cttcagtcag gtggtcgcta gccaccgggt ggccacgccg    420
caggtctcag gagaggatac ccagcccacg acctacgccg ccgaggctca ggggcccacc    480
cctgagccac cccttgcttc tccgcagacc tcccagatgt tagtcaccag taagatggct    540
gcccccgagg ctccggcaac ctccgcacag tcccagacag gctccccggc ccaggaggct    600
gctactgagg gccctagtag cgcctgtgct ttctctcagg ctccgtgtgc cagggaggtg    660
gacgccaacc ggcccagcac agccttcctg ggccagaatg atgtcttcga tttcactcag    720
ccggcaggtg tcagtggcat ggccttcccg cgccccaaga gacctgcccc agcccaagag    780
gctgccacag agggccccag tgctgcctct ggtgtgcccc agacgggacc tggcagggag    840
gtggcagcca cccggcccaa gaccaccaag tcggggaagg cgctggccaa gactcggtgg    900
gtggagcctc agaatgttgt ggcagcagct gctgccaagg ccaagatggc cacgagcatc    960
cctgagccgg agggtgcagc tgctgccact gctcagcaca gtgctgagcc ctgggccagg   1020
atgggaggca agaggaccaa gaagtccaag cacctggatg atgagtatga gagcagcgag   1080
gaggagagag agactcccgc ggtcccaccc acctggagag catcacagcc ctcattgacg   1140
gtgcgggctc agttggcccc tcggccccccg atggccccga ggtcccagat accctcaagg   1200
cacgtactgt gcctgccccc ccgcaacgtg acccttctgc aggagagggc aaataagttg   1260
gtgaaatacc tgatgattaa ggactacaag aagatcccca tcaagcgcgc agacatgctg   1320
aaggatgtca tcagagaata tgatgaacat ttccctgaga tcattgaacg agcaacgtac   1380
accctggaaa agaagtttgg gatccacctg aaggagatcg acaaggaaga acacctgtat   1440
attcttgtct gcacacggga ctcctcagct cgcctccttg gaaaaaccaa ggacactccc   1500
aggctgagtc tcctcttggt gattctgggc gtcatcttca tgaatggcaa ccgtgccagc   1560
gaggctgtcc tctgggaggc actacgcaag atgggactgc gccctggggt gaggcaccca   1620
ttcctcggcg atctgaggaa gctcatcaca gatgactttg tgaagcagaa gtacctggaa   1680
tacaagaaga tccccaacag caacccacct gagtatgaat tcctctgggg cctgcgagcc   1740
cgccatgaga ccagcaagat gagggtcctg agattcatcg cccagaatca gaaccgagac   1800
ccccgggaat ggaaggctca tttcttggag gctgtggatg atgctttcaa gacaatggat   1860
gtggatatgg ccgaggaaca tgccagggcc cagatgaggg cccagatgaa tatcggggat   1920
gaagcgctga ttggacggtg gagctgggat gacatacaag tcgagctcct gacctgggat   1980
gaggacggag attttggcga tgcctgggcc aggatcccct ttgctttctg ggccagatac   2040
catcagtaca ttctgaatag caaccgtgcc aacaggaggg ccacgtggag agctggcgtc   2100
agcagtggca ccaatggagg ggccagcacc agcgtcctag atggccccag caccagctcc   2160
accatccgga ccagaaatgc tgccagagct ggcgccagct tcttctcctg gatccagcac   2220
cgttga                                                              2226
```

<210> SEQ ID NO 17
<211> LENGTH: 2226
<212> TYPE: DNA
<213> ORGANISM: Homo sapiens

<400> SEQUENCE: 17

```
atggccgagg gatctttttc tgtgcagagc gaaagctaca gcgtcgagga catggacgag     60
ggttctgatg aagttggcga agaagaaatg gtggaaggaa atgactacga ggagttcggc    120
gccttcggcg gctacggcac cctgacatcc ttcgacatcc acatcctaag agccttcggc    180
tctctgggcc ctggtcttcg gatcctgtct aatgagcctt gggagctgga aaaccccgtg    240
ctggctcaaa ccctggtgga agcactccag ctggatcctg aaaccctggc caacgagaca    300
gctgcgcgtg ctgccaatgt ggccagagct gctgcaagca acagagctgc tcgcgccgcc    360
gctgctgccg cccggacagc ctttagccag gtggtggcca gccacagagt ggccactcct    420
caggttagcg gcgaggatac acagcctacc acctacgccg ccgaagccca gggccccacc    480
cctgaacccc ctctggcctc ccctcagacc tcccagatgc tggtgacaag caaaatggcc    540
gcacctgagg cccctgccac atcagcccaa agccagacag gcagccctgc tcaggaggcc    600
gctactgagg gccctagctc agcttgtgcc ttcagccagg ccccgtgcgc cagagaggtg    660
gacgccaaca gacctagcac cgccttcctg ggccagaacg acgtctttga tttcacccag    720
ccagccggag tgtccggcat ggcctttcct agacccaaga gacctgcccc tgcccaggag    780
gccgccaccg agggccctag cgccgccagc ggagttccac agaccggccc cggcagagaa    840
gtggccgcca cgagacctaa gaccacaaag agcggcaaag ccctggctaa gacaagatgg    900
gtcgaaccgc aaaacgtggt ggccgccgct gccgccaagg ccaaaatggc tacaagtatc    960
cctgagcctg agggcgctgc cgcggccacc gcccagcaca gcgccgagcc ctgggcccgg   1020
atgggcggaa agagaaccaa aaaaagcaag cacctcgatg atgagtacga gagctctgag   1080
gaagagcggg aaacacctgc cgtgcccccc acctggagag ccagccagcc tagcctgacc   1140
gtgcgggccc agctggcccc tcgcccacct atggccccta gaagccagat ccctagcaga   1200
cacgtgctgt gcctgcctcc ccggaacgtg accctgctgc aggagagagc caacaagctg   1260
gtgaagtacc tgatgatcaa ggactataag aagatcccca tcaagcgggc cgacatgctg   1320
aaggatgtga ttagagagta cgacgagcac ttccccgaga tcatcgagcg ggccacgtac   1380
accctggaaa agaaattcgg catccacctg aaagagatcg acaaggaaga acacctgtac   1440
atcctggtgt gcaccagaga cagcagcgct cggctgctgg gaaaaaccaa ggacacccct   1500
cggctgagcc tgctgctcgt gatcctgggc gtgattttca tgaacggcaa cagagcttct   1560
gaggcagtgc tgtgggaagc cctcagaaag atgggcctga gacccggagt cagacatcct   1620
ttcctgggcg acctgagaaa gctgatcacc gacgacttcg tgaagcagaa gtacctggaa   1680
tacaagaaga tccctaatag caatcctcca gagtacgagt tcctgtgggg cctgcgggcc   1740
cgccacgaga catccaagat gagagtgctg aggttcatcg cccagaacca gaaccgcgac   1800
cccagagagt ggaaggccca cttcctggaa gccgtggatg acgcttttaa gacaatggat   1860
gtggacatgg ccgaggaaca cgcccgagct cagatgcggg cccaaatgaa catcggcgac   1920
gaggccctga tcggcagatg gtcctgggac gatatccagg tggaactgct gacctgggat   1980
gaggacggcg atttcggcga cgcctgggcc cgaatcccat tcgccttctg ggctagatac   2040
caccagtaca tcctgaacag caacagagct aaccgtagag ccacctggcg ggccggcgtg   2100
tccagcggca caaacggcgg cgcctctaca agcgtgctgg acggcccaag cacaagcagc   2160
accatcagaa ccagaaacgc cgctagagcc ggcgccagct tcttcagctg gatccagcat   2220
agatga                                                              2226
```

<210> SEQ ID NO 18
<211> LENGTH: 3072

<212> TYPE: DNA
<213> ORGANISM: Homo sapiens

<400> SEQUENCE: 18
atgggttgga gctgtatcat cttctttctg gtagcaacag ctacaggtgt gcactccaaa 60
aaccttgatt gttgggtcga caacgaagaa gacatcgatg ttatcctgaa aaagtctacc 120
attctgaact tggacatcaa caacgatatt atctccgaca tctctggttt caactcctct 180
gttatcacat atccagatgc tcaattggtg ccgggcatca acggcaaagc tatccacctg 240
gttaacaacg aatcttctga agttatcgtg cacaaggcca tggacatcga atacaacgac 300
atgttcaaca acttcaccgt tagcttctgg ctgcgcgttc cgaaagtttc tgcttcccac 360
ctggaacagt acggcactaa cgagtactcc atcatcagct ctatgaagaa acactccctg 420
tccatcggct ctggttggtc tgtttccctg aagggtaaca acctgatctg gactctgaaa 480
gactccgcgg gcgaagttcg tcagatcact ttccgcgacc tgccggacaa gttcaacgcg 540
tacctggcta acaaatgggt tttcatcact atcactaacg atcgtctgtc ttctgctaac 600
ctgtacatca acggcgttct gatgggctcc gctgaaatca ctggtctggg cgctatccgt 660
gaggacaaca acatcactct taagctggac cgttgcaaca acaacaacca gtacgtatcc 720
atcgacaagt tccgtatctt ctgcaaagca ctgaacccga aagagatcga aaaactgtat 780
accagctacc tgtctatcac cttcctgcgt gacttctggg gtaacgcggc cgctggaccc 840
ggacctatgg ctgagggaag cttcagcgtg caatcggaaa gctacagtgt tgaagacatg 900
gatgagggta gcgacgaagt cggggaggaa gagatggttg aaggcaacga ctatgaagaa 960
ttcggtgcgt ttggtggcta tggcaccctc accagctttg acatccatat cctcagagcc 1020
ttcggaagct tgggtccagg ccttcgcatc ttatcgaatg agccctggga actggaaaac 1080
cctgtgctgg cccagaccct ggtggaggca ttgcagctgg atccggaaac acttgccaat 1140
gagacggccg cccgtgctgc caacgtagcc cgcgccgccg cctccaaccg tgcggctcgg 1200
gccgctgccg ccgctgcccg taccgccttc agtcaggtgg tcgctagcca ccgggtggcc 1260
acgccgcagg tctcaggaga ggataccccag cccacgacct acgccgccga ggctcagggg 1320
cccacccctg agccacccct tgcttctccg cagacctccc agatgttagt caccagtaag 1380
atggctgccc ccgaggctcc ggcaacctcc gcacagtccc agacaggctc cccggcccag 1440
gaggctgcta ctgagggccc tagtagcgcc tgtgctttct ctcaggctcc gtgtgccagg 1500
gaggtggacg ccaaccggcc cagcacagcc ttcctgggcc agaatgatgt cttcgatttc 1560
actcagccgg caggtgtcag tggcatggcc ttcccgcgcc ccaagagacc tgccccagcc 1620
caagaggctg ccacagaggg ccccagtgct gcctctggtg tgccccagac gggacctggc 1680
agggaggtgg cagccacccg gcccaagacc accaagtcgg ggaaggcgct ggccaagact 1740
cggtgggtgg agcctcagaa tgttgtggca gcagctgctg ccaaggccaa gatggccacg 1800
agcatccctg agccggaggg tgcagctgct gccactgctc agcacagtgc tgagccctgg 1860
gccaggatgg gaggcaagag gaccaagaag tccaagcacc tggatgatga gtatgagagc 1920
agcgaggagg agagagagac tcccgcggtc ccacccacct ggagagcatc acagccctca 1980
ttgacggtgc gggctcagtt ggcccctcgg cccccgatgg ccccgaggtc ccagataccc 2040
tcaaggcacg tactgtgcct gcccccccgc aacgtgaccc ttctgcagga gagggcaaat 2100
aagttggtga aatacctgat gattaaggac tacaagaaga tccccatcaa gcgcgcagac 2160
atgctgaagg atgtcatcag agaatatgat gaacatttcc ctgagatcat tgaacgagca 2220

```
acgtacaccc tggaaaagaa gtttgggatc cacctgaagg agatcgacaa ggaagaacac   2280

ctgtatattc ttgtctgcac acgggactcc tcagctcgcc tccttggaaa aaccaaggac   2340

actcccaggc tgagtctcct cttggtgatt ctgggcgtca tcttcatgaa tggcaaccgt   2400

gccagcgagg ctgtcctctg ggaggcacta cgcaagatgg gactgcgccc tggggtgagg   2460

cacccattcc tcggcgatct gaggaagctc atcacagatg actttgtgaa gcagaagtac   2520

ctggaataca agaagatccc caacagcaac ccacctgagt atgaattcct ctggggcctg   2580

cgagcccgcc atgagaccag caagatgagg gtcctgagat tcatcgccca gaatcagaac   2640

cgagaccccc gggaatggaa ggctcatttc ttggaggctg tggatgatgc tttcaagaca   2700

atggatgtgg atatggccga ggaacatgcc agggcccaga tgagggccca gatgaatatc   2760

ggggatgaag cgctgattgg acggtggagc tgggatgaca tacaagtcga gctcctgacc   2820

tgggatgagg acggagattt tggcgatgcc tgggccagga tcccctttgc tttctgggcc   2880

agataccatc agtacattct gaatagcaac cgtgccaaca ggagggccac gtggagagct   2940

ggcgtcagca gtggcaccaa tggaggggcc agcaccagcg tcctagatgg ccccagcacc   3000

agctccacca tccggaccag aaatgctgcc agagctggcg ccagcttctt ctcctggatc   3060

cagcaccgtt ga                                                       3072
```

```
<210> SEQ ID NO 19
<211> LENGTH: 3072
<212> TYPE: DNA
<213> ORGANISM: Homo sapiens

<400> SEQUENCE: 19

atgggttgga gctgtatcat cttctttctg gtagcaacag ctacaggtgt gcactccaaa     60

aaccttgatt gttgggtcga caacgaagaa gacatcgatg ttatcctgaa aaagtctacc    120

attctgaact tggacatcaa caacgatatt atctccgaca tctctggttt caactcctct    180

gttatcacat atccagatgc tcaattggtg ccgggcatca acggcaaagc tatccacctg    240

gttaacaacg aatcttctga agttatcgtg cacaaggcca tggacatcga atacaacgac    300

atgttcaaca acttcaccgt tagcttctgg ctgcgcgttc cgaaagtttc tgcttcccac    360

ctggaacagt acggcactaa cgagtactcc atcatcagct ctatgaagaa acactccctg    420

tccatcggct ctggttggtc tgtttccctg aagggtaaca acctgatctg gactctgaaa    480

gactccgcgg gcgaagttcg tcagatcact ttccgcgacc tgccggacaa gttcaacgcg    540

tacctggcta acaaatgggt tttcatcact atcactaacg atcgtctgtc ttctgctaac    600

ctgtacatca acggcgttct gatgggctcc gctgaaatca ctggtctggg cgctatccgt    660

gaggacaaca acatcactct taagctggac cgttgcaaca acaacaacca gtacgtatcc    720

atcgacaagt tccgtatctt ctgcaaagca ctgaacccga aagagatcga aaaactgtat    780

accagctacc tgtctatcac cttcctgcgt gacttctggg gtaacgcggc cgctggaccc    840

ggacctatgg ccgagggatc tttttctgtg cagagcgaaa gctacagcgt cgaggacatg    900

gacgagggtt ctgatgaagt tggcgaagaa gaaatggtgg aaggaaatga ctacgaggag    960

ttcggcgcct tcggcggcta cggcaccctg acatccttcg acatccacat cctaagagcc   1020

ttcggctctc tgggccctgg tcttcggatc ctgtctaatg agccttggga gctggaaaac   1080

cccgtgctgg ctcaaaccct ggtggaagca ctccagctgg atcctgaaac cctggccaac   1140

gagacagctg cgcgtgctgc caatgtggcc agagctgctg caagcaacag agctgctcgc   1200

gccgccgctg ctgccgcccg gacagccttt agccaggtgg tggccagcca cagagtggcc   1260
```

```
actcctcagg ttagcggcga ggatacacag cctaccacct acgccgccga agcccagggc   1320

cccaccccctg aaccccctct ggcctcccct cagacctccc agatgctggt gacaagcaaa   1380

atggccgcac ctgaggcccc tgccacatca gcccaaagcc agacaggcag ccctgctcag   1440

gaggccgcta ctgagggccc tagctcagct tgtgccttca gccaggcccc gtgcgccaga   1500

gaggtggacg ccaacagacc tagcaccgcc ttcctgggcc agaacgacgt ctttgatttc   1560

acccagccag ccggagtgtc cggcatggcc tttcctagac ccaagagacc tgcccctgcc   1620

caggaggccg ccaccgaggg ccctagcgcc gccagcggag ttccacagac cggccccggc   1680

agagaagtgg ccgccacgag acctaagacc acaaagagcg gcaaagccct ggctaagaca   1740

agatgggtcg aaccgcaaaa cgtggtggcc gccgctgccg ccaaggccaa aatggctaca   1800

agtatccctg agcctgaggg cgctgccgcg gccaccgccc agcacagcgc cgagccctgg   1860

gcccggatgg gcggaaagag aaccaaaaaa agcaagcacc tcgatgatga gtacgagagc   1920

tctgaggaag agcgggaaac acctgccgtg ccccccacct ggagagccag ccagcctagc   1980

ctgaccgtgc gggcccagct ggcccctcgc ccacctatgg cccctagaag ccagatccct   2040

agcagacacg tgctgtgcct gcctccccgg aacgtgaccc tgctgcagga gagagccaac   2100

aagctggtga agtacctgat gatcaaggac tataagaaga tccccatcaa gcgggccgac   2160

atgctgaagg atgtgattag agagtacgac gagcacttcc ccgagatcat cgagcgggcc   2220

acgtacaccc tggaaaagaa attcggcatc cacctgaaag agatcgacaa ggaagaacac   2280

ctgtacatcc tggtgtgcac cagagacagc agcgctcggc tgctgggaaa aaccaaggac   2340

acccctcggc tgagcctgct gctcgtgatc ctgggcgtga ttttcatgaa cggcaacaga   2400

gcttctgagg cagtgctgtg ggaagccctc agaaagatgg gcctgagacc cggagtcaga   2460

catcctttcc tgggcgacct gagaaagctg atcaccgacg acttcgtgaa gcagaagtac   2520

ctggaataca agaagatccc taatagcaat cctccagagt acgagttcct gtggggcctg   2580

cgggcccgcc acgagacatc caagatgaga gtgctgaggt tcatcgccca gaaccagaac   2640

cgcgacccca gagagtggaa ggcccacttc ctggaagccg tggatgacgc ttttaagaca   2700

atggatgtgg acatggccga ggaacacgcc cgagctcaga tgcgggccca aatgaacatc   2760

ggcgacgagg ccctgatcgg cagatggtcc tgggacgata tccaggtgga actgctgacc   2820

tgggatgagg acggcgattt cggcgacgcc tgggcccgaa tcccattcgc cttctgggct   2880

agataccacc agtacatcct gaacagcaac agagctaacc gtagagccac ctggcgggcc   2940

ggcgtgtcca gcggcacaaa cggcggcgcc tctacaagcg tgctggacgg cccaagcaca   3000

agcagcacca tcagaaccag aaacgccgct agagccggcg ccagcttctt cagctggatc   3060

cagcatagat ga                                                      3072
```

<210> SEQ ID NO 20
<211> LENGTH: 1314
<212> TYPE: DNA
<213> ORGANISM: Homo sapiens

<400> SEQUENCE: 20

```
atgggcagga ggatgcgggg cgccgccgcc accgcggggc tctggctgct ggcgctgggc     60

tcgctgctgg cgctgtgggg agggctcctg ccgccgcgga ccgagctgcc cgcctcccgg    120

ccgcccgaag accgactccc acggcgcccg gcccggagcg gcggccccgc gcccgcgcct    180

cgcttccctc tgcccccgcc cctggcgtgg gacgcccgcg gcggctccct gaaaactttc    240
```

```
cgggcgctgc tcaccctggc ggccggcgcg gacggcccgc cccggcagtc ccggagcgag    300

cccaggtggc acgtgtcagc caggcagccc cggccggagg agagcgccgc ggtgcacggg    360

ggcgtcttct ggagccgcgg cctggaggag caggtgcccc cgggctttc ggaggcccag     420

gcggcggcgt ggctggaggc ggctcgcggc gcccggatgg tggccctgga gcgcgggggt    480

tgcgggcgca gctccaaccg actggcccgt tttgccgacg gcacccgcgc ctgcgtgcgc    540

tacggcatca acccggagca gattcagggc gaggccctgt cttactatct ggcgcgcctg    600

ctgggcctcc agcgccacgt gccgccgctg gcactggctc gggtggaggc tcggggcgcg    660

cagtgggcgc aggtgcagga ggagctgcgc gctgcgcact ggaccgaggg cagcgtggtg    720

agcctgacac gctggctgcc caacctcacg gacgtggtgg tgcccgcgcc ctggcgctcg    780

gaggacggcc gtctgcgccc cctccgggat gccgggggtg agctggccaa cctcagccag    840

gcggagctgg tggacctagt acaatggacc gacttaatcc ttttcgacta cctgacggcc    900

aacttcgacc ggctcgtaag caacctcttc agcctgcagt gggacccgcg cgtcatgcag    960

cgtgccacca gcaacctgca ccgcggtccg ggcggggcgc tggtctttct ggacaatgag   1020

gcgggcttgg tgcacggcta ccgggtagca ggcatgtggg acaagtataa cgagccgctg   1080

ttgcagtcag tgtgcgtgtt ccgcgagcgg accgcgcggc gcgtcctgga gctgcaccgc   1140

ggacaggacg ccgcggcccg gctgctgcgc ctctaccggc gccacgagcc tcgcttcccc   1200

gagctggccg cccttgcaga cccccacgct cagctgctac agcgccgcct cgacttcctc   1260

gccaagcaca ttttgcactg taaggccaag tacggccgcc ggtctgggac ttag         1314
```

<210> SEQ ID NO 21
<211> LENGTH: 1314
<212> TYPE: DNA
<213> ORGANISM: Homo sapiens

<400> SEQUENCE: 21

```
atgggcagaa gaatgagagg cgccgctgcc accgccggac tctggctact ggctctgggc     60

agcctgctgg ctctgtgggg cggcctgctg cctccacgaa cagagctgcc cgctagcaga    120

cctccagaag atagactgcc tcggcggcct gccagaagcg gcggacctgc accagcccct    180

agattccccc tgcctcctcc tcttgcctgg gatgccagag gcggaagcct gaagaccttc    240

agagccctgc tcaccctggc agctggagcc gacggccctc ctagacagag cagatcagag    300

cctcggtggc acgtgtccgc ccggcagcct cggcccgagg aaagcgccgc cgtgcacggc    360

ggcgtgttct ggtccagagg cctggaagaa caggtgcctc ccggcttctc agaggcccag    420

gccgctgcct ggctggaagc tgctagaggc gccagaatgg tggccctcga gcggggcggt    480

tgtggcagaa gcagcaatag actggctcgg ttcgccgatg gcaccagagc ctgcgtgcgg    540

tacggcatca accccgagca gatccagggc gaggccctca gctactacct ggccagactg    600

ctgggactgc aaagacacgt gccacctctg gccctcgcca gggtggaagc cagaggggcc    660

cagtgggccc aagtgcagga ggaactgaga gccgcccact ggaccgaggg cagcgtggtc    720

agcctgacca gatggctgcc caacctgacc gacgtggtgg ttcctgcccc ttggcggtct    780

gaagatggaa gactgagacc cctgcgcgat gccggcggcg agctggccaa tctgagccag    840

gccgagctgg tcgacctggt gcagtggaca gacctgatcc tgtttgatta cctgaccgcc    900

aacttcgacc ggctggtgtc caacctgttc agcctgcagt gggaccctag agtgatgcag    960

cgggccacaa gcaacctcca ccggggtcct ggcggcgccc tcgtgtttct ggacaacgag   1020

gccggactgg ttcatggcta cagagtggcc ggcatgtggg acaagtacaa cgagcccctg   1080
```

```
cttcaaagcg tgtgcgtgtt ccgcgagaga accgccagaa gagtgctgga actgcacaga   1140

ggacaggacg ccgccgccag actgctgcgg ctgtaccggc ggcacgagcc tagattccct   1200

gaactggccg ctctggccga cccccacgcc cagctgctgc agagaaggct cgacttcctg   1260

gctaagcaca tcctgcactg caaggccaag tacggcagac ggagcggaac atga         1314


<210> SEQ ID NO 22
<211> LENGTH: 2160
<212> TYPE: DNA
<213> ORGANISM: Homo sapiens

<400> SEQUENCE: 22

atgggttgga gctgtatcat cttctttctg gtagcaacag ctacaggtgt gcactccaaa     60

aaccttgatt gttgggtcga caacgaagaa gacatcgatg ttatcctgaa aaagtctacc    120

attctgaact tggacatcaa caacgatatt atctccgaca tctctggttt caactcctct    180

gttatcacat atccagatgc tcaattggtg ccgggcatca acggcaaagc tatccacctg    240

gttaacaacg aatcttctga agttatcgtg cacaaggcca tggacatcga atacaacgac    300

atgttcaaca acttcaccgt tagcttctgg ctgcgcgttc cgaaagtttc tgcttcccac    360

ctggaacagt acggcactaa cgagtactcc atcatcagct ctatgaagaa acactccctg    420

tccatcggct ctggttggtc tgtttccctg aagggtaaca acctgatctg gactctgaaa    480

gactccgcgg gcgaagttcg tcagatcact ttccgcgacc tgccggacaa gttcaacgcg    540

tacctggcta acaaatgggt tttcatcact atcactaacg atcgtctgtc ttctgctaac    600

ctgtacatca acggcgttct gatgggctcc gctgaaatca ctggtctggg cgctatccgt    660

gaggacaaca acatcactct taagctggac cgttgcaaca acaacaacca gtacgtatcc    720

atcgacaagt tccgtatctt ctgcaaagca ctgaacccga aagagatcga aaaactgtat    780

accagctacc tgtctatcac cttcctgcgt gacttctggg gtaacgcggc cgctggaccc    840

ggacctatgg gcaggaggat gcggggcgcc gccgccaccg cggggctctg gctgctggcg    900

ctgggctcgc tgctggcgct gtggggaggg ctcctgccgc cgcggaccga gctgcccgcc    960

tcccggccgc ccgaagaccg actcccacgg cgcccggccc ggagcggcgg ccccgcgccc   1020

gcgcctcgct tccctctgcc cccgcccctg gcgtgggacg cccgcggcgg ctccctgaaa   1080

actttccggg cgctgctcac cctggcggcc ggcgcggacg gcccgccccg gcagtcccgg   1140

agcgagccca ggtggcacgt gtcagccagg cagccccggc cggaggagag cgccgcggtg   1200

cacgggggcg tcttctggag ccgcggcctg gaggagcagg tgcccccggg cttttcggag   1260

gcccaggcgg cggcgtggct ggaggcggct cgcggcgccc ggatggtggc cctggagcgc   1320

gggggttgcg ggcgcagctc caaccgactg gcccgttttg ccgacggcac ccgcgcctgc   1380

gtgcgctacg gcatcaaccc ggagcagatt cagggcgagg ccctgtctta ctatctggcg   1440

cgcctgctgg gcctccagcg ccacgtgccg ccgctggcac tggctcgggt ggaggctcgg   1500

ggcgcgcagt gggcgcaggt gcaggaggag ctgcgcgctg cgcactggac cgagggcagc   1560

gtggtgagcc tgacacgctg gctgcccaac ctcacggacg tggtggtgcc cgcgccctgg   1620

cgctcggagg acggccgtct gcgccccctc cgggatgccg ggggtgagct ggccaacctc   1680

agccaggcgg agctggtgga cctagtacaa tggaccgact taatcctttt cgactacctg   1740

acggccaact tcgaccggct cgtaagcaac ctcttcagcc tgcagtggga cccgcgcgtc   1800

atgcagcgtg ccaccagcaa cctgcaccgc ggtccgggcg ggcgctggt ctttctggac    1860
```

aatgaggcgg gcttggtgca cggctaccgg gtagcaggca tgtgggacaa gtataacgag 1920
ccgctgttgc agtcagtgtg cgtgttccgc gagcggaccg cgcggcgcgt cctggagctg 1980
caccgcggac aggacgccgc ggcccggctg ctgcgcctct accggcgcca cgagcctcgc 2040
ttccccgagc tggccgccct tgcagacccc cacgctcagc tgctacagcg ccgcctcgac 2100
ttcctcgcca agcacatttt gcactgtaag gccaagtacg gccgccggtc tgggacttag 2160

<210> SEQ ID NO 23
<211> LENGTH: 2160
<212> TYPE: DNA
<213> ORGANISM: Homo sapiens

<400> SEQUENCE: 23
atgggttgga gctgtatcat cttctttctg gtagcaacag ctacaggtgt gcactccaaa 60
aaccttgatt gttgggtcga caacgaagaa gacatcgatg ttatcctgaa aaagtctacc 120
attctgaact tggacatcaa caacgatatt atctccgaca tctctggttt caactcctct 180
gttatcacat atccagatgc tcaattggtg ccgggcatca acggcaaagc tatccacctg 240
gttaacaacg aatcttctga agttatcgtg cacaaggcca tggacatcga atacaacgac 300
atgttcaaca acttcaccgt tagcttctgg ctgcgcgttc cgaaagtttc tgcttcccac 360
ctggaacagt acggcactaa cgagtactcc atcatcagct ctatgaagaa acactccctg 420
tccatcggct ctggttggtc tgtttccctg aagggtaaca acctgatctg gactctgaaa 480
gactccgcgg gcgaagttcg tcagatcact ttccgcgacc tgccggacaa gttcaacgcg 540
tacctggcta acaaatgggt tttcatcact atcactaacg atcgtctgtc ttctgctaac 600
ctgtacatca acggcgttct gatgggctcc gctgaaatca ctggtctggg cgctatccgt 660
gaggacaaca acatcactct taagctggac cgttgcaaca acaacaacca gtacgtatcc 720
atcgacaagt tccgtatctt ctgcaaagca ctgaacccga aagagatcga aaaactgtat 780
accagctacc tgtctatcac cttcctgcgt gacttctggg gtaacgcggc cgctggaccc 840
ggacctatgg gcagaagaat gagaggcgcc gctgccaccg ccggactctg gctactggct 900
ctgggcagcc tgctggctct gtggggcggc ctgctgcctc cacgaacaga gctgcccgct 960
agcagacctc cagaagatag actgcctcgg cggcctgcca gaagcggcgg acctgcacca 1020
gcccctagat tcccccctgcc tcctcctctt gcctgggatg ccagaggcgg aagcctgaag 1080
accttcagag ccctgctcac cctggcagct ggagccgacg gccctcctag acagagcaga 1140
tcagagcctc ggtggcacgt gtccgcccgg cagcctcggc ccgaggaaag cgccgccgtg 1200
cacggcggcg tgttctggtc cagaggcctg gaagaacagg tgcctcccgg cttctcagag 1260
gcccaggccg ctgcctggct ggaagctgct agaggcgcca gaatggtggc cctcgagcgg 1320
ggcggttgtg gcagaagcag caatagactg gctcggttcg ccgatggcac cagagcctgc 1380
gtgcggtacg gcatcaaccc cgagcagatc cagggcgagg ccctcagcta ctacctggcc 1440
agactgctgg gactgcaaag acacgtgcca cctctggccc tcgccagggt ggaagccaga 1500
ggggcccagt gggcccaagt gcaggaggaa ctgagagccg cccactggac cgagggcagc 1560
gtggtcagcc tgaccagatg gctgcccaac ctgaccgacg tggtggttcc tgccccttgg 1620
cggtctgaag atggaagact gagacccctg cgcgatgccg gcggcgagct ggccaatctg 1680
agccaggccg agctggtcga cctggtgcag tggacagacc tgatcctgtt tgattacctg 1740
accgccaact tcgaccggct ggtgtccaac ctgttcagcc tgcagtggga ccctagagtg 1800
atgcagcggg ccacaagcaa cctccaccgg ggtcctggcg gcgccctcgt gtttctggac 1860
aacgaggccg gactggttca tggctacaga gtggccggca tgtgggacaa gtacaacgag 1920
cccctgcttc aaagcgtgtg cgtgttccgc gagagaaccg ccagaagagt gctggaactg 1980
cacagaggac aggacgccgc cgccagactg ctgcggctgt accggcggca cgagcctaga 2040
ttccctgaac tggccgctct ggccgacccc cacgcccagc tgctgcagag aaggctcgac 2100
ttcctggcta agcacatcct gcactgcaag gccaagtacg gcagacggag cggaacatga 2160

<210> SEQ ID NO 24
<211> LENGTH: 1437
<212> TYPE: DNA
<213> ORGANISM: Homo sapiens

<400> SEQUENCE: 24
atggctgagg gaagcttcag cgtgcaatcg gaaagctaca gtgttgaaga catggatgag 60
ggtagcgacg aagtcgggga ggaagagatg gttgaaggca acgactatga agaattcggt 120
gcgtttggtg gctatggcac cctcaccagc tttgacatcc atatcctcag agccttcgga 180
agcttgggtc caggccttcg catcttatcg aatgagccct gggaactgga aaaccctgtg 240
ctggcccaga ccctggtgga ggcattgcag ctggatccgg aaacacttgc caatgagacg 300
gccgcccgtg ctgccaacgt agcccgcgcc gccgcctcca accgtgcggc tcgggccgct 360
gccgccgctg cccgtaccgc cttcagtcag gtggtcgcta gccaccgggt ggccacgccg 420
caggtctcag gagaggatac ccagcccacg acctacgccg ccgaggctca ggggcccacc 480
cctgagccac cccttgcttc tccgcagacc tcccagatgt tagtcaccag taagatggct 540
gcccccgagg ctccggcaac ctccgcacag tcccagacag gctccccggc ccaggaggct 600
gctactgagg gccctagtag cgcctgtgct ttctctcagg ctccgtgtgc cagggaggtg 660
gacgccaacc ggcccagcac agccttcctg ggccagaatg atgtcttcga tttcactcag 720
ccggcaggtg tcagtggcat ggccttcccg cgccccaaga gacctgcccc agcccaagag 780
gctgccacag agggccccag tgctgcctct ggtgtgcccc agacgggacc tggcagggag 840
gtggcagcca cccggcccaa gaccaccaag tcggggaagg cgctggccaa gactcggtgg 900
gtggagcctc agaatgttgt ggcagcagct gctgccaagg ccaagatggc cacgagcatc 960
cctgagccgg agggtgcagc tgctgccact gctcagcaca gtgctgagcc ctgggccagg 1020
atgggaggca agaggaccaa gaagtccaag cacctggatg atgagtatga gagcagcgag 1080
gaggagagag agactcccgc ggtcccaccc acctggagag catcacagcc ctcattgacg 1140
gtgcgggctc agttggcccc tcggcccccg atggccccga ggtcccagat accctcaagg 1200
cacgtactgt gcctgccccc ccgcaacgtg accagactgt ctctgctgct ggtcatcctg 1260
tacattctga atagcaaccg tgccaacagg agggccacgt ggagagctgg cgtcagcagt 1320
ggcaccaatg gaggggccag caccagcgtc ctagatggcc ccagcaccag ctccaccatc 1380
cggaccagaa atgctgccag agctggcgcc agcttcttct cctggatcca gcaccgt 1437

<210> SEQ ID NO 25
<211> LENGTH: 1956
<212> TYPE: DNA
<213> ORGANISM: Homo sapiens

<400> SEQUENCE: 25
atggctgagg gaagcttcag cgtgcaatcg gaaagctaca gtgttgaaga catggatgag 60
ggtagcgacg aagtcgggga ggaagagatg gttgaaggca acgactatga agaattcggt 120

```
gcgtttggtg gctatggcac cctcaccagc tttgacatcc atatcctcag agccttcgga    180

agcttgggtc caggccttcg catcttatcg aatgagccct gggaactgga aaaccctgtg    240

ctggcccaga ccctggtgga ggcattgcag ctggatccgg aaacacttgc caatgagacg    300

gccgcccgtg ctgccaacgt agcccgcgcc gccgcctcca accgtgcggc tcgggccgct    360

gccgccgctg cccgtaccgc cttcagtcag gtggtcgcta gccaccgggt ggccacgccg    420

caggtctcag gagaggatac ccagcccacg acctacgccg ccgaggctca ggggcccacc    480

cctgagccac cccttgcttc tccgcagacc tcccagatgt tagtcaccag taagatggct    540

gcccccgagg ctccggcaac ctccgcacag tcccagacag gctccccggc ccaggaggct    600

gctactgagg gccctagtag cgcctgtgct ttctctcagg ctccgtgtgc cagggaggtg    660

gacgccaacc ggcccagcac agccttcctg ggccagaatg atgtcttcga tttcactcag    720

ccggcaggtg tcagtggcat ggccttcccg cgccccaaga gacctgcccc agcccaagag    780

gctgccacag agggccccag tgctgcctct ggtgtgcccc agacgggacc tggcagggag    840

gtggcagcca cccggcccaa gaccaccaag tcggggaagg cgctggccaa gactcggtgg    900

gtggagcctc agaatgttgt ggcagcagct gctgccaagg ccaagatggc cacgagcatc    960

cctgagccgg agggtgcagc tgctgccact gctcagcaca gtgctgagcc ctgggccagg   1020

atgggaggca agaggaccaa gaagtccaag cacctggatg atgagtatga gagcagcgag   1080

gaggagagag agactcccgc ggtcccaccc acctggagag catcacagcc ctcattgacg   1140

gtgcgggctc agttggcccc tcggcccccg atggccccga ggtcccagat accctcaagg   1200

cacgtactgt gcctgccccc ccgcaacgtg accaggctga gtctcctctt ggtgattctg   1260

ggcgtcatct tcatgaatgg caaccgtgcc agcgaggctg tcctctggga ggcactacgc   1320

aagatgggac tgcgccctgg ggtgaggcac ccattcctcg gcgatctgag gaagctcatc   1380

acagatgact ttgtgaagca gaagtacctg gaatacaaga agatccccaa cagcaaccca   1440

cctgagtatg aattcctctg gggcctgcga gcccgccatg agaccagcaa gatgagggtc   1500

ctgagattca tcgcccagaa tcagaaccga gacccccggg aatggaaggc tcatttcttg   1560

gaggctgtgg atgatgcttt caagacaatg gatgtggata tggccgagga acatgccagg   1620

gcccagatga gggcccagat gaatatcggg gatgaagcgc tgattggacg gtggagctgg   1680

gatgacatac aagtcgagct cctgacctgg gatgaggacg gagattttgg cgatgcctgg   1740

gccaggatcc cctttgcttt ctgggccaga taccatcagt acattctgaa tagcaaccgt   1800

gccaacagga gggccacgtg gagagctggc gtcagcagtg gcaccaatgg aggggccagc   1860

accagcgtcc tagatggccc cagcaccagc tccaccatcc ggaccagaaa tgctgccaga   1920

gctggcgcca gcttcttctc ctggatccag caccgt                             1956
```

<210> SEQ ID NO 26
<211> LENGTH: 1704
<212> TYPE: DNA
<213> ORGANISM: Homo sapiens

<400> SEQUENCE: 26

```
atggctgagg gaagcttcag cgtgcaatcg gaaagctaca gtgttgaaga catggatgag     60

ggtagcgacg aagtcgggga ggaagagatg gttgaaggca acgactatga agaattcggt    120

gcgtttggtg gctatggcac cctcaccagc tttgacatcc atatcctcag agccttcgga    180

agcttgggtc caggccttcg catcttatcg aatgagccct gggaactgga aaaccctgtg    240

ctggcccaga ccctggtgga ggcattgcag ctggatccgg aaacacttgc caatgagacg    300
```

```
gccgcccgtg ctgccaacgt agcccgcgcc gccgcctcca accgtgcggc tcgggccgct    360

gccgccgctg cccgtaccgc cttcagtcag gtggtcgcta gccaccgggt ggccacgccg    420

caggtctcag gagaggatac ccagcccacg acctacgccg ccgaggctca ggggcccacc    480

cctgagccac cccttgcttc tccgcagacc tcccagatgt tagtcaccag taagatggct    540

gcccccgagg ctccggcaac ctccgcacag tcccagacag gctccccggc ccaggaggct    600

gctactgagg gccctagtag cgcctgtgct ttctctcagg ctccgtgtgc cagggaggtg    660

gacgccaacc ggcccagcac agccttcctg ggccagaatg atgtcttcga tttcactcag    720

ccggcaggtg tcagtggcat ggccttcccg cgccccaaga gacctgcccc agcccaagag    780

gctgccacag agggccccag tgctgcctct ggtgtgcccc agacgggacc tggcagggag    840

gtggcagcca cccggcccaa gaccaccaag tcggggaagg cgctggccaa gactcggtgg    900

gtggagcctc agaatgttgt ggcagcagct gctgccaagg ccaagatggc cacgagcatc    960

cctgagccgg agggtgcagc tgctgccact gctcagcaca gtgctgagcc ctgggccagg   1020

atgggaggca agaggaccaa gaagtccaag cacctggatg atgagtatga gagcagcgag   1080

gaggagagag agactcccgc ggtcccaccc acctggagag catcacagcc ctcattgacg   1140

gtgcgggctc agttggcccc tcggcccccg atggccccga ggtcccagat accctcaagg   1200

cacgtactgt gcctgccccc ccgcaacgtg acccttctgc aggagagggc aaataagttg   1260

gtgaaatacc tgatgattaa ggactacaag aagatcccca tcaagcgcgc agacatgctg   1320

aaggatgtca tcagagaata tgatgaacat ttccctgaga tcattgaacg agcaacgtac   1380

accctggaaa agaagtttgg gatccacctg aaggagatcg acaaggaaga acacctgtat   1440

attcttgtct gcacacggga ctcctcagct cgcctccttg gaaaaaccaa ggacactccc   1500

aggctgagtc tcctcttggt gattctgtac attctgaata gcaaccgtgc caacaggagg   1560

gccacgtgga gagctggcgt cagcagtggc accaatggag ggccagcac cagcgtccta     1620

gatggcccca gcaccagctc caccatccgg accagaaatg ctgccagagc tggcgccagc   1680

ttcttctcct ggatccagca ccgt                                          1704
```

<210> SEQ ID NO 27
<211> LENGTH: 57
<212> TYPE: DNA
<213> ORGANISM: Homo sapiens

<400> SEQUENCE: 27

```
atgggttgga gctgtatcat cttctttctg gtagcaacag ctacaggtgt gcactcc        57
```

<210> SEQ ID NO 28
<211> LENGTH: 711
<212> TYPE: DNA
<213> ORGANISM: Homo sapiens

<400> SEQUENCE: 28

```
atgagcgccc ctgcctctac aacacagcct atcggcagca ccacctccac caccacaaaa     60

acagctggcg ctacccctgc cacagcctct ggcctgttta caatccctga cggcgacttc    120

ttcagcaccg ccagagctat cgtggcctct aacgccgtgg ccacaaacga ggacctgagc    180

aagatcgagg ccatctggaa ggacatgaag gtgcccaccg acacaatggc ccaggctgct    240

tgggatctcg tcagacactg tgccgatgtg ggcagctctg cccagacaga gatgatcgac    300

acaggcccct acagcaacgg catcagcaga gctagactgg ccgctgccat caaagaagtg    360
```

```
tgcaccctga gacagttctg catgaagtac gcccctgtcg tgtggaactg gatgctgacc    420

aacaacagcc ctcctgccaa ctggcaggct cagggcttta agccagagca caagttcgcc    480

gccttcgatt tcttcaacgg cgtgacaaac cctgccgcca tcatgcctaa agagggcctg    540

atcagacctc ctagcgaggc cgagatgaac gccgctcaga ctgctgcctt cgtgaagatc    600

accaaggcca gggctcagag caacgacttc gcctctcttg atgccgccgt gaccagaggc    660

agaatcaccg gaaccacaac agccgaggct gtcgtgacat tgcctcctcc a             711


<210> SEQ ID NO 29
<211> LENGTH: 288
<212> TYPE: DNA
<213> ORGANISM: Homo sapiens

<400> SEQUENCE: 29

atgtgctgta ccaagtctct gctgctggcc gctctgatgt ctgtgctgct gctgcatctg     60

tgtggcgagt ctgaggccgc cagcaacttc gactgttgtc tgggctacac cgacagaatc    120

ctgcatccta agttcatcgt gggcttcacc agacagctgg ccaacgaggg ctgtgacatc    180

aacgccatca tcttccacac caagaagaag ctgagcgtct gcgctaaccc caagcagacc    240

tgggtcaagt acatcgtgcg gctgctgagc aagaaagtga agaacatg                 288


<210> SEQ ID NO 30
<211> LENGTH: 165
<212> TYPE: DNA
<213> ORGANISM: Homo sapiens

<400> SEQUENCE: 30

atcgtgggaa ttgtggctgg actggccctg tttggcgccg tgattacagg tgctgtggtg     60

gccgctgtta tgtggcggag aaagagcagc gacagaaaag gcggcagcta ctctcaggcc    120

gccagctctg attctgccca gggctctgat gtgtccctga cagct                    165


<210> SEQ ID NO 31
<211> LENGTH: 741
<212> TYPE: PRT
<213> ORGANISM: Homo sapiens

<400> SEQUENCE: 31

Met Ala Glu Gly Ser Phe Ser Val Gln Ser Glu Ser Tyr Ser Val Glu
1               5                   10                  15

Asp Met Asp Glu Gly Ser Asp Glu Val Gly Glu Glu Glu Met Val Glu
            20                  25                  30

Gly Asn Asp Tyr Glu Glu Phe Gly Ala Phe Gly Gly Tyr Gly Thr Leu
        35                  40                  45

Thr Ser Phe Asp Ile His Ile Leu Arg Ala Phe Gly Ser Leu Gly Pro
    50                  55                  60

Gly Leu Arg Ile Leu Ser Asn Glu Pro Trp Glu Leu Glu Asn Pro Val
65                  70                  75                  80

Leu Ala Gln Thr Leu Val Glu Ala Leu Gln Leu Asp Pro Glu Thr Leu
                85                  90                  95

Ala Asn Glu Thr Ala Ala Arg Ala Ala Asn Val Ala Arg Ala Ala Ala
            100                 105                 110

Ser Asn Arg Ala Ala Arg Ala Ala Ala Ala Ala Ala Arg Thr Ala Phe
        115                 120                 125

Ser Gln Val Val Ala Ser His Arg Val Ala Thr Pro Gln Val Ser Gly
    130                 135                 140
```

```
Glu Asp Thr Gln Pro Thr Thr Tyr Ala Ala Glu Ala Gln Gly Pro Thr
145                 150                 155                 160

Pro Glu Pro Pro Leu Ala Ser Pro Gln Thr Ser Gln Met Leu Val Thr
                165                 170                 175

Ser Lys Met Ala Ala Pro Glu Ala Pro Ala Thr Ser Ala Gln Ser Gln
            180                 185                 190

Thr Gly Ser Pro Ala Gln Glu Ala Ala Thr Glu Gly Pro Ser Ser Ala
        195                 200                 205

Cys Ala Phe Ser Gln Ala Pro Cys Ala Arg Glu Val Asp Ala Asn Arg
    210                 215                 220

Pro Ser Thr Ala Phe Leu Gly Gln Asn Asp Val Phe Asp Phe Thr Gln
225                 230                 235                 240

Pro Ala Gly Val Ser Gly Met Ala Phe Pro Arg Pro Lys Arg Pro Ala
                245                 250                 255

Pro Ala Gln Glu Ala Ala Thr Glu Gly Pro Ser Ala Ala Ser Gly Val
            260                 265                 270

Pro Gln Thr Gly Pro Gly Arg Glu Val Ala Ala Thr Arg Pro Lys Thr
        275                 280                 285

Thr Lys Ser Gly Lys Ala Leu Ala Lys Thr Arg Trp Val Glu Pro Gln
    290                 295                 300

Asn Val Val Ala Ala Ala Ala Ala Lys Ala Lys Met Ala Thr Ser Ile
305                 310                 315                 320

Pro Glu Pro Glu Gly Ala Ala Ala Ala Thr Ala Gln His Ser Ala Glu
                325                 330                 335

Pro Trp Ala Arg Met Gly Gly Lys Arg Thr Lys Lys Ser Lys His Leu
            340                 345                 350

Asp Asp Glu Tyr Glu Ser Ser Glu Glu Glu Arg Glu Thr Pro Ala Val
        355                 360                 365

Pro Pro Thr Trp Arg Ala Ser Gln Pro Ser Leu Thr Val Arg Ala Gln
    370                 375                 380

Leu Ala Pro Arg Pro Pro Met Ala Pro Arg Ser Gln Ile Pro Ser Arg
385                 390                 395                 400

His Val Leu Cys Leu Pro Pro Arg Asn Val Thr Leu Leu Gln Glu Arg
                405                 410                 415

Ala Asn Lys Leu Val Lys Tyr Leu Met Ile Lys Asp Tyr Lys Lys Ile
            420                 425                 430

Pro Ile Lys Arg Ala Asp Met Leu Lys Asp Val Ile Arg Glu Tyr Asp
        435                 440                 445

Glu His Phe Pro Glu Ile Ile Glu Arg Ala Thr Tyr Thr Leu Glu Lys
    450                 455                 460

Lys Phe Gly Ile His Leu Lys Glu Ile Asp Lys Glu Glu His Leu Tyr
465                 470                 475                 480

Ile Leu Val Cys Thr Arg Asp Ser Ser Ala Arg Leu Leu Gly Lys Thr
                485                 490                 495

Lys Asp Thr Pro Arg Leu Ser Leu Leu Leu Val Ile Leu Gly Val Ile
            500                 505                 510

Phe Met Asn Gly Asn Arg Ala Ser Glu Ala Val Leu Trp Glu Ala Leu
        515                 520                 525

Arg Lys Met Gly Leu Arg Pro Gly Val Arg His Pro Phe Leu Gly Asp
    530                 535                 540

Leu Arg Lys Leu Ile Thr Asp Asp Phe Val Lys Gln Lys Tyr Leu Glu
545                 550                 555                 560

Tyr Lys Lys Ile Pro Asn Ser Asn Pro Pro Glu Tyr Glu Phe Leu Trp
```

```
                565                 570                 575

Gly Leu Arg Ala Arg His Glu Thr Ser Lys Met Arg Val Leu Arg Phe
            580                 585                 590

Ile Ala Gln Asn Gln Asn Arg Asp Pro Arg Glu Trp Lys Ala His Phe
        595                 600                 605

Leu Glu Ala Val Asp Asp Ala Phe Lys Thr Met Asp Val Asp Met Ala
    610                 615                 620

Glu Glu His Ala Arg Ala Gln Met Arg Ala Gln Met Asn Ile Gly Asp
625                 630                 635                 640

Glu Ala Leu Ile Gly Arg Trp Ser Trp Asp Asp Ile Gln Val Glu Leu
                645                 650                 655

Leu Thr Trp Asp Glu Asp Gly Asp Phe Gly Asp Ala Trp Ala Arg Ile
            660                 665                 670

Pro Phe Ala Phe Trp Ala Arg Tyr His Gln Tyr Ile Leu Asn Ser Asn
        675                 680                 685

Arg Ala Asn Arg Arg Ala Thr Trp Arg Ala Gly Val Ser Ser Gly Thr
    690                 695                 700

Asn Gly Gly Ala Ser Thr Ser Val Leu Asp Gly Pro Ser Thr Ser Ser
705                 710                 715                 720

Thr Ile Arg Thr Arg Asn Ala Ala Arg Ala Gly Ala Ser Phe Phe Ser
                725                 730                 735

Trp Ile Gln His Arg
            740


<210> SEQ ID NO 32
<211> LENGTH: 1023
<212> TYPE: PRT
<213> ORGANISM: Homo sapiens

<400> SEQUENCE: 32

Met Gly Trp Ser Cys Ile Ile Phe Phe Leu Val Ala Thr Ala Thr Gly
1               5                   10                  15

Val His Ser Lys Asn Leu Asp Cys Trp Val Asp Asn Glu Glu Asp Ile
            20                  25                  30

Asp Val Ile Leu Lys Lys Ser Thr Ile Leu Asn Leu Asp Ile Asn Asn
        35                  40                  45

Asp Ile Ile Ser Asp Ile Ser Gly Phe Asn Ser Ser Val Ile Thr Tyr
    50                  55                  60

Pro Asp Ala Gln Leu Val Pro Gly Ile Asn Gly Lys Ala Ile His Leu
65                  70                  75                  80

Val Asn Asn Glu Ser Ser Glu Val Ile Val His Lys Ala Met Asp Ile
                85                  90                  95

Glu Tyr Asn Asp Met Phe Asn Asn Phe Thr Val Ser Phe Trp Leu Arg
            100                 105                 110

Val Pro Lys Val Ser Ala Ser His Leu Glu Gln Tyr Gly Thr Asn Glu
        115                 120                 125

Tyr Ser Ile Ile Ser Ser Met Lys Lys His Ser Leu Ser Ile Gly Ser
    130                 135                 140

Gly Trp Ser Val Ser Leu Lys Gly Asn Asn Leu Ile Trp Thr Leu Lys
145                 150                 155                 160

Asp Ser Ala Gly Glu Val Arg Gln Ile Thr Phe Arg Asp Leu Pro Asp
                165                 170                 175

Lys Phe Asn Ala Tyr Leu Ala Asn Lys Trp Val Phe Ile Thr Ile Thr
            180                 185                 190
```

```
Asn Asp Arg Leu Ser Ser Ala Asn Leu Tyr Ile Asn Gly Val Leu Met
        195                 200                 205

Gly Ser Ala Glu Ile Thr Gly Leu Gly Ala Ile Arg Glu Asp Asn Asn
    210                 215                 220

Ile Thr Leu Lys Leu Asp Arg Cys Asn Asn Asn Asn Gln Tyr Val Ser
225                 230                 235                 240

Ile Asp Lys Phe Arg Ile Phe Cys Lys Ala Leu Asn Pro Lys Glu Ile
                245                 250                 255

Glu Lys Leu Tyr Thr Ser Tyr Leu Ser Ile Thr Phe Leu Arg Asp Phe
            260                 265                 270

Trp Gly Asn Ala Ala Ala Gly Pro Gly Pro Met Ala Glu Gly Ser Phe
        275                 280                 285

Ser Val Gln Ser Glu Ser Tyr Ser Val Glu Asp Met Asp Glu Gly Ser
    290                 295                 300

Asp Glu Val Gly Glu Glu Glu Met Val Glu Gly Asn Asp Tyr Glu Glu
305                 310                 315                 320

Phe Gly Ala Phe Gly Gly Tyr Gly Thr Leu Thr Ser Phe Asp Ile His
                325                 330                 335

Ile Leu Arg Ala Phe Gly Ser Leu Gly Pro Gly Leu Arg Ile Leu Ser
            340                 345                 350

Asn Glu Pro Trp Glu Leu Glu Asn Pro Val Leu Ala Gln Thr Leu Val
        355                 360                 365

Glu Ala Leu Gln Leu Asp Pro Glu Thr Leu Ala Asn Glu Thr Ala Ala
    370                 375                 380

Arg Ala Ala Asn Val Ala Arg Ala Ala Ala Ser Asn Arg Ala Ala Arg
385                 390                 395                 400

Ala Ala Ala Ala Ala Ala Arg Thr Ala Phe Ser Gln Val Val Ala Ser
                405                 410                 415

His Arg Val Ala Thr Pro Gln Val Ser Gly Glu Asp Thr Gln Pro Thr
            420                 425                 430

Thr Tyr Ala Ala Glu Ala Gln Gly Pro Thr Pro Glu Pro Pro Leu Ala
        435                 440                 445

Ser Pro Gln Thr Ser Gln Met Leu Val Thr Ser Lys Met Ala Ala Pro
    450                 455                 460

Glu Ala Pro Ala Thr Ser Ala Gln Ser Gln Thr Gly Ser Pro Ala Gln
465                 470                 475                 480

Glu Ala Ala Thr Glu Gly Pro Ser Ser Ala Cys Ala Phe Ser Gln Ala
                485                 490                 495

Pro Cys Ala Arg Glu Val Asp Ala Asn Arg Pro Ser Thr Ala Phe Leu
            500                 505                 510

Gly Gln Asn Asp Val Phe Asp Phe Thr Gln Pro Ala Gly Val Ser Gly
        515                 520                 525

Met Ala Phe Pro Arg Pro Lys Arg Pro Ala Pro Ala Gln Glu Ala Ala
    530                 535                 540

Thr Glu Gly Pro Ser Ala Ala Ser Gly Val Pro Gln Thr Gly Pro Gly
545                 550                 555                 560

Arg Glu Val Ala Ala Thr Arg Pro Lys Thr Thr Lys Ser Gly Lys Ala
                565                 570                 575

Leu Ala Lys Thr Arg Trp Val Glu Pro Gln Asn Val Val Ala Ala Ala
            580                 585                 590

Ala Ala Lys Ala Lys Met Ala Thr Ser Ile Pro Glu Pro Glu Gly Ala
        595                 600                 605

Ala Ala Ala Thr Ala Gln His Ser Ala Glu Pro Trp Ala Arg Met Gly
```

```
    610                 615                 620

Gly Lys Arg Thr Lys Lys Ser Lys His Leu Asp Asp Glu Tyr Glu Ser
625                 630                 635                 640

Ser Glu Glu Glu Arg Glu Thr Pro Ala Val Pro Pro Thr Trp Arg Ala
                645                 650                 655

Ser Gln Pro Ser Leu Thr Val Arg Ala Gln Leu Ala Pro Arg Pro Pro
            660                 665                 670

Met Ala Pro Arg Ser Gln Ile Pro Ser Arg His Val Leu Cys Leu Pro
        675                 680                 685

Pro Arg Asn Val Thr Leu Leu Gln Glu Arg Ala Asn Lys Leu Val Lys
    690                 695                 700

Tyr Leu Met Ile Lys Asp Tyr Lys Lys Ile Pro Ile Lys Arg Ala Asp
705                 710                 715                 720

Met Leu Lys Asp Val Ile Arg Glu Tyr Asp Glu His Phe Pro Glu Ile
                725                 730                 735

Ile Glu Arg Ala Thr Tyr Thr Leu Glu Lys Lys Phe Gly Ile His Leu
            740                 745                 750

Lys Glu Ile Asp Lys Glu Glu His Leu Tyr Ile Leu Val Cys Thr Arg
        755                 760                 765

Asp Ser Ser Ala Arg Leu Leu Gly Lys Thr Lys Asp Thr Pro Arg Leu
    770                 775                 780

Ser Leu Leu Leu Val Ile Leu Gly Val Ile Phe Met Asn Gly Asn Arg
785                 790                 795                 800

Ala Ser Glu Ala Val Leu Trp Glu Ala Leu Arg Lys Met Gly Leu Arg
                805                 810                 815

Pro Gly Val Arg His Pro Phe Leu Gly Asp Leu Arg Lys Leu Ile Thr
            820                 825                 830

Asp Asp Phe Val Lys Gln Lys Tyr Leu Glu Tyr Lys Lys Ile Pro Asn
        835                 840                 845

Ser Asn Pro Pro Glu Tyr Glu Phe Leu Trp Gly Leu Arg Ala Arg His
    850                 855                 860

Glu Thr Ser Lys Met Arg Val Leu Arg Phe Ile Ala Gln Asn Gln Asn
865                 870                 875                 880

Arg Asp Pro Arg Glu Trp Lys Ala His Phe Leu Glu Ala Val Asp Asp
                885                 890                 895

Ala Phe Lys Thr Met Asp Val Asp Met Ala Glu Glu His Ala Arg Ala
            900                 905                 910

Gln Met Arg Ala Gln Met Asn Ile Gly Asp Glu Ala Leu Ile Gly Arg
        915                 920                 925

Trp Ser Trp Asp Asp Ile Gln Val Glu Leu Leu Thr Trp Asp Glu Asp
    930                 935                 940

Gly Asp Phe Gly Asp Ala Trp Ala Arg Ile Pro Phe Ala Phe Trp Ala
945                 950                 955                 960

Arg Tyr His Gln Tyr Ile Leu Asn Ser Asn Arg Ala Asn Arg Arg Ala
                965                 970                 975

Thr Trp Arg Ala Gly Val Ser Ser Gly Thr Asn Gly Gly Ala Ser Thr
            980                 985                 990

Ser Val Leu Asp Gly Pro Ser Thr  Ser Ser Thr Ile Arg  Thr Arg Asn
        995                 1000                1005

Ala Ala  Arg Ala Gly Ala Ser  Phe Phe Ser Trp Ile  Gln His Arg
    1010                1015                1020
```

<210> SEQ ID NO 33

```
<211> LENGTH: 437
<212> TYPE: PRT
<213> ORGANISM: Homo sapiens

<400> SEQUENCE: 33

Met Gly Arg Arg Met Arg Gly Ala Ala Ala Thr Ala Gly Leu Trp Leu
1               5                   10                  15

Leu Ala Leu Gly Ser Leu Leu Ala Leu Trp Gly Gly Leu Leu Pro Pro
            20                  25                  30

Arg Thr Glu Leu Pro Ala Ser Arg Pro Pro Glu Asp Arg Leu Pro Arg
        35                  40                  45

Arg Pro Ala Arg Ser Gly Gly Pro Ala Pro Ala Pro Arg Phe Pro Leu
    50                  55                  60

Pro Pro Pro Leu Ala Trp Asp Ala Arg Gly Gly Ser Leu Lys Thr Phe
65                  70                  75                  80

Arg Ala Leu Leu Thr Leu Ala Ala Gly Ala Asp Gly Pro Pro Arg Gln
                85                  90                  95

Ser Arg Ser Glu Pro Arg Trp His Val Ser Ala Arg Gln Pro Arg Pro
            100                 105                 110

Glu Glu Ser Ala Ala Val His Gly Gly Val Phe Trp Ser Arg Gly Leu
        115                 120                 125

Glu Glu Gln Val Pro Pro Gly Phe Ser Glu Ala Gln Ala Ala Ala Trp
    130                 135                 140

Leu Glu Ala Ala Arg Gly Ala Arg Met Val Ala Leu Glu Arg Gly Gly
145                 150                 155                 160

Cys Gly Arg Ser Ser Asn Arg Leu Ala Arg Phe Ala Asp Gly Thr Arg
                165                 170                 175

Ala Cys Val Arg Tyr Gly Ile Asn Pro Glu Gln Ile Gln Gly Glu Ala
            180                 185                 190

Leu Ser Tyr Tyr Leu Ala Arg Leu Leu Gly Leu Gln Arg His Val Pro
        195                 200                 205

Pro Leu Ala Leu Ala Arg Val Glu Ala Arg Gly Ala Gln Trp Ala Gln
    210                 215                 220

Val Gln Glu Glu Leu Arg Ala Ala His Trp Thr Glu Gly Ser Val Val
225                 230                 235                 240

Ser Leu Thr Arg Trp Leu Pro Asn Leu Thr Asp Val Val Val Pro Ala
                245                 250                 255

Pro Trp Arg Ser Glu Asp Gly Arg Leu Arg Pro Leu Arg Asp Ala Gly
            260                 265                 270

Gly Glu Leu Ala Asn Leu Ser Gln Ala Glu Leu Val Asp Leu Val Gln
        275                 280                 285

Trp Thr Asp Leu Ile Leu Phe Asp Tyr Leu Thr Ala Asn Phe Asp Arg
    290                 295                 300

Leu Val Ser Asn Leu Phe Ser Leu Gln Trp Asp Pro Arg Val Met Gln
305                 310                 315                 320

Arg Ala Thr Ser Asn Leu His Arg Gly Pro Gly Gly Ala Leu Val Phe
                325                 330                 335

Leu Asp Asn Glu Ala Gly Leu Val His Gly Tyr Arg Val Ala Gly Met
            340                 345                 350

Trp Asp Lys Tyr Asn Glu Pro Leu Leu Gln Ser Val Cys Val Phe Arg
        355                 360                 365

Glu Arg Thr Ala Arg Arg Val Leu Glu Leu His Arg Gly Gln Asp Ala
    370                 375                 380

Ala Ala Arg Leu Leu Arg Leu Tyr Arg Arg His Glu Pro Arg Phe Pro
```

```
385                 390                 395                 400

Glu Leu Ala Ala Leu Ala Asp Pro His Ala Gln Leu Leu Gln Arg Arg
                405                 410                 415

Leu Asp Phe Leu Ala Lys His Ile Leu His Cys Lys Ala Lys Tyr Gly
            420                 425                 430

Arg Arg Ser Gly Thr
        435


<210> SEQ ID NO 34
<211> LENGTH: 719
<212> TYPE: PRT
<213> ORGANISM: Homo sapiens

<400> SEQUENCE: 34

Met Gly Trp Ser Cys Ile Ile Phe Phe Leu Val Ala Thr Ala Thr Gly
1               5                   10                  15

Val His Ser Lys Asn Leu Asp Cys Trp Val Asp Asn Glu Glu Asp Ile
            20                  25                  30

Asp Val Ile Leu Lys Lys Ser Thr Ile Leu Asn Leu Asp Ile Asn Asn
        35                  40                  45

Asp Ile Ile Ser Asp Ile Ser Gly Phe Asn Ser Ser Val Ile Thr Tyr
    50                  55                  60

Pro Asp Ala Gln Leu Val Pro Gly Ile Asn Gly Lys Ala Ile His Leu
65                  70                  75                  80

Val Asn Asn Glu Ser Ser Glu Val Ile Val His Lys Ala Met Asp Ile
                85                  90                  95

Glu Tyr Asn Asp Met Phe Asn Asn Phe Thr Val Ser Phe Trp Leu Arg
            100                 105                 110

Val Pro Lys Val Ser Ala Ser His Leu Glu Gln Tyr Gly Thr Asn Glu
        115                 120                 125

Tyr Ser Ile Ile Ser Ser Met Lys Lys His Ser Leu Ser Ile Gly Ser
    130                 135                 140

Gly Trp Ser Val Ser Leu Lys Gly Asn Asn Leu Ile Trp Thr Leu Lys
145                 150                 155                 160

Asp Ser Ala Gly Glu Val Arg Gln Ile Thr Phe Arg Asp Leu Pro Asp
                165                 170                 175

Lys Phe Asn Ala Tyr Leu Ala Asn Lys Trp Val Phe Ile Thr Ile Thr
            180                 185                 190

Asn Asp Arg Leu Ser Ser Ala Asn Leu Tyr Ile Asn Gly Val Leu Met
        195                 200                 205

Gly Ser Ala Glu Ile Thr Gly Leu Gly Ala Ile Arg Glu Asp Asn Asn
    210                 215                 220

Ile Thr Leu Lys Leu Asp Arg Cys Asn Asn Asn Asn Gln Tyr Val Ser
225                 230                 235                 240

Ile Asp Lys Phe Arg Ile Phe Cys Lys Ala Leu Asn Pro Lys Glu Ile
                245                 250                 255

Glu Lys Leu Tyr Thr Ser Tyr Leu Ser Ile Thr Phe Leu Arg Asp Phe
            260                 265                 270

Trp Gly Asn Ala Ala Ala Gly Pro Gly Pro Met Gly Arg Arg Met Arg
        275                 280                 285

Gly Ala Ala Ala Thr Ala Gly Leu Trp Leu Leu Ala Leu Gly Ser Leu
    290                 295                 300

Leu Ala Leu Trp Gly Gly Leu Leu Pro Pro Arg Thr Glu Leu Pro Ala
305                 310                 315                 320
```

```
Ser Arg Pro Pro Glu Asp Arg Leu Pro Arg Arg Pro Ala Arg Ser Gly
                325                 330                 335

Gly Pro Ala Pro Ala Pro Arg Phe Pro Leu Pro Pro Pro Leu Ala Trp
            340                 345                 350

Asp Ala Arg Gly Gly Ser Leu Lys Thr Phe Arg Ala Leu Leu Thr Leu
        355                 360                 365

Ala Ala Gly Ala Asp Gly Pro Pro Arg Gln Ser Arg Ser Glu Pro Arg
    370                 375                 380

Trp His Val Ser Ala Arg Gln Pro Arg Pro Glu Glu Ser Ala Ala Val
385                 390                 395                 400

His Gly Gly Val Phe Trp Ser Arg Gly Leu Glu Glu Gln Val Pro Pro
                405                 410                 415

Gly Phe Ser Glu Ala Gln Ala Ala Ala Trp Leu Glu Ala Ala Arg Gly
            420                 425                 430

Ala Arg Met Val Ala Leu Glu Arg Gly Gly Cys Gly Arg Ser Ser Asn
        435                 440                 445

Arg Leu Ala Arg Phe Ala Asp Gly Thr Arg Ala Cys Val Arg Tyr Gly
    450                 455                 460

Ile Asn Pro Glu Gln Ile Gln Gly Glu Ala Leu Ser Tyr Tyr Leu Ala
465                 470                 475                 480

Arg Leu Leu Gly Leu Gln Arg His Val Pro Pro Leu Ala Leu Ala Arg
                485                 490                 495

Val Glu Ala Arg Gly Ala Gln Trp Ala Gln Val Gln Glu Glu Leu Arg
            500                 505                 510

Ala Ala His Trp Thr Glu Gly Ser Val Val Ser Leu Thr Arg Trp Leu
        515                 520                 525

Pro Asn Leu Thr Asp Val Val Val Pro Ala Pro Trp Arg Ser Glu Asp
    530                 535                 540

Gly Arg Leu Arg Pro Leu Arg Asp Ala Gly Gly Glu Leu Ala Asn Leu
545                 550                 555                 560

Ser Gln Ala Glu Leu Val Asp Leu Val Gln Trp Thr Asp Leu Ile Leu
                565                 570                 575

Phe Asp Tyr Leu Thr Ala Asn Phe Asp Arg Leu Val Ser Asn Leu Phe
            580                 585                 590

Ser Leu Gln Trp Asp Pro Arg Val Met Gln Arg Ala Thr Ser Asn Leu
        595                 600                 605

His Arg Gly Pro Gly Gly Ala Leu Val Phe Leu Asp Asn Glu Ala Gly
    610                 615                 620

Leu Val His Gly Tyr Arg Val Ala Gly Met Trp Asp Lys Tyr Asn Glu
625                 630                 635                 640

Pro Leu Leu Gln Ser Val Cys Val Phe Arg Glu Arg Thr Ala Arg Arg
                645                 650                 655

Val Leu Glu Leu His Arg Gly Gln Asp Ala Ala Ala Arg Leu Leu Arg
            660                 665                 670

Leu Tyr Arg Arg His Glu Pro Arg Phe Pro Glu Leu Ala Ala Leu Ala
        675                 680                 685

Asp Pro His Ala Gln Leu Leu Gln Arg Arg Leu Asp Phe Leu Ala Lys
    690                 695                 700

His Ile Leu His Cys Lys Ala Lys Tyr Gly Arg Arg Ser Gly Thr
705                 710                 715
```

<210> SEQ ID NO 35
<211> LENGTH: 479
<212> TYPE: PRT

<213> ORGANISM: Homo sapiens

<400> SEQUENCE: 35

```
Met Ala Glu Gly Ser Phe Ser Val Gln Ser Glu Ser Tyr Ser Val Glu
1               5                   10                  15

Asp Met Asp Glu Gly Ser Asp Glu Val Gly Glu Glu Glu Met Val Glu
            20                  25                  30

Gly Asn Asp Tyr Glu Glu Phe Gly Ala Phe Gly Gly Tyr Gly Thr Leu
        35                  40                  45

Thr Ser Phe Asp Ile His Ile Leu Arg Ala Phe Gly Ser Leu Gly Pro
    50                  55                  60

Gly Leu Arg Ile Leu Ser Asn Glu Pro Trp Glu Leu Glu Asn Pro Val
65                  70                  75                  80

Leu Ala Gln Thr Leu Val Glu Ala Leu Gln Leu Asp Pro Glu Thr Leu
                85                  90                  95

Ala Asn Glu Thr Ala Ala Arg Ala Ala Asn Val Ala Arg Ala Ala Ala
            100                 105                 110

Ser Asn Arg Ala Ala Arg Ala Ala Ala Ala Ala Ala Arg Thr Ala Phe
        115                 120                 125

Ser Gln Val Val Ala Ser His Arg Val Ala Thr Pro Gln Val Ser Gly
    130                 135                 140

Glu Asp Thr Gln Pro Thr Thr Tyr Ala Ala Glu Ala Gln Gly Pro Thr
145                 150                 155                 160

Pro Glu Pro Pro Leu Ala Ser Pro Gln Thr Ser Gln Met Leu Val Thr
                165                 170                 175

Ser Lys Met Ala Ala Pro Glu Ala Pro Ala Thr Ser Ala Gln Ser Gln
            180                 185                 190

Thr Gly Ser Pro Ala Gln Glu Ala Ala Thr Glu Gly Pro Ser Ser Ala
        195                 200                 205

Cys Ala Phe Ser Gln Ala Pro Cys Ala Arg Glu Val Asp Ala Asn Arg
    210                 215                 220

Pro Ser Thr Ala Phe Leu Gly Gln Asn Asp Val Phe Asp Phe Thr Gln
225                 230                 235                 240

Pro Ala Gly Val Ser Gly Met Ala Phe Pro Arg Pro Lys Arg Pro Ala
                245                 250                 255

Pro Ala Gln Glu Ala Ala Thr Glu Gly Pro Ser Ala Ala Ser Gly Val
            260                 265                 270

Pro Gln Thr Gly Pro Gly Arg Glu Val Ala Ala Thr Arg Pro Lys Thr
        275                 280                 285

Thr Lys Ser Gly Lys Ala Leu Ala Lys Thr Arg Trp Val Glu Pro Gln
    290                 295                 300

Asn Val Val Ala Ala Ala Ala Ala Lys Ala Lys Met Ala Thr Ser Ile
305                 310                 315                 320

Pro Glu Pro Glu Gly Ala Ala Ala Ala Thr Ala Gln His Ser Ala Glu
                325                 330                 335

Pro Trp Ala Arg Met Gly Gly Lys Arg Thr Lys Lys Ser Lys His Leu
            340                 345                 350

Asp Asp Glu Tyr Glu Ser Ser Glu Glu Glu Arg Glu Thr Pro Ala Val
        355                 360                 365

Pro Pro Thr Trp Arg Ala Ser Gln Pro Ser Leu Thr Val Arg Ala Gln
    370                 375                 380

Leu Ala Pro Arg Pro Pro Met Ala Pro Arg Ser Gln Ile Pro Ser Arg
385                 390                 395                 400
```

```
His Val Leu Cys Leu Pro Pro Arg Asn Val Thr Arg Leu Ser Leu Leu
                405                 410                 415

Leu Val Ile Leu Tyr Ile Leu Asn Ser Asn Arg Ala Asn Arg Arg Ala
            420                 425                 430

Thr Trp Arg Ala Gly Val Ser Ser Gly Thr Asn Gly Gly Ala Ser Thr
        435                 440                 445

Ser Val Leu Asp Gly Pro Ser Thr Ser Ser Thr Ile Arg Thr Arg Asn
    450                 455                 460

Ala Ala Arg Ala Gly Ala Ser Phe Phe Ser Trp Ile Gln His Arg
465                 470                 475


<210> SEQ ID NO 36
<211> LENGTH: 652
<212> TYPE: PRT
<213> ORGANISM: Homo sapiens

<400> SEQUENCE: 36

Met Ala Glu Gly Ser Phe Ser Val Gln Ser Glu Ser Tyr Ser Val Glu
1               5                   10                  15

Asp Met Asp Glu Gly Ser Asp Glu Val Gly Glu Glu Glu Met Val Glu
            20                  25                  30

Gly Asn Asp Tyr Glu Glu Phe Gly Ala Phe Gly Gly Tyr Gly Thr Leu
        35                  40                  45

Thr Ser Phe Asp Ile His Ile Leu Arg Ala Phe Gly Ser Leu Gly Pro
    50                  55                  60

Gly Leu Arg Ile Leu Ser Asn Glu Pro Trp Glu Leu Glu Asn Pro Val
65                  70                  75                  80

Leu Ala Gln Thr Leu Val Glu Ala Leu Gln Leu Asp Pro Glu Thr Leu
                85                  90                  95

Ala Asn Glu Thr Ala Ala Arg Ala Ala Asn Val Ala Arg Ala Ala Ala
            100                 105                 110

Ser Asn Arg Ala Ala Arg Ala Ala Ala Ala Ala Ala Arg Thr Ala Phe
        115                 120                 125

Ser Gln Val Val Ala Ser His Arg Val Ala Thr Pro Gln Val Ser Gly
    130                 135                 140

Glu Asp Thr Gln Pro Thr Thr Tyr Ala Ala Glu Ala Gln Gly Pro Thr
145                 150                 155                 160

Pro Glu Pro Pro Leu Ala Ser Pro Gln Thr Ser Gln Met Leu Val Thr
                165                 170                 175

Ser Lys Met Ala Ala Pro Glu Ala Pro Ala Thr Ser Ala Gln Ser Gln
            180                 185                 190

Thr Gly Ser Pro Ala Gln Glu Ala Ala Thr Glu Gly Pro Ser Ser Ala
        195                 200                 205

Cys Ala Phe Ser Gln Ala Pro Cys Ala Arg Glu Val Asp Ala Asn Arg
    210                 215                 220

Pro Ser Thr Ala Phe Leu Gly Gln Asn Asp Val Phe Asp Phe Thr Gln
225                 230                 235                 240

Pro Ala Gly Val Ser Gly Met Ala Phe Pro Arg Pro Lys Arg Pro Ala
                245                 250                 255

Pro Ala Gln Glu Ala Ala Thr Glu Gly Pro Ser Ala Ala Ser Gly Val
            260                 265                 270

Pro Gln Thr Gly Pro Gly Arg Glu Val Ala Ala Thr Arg Pro Lys Thr
        275                 280                 285

Thr Lys Ser Gly Lys Ala Leu Ala Lys Thr Arg Trp Val Glu Pro Gln
    290                 295                 300
```

```
Asn Val Val Ala Ala Ala Ala Ala Lys Ala Lys Met Ala Thr Ser Ile
305                 310                 315                 320

Pro Glu Pro Glu Gly Ala Ala Ala Ala Thr Ala Gln His Ser Ala Glu
                325                 330                 335

Pro Trp Ala Arg Met Gly Gly Lys Arg Thr Lys Lys Ser Lys His Leu
            340                 345                 350

Asp Asp Glu Tyr Glu Ser Ser Glu Glu Glu Arg Glu Thr Pro Ala Val
        355                 360                 365

Pro Pro Thr Trp Arg Ala Ser Gln Pro Ser Leu Thr Val Arg Ala Gln
    370                 375                 380

Leu Ala Pro Arg Pro Pro Met Ala Pro Arg Ser Gln Ile Pro Ser Arg
385                 390                 395                 400

His Val Leu Cys Leu Pro Pro Arg Asn Val Thr Arg Leu Ser Leu Leu
                405                 410                 415

Leu Val Ile Leu Gly Val Ile Phe Met Asn Gly Asn Arg Ala Ser Glu
            420                 425                 430

Ala Val Leu Trp Glu Ala Leu Arg Lys Met Gly Leu Arg Pro Gly Val
        435                 440                 445

Arg His Pro Phe Leu Gly Asp Leu Arg Lys Leu Ile Thr Asp Asp Phe
    450                 455                 460

Val Lys Gln Lys Tyr Leu Glu Tyr Lys Lys Ile Pro Asn Ser Asn Pro
465                 470                 475                 480

Pro Glu Tyr Glu Phe Leu Trp Gly Leu Arg Ala Arg His Glu Thr Ser
                485                 490                 495

Lys Met Arg Val Leu Arg Phe Ile Ala Gln Asn Gln Asn Arg Asp Pro
            500                 505                 510

Arg Glu Trp Lys Ala His Phe Leu Glu Ala Val Asp Asp Ala Phe Lys
        515                 520                 525

Thr Met Asp Val Asp Met Ala Glu Glu His Ala Arg Ala Gln Met Arg
    530                 535                 540

Ala Gln Met Asn Ile Gly Asp Glu Ala Leu Ile Gly Arg Trp Ser Trp
545                 550                 555                 560

Asp Asp Ile Gln Val Glu Leu Leu Thr Trp Asp Glu Asp Gly Asp Phe
                565                 570                 575

Gly Asp Ala Trp Ala Arg Ile Pro Phe Ala Phe Trp Ala Arg Tyr His
            580                 585                 590

Gln Tyr Ile Leu Asn Ser Asn Arg Ala Asn Arg Arg Ala Thr Trp Arg
        595                 600                 605

Ala Gly Val Ser Ser Gly Thr Asn Gly Gly Ala Ser Thr Ser Val Leu
    610                 615                 620

Asp Gly Pro Ser Thr Ser Ser Thr Ile Arg Thr Arg Asn Ala Ala Arg
625                 630                 635                 640

Ala Gly Ala Ser Phe Phe Ser Trp Ile Gln His Arg
                645                 650


<210> SEQ ID NO 37
<211> LENGTH: 568
<212> TYPE: PRT
<213> ORGANISM: Homo sapiens

<400> SEQUENCE: 37

Met Ala Glu Gly Ser Phe Ser Val Gln Ser Glu Ser Tyr Ser Val Glu
1               5                   10                  15

Asp Met Asp Glu Gly Ser Asp Glu Val Gly Glu Glu Glu Met Val Glu
```

```
            20                  25                  30

Gly Asn Asp Tyr Glu Glu Phe Gly Ala Phe Gly Gly Tyr Gly Thr Leu
        35                  40                  45

Thr Ser Phe Asp Ile His Ile Leu Arg Ala Phe Gly Ser Leu Gly Pro
    50                  55                  60

Gly Leu Arg Ile Leu Ser Asn Glu Pro Trp Glu Leu Glu Asn Pro Val
65                  70                  75                  80

Leu Ala Gln Thr Leu Val Glu Ala Leu Gln Leu Asp Pro Glu Thr Leu
                85                  90                  95

Ala Asn Glu Thr Ala Ala Arg Ala Ala Asn Val Ala Arg Ala Ala Ala
            100                 105                 110

Ser Asn Arg Ala Ala Arg Ala Ala Ala Ala Ala Ala Arg Thr Ala Phe
        115                 120                 125

Ser Gln Val Val Ala Ser His Arg Val Ala Thr Pro Gln Val Ser Gly
    130                 135                 140

Glu Asp Thr Gln Pro Thr Thr Tyr Ala Ala Glu Ala Gln Gly Pro Thr
145                 150                 155                 160

Pro Glu Pro Pro Leu Ala Ser Pro Gln Thr Ser Gln Met Leu Val Thr
                165                 170                 175

Ser Lys Met Ala Ala Pro Glu Ala Pro Ala Thr Ser Ala Gln Ser Gln
            180                 185                 190

Thr Gly Ser Pro Ala Gln Glu Ala Ala Thr Glu Gly Pro Ser Ser Ala
        195                 200                 205

Cys Ala Phe Ser Gln Ala Pro Cys Ala Arg Glu Val Asp Ala Asn Arg
    210                 215                 220

Pro Ser Thr Ala Phe Leu Gly Gln Asn Asp Val Phe Asp Phe Thr Gln
225                 230                 235                 240

Pro Ala Gly Val Ser Gly Met Ala Phe Pro Arg Pro Lys Arg Pro Ala
                245                 250                 255

Pro Ala Gln Glu Ala Ala Thr Glu Gly Pro Ser Ala Ala Ser Gly Val
            260                 265                 270

Pro Gln Thr Gly Pro Gly Arg Glu Val Ala Ala Thr Arg Pro Lys Thr
        275                 280                 285

Thr Lys Ser Gly Lys Ala Leu Ala Lys Thr Arg Trp Val Glu Pro Gln
    290                 295                 300

Asn Val Val Ala Ala Ala Ala Ala Lys Ala Lys Met Ala Thr Ser Ile
305                 310                 315                 320

Pro Glu Pro Glu Gly Ala Ala Ala Ala Thr Ala Gln His Ser Ala Glu
                325                 330                 335

Pro Trp Ala Arg Met Gly Gly Lys Arg Thr Lys Lys Ser Lys His Leu
            340                 345                 350

Asp Asp Glu Tyr Glu Ser Ser Glu Glu Glu Arg Glu Thr Pro Ala Val
        355                 360                 365

Pro Pro Thr Trp Arg Ala Ser Gln Pro Ser Leu Thr Val Arg Ala Gln
    370                 375                 380

Leu Ala Pro Arg Pro Pro Met Ala Pro Arg Ser Gln Ile Pro Ser Arg
385                 390                 395                 400

His Val Leu Cys Leu Pro Pro Arg Asn Val Thr Leu Leu Gln Glu Arg
                405                 410                 415

Ala Asn Lys Leu Val Lys Tyr Leu Met Ile Lys Asp Tyr Lys Lys Ile
            420                 425                 430

Pro Ile Lys Arg Ala Asp Met Leu Lys Asp Val Ile Arg Glu Tyr Asp
        435                 440                 445
```

```
Glu His Phe Pro Glu Ile Ile Glu Arg Ala Thr Tyr Thr Leu Glu Lys
    450                 455                 460

Lys Phe Gly Ile His Leu Lys Glu Ile Asp Lys Glu Glu His Leu Tyr
465                 470                 475                 480

Ile Leu Val Cys Thr Arg Asp Ser Ser Ala Arg Leu Leu Gly Lys Thr
                485                 490                 495

Lys Asp Thr Pro Arg Leu Ser Leu Leu Leu Val Ile Leu Tyr Ile Leu
            500                 505                 510

Asn Ser Asn Arg Ala Asn Arg Arg Ala Thr Trp Arg Ala Gly Val Ser
        515                 520                 525

Ser Gly Thr Asn Gly Gly Ala Ser Thr Ser Val Leu Asp Gly Pro Ser
    530                 535                 540

Thr Ser Ser Thr Ile Arg Thr Arg Asn Ala Ala Arg Ala Gly Ala Ser
545                 550                 555                 560

Phe Phe Ser Trp Ile Gln His Arg
                565


<210> SEQ ID NO 38
<211> LENGTH: 237
<212> TYPE: PRT
<213> ORGANISM: Homo sapiens

<400> SEQUENCE: 38

Met Ser Ala Pro Ala Ser Thr Thr Gln Pro Ile Gly Ser Thr Thr Ser
1               5                   10                  15

Thr Thr Thr Lys Thr Ala Gly Ala Thr Pro Ala Thr Ala Ser Gly Leu
            20                  25                  30

Phe Thr Ile Pro Asp Gly Asp Phe Phe Ser Thr Ala Arg Ala Ile Val
        35                  40                  45

Ala Ser Asn Ala Val Ala Thr Asn Glu Asp Leu Ser Lys Ile Glu Ala
    50                  55                  60

Ile Trp Lys Asp Met Lys Val Pro Thr Asp Thr Met Ala Gln Ala Ala
65                  70                  75                  80

Trp Asp Leu Val Arg His Cys Ala Asp Val Gly Ser Ser Ala Gln Thr
                85                  90                  95

Glu Met Ile Asp Thr Gly Pro Tyr Ser Asn Gly Ile Ser Arg Ala Arg
            100                 105                 110

Leu Ala Ala Ala Ile Lys Glu Val Cys Thr Leu Arg Gln Phe Cys Met
        115                 120                 125

Lys Tyr Ala Pro Val Val Trp Asn Trp Met Leu Thr Asn Asn Ser Pro
    130                 135                 140

Pro Ala Asn Trp Gln Ala Gln Gly Phe Lys Pro Glu His Lys Phe Ala
145                 150                 155                 160

Ala Phe Asp Phe Phe Asn Gly Val Thr Asn Pro Ala Ala Ile Met Pro
                165                 170                 175

Lys Glu Gly Leu Ile Arg Pro Pro Ser Glu Ala Glu Met Asn Ala Ala
            180                 185                 190

Gln Thr Ala Ala Phe Val Lys Ile Thr Lys Ala Arg Ala Gln Ser Asn
        195                 200                 205

Asp Phe Ala Ser Leu Asp Ala Ala Val Thr Arg Gly Arg Ile Thr Gly
    210                 215                 220

Thr Thr Thr Ala Glu Ala Val Val Thr Leu Pro Pro Pro
225                 230                 235
```

```
<210> SEQ ID NO 39
<211> LENGTH: 96
<212> TYPE: PRT
<213> ORGANISM: Homo sapiens

<400> SEQUENCE: 39

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
        35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95


<210> SEQ ID NO 40
<211> LENGTH: 55
<212> TYPE: PRT
<213> ORGANISM: Homo sapiens

<400> SEQUENCE: 40

Ile Val Gly Ile Val Ala Gly Leu Ala Leu Phe Gly Ala Val Ile Thr
1               5                   10                  15

Gly Ala Val Val Ala Ala Val Met Trp Arg Arg Lys Ser Ser Asp Arg
            20                  25                  30

Lys Gly Gly Ser Tyr Ser Gln Ala Ala Ser Ser Asp Ser Ala Gln Gly
        35                  40                  45

Ser Asp Val Ser Leu Thr Ala
    50                  55


<210> SEQ ID NO 41
<211> LENGTH: 739
<212> TYPE: PRT
<213> ORGANISM: Homo sapiens

<400> SEQUENCE: 41

Met Ala Glu Gly Ser Phe Ser Val Gln Ser Glu Ser Tyr Ser Val Glu
1               5                   10                  15

Asp Met Asp Glu Gly Ser Asp Glu Val Gly Glu Glu Glu Met Val Glu
            20                  25                  30

Gly Asn Asp Tyr Glu Glu Phe Gly Ala Phe Gly Gly Tyr Gly Thr Leu
        35                  40                  45

Thr Ser Phe Asp Ile His Ile Leu Arg Ala Phe Gly Ser Leu Gly Pro
    50                  55                  60

Gly Leu Arg Ile Leu Ser Asn Glu Pro Trp Glu Leu Glu Asn Pro Val
65                  70                  75                  80

Leu Ala Gln Thr Leu Val Glu Ala Leu Gln Leu Asp Pro Glu Thr Leu
                85                  90                  95

Ala Asn Glu Thr Ala Ala Arg Ala Ala Asn Val Ala Arg Ala Ala Ala
            100                 105                 110

Ser Asn Arg Ala Ala Arg Ala Ala Ala Ala Ala Ala Arg Thr Ala Phe
        115                 120                 125

Ser Gln Val Val Ala Ser His Arg Val Ala Thr Pro Gln Val Ser Gly
    130                 135                 140
```

```
Glu Asp Thr Gln Pro Thr Thr Tyr Ala Ala Glu Ala Gln Gly Pro Thr
145                 150                 155                 160

Pro Glu Pro Pro Leu Ala Ser Pro Gln Thr Ser Gln Met Leu Val Thr
                165                 170                 175

Ser Lys Met Ala Ala Pro Glu Ala Pro Ala Thr Ser Ala Gln Ser Gln
            180                 185                 190

Thr Gly Ser Pro Ala Gln Glu Ala Ala Thr Glu Gly Pro Ser Ser Ala
        195                 200                 205

Cys Ala Phe Ser Gln Ala Pro Cys Ala Arg Glu Val Asp Ala Asn Arg
    210                 215                 220

Pro Ser Thr Ala Phe Leu Gly Gln Asn Asp Val Phe Asp Phe Thr Gln
225                 230                 235                 240

Pro Ala Gly Val Ser Gly Met Ala Phe Pro Arg Pro Lys Arg Pro Ala
                245                 250                 255

Pro Ala Gln Glu Ala Ala Thr Glu Gly Pro Ser Ala Ala Ser Gly Val
            260                 265                 270

Pro Gln Thr Gly Pro Gly Arg Glu Val Ala Ala Thr Arg Pro Lys Thr
        275                 280                 285

Thr Lys Ser Gly Lys Ala Leu Ala Lys Thr Arg Trp Val Glu Pro Gln
    290                 295                 300

Asn Val Val Ala Ala Ala Ala Ala Lys Ala Lys Met Ala Thr Ser Ile
305                 310                 315                 320

Pro Glu Pro Glu Gly Ala Ala Ala Ala Thr Ala Gln His Ser Ala Glu
                325                 330                 335

Pro Trp Ala Arg Met Gly Gly Lys Arg Thr Lys Lys Ser Lys His Leu
            340                 345                 350

Asp Asp Glu Tyr Glu Ser Ser Glu Glu Glu Arg Glu Thr Pro Ala Val
        355                 360                 365

Pro Pro Thr Trp Arg Ala Ser Gln Pro Ser Leu Thr Val Arg Ala Gln
    370                 375                 380

Leu Ala Pro Arg Pro Pro Met Ala Pro Arg Ser Gln Ile Pro Ser Arg
385                 390                 395                 400

His Val Leu Cys Leu Pro Pro Arg Asn Val Thr Leu Leu Gln Glu Arg
                405                 410                 415

Ala Asn Lys Leu Val Lys Tyr Leu Met Ile Lys Asp Tyr Lys Lys Ile
            420                 425                 430

Pro Ile Lys Arg Ala Asp Met Leu Lys Asp Val Ile Arg Glu Tyr Asp
        435                 440                 445

Glu His Phe Pro Glu Ile Ile Glu Arg Ala Thr Tyr Thr Leu Glu Lys
    450                 455                 460

Lys Phe Gly Ile His Leu Lys Glu Ile Asp Lys Glu Glu His Leu Tyr
465                 470                 475                 480

Ile Leu Val Cys Thr Arg Asp Ser Ser Ala Arg Leu Leu Gly Lys Thr
                485                 490                 495

Lys Asp Thr Pro Arg Leu Ser Leu Leu Leu Val Ile Leu Gly Val Ile
            500                 505                 510

Phe Met Asn Gly Asn Arg Ala Ser Glu Ala Val Leu Trp Glu Ala Leu
        515                 520                 525

Arg Lys Met Gly Leu Arg Pro Gly Val Arg His Pro Phe Leu Gly Asp
    530                 535                 540

Leu Arg Lys Leu Ile Thr Asp Asp Phe Val Lys Gln Lys Tyr Leu Glu
545                 550                 555                 560
```

```
Tyr Lys Lys Ile Pro Asn Ser Asn Pro Pro Glu Tyr Glu Phe Leu Trp
                565                 570                 575

Gly Leu Arg Ala Arg His Glu Thr Ser Lys Met Arg Val Leu Arg Phe
            580                 585                 590

Ile Ala Gln Asn Gln Asn Arg Asp Pro Arg Glu Trp Lys Ala His Phe
        595                 600                 605

Leu Glu Ala Val Asp Asp Ala Phe Lys Thr Met Asp Val Asp Met Ala
    610                 615                 620

Glu Glu His Ala Arg Ala Gln Met Arg Ala Gln Met Asn Ile Gly Asp
625                 630                 635                 640

Glu Ala Leu Ile Gly Arg Trp Ser Trp Asp Asp Ile Gln Val Glu Leu
                645                 650                 655

Leu Thr Trp Asp Glu Asp Gly Asp Phe Gly Asp Ala Trp Ala Arg Ile
            660                 665                 670

Pro Phe Ala Phe Trp Ala Arg Tyr His Gln Tyr Ile Leu Asn Ser Asn
        675                 680                 685

Arg Ala Asn Arg Arg Ala Thr Trp Arg Ala Gly Val Ser Ser Gly Thr
    690                 695                 700

Asn Gly Gly Ala Ser Thr Ser Val Leu Asp Gly Pro Ser Thr Ser Ser
705                 710                 715                 720

Thr Ile Arg Thr Arg Asn Ala Ala Arg Ala Gly Ala Ser Phe Phe Ser
                725                 730                 735

Trp Ile Gln


<210> SEQ ID NO 42
<211> LENGTH: 414
<212> TYPE: PRT
<213> ORGANISM: Homo sapiens

<400> SEQUENCE: 42

Met Ala Glu Gly Ser Phe Ser Val Gln Ser Glu Ser Tyr Ser Val Glu
1               5                   10                  15

Asp Met Asp Glu Gly Ser Asp Glu Val Gly Glu Glu Glu Met Val Glu
            20                  25                  30

Gly Asn Asp Tyr Glu Glu Phe Gly Ala Phe Gly Gly Tyr Gly Thr Leu
        35                  40                  45

Thr Ser Phe Asp Ile His Ile Leu Arg Ala Phe Gly Ser Leu Gly Pro
    50                  55                  60

Gly Leu Arg Ile Leu Ser Asn Glu Pro Trp Glu Leu Glu Asn Pro Val
65                  70                  75                  80

Leu Ala Gln Thr Leu Val Glu Ala Leu Gln Leu Asp Pro Glu Thr Leu
                85                  90                  95

Ala Asn Glu Thr Ala Ala Arg Ala Ala Asn Val Ala Arg Ala Ala Ala
            100                 105                 110

Ser Asn Arg Ala Ala Arg Ala Ala Ala Ala Ala Ala Arg Thr Ala Phe
        115                 120                 125

Ser Gln Val Val Ala Ser His Arg Val Ala Thr Pro Gln Val Ser Gly
    130                 135                 140

Glu Asp Thr Gln Pro Thr Thr Tyr Ala Ala Glu Ala Gln Gly Pro Thr
145                 150                 155                 160

Pro Glu Pro Pro Leu Ala Ser Pro Gln Thr Ser Gln Met Leu Val Thr
                165                 170                 175

Ser Lys Met Ala Ala Pro Glu Ala Pro Ala Thr Ser Ala Gln Ser Gln
            180                 185                 190
```

```
Thr Gly Ser Pro Ala Gln Glu Ala Ala Thr Glu Gly Pro Ser Ser Ala
        195                 200                 205

Cys Ala Phe Ser Gln Ala Pro Cys Ala Arg Glu Val Asp Ala Asn Arg
    210                 215                 220

Pro Ser Thr Ala Phe Leu Gly Gln Asn Asp Val Phe Asp Phe Thr Gln
225                 230                 235                 240

Pro Ala Gly Val Ser Gly Met Ala Phe Pro Arg Pro Lys Arg Pro Ala
                245                 250                 255

Pro Ala Gln Glu Ala Ala Thr Glu Gly Pro Ser Ala Ala Ser Gly Val
            260                 265                 270

Pro Gln Thr Gly Pro Gly Arg Glu Val Ala Ala Thr Arg Pro Lys Thr
        275                 280                 285

Thr Lys Ser Gly Lys Ala Leu Ala Lys Thr Arg Trp Val Glu Pro Gln
    290                 295                 300

Asn Val Val Ala Ala Ala Ala Ala Lys Ala Lys Met Ala Thr Ser Ile
305                 310                 315                 320

Pro Glu Pro Glu Gly Ala Ala Ala Ala Thr Ala Gln His Ser Ala Glu
                325                 330                 335

Pro Trp Ala Arg Met Gly Gly Lys Arg Thr Lys Lys Val Arg Ser Pro
            340                 345                 350

Cys Pro Leu Pro Pro Pro His Pro Leu Ala Pro Val Leu Ser Phe Ser
        355                 360                 365

Ser Leu Ser Cys Ser Ser Pro Pro Ser Pro Leu Pro Leu Leu Pro Leu
    370                 375                 380

Phe Ser Ser Phe Pro Ser Phe Ser Pro His Leu Pro Ser Pro Pro Leu
385                 390                 395                 400

Leu Ser Ser Gln Leu Val His Val Ser Pro Thr Gln Val Cys
                405                 410


<210> SEQ ID NO 43
<211> LENGTH: 757
<212> TYPE: PRT
<213> ORGANISM: Homo sapiens

<400> SEQUENCE: 43

Met Ala Glu Gly Ser Phe Ser Val Gln Ser Glu Ser Tyr Ser Val Glu
1               5                   10                  15

Asp Met Asp Glu Gly Ser Asp Glu Val Gly Glu Glu Glu Met Val Glu
            20                  25                  30

Gly Asn Asp Tyr Glu Glu Phe Gly Ala Phe Gly Gly Tyr Gly Thr Leu
        35                  40                  45

Thr Ser Phe Asp Ile His Ile Leu Arg Ala Phe Gly Ser Leu Gly Pro
    50                  55                  60

Gly Leu Arg Ile Leu Ser Asn Glu Pro Trp Glu Leu Glu Asn Pro Val
65                  70                  75                  80

Leu Ala Gln Thr Leu Val Glu Ala Leu Gln Leu Asp Pro Glu Thr Leu
                85                  90                  95

Ala Asn Glu Thr Ala Ala Arg Ala Ala Asn Val Ala Arg Ala Ala Ala
            100                 105                 110

Ser Asn Arg Ala Ala Arg Ala Ala Ala Ala Ala Ala Arg Thr Ala Phe
        115                 120                 125

Ser Gln Val Val Ala Ser His Arg Val Ala Thr Pro Gln Val Ser Gly
    130                 135                 140

Glu Asp Thr Gln Pro Thr Thr Tyr Ala Ala Glu Ala Gln Gly Pro Thr
145                 150                 155                 160
```

```
Pro Glu Pro Pro Leu Ala Ser Pro Gln Thr Ser Gln Met Leu Val Thr
                165                 170                 175

Ser Lys Met Ala Ala Pro Glu Ala Pro Ala Thr Ser Ala Gln Ser Gln
            180                 185                 190

Thr Gly Ser Pro Ala Gln Glu Ala Ala Thr Glu Gly Pro Ser Ser Ala
        195                 200                 205

Cys Ala Phe Ser Gln Ala Pro Cys Ala Arg Glu Val Asp Ala Asn Arg
    210                 215                 220

Pro Ser Thr Ala Phe Leu Gly Gln Asn Asp Val Phe Asp Phe Thr Gln
225                 230                 235                 240

Pro Ala Gly Val Ser Gly Met Ala Phe Pro Arg Pro Lys Arg Pro Ala
                245                 250                 255

Pro Ala Gln Glu Ala Ala Thr Glu Gly Pro Ser Ala Ala Ser Gly Val
            260                 265                 270

Pro Gln Thr Gly Pro Gly Arg Glu Val Ala Ala Thr Arg Pro Lys Thr
        275                 280                 285

Thr Lys Ser Gly Lys Ala Leu Ala Lys Thr Arg Trp Val Glu Pro Gln
    290                 295                 300

Asn Val Val Ala Ala Ala Ala Ala Lys Ala Lys Met Ala Thr Ser Ile
305                 310                 315                 320

Pro Glu Pro Glu Gly Ala Ala Ala Ala Thr Ala Gln His Ser Ala Glu
                325                 330                 335

Pro Trp Ala Arg Met Gly Gly Lys Arg Thr Lys Lys Ser Lys His Leu
            340                 345                 350

Asp Asp Glu Tyr Glu Ser Ser Glu Glu Glu Arg Glu Thr Pro Ala Val
        355                 360                 365

Pro Pro Thr Trp Arg Ala Ser Gln Pro Ser Leu Thr Val Arg Ala Gln
    370                 375                 380

Leu Ala Pro Arg Pro Pro Met Ala Pro Arg Ser Gln Ile Pro Ser Arg
385                 390                 395                 400

His Val Leu Cys Leu Pro Pro Arg Asn Val Thr Leu Leu Gln Glu Arg
                405                 410                 415

Ala Asn Lys Leu Val Lys Tyr Leu Met Ile Lys Asp Tyr Lys Lys Ile
            420                 425                 430

Pro Ile Lys Arg Ala Asp Met Leu Lys Asp Val Ile Arg Glu Tyr Asp
        435                 440                 445

Glu His Phe Pro Glu Ile Ile Glu Arg Ala Thr Tyr Thr Leu Glu Lys
    450                 455                 460

Lys Phe Gly Ile His Leu Lys Glu Ile Asp Lys Glu Glu His Leu Tyr
465                 470                 475                 480

Ile Leu Val Cys Thr Arg Asp Ser Ser Ala Arg Leu Leu Gly Lys Thr
                485                 490                 495

Lys Asp Thr Pro Arg Leu Ser Leu Leu Leu Val Ile Leu Gly Val Ile
            500                 505                 510

Phe Met Asn Gly Asn Arg Ala Ser Glu Ala Val Leu Trp Glu Ala Leu
        515                 520                 525

Arg Lys Met Gly Leu Arg Pro Gly Val Arg His Pro Phe Leu Gly Asp
    530                 535                 540

Leu Arg Lys Leu Ile Thr Asp Asp Phe Val Lys Gln Lys Asn Pro Glu
545                 550                 555                 560

Leu Arg Glu Glu Thr Pro Leu Ser Met Ala Pro Ser Trp Tyr Leu Glu
                565                 570                 575
```

-continued

```
Tyr Lys Lys Ile Pro Asn Ser Asn Pro Pro Glu Tyr Glu Phe Leu Trp
            580                 585                 590

Gly Leu Arg Ala Arg His Glu Thr Ser Lys Met Arg Val Leu Arg Phe
        595                 600                 605

Ile Ala Gln Asn Gln Asn Arg Asp Pro Arg Glu Trp Lys Ala His Phe
    610                 615                 620

Leu Glu Ala Val Asp Asp Ala Phe Lys Thr Met Asp Val Asp Met Ala
625                 630                 635                 640

Glu Glu His Ala Arg Ala Gln Met Arg Ala Gln Met Asn Ile Gly Asp
                645                 650                 655

Glu Ala Leu Ile Gly Arg Trp Ser Trp Asp Asp Ile Gln Val Glu Leu
            660                 665                 670

Leu Thr Trp Asp Glu Asp Gly Asp Phe Gly Asp Ala Trp Ala Arg Ile
        675                 680                 685

Pro Phe Ala Phe Trp Ala Arg Tyr His Gln Tyr Ile Leu Asn Ser Asn
    690                 695                 700

Arg Ala Asn Arg Arg Ala Thr Trp Arg Ala Gly Val Ser Ser Gly Thr
705                 710                 715                 720

Asn Gly Gly Ala Ser Thr Ser Val Leu Asp Gly Pro Ser Thr Ser Ser
                725                 730                 735

Thr Ile Arg Thr Arg Asn Ala Ala Arg Ala Gly Ala Ser Phe Phe Ser
            740                 745                 750

Trp Ile Gln His Arg
        755
```

CANCER VACCINE

CROSS-REFERENCE TO RELATED APPLICATIONS

This application is the National Phase of PCT International Application No. PCT/GB2020/052631, filed on Oct. 19, 2020, under 35 U.S.C. § 119(a) to Patent Application No. 1915163.8, filed in Great Britain on Oct. 18, 2019, all of which are hereby expressly incorporated by reference into the present application.

REFERENCE TO ELECTRONIC SEQUENCE LISTING

The application contains a Sequence Listing which has been submitted electronically in .txt format and is hereby incorporated by reference in its entirety. Said .txt copy, created on Nov. 24, 2020, is named "100652 SEQ listing_ST25" and is 154,287 bytes in size. The sequence listing contained in this .txt file is part of the specification and is hereby incorporated by reference herein in its entirety.

The present invention relates to a nucleic acid based cancer vaccine, it use, and methods of treatment or prevention of cancer, particularly oral cancer, and associated combination therapies. The inventors have demonstrated the utility of the nucleic acid based cancer vaccine for several cancer types. Particular combination therapies of interest include immunotherapies, radiotherapy, targeted therapies and chemotherapies.

The present invention relates to nucleic acid vaccines which encode at least a MAGED4B protein, for use in the treatment of cancer in particular. Synergistic combinations with other anti-cancer agents are described, particularly immune checkpoint inhibitors. The cancer vaccine may further comprise an immunologically active fragment to enhance the immune response, and an additional cancer antigen, such as FJX1.

One particular cancer of interest, although not the only cancer suitable for treatment with the vaccine described herein is oral and oropharyngeal cancer. Oral and oropharyngeal cancer (commonly referred to as head and neck cancer; HNSCC), grouped together, is the sixth most common cancer in the world (annual estimated incidence 275,000 for oral (OSCC) and 130,300 for oropharyngeal cancers (OPSCC). In the UK incidence of HNSCC has risen dramatically since the late 1970s (+92%) to over 7500 cases/year; while the rising UK incidence of OPSCC is related to human papillomavirus (HPV) infection, the cause of the increased incidence of OSCC is unclear, and, it is estimated that rates will continue to rise significantly. Management of patients is often by a costly multidisciplinary approach involving surgery and/or radiotherapy followed by reconstruction and rehabilitation. Treatment results in considerable physical and psychological morbidity and may not prolong life for many of the patients. Surgery and radiotherapy, remain the standard treatments, but despite improvements, are associated with significant morbidity and a relatively static 5-year survival rate of around 50-60%. Immune checkpoint inhibitors against CTLA4 and PD1/PDL1, predicated upon boosting a pre-existing anti-tumour immune response, have shown efficacy across cancer types, and the recent KEYNOTE 012 trial treating HNSCC patients with α-PD1 produced an overall response rate of 18% (J. Clin. Oncol. 34, 3838-3845 (2016). British Journal of Cancer119, 153-159 (2018). However, most patients do not respond to checkpoint inhibitor therapy, likely through lack of a sufficiently strong pre-existing anti-tumour immune response. Experimental approaches to treatment of HPV driven HNSCC targeting HPV antigens are been developed by several companies. These include peptide vaccines, mRNA and DNA vaccines. The majority of oral and oropharyngeal cancers however are HPV-negative; the survival in this patient group is significantly poorer than in those with HPV-positive tumours. 6,000,000 patients annually HPV negative HNSCC require treatment worldwide. So far, a very small number vaccination approaches have been explored in this disease.

While there is intriguing potential for the development of patient-specific vaccines based on an individual's tumour mutanome, the costliness and technical difficulty of such an approach means that, even if successful, it is unlikely to benefit most patients. Identifying common tumour antigens that are shared between patients, to the production of generic cancer vaccines that would provide a cheap and widely available treatment for OSCC. Among the different types of TAA, cancer/testis (CT) antigens are highly promising therapeutic targets; cellular and humoral immune responses to CT antigens are frequently observed in cancer patients, and there is an association between CT antigen expression and cytolytic activity of tumour immune infiltrates. The immunogenicity and cancer-specificity of CT antigens have made them prioritised targets for cancer immunotherapy, and their therapeutic function has been tested in a variety of clinical settings. CT antigen vaccines are generally well tolerated, and there are presently a large number of ongoing cancer vaccination trials assessing their therapeutic efficacy. A need exists for identifying tumour antigens that can be effectively targeted for treatment or prevention of cancers, such as oral and oropharyngeal cancer.

The inventors have also identified other cancer types which express the cancer antigens described herein, or may be suitable for treatment with the cancer vaccine described herein. Such cancers could include head and neck cancer, oral cancer, oropharyngeal cancer, nasopharyngeal cancer, lung cancer, breast cancer, oesophageal cancer, stomach cancer, liver cancer, colon cancer, kidney cancer, cholangiocarcinoma, cutaneous melanoma, rectal cancer, thyroid cancer, bladder urothelial carcinoma, renal cancer and stomach adenocarcinoma. Those skilled in the art may appreciate further cancer types in which the cancer vaccine may be efficacious, based upon mechanism of action of the vaccine. Evidence that the cancer antigens are expressed in various cancer types is included in FIG. 29.

The cancer antigen of primary interest herein is the MAGED4B antigen. This may be expressed on the surface of one or more cells associated with cancer, including the tumour cells or cancer associated cells. Another cancer antigen of interest herein is the FJX1 antigen. These may be both expressed in the same cancer, for example be expressed on the surface one or more cell of the cancer or cell associated with the cancer, or in the cancer microenvironment of a tumour. Thus, the vaccine can include one or both cancer antigens.

Previously, it has been identified that MAGED4B and/or FJX1 proteins can be split into small peptides for vaccination (WO2018/169385), by cleaving the protein such that peptides are capable of binding to a MHC class I molecule to induce an anti-cancer immune response in a subject. These peptides are restricted to those that can bind to MHC class I molecules which imposes a limitation on size since the groove of an MHC class I molecule may accept peptides of 8 to 10 amino acids or slightly longer.

However, it is thought that such peptides do not activate a sufficiently sustained immune response in order to help patients induce a durable anti-cancer response.

Since MAGED4B and FJX1 are both self-proteins a major issue with developing a successful cancer vaccine to any one or more of these targets is that patients in need of vaccination are already self-tolerised to these antigens. Further, the targeting of solely MHC class I molecules has been found not to produce a sufficient immune response to produce the anti-cancer response. Such a vaccine approach does not elicit the potent, balanced, and durable CD4 plus CD8 T cell expansion necessary for clinical efficacy. Despite these antigens being identified as good targets for a cancer vaccine, it is regrettable that current technology to date has not produced a vaccine which could be used in a clinical setting.

Further, by providing a vaccine as a small peptide, the vaccine works in a very specific way, and targets a particular type of human leukocyte antigen (HLA) which can limit the usefulness of the vaccine to specific parts of the population. Thus, a vaccine derived from peptides can never provide a pan-population vaccine, meaning that patients would need to be tested to see if the vaccine was suitable for them, missing parts of the population in need thereof.

Therapeutic cancer vaccines in general have to overcome three major hurdles: low immunogenicity; established disease burden; and the immunosuppressive tumour microenvironment. Aberrantly expressed self-antigens, such as MAGED4B and FJX1 face this hurdle, high-affinity T cells recognising these self-antigens are eliminated by central and peripheral tolerance mechanisms. Thus, the peptide vaccines have, as yet, activated sufficient low affinity T cells. However, high doses of adjuvant needed to stimulate the immune response will have significant side effects for the patient. There is thus still a long-unmet need to be able to help patients with cancers expressing MAGED4B and/or FJX1 to eliminate their tumours.

These issues are such that there was a large risk that a vaccine directed to these antigens in isolation is unlikely to be effective on its own in the treatment of these patients. However, the present inventors have surprisingly found that it is possible to develop a vaccine that demonstrates a good immunological response, providing a CD4 plus CD8 T cell response required for clinical efficacy, and furthermore provides a pan-population effect which means that this can be of general, rather than specific use. Further, they have noted some additional beneficial effects in using the vaccine of the invention that may make the cancer more susceptible in general to additional chemotherapeutic or immunotherapeutic agents, by targeting cells that are associated with the cancer and protecting it from the effects of other anti-cancer agents. This exciting development is of great interest in the treatment of patients in need thereof.

Moreover, there is some evidence that the cancer vaccine described herein may act in a synergistic way with additional anti-cancer agents, which is an exciting development in the treatment of these cancer types, as a combined approach is often clinically recommended to ensure complete remission of the cancer.

In order to provide a successful cancer vaccine, the vaccine must enter the cells and be expressed in vivo, thereby enabling antigen presentation on major histocompatibility molecules (MHC) and T cell recognition. Co-induction of T helper cells (with the surface marker CD4) to cytotoxic T cells (with the surface marker CD8) is critical. Both CD4+ and CD8+ T cells contain several subsets. Therefore, and DNA vaccine must fulfil many requirements before it can be considered to be a good clinical candidate.

The inventors have shown in relevant models and with preclinical data presented here that the desired immunological responses are obtained using the vaccine of the invention. Particularly, the inventors have shown effective tumour infiltration by CD8+ T cells following vaccination, and that circulating T cells exist in human samples that have the potential to be stimulated by the administration 5 of the vaccine, whilst also provoking the formation of newly primed T cells. Data significantly demonstrates good expression and secretion of the protein from the cells transfected with nucleic acid vaccine, which is appropriate, processed to present relevant epitopes thereof to immune surveillance. Further, in mouse tumour models, where the mice had palpable tumours expressing at least one human antigen, the impact of the vaccine on the reduction of tumour size can be seen. Since the tumours associated with at least the MAGED4B protein are known to be particularly aggressive, such mouse model data is hugely encouraging to the inventors.

The vaccine of the present invention has therefore been demonstrated to have the capacity to alter the microenvironment surrounding a tumour, making it "visible" to the immune system, permitting T cell infiltration, not only to provoke an immune response to the tumour itself, but further to cancer associated fibroblasts which entirely unexpectedly have been shown to express the MAGED4B protein too. Thus, a vaccine according to the present invention has the capacity to alter cells surrounding the tumour that act to protect such cancer cells from the immune system and anti-cancer agents. Thus, the vaccine of the invention has far-reaching implications for the modulation of the cancer microenvironment, exposing the tumour to the immune system, enhancing the immune response against the tumour and thus greatly assisting tumour cell death.

Notably, the present inventors have found that the vaccine of the invention is very unlikely to cause harm to the normal tissues in the body, since patterns of expression in other tissues is minimal. Thus, this makes the vaccine clinically relevant.

Thus, the present invention provides vaccines that treat and provide protection against tumour growth.

An aim of the present invention is to provide a cancer vaccine that can provide an appropriate immune response against cancer cells, particularly oral and oropharyngeal cancer cells.

SUMMARY OF THE PRESENT INVENTION

The present invention relates to the provision of a nucleic acid vaccine. The vaccine according to any part hereof may be formulated as a vaccine composition. The nucleic acid vaccine is a cancer vaccine, for use in treating cancer. Various alternative vaccines are described. As used herein, either protein may be described as a cancer antigen.

The cancer vaccine may comprise a nucleic acid which encodes a MAGED4B protein or a variant thereof. This may be the full length protein as described in SEQ ID No. 3 or SEQ ID No. 31, but this can be truncated or modified, such that a sufficient amount of the protein is provided by the nucleic acid, to enable the protein to be processed within the cell and presented to the immune system. Suitable truncations are described in SEQ ID No. 35 to SEQ ID No. 37. Thus, the MAGED4B protein may be an immunogenic fragment of the full length protein as described herein. The sequence MADGED4B protein may further be modified, such that amino acid substitutions are made. Such variants, modifications and truncations are discussed further herein.

Known isoforms (variants) of MAGED4B are described in No. 41-43.

Alternatively defined, the cancer vaccine may include a nucleic acid encoding a MAGED4B protein, said nucleic acid sequence as described in SEQ ID No. 7, SEQ ID No. 16, SEQ ID No. 17, SEQ ID No. 24, SEQ ID No. 25 or SEQ ID No. 26, or variants and truncated versions thereof. Variants and truncations are as defined herein.

Optionally, the composition may also include a nucleic acid which encodes a FJX1 protein or a variant thereof. The protein may be a full length protein as described in SEQ ID No. 4 or SEQ ID No. 33 or may be truncated or modified. Such variants, modifications and truncations are discussed further herein.

Alternatively defined, the cancer vaccine may include a nucleic acid encoding a FJX1 protein, said nucleic acid sequence as described in SEQ ID No. 8, SEQ ID No. 20 or SEQ ID No. 21, or variants and truncated versions thereof. Variants and truncations are as defined herein.

Optionally, if the vaccine comprises a nucleic acid encoding a MAGED4B protein or a variant thereof and a nucleic acid which encodes a FJX1 protein or a variant thereof, these may be provided separately, i.e. as separate nucleic acids, or on the same nucleic acid, either under the control of the same or different promoters, or present as a fusion between the two proteins.

The present invention relates to the provision of a nucleic acid vaccine. The nucleic acid encodes a FJX1 protein or a variant thereof. The protein may be the full length protein as described in SEQ ID No. 4 or SEQ ID No. 33, or may be truncated or modified. Such variants, modifications and truncations are discussed further herein. Optionally, the composition may also include a nucleic acid which encodes a MAGED4B protein or variant thereof. The protein may be a full length protein as described in SEQ ID No. 3 or SEQ ID No. 31, or may be truncated (such as described in SEQ ID No. 35 to SEQ ID No. 37) or modified. Such terms are as discussed herein.

The present invention relates to the provision of a nucleic acid vaccine composition. The composition may include a nucleic acid that encodes a MAGED4B protein or variant thereof, and a nucleic acid that encodes a FJX1 protein or variant thereof. The nucleic acid may encode both the MADGED4B and the FJX1 protein as a fusion protein. The composition may be two separate nucleic acid constructs, each encoding either a MAGED4B protein or variant thereof or a FJX1 protein or variant thereof, for separate, simultaneous or sequential administration as a vaccine to a patient in need thereof.

Alternatively defined, the cancer vaccine may include a nucleic acid encoding a MAGED4B protein, said nucleic acid sequence as described in SEQ ID No. 7, SEQ ID No. 16, SEQ ID No. 17, SEQ ID No. 24, SEQ ID No. 25 or SEQ ID No. 26, or variants and truncated versions thereof, together with a nucleic acid encoding a FJX1 protein, said nucleic acid sequence as described in SEQ ID No. 8, SEQ ID No. 20 or SEQ ID No. 21, or variants and truncated versions thereof. Variants and truncations are as defined herein. The nucleic acids may be separate or present on the same nucleic acid construct.

A fusion protein is a protein consisting of at least two domains that are encoded by separate coding sequences that have been joined so that they are transcribed and translated as a single unit, producing a single polypeptide. Thus, the nucleic acid encoding for a MAGED4B protein or variant thereof, and a FJX1 protein or variant thereof may be fused such that they are produced as a single polypeptide when administered. Thus, in a nucleic acid encoding the fusion protein, the fusion protein is expressed under the control of one promoter. The gene order in the fusion may be in either direction, i.e. a FJX1 protein or variant thereof followed by a MAGED4B protein or variant thereof, or vice versa. It may be preferred that the MAGED4B protein or variant thereof precedes the FJX1 protein or variant thereof.

It may be preferred that any of the nucleic acid vaccine compositions described herein further comprises a helper motif. A helper motif may be defined as a nucleic acid sequence that stimulates an immune response either directly (for example the DNA sequence is in itself capable of stimulating an immune response) or the motif encodes an immunogenic protein or fragment thereof. Said helped motif acts to boost the immune response to the proteins encoded by the nucleic acid vaccine. Suitable helper motifs are discussed herein. One helper motif is an immunogenic fragment of the tetanus toxin, known as DOM.

Thus, the cancer vaccine may comprise nucleic acid encoding MAGED4B protein or a variant thereof together with helper motif. The helper motif may be any suitable helper motif as described here. The helper motif may be DOM. An exemplary vaccine may comprise a sequence described in SEQ ID No. 18 or SEQ ID No. 19, or variants or truncations thereof. An exemplary vaccine may encode a protein sequence described in SEQ ID No. 32 or variants or truncations thereof.

Alternatively, the cancer vaccine may comprise nucleic acid encoding FJX-1 protein or a variant thereof together with helper motif. The helper motif may be any suitable helper motif as described here. The helper motif may be DOM. An exemplary vaccine may comprise a nucleic sequence described in SEQ ID No. 22 or SEQ ID No. 23, or variants or truncations thereof. An exemplary vaccine may encode a protein sequence described in SEQ ID No. 34 or variants or truncations thereof.

Further, the cancer vaccine may comprise nucleic acid encoding MAGED4B protein or a variant thereof and nucleic acid encoding FJX-1 protein or a variant thereof together with helper motif. The helper motif may be any suitable helper motif as described here. The helper motif may be DOM. An exemplary vaccine may comprise a MAGED4B sequence described in SEQ ID No. 18 or SEQ ID No. 19, or variants or truncations thereof. An exemplary vaccine may encode a MAGED4B protein sequence described in SEQ ID No. 32 or variants or truncations thereof. An exemplary vaccine may comprise a nucleic sequence described in SEQ ID No. 22 or SEQ ID No. 23, or variants or truncations thereof. An exemplary vaccine may encode a protein sequence described in SEQ ID No. 34 or variants or truncations thereof.

Where the cancer vaccine as described here includes a fusion protein, a linker may be used between the coding sequences. This fusion may be between cancer antigens MAGED4B and FJX1 or may be between a cancer antigen and helper motif. Any suitable linker sequences may be used. Exemplary linker sequences are given in SEQ ID No. 5, 6, 10 and 11.

The nucleic acid sequence encoding the cancer antigen may include a signal or leader sequence. Such may improve the secretion of the protein from a transfected cell. Exemplary leader sequences are given in SEQ ID No. 1 and 27.

The nucleic acid of the cancer vaccine described here may further comprise a promoter operably linked to the encoding sequences, and optionally further comprising a polyadenylation signal downstream of the encoding sequences. Suitable promoter and polyadenylation signals are described here. Suitable promoters include the sequences described in SEQ ID No. 9 and SEQ ID No. 15.

A cancer vaccine as described here may be a DNA vaccine or an RNA vaccine. The vaccine may also be a non-natural nucleic acid as described here.

The cancer vaccine as described here may be presented as any appropriate nucleic acid construct, including plasmid, minicircle, single stranded circle, closed linear DNA or single stranded RNA. The construct may include any other components in order to promote the expression of the coding sequence, such as enhancers and the like.

Any one of these vaccines is described further below:

A cancer vaccine as described here may be provided as a vaccine composition. A composition may include any suitable excipients or additives which may be supplied in order to stabilise the vaccine composition, making it suitable for storage and transportation, and/or making it suitable for administration, by including buffer solutions and the like to ensure a correct pH.

A cancer vaccine as described here may be used to treat cancer in an animal, including a human. Optionally, the cancer vaccine is for use in treating cancer in a human. Optionally, the cancer vaccine is for use in treating cancer in a non-human animal, such as a domestic, livestock or wild animal. Suitable animals may include cats and dogs, guinea pigs, cattle, horses, sheep, rabbits, and non-human primates. Non-human primates may include chimpanzees and monkeys.

Also envisaged is a method of treating cancer in an animal, including a human, comprising administering the cancer vaccine described here to a patient in need thereof. Suitable animals may include cats and dogs, guinea pigs, cattle, horses, sheep, rabbits, and non-human primates. Non-human primates may include chimpanzees and monkeys.

The cancer vaccine described here may be for use in medicine, optionally for use in treating or preventing cancer.

The cancer vaccine described here may be for use in revealing a tumour to the immune system.

The cancer vaccine described here may be for use in sensitising a tumour to an anticancer agent, optionally an immunotherapy such as a checkpoint inhibitor.

The cancer vaccine described here may be for use in combination with an anti-cancer agent, optionally an immunotherapy such as a checkpoint inhibitor, or chemotherapy.

The cancer vaccine described here may be for a method of sensitising a tumour to infiltration by $CD8^+$ T cells, the method comprising administering the cancer vaccine to a human or animal subject.

The method of treatments described here may further comprise the use of an anti-cancer agent, optionally an immunotherapy such as a checkpoint inhibitor.

As used herein, a checkpoint inhibitor is an agent capable of blocking the action of PD-1, PD-L1, PD-L2 or CTLA-4, optionally wherein said agent is an antibody or aptamer.

The cancer vaccine described here may be used in a method of increasing the efficacy of immune checkpoint blockade in a patient in need thereof, said method comprising administering a cancer vaccine as described here to a human or animal subject.

The cancer vaccine described herein may be used to co-induce CD4 and CD8 T cells.

The cancer vaccine, uses and methods of treatment described here may be effective for use in the treatment of a multitude of cancer types, including but not limited to head and neck cancer, oral cancer, oropharyngeal cancer, nasopharyngeal cancer, lung cancer, breast cancer, oesophageal cancer, stomach cancer, liver cancer, colon cancer, kidney cancer, cholangiocarcinoma, cutaneous melanoma, rectal cancer, thyroid cancer, bladder urothelial carcinoma, renal cancer and stomach adenocarcinoma.

According to a first aspect of the present invention, there is provided a cancer vaccine comprising nucleic acid encoding the proteins MAGED4B and/or FJX1, or variants thereof, and further encoding an immunogenic fragment of tetanus toxin.

Advantageously, two cancer testis antigens MAGED4B and FJX1 are found to be frequently expressed in OSCC. Overall the two antigens are expressed at 96% of OSCC cases at the RNA level. Furthermore the present study has confirmed the expression of both antigens at protein levels in oral dysplasia and OSCC cases (10/10 were positive; 5 for each condition) with no expression in non-malignant oral mucosa. Examination of expression in healthy tissues at protein levels demonstrated low expression. These expression data have been paralleled by study of pre-existing immunity to the antigens in patients with HPV independent HNSCC using an HLA-A2 tetramer (at present available for MAGED4B only) and overlapping peptide pools (OPP) for the entire amino acid sequence of each antigen. These were measured in both blood and the tumour using expanded tumour infiltrating lymphocytes. Circulating MAGED-4B tetramer positive CD8+ T cells were observed in 5/7 HLA-A2 patients (0.04-0.1% of total CD8+ T cells) with 2/2 expanded TILs also having the tetramer positive at a similar frequency. Higher levels of MAGED4B positive CD8 T cells (5-10 times) was detected in HLA-A2 negative HLA-A1 positive TIL samples using OPP indicating reactivity beyond HLA-A2 restriction. For FJX1 CD8 T cell reactivity has been evaluated in expanded TIL samples using OPP with demonstration of CD8 reactivity in HLA-A1 patients coexisting with MAGED4B CD8 T cells. The patients' data indicate a significant immunogenicity of both antigens more so pronounced for MAGED4B. DNA vaccines encoding full length MAGED4B and FJX1 antigens (e.g. p.Dom-MAGED4BFL and p.Dom-FJX1FL described herein) have been developed and the preclinical data demonstrates the DNA vaccines targeting MAGED4B/FJX1 have a significant potential to suppress the growth of tumour expressing these antigens.

Further advantageously, the provision of an immunogenic fragment of tetanus toxin of *Clostridium tetani* can help to induce strong CD4+ helper T cell responses required for induction of tumour-specific CD4+ and CD8+ T cell responses via activation of dendritic cells (the so called linked T cell mechanisms). Such CD4 and CD8 epitopes are known to be able to bind to a range of mouse and human MHC class II molecules.

DETAILED DESCRIPTION

The cancer vaccine described here can induce antigen-specific T cell responses, notably a $CD4^+$ and $CD8^+$ T cell response critical for an enduring response, thereby eliciting an immune response that is directed to the tumour expressing the antigen. The cancer vaccine described herein can additionally or alternatively affect the tumour microenvironment, increasing the immune visibility of the tumour and promoting infiltration of CD8 T cells into the tumour mass, thereby making tumour cells more vulnerable to anti-cancer agents, either alone or in combination with said anti-cancer agents. Effectively the vaccine changes the microenvironment of the tumour, making it more susceptible to immune attack.

Lack of intra-tumoural T cells is a major barrier to the efficacy of immune checkpoint inhibitors and other immunotherapies in patients with cancer; this may result from poor tumour immunogenicity (i.e. a lack of T cells) or because T cells fail to infiltrate the tumour (i.e. T cells in the wrong place). The inventors have clearly demonstrated that the cancer vaccine described here increases intra-tumoural T cells (FIGS. 10B and C). Therefore, the invention extends to a method for increasing the efficacy of immune checkpoint blockade in a patient in need thereof, comprising administering a cancer vaccine described here to a human or animal subject. The cancer vaccine described here may be for use in sensitising a tumour to the immune system or to an anti-cancer agent. Data is presented here that demonstrates, when the cancer vaccine described here is used with an agent capable of causing an immune checkpoint blockade, that a synergistic effect occurs (FIG. 9B) which is of great importance.

The vaccine as described here may produce an induced or elicited immune response which may be a cellular immune response. The induced or elicited immune response may include induction or secretion of interferon-gamma (IFN-γ), and/or CD107a/b which is a marker of cytotoxic T cells (FIGS. 21 and 22).

In particular, where the antigen in the cancer vaccine is a MAGED4B protein antigen, the cancer vaccine can induce an antigen specific response that is additionally directed against cancer-associated fibroblasts (CAF) which have been demonstrated by the inventors to also express this antigen (FIGS. 27 and 28). A human tumour contains many different types of cell, apart from cancerous cells, including cancer-associated fibroblasts (CAF), endothelial cells, immune cells, adipocytes, and pericytes, which shape the immune microenvironment and promote cancer progression. Thus, the ability to target such cells in the tumour microenvironment is of particular use in the treatment of cancer in general, and may not be limited to the cancer subtypes that themselves express MAGED4B.

All types of solid cancers (tumours) contain CAF-rich subgroups; this ranges from greater than 95% in pancreatic cancers to approximately 50% in head and neck cancers. The proportion of CAF in the tumour is around 25-50% of the tumours, and can be higher in some cancers such as pancreatic cancer where most tumours are CAF-rich. Notably, CAF accumulation in cancers is associated with poor clinical outcome; CAF-rich tumours are clinically aggressive, respond poorly to treatment and are associated with poor survival. This is because CAF promote many of the 'hallmarks of malignancy', promoting tumour growth, invasion, metastasis and angiogenesis. A consistent finding in multiple cancer types has been the inverse correlation between CAF and CD8 T cells suggesting a role for CAF in tumour immune evasion. Recent studies, including those by the applicants, have shown that CAF exclude CD8 T cells from tumours, and thereby promote resistance to anti-PD1/PDL1 checkpoint immunotherapy (and vaccine-based immunotherapy; Ford et al., Cancer Res 80, 1846-1860 (2020)). A number of clinical studies have identified CAF gene signatures in patients that do not respond to anti-PD1/PDL1 (Mariathasan, S. et al. Nature 554, 544-548 (2018)). CAF-mediated CD8 T cell exclusion is now recognised as a major contributor to checkpoint immunotherapy resistance, and CAF have become an important immunotherapeutic target to improve checkpoint immunotherapy response rates (which currently are around 20% across cancer types). Therapeutic possibilities suggested for targeting CAF include CAF depletion, inhibiting CAF function or CAF normalisation, but previous attempts to specifically target CAF clinically have been unsuccessful.

The fact that the inventors have demonstrated that CAF appear to consistently express MAGED4B is very surprising. Expression is uniformly high across the CAF population, and consistent between tumours; 70% of HNSCC analysed contained MAGED4B-positive CAF. This CAF MAGED4B expression was confirmed by analysing scRNASeq HNSCC transcriptomic data (FIG. 28) (Puram et al., Cell. 2017; 171(7):1611-1624 which also confirmed MAGED4B expression by HNSCC cells).

Generating an immune response that specifically targets CAF is a highly attractive therapeutic, and there have been previous attempts to target CAF by vaccination, for example vaccinating against FAP (fibroblast activated protein). However, FAP is now known to be expressed by other cell types (such as multipotent bone marrow stromal cells) and is not CAF specific. No CAF-specific antigen has yet been identified, but one which the cancer vaccine of the present invention may supply, wherein the antigen the cancer vaccine supplies is a MAGED4B protein or variant thereof.

The present invention is directed to vaccines and methods useful for the restoration of responsiveness to other anti-cancer agents, notably targeted therapies, immunotherapy and chemotherapy, in particular for the restoration of responsiveness to T cell based immunotherapies, including immune checkpoint blockade such as with PD-1 inhibitors, PD-L1 inhibitors, CTLA-4 inhibitors, TIM3 inhibitors, LAG 3 inhibitors, TIGIT inhibitors etc., T cell agonists, such as aCD40, aCD27, OX40 etc., chimeric antigen receptor (CAR) T cells and vaccines.

T cell-mediated elimination of tumours requires signals from the T cell receptor and co-stimulatory molecules to permit effector functions of tumour-antigen specific T cells. There is also an array of immune suppressive mechanisms within the tumour microenvironment that can suppress anti-tumour immunity. The use of monoclonal antibodies to overcome this suppression, in particular targeting co-stimulatory members of the tumour necrosis factor receptor (TNFR) family with agonist Abs enhances T cell function, which has led to encouraging therapeutic results. TNFRs may be important targets for enhancing tumour-specific immune responses and specific TNFRs include OX40, 4-1BB, and CD40.

The cancer vaccines described herein can be administered in therapeutically effective dosages alone or in combination with adjunct cancer therapy such as chemotherapy, radiotherapy, immunotherapy, laser therapy, targeted therapy and/or surgery, all of which may be herein described as an anti-cancer agent. The cancer vaccines described may provide a beneficial effect, such as a reduction in tumour size, slowing rate of tumour growth, inhibiting or slowing metastasis, sensitizing tumours to the immune response or to anti-cancer treatments, or otherwise improving overall clinical condition, without necessarily eradicating the tumour.

Specifically contemplated for combination therapy are cytostatic and cytotoxic agents that target the tumour cells, agents that target angiogenesis (such as angiogenesis inhibitors lenvatinib and sorafenib), agents that target markers that the cancer cells are specifically expressing (i.e. Herceptin that target HER2 positive cells), immune therapies targeting macrophages, immune therapies targeting T cell checkpoint or agonist pathways, adoptive cell therapy (ACT) using T cells engineered to express chimeric antigen receptors (CAR T cells),T-cell receptor (TCR) or in vitro expanded T cells and vaccines.

The combination described here can further comprise immune checkpoint inhibitor, for example agents that are active against cytotoxic T-lymphocyte associated protein 4 (CTLA-4), PD-1 and PDL-1, since these may prevent the suppression of elements in the immune system such as MHC class presentation, T cell presentation and/or differentiation, and cytokine, chemokine or signalling for immune cell proliferation and/or differentiation.

Thus, the cancer vaccine described here may be combined with checkpoint inhibitors such as antibodies directed to CTLA-4, PD-1, PD-L1 and PD-L2 to increase the stimulation of both the cellular and humoral immune responses, but any suitable inhibitor may be used.

Thus, the cancer vaccine described here may be combined with cytostatic and cytotoxic agents that target the tumour cells, agents that target angiogenesis, immune therapies targeting macrophages, immune therapies targeting T cell checkpoint or agonist pathways, adoptive cell therapy (ACT) using T cells engineered to express chimeric antigen receptors (CAR T cells), T cell receptor (TCR) or in vitro expanded T cells, T cell agonists and vaccines.

MAGED4B Antigen

MAGED4B is part of a superfamily termed MAGE (melanoma antigen-encoding gene) proteins. MAGE proteins share a conserved domain known as the MAGE homology domain (MHD). The cancer vaccine may comprise a nucleic acid which encodes a MAGED4B protein or a variant thereof. This may be the full length protein as described in SEQ ID No. 3 or SEQ ID No. 31, but this can be truncated or modified, such that a sufficient amount of the protein is provided by the nucleic acid, to enable the protein to be processed within the cell and presented to the immune system. Suitable truncations are described in SEQ ID No. 35 to SEQ ID No. 37. Thus, the MAGED4B protein may be an immunogenic fragment of the full length protein as described herein. The sequence MADGED4B protein may further be modified, such that amino acid substitutions are made. Such variants, modifications and truncations are discussed further herein.

Alternatively defined, the cancer vaccine may include a nucleic acid encoding a MAGED4B protein, said nucleic acid sequence as described in SEQ ID No. 7, SEQ ID No. 16, SEQ ID No. 17, SEQ ID No. 24, SEQ ID No. 25 or SEQ ID No. 26, or variants and truncated versions thereof. Variants and truncations are as defined herein.

The MAGED4B protein may comprise or consist of the full length MAGED4B protein sequence. The MAGED4B protein may comprise or consist of the sequence of SEQ ID NO: 3 or SEQ ID No. 31, or a variant thereof. In another embodiment, the MAGED4B protein may be encoded by a nucleic acid comprising or consisting of the sequence of SEQ ID NO: 7, SEQ ID No. 16, SEQ ID No. 17, SEQ ID No. 24, SEQ ID No. 25 or SEQ ID No. 26 or a variant thereof.

Advantageously, the full length antigen design can achieve wider population coverage, where it is not focused on targeting individual HLA alleles such as the HLA-A2 allele for example.

Advantageously, the MAGED4B protein may be truncated. The truncation may involve the removal of all or a part or portion of the MAGE homology domain. Two potential regions of homology are found in MAGED4B proteins, and both represent areas which may permit truncation, since they are common across MAGE proteins. The two homology domains have been identified at amino acids 412-500 and amino acids 510-682 in isoform 1 which is represented in SEQ ID No. 3. This sequence is 741 amino acids in length. If both homology domains are removed, this would reduce the length of MAGED4B by 260 amino acids and still provide a functional immunological fragment thereof. Thus, up to 40% of the full length protein can be removed, optionally up to 50%, and the remaining sequence may still be sufficiently immunogenic to act as a vaccine. Possible truncations are depicted in FIG. 16. It may be preferred that known epitopes from the MHD are retained, such as the HLA-2 defined epitope RLSLLLVL. This sits between the two MHDs. As depicted, each of the MHDs have been successfully removed in vaccines, but any portion thereof may be removed. Thus, a truncated version of MAGED4B may include an immunological fragment in which a portion or whole of a MHD is removed. Indeed, in removing the MHD further residues may also be truncated. As a minimum, 450 amino acids of the MAGED4B sequence as described in SEQ ID No. 3 are included. The immunogenic fragment may be 400, 450, 500, 550, 600, 650 or 700 amino acids in length or any number there-between. Various truncations are detailed in SEQ ID No. 35 to SEQ ID No. 37. Other truncations are possible. The inventors postulate that removing the MHD may permit the immune system to recognise the MAGED4B specific epitopes more clearly.

The work here is based on MAGED4B isoform 1 (SEQ ID No. 3). However, 4 isoforms exist, and are included in SEQ ID No. 41-43. Of these, isoform 3 (SEQ ID No. 42) is a very rare alternative splicing, which has a frame shift at position 349, and terminated at position 414. Sequence ID No. 42 has 85% identity sequence to SEQ ID No. 3, due to these alternative splicing and therefor truncations. Thus, in an alternative definition, the truncations may have a sequence identity of at least 50%, 55%, 60%, 65%, 70%, 75%, 80%, 85%, 90% or 95% of the sequence shown in SEQ ID No. 3.

The cancer vaccine described here may include nucleic acid coding for any one of the MAGED4B proteins described in SEQ ID No. 41-43. These are variants of SEQ ID No. 3.

A variant of MAGED4B may comprise a modified and/or truncated variant of MAGED4B. In particular, the skilled person will understand that some modifications or variants of a sequence may provide the same or substantially similar immunogenic function as the unmodified sequence (i.e. the MAGED4B sequence described herein). Modifications may comprise amino acid residue additions, substitutions, or deletions. In one embodiment, the modification may comprise or consist of no more than 20 amino acid residue additions, substitutions, or deletions. In another embodiment, the modification may comprise or consist of no more than 15 amino acid residue additions, substitutions, or deletions. In another embodiment, the modification may comprise or consist of no more than 10 amino acid residue additions, substitutions, or deletions. In another embodiment, the modification may comprise or consist of no more than 8 amino acid residue additions, substitutions, or deletions. In another embodiment, the modification may comprise or consist of no more than 6 amino acid residue additions, substitutions, or deletions. In another embodiment, the modification may comprise or consist of no more than 5 amino acid residue additions, substitutions, or deletions. In another embodiment, the modification may comprise or consist of no more than 4 amino acid residue additions, substitutions, or deletions. In another embodiment, the modification may comprise or consist of no more than 3 amino acid residue additions, substitutions, or deletions. In another embodiment, the modification may comprise or consist of no more than 2 amino acid residue additions, substitutions, or deletions. In another embodiment, the modification may comprise or consist of no more than one amino acid residue addition, substitution, or deletion. The amino acid residue additions, substitutions, or deletions may involve consecutive amino acids, multiple groups of amino acids, or non-consecutive amino acid residues, or combinations thereof.

Variants of MAGED4B may comprise or consist of a sequence having at least 80% identity with SEQ ID NO: 3. Alternatively, variants of MAGED4B may comprise or consist of a sequence having at least 85% identity with SEQ ID NO: 3. Alternatively, variants of MAGED4B may comprise or consist of a sequence having at least 90% identity with SEQ ID NO: 3. Alternatively, variants of MAGED4B may comprise or consist of a sequence having at least 95% identity with SEQ ID NO: 3. Alternatively, variants of MAGED4B may comprise or consist of a sequence having at least 98% identity with SEQ ID NO: 3. Alternatively, variants of MAGED4B may comprise or consist of a sequence having at least 99% identity with SEQ ID NO: 3. Alternatively, variants of MAGED4B may comprise or consist of a sequence having at least 99.5% identity with SEQ ID NO: 3.

Nucleic acid variations/modifications may comprise conservative substitutions of nucleotides using codon redundancy to encode the same MAGED4B protein, or part thereof, as encoded by SEQ ID NO: 7.

Also included are the nucleic acids disclosed in SEQ ID No. 7, SEQ ID No. 16, SEQ ID No. 17, SEQ ID No. 24, SEQ ID No. 25 or SEQ ID No. 26, or variants thereof. Variants may have a sequence identity of at least 50%, 55%, 60%, 65%, 70%, 75%, 80%, 85%, 90% or 95% of the sequence shown in any one of these sequences. These variants therefore cover the truncations listed above in the protein.

The nucleic acid of the cancer vaccine may be codon optimised, such as the sequence described in SEQ ID No. 17. Codon optimised sequences may code for the same peptide sequence, but is possible because most amino acids are encoded by more than one codon. This may be done to aid synthesis of the nucleic acid, or to prevent a perfect homology with the host genome. As shown in the data, the codon optimised vaccines performed well. Coding sequences can be optimised for stability and high levels of expression.

Variants of the nucleic acid encoding MAGED4B may comprise or consist of a sequence having at least 80% identity with SEQ ID NO: 7. Alternatively, variants of the nucleic acid encoding MAGED4B may comprise or consist of a sequence having at least 85% identity with SEQ ID NO: 7. Alternatively, variants of the nucleic acid encoding MAGED4B may comprise or consist of a sequence having at least 90% identity with SEQ ID NO: 7. Alternatively, variants of the nucleic acid encoding MAGED4B may comprise or consist of a sequence having at least 95% identity with SEQ ID NO: 7. Alternatively, variants of the nucleic acid encoding the MAGED4B may comprise or consist of a sequence having at least 98% identity with SEQ ID NO: 7. Alternatively, variants of the nucleic acid encoding the MAGED4B may comprise or consist of a sequence having at least 99% identity with SEQ ID NO: 7. Alternatively, variants of the nucleic acid encoding the MAGED4B may comprise or consist of a sequence having at least 99.5% identity with SEQ ID NO: 7.

The sequence identity may be over at least 600 consecutive nucleotides or amino acid residues. Alternatively, the sequence identity may be over at least 700 consecutive nucleotides or amino acid residues. Alternatively, the sequence identity may be over the whole MAGED4B sequence.

The sequence identity may be over at least 400 consecutive amino acids, at least 450 amino acids, at least 500 amino acids, or at least 550 amino acids.

In another embodiment, variants of MAGED4B may comprise or consist of a truncated sequence of SEQ ID NO: 3. For example, the sequence of SEQ ID NO: 3 herein may be truncated and still provide immunogenicity. The truncated sequence may comprise at least 200 amino acids of the sequence of SEQ ID NO: 3. The truncated sequence may comprise at least 300 amino acids of the sequence of SEQ ID NO: 3. The truncated sequence may comprise at least 400 amino acids of the sequence of SEQ ID NO: 3. The truncated sequence may comprise at least 500 amino acids of the sequence of SEQ ID NO: 3. Alternatively, the truncated sequence may comprise at least 600 amino acids of the sequence of SEQ ID NO: 3. Alternatively, the truncated sequence may comprise at least 700 amino acids of the sequence of SEQ ID NO: 3. Suitable truncations are depicted in FIG. 16.

FJX1 Antigen

The cancer vaccine may comprise or additionally comprise a nucleic acid which encodes a FJX1 (Four-jointed box protein 1) protein or a variant thereof. The protein may be a full length protein as described in SEQ ID No. 4 or SEQ ID No. 33 or may be truncated or modified. Such variants, modifications and truncations are discussed further herein.

Alternatively defined, the cancer vaccine may include or further include a nucleic acid encoding a FJX1 protein, said nucleic acid sequence as described in SEQ ID No. 8, SEQ ID No. 20 or SEQ ID No. 21, or variants and truncated versions thereof. Variants and truncations are as defined herein.

The FJX1 protein may comprise or consist of the full length FJX1 protein sequence. The FJX1 protein may comprise or consist of the sequence of SEQ ID NO: 4, or a variant thereof. In another embodiment, the FJX1 protein may be encoded by a nucleic acid comprising or consisting of the sequence of SEQ ID NO: 8, or a variant thereof.

As previously discussed, the full length antigen design can achieve a wider population coverage, where it is not focused on targeting individual HLA alleles such as HLA-A2 for example.

A variant of FJX1 may comprise a modified and/or truncated variant of FJX1. In particular, the skilled person will understand that some modifications or variants of a sequence may provide the same or substantially similar immunogenic function as the unmodified sequence (i.e. the FJX1 sequence described herein). Modifications may comprise amino acid residue additions, substitutions, or deletions. In one embodiment, the modification may comprise or consist of no more than 20 amino acid residue additions, substitutions, or deletions. In another embodiment, the modification may comprise or consist of no more than 15 amino acid residue additions, substitutions, or deletions. In another embodiment, the modification may comprise or consist of no more than 10 amino acid residue additions, substitutions, or deletions. In another embodiment, the modification may comprise or consist of no more than 8 amino acid residue additions, substitutions, or deletions. In another embodiment, the modification may comprise or consist of no more than 6 amino acid residue additions, substitutions, or deletions. In another embodiment, the modification may comprise or consist of no more than 5 amino acid residue additions, substitutions, or deletions. In another embodiment, the modification may comprise or consist of no more than 4 amino acid residue additions, substitutions, or deletions. In another embodiment, the modification may comprise or consist of no more than 3 amino acid residue additions, substitutions, or deletions. In another embodiment, the modification may comprise or consist of no more than 2 amino acid residue additions, substitutions, or deletions. In another embodiment, the modification may comprise or consist of no more than one amino acid residue addition, substitution, or deletion. The amino acid residue additions, substitutions, or deletions may involve consecutive amino acids, multiple groups of amino acids, or non-consecutive amino acid residues, or combinations thereof.

Variants of FJX1 may comprise or consist of a sequence having at least 80% identity with SEQ ID NO: 4 or SEQ ID No. 33. Alternatively, variants of FJX1 may comprise or consist of a sequence having at least 85% identity with SEQ ID NO: 4 or SEQ ID No. 33. Alternatively, variants of FJX1 may comprise or consist of a sequence having at least 90% identity with SEQ ID NO: 4 or SEQ ID No. 33. Alternatively, variants of FJX1 may comprise or consist of a sequence having at least 95% identity with SEQ ID NO: 4 or SEQ ID No. 33. Alternatively, variants of FJX1 may comprise or consist of a sequence having at least 98% identity with SEQ ID NO: 4 or SEQ ID No. 33. Alternatively, variants of FJX1 may comprise or consist of a sequence having at least 99% identity with SEQ ID NO: 4 or SEQ ID No. 33. Alternatively, variants of FJX1 may comprise or consist of a sequence having at least 99.5% identity with SEQ ID NO: 4 or SEQ ID No. 33.

Nucleic acid variations/modifications may comprise conservative substitutions of nucleotides using codon redundancy to encode the same FJX1 protein, or part thereof, as encoded by SEQ ID NO: 8 or SEQ ID No. 20 or SEQ ID No. 21.

The nucleic acid of the cancer vaccine may be codon optimised, such as the sequence described in SEQ ID No. 21. Codon optimised sequences may code for the same peptide sequence, but is possible because most amino acids are encoded by more than one codon. This may be done to aid synthesis of the nucleic acid, or to prevent a perfect homology with the host genome.

Variants of the nucleic acid encoding FJX1 may comprise or consist of a sequence having at least 80% identity with SEQ ID NO: 8. Alternatively, variants of the nucleic acid encoding FJX1 may comprise or consist of a sequence having at least 85% identity with SEQ ID NO: 8. Alternatively, variants of the nucleic acid encoding FJX1 may comprise or consist of a sequence having at least 90% identity with SEQ ID NO: 8. Alternatively, variants of the nucleic acid encoding FJX1 may comprise or consist of a sequence having at least 95% identity with SEQ ID NO: 8. Alternatively, variants of the nucleic acid encoding the FJX1 may comprise or consist of a sequence having at least 98% identity with SEQ ID NO: 8. Alternatively, variants of the nucleic acid encoding the FJX1 may comprise or consist of a sequence having at least 99% identity with SEQ ID NO: 8. Alternatively, variants of the nucleic acid encoding the FJX1 may comprise or consist of a sequence having at least 99.5% identity with SEQ ID NO: 8. SED ID No. 8 in this paragraph can be can be substituted with SEQ ID No. 20 or SEQ ID No. 21.

The sequence identity may be over at least 300 consecutive nucleotides or amino acid residues. Alternatively, the sequence identity may be over at least 400 consecutive nucleotides or amino acid residues. Alternatively, the sequence identity may be over the whole FJX1 sequence.

In another embodiment, variants of FJX1 may comprise or consist of a truncated sequence of SEQ ID NO: 4. For example, the sequence of SEQ ID NO: 4 herein may be truncated and still provide immunogenicity. The truncated sequence may comprise at least 200 amino acids of the sequence of SEQ ID NO: 4. The truncated sequence may comprise at least 300 amino acids of the sequence of SEQ ID NO: 4. The truncated sequence may comprise at least 400 amino acids of the sequence of SEQ ID NO: 4. Thus, also encompassed is a immunogenic fragment of FJX1 according to any sequence disclosed herein.

MAGED4B and FJX1 Combined

In one embodiment, the nucleic acid encodes both MAGED4B and FJX1, or variants thereof. In one embodiment, the nucleic acid encodes both MAGED4B and FJX1, or variants thereof with a linker therebetween.

The MAGED4B and FJX1 antigens may be encoded as a single fusion protein, or encoded for separate expression. The MAGED4B may be encoded N-terminal to FJX1.

The combination may extend to a single transcription unit such as MAGED4B-2A peptide-FJX1. 2A self-cleaving peptides, or 2A peptides, are a class of 18-22 aa-long peptides, which can induce ribosomal skipping during translation of a protein in a cell. These peptides share a core sequence motif of DxExNPGP, and are found in a wide range of viral families. They help generating polyproteins by causing the ribosome to fail at making a peptide bond.

Helper Motif

The cancer vaccine described here may be provided with a nucleic acid providing a helper motif. A helper motif as used herein is a motif which enhances or improves the immunogenicity of the cancer vaccine. Such may be defined as an adjuvant, a helper epitope, an immunogenic fragment, a cytokine, The inflammatory signal upon cytosolic nucleic acid recognition may enhance immunogenicity per se via the activation of major pro-inflammatory pathways, but this can be further provoked if the nucleic acid vaccine includes a helper motif which is a sequence motif such as CpG motifs. Unmethylated CpG motifs may have an immune stimulating effect by themselves via stimulating the innate immune system through Toll-like receptor (TLR) 9.

Thus, the helper motif may be a nucleic motif known to stimulate the immune system without the need for expression.

The helper motif may encode a protein or polypeptide, or an immunogenic fragment thereof which stimulates the immune system. Thus, the helper motif is expressed in the cell. The helper motif may be present on the same construct as the cancer vaccine antigen, or may be provided on a separate construct. Advantageously, both may be supplied together on the same nucleic acid construct. If both are provided together, they may be under the control of the same or different promoters. Advantageously, these may be provided as a transcriptional or translational fusion. Transcriptional fusions permit the coding sequences to be combined, but does not result in the production of hybrid or fusion proteins. Translational fusions may also be provided, wherein the product of the expression is a hybrid protein. Such may be preferred for vaccination. A linker molecule as described here may be used to link the cancer antigen and the helper motif together in the genetic fusion, and polypeptide fusion.

For example, nucleic acid sequence encoding a cytokine or chemokine can also be delivered directly with the nucleic vaccine, either on the construct or on a separate construct. This enables the appearance of the cytokine or chemokine at the same time and in the same area as the cancer vaccine antigen. Suitable nucleic acids encode cytokines or chemokines such as interleukin (IL)-10, IL-12, dendritic cell-targeting chemokine MIP3α, or IFN-γ, or those discussed further below. Thus, the helper motif may be a nucleic acid encoding a cytokine.

Further, the nucleic acid sequence may encode an immune system stimulator, which can also be delivered directly with the vaccine. Such may include sequences that include trafficking signals (such as MHC class I trafficking signal (MITD)) and the like.

Alternatively, the helper motif may provide immune stimulation by other means, such as by the formation of particles. PVXCP encodes the potato virus X coat protein which provides immune stimulation through the mechanism of linked T-cell help similarly to DOM and permits the formation of particles which enhance the immunogenicity of the expressed polypeptide.

As further example, the helper motif may encode for a protein, polypeptide or an immunogenic fragment thereof which are known to induce a strong immune response. As detailed herein, such includes an immunogenic fragment of the tetanus toxin, in particular DOM. Other suitable helper eptiopes may be derived from the B subunit of *Escherichia coli* heat labile toxin, fragment C of tetanus toxin, diphtheria toxin B subunit, *E. coli* labile toxin fragment, cholera toxin fragment, OVA peptides and/or calreticulin, HIV protein NEF (Negative regulatory factor), HBV surface antigen, promiscuous CD4 epitope PADRE.

Examples are presented herein in which various helper motifs such as CpG motifs, MITD, PVXCP and MIP3α are used in combination with the cancer vaccine.

Suitable helper motifs include nucleic acid sequences encoding: Flt3L, Flt3L-Fc fusion, CD80, CD80-Fc fusion, OX40L, IL-15, 4-1BBL, GM-CSF, CCL21a, IL-23, CCL27, CXCL10, CCL5, CCL3, LAG3, IL-15RA, CXCL10, CpG, *E. coli* Labile toxin fragment, cholera toxin fragment, calreticulin, HIV NEF, HBV sAg, PADRE, IRF1, CCL25, IL-33 and/or IL-28B.

Particular results have been obtained when the helper motif is an immunogenic fragment of a tetanus toxin, as described herein.

Immunogenic Fragment of Tetanus Toxin DOM

The immunogenic fragment of tetanus toxin may not have the toxic functionality of full length tetanus toxin. In one embodiment, the immunogenic fragment of tetanus toxin may not comprise a neuron binding domain, or may not comprise a functional binding domain. In one embodiment, the immunogenic fragment of tetanus toxin may comprise or consist of the p30 MHC II epitope of tetanus toxin. In one embodiment, the immunogenic fragment of tetanus toxin comprises or consists of DOM. DOM may comprise or consist of the sequence of SEQ ID NO: 2, or a variant thereof.

DOM is an immunogenic fragment of tetanus toxin of *Clostridium tetani* (1), which is safe for human use, because it does not contain a neuron binding domain that is responsible for spastic paralysis. Advantageously, DOM contains a 'promiscuous' p30 MHC II epitope and potentially other CD4 T cell epitopes. P30 is known to be able to bind to a range of mouse and human MHC class II molecules and induce strong CD4+ helper T cell responses required for induction of tumour-specific CD4 and CD8 T cell responses via activation of dendritic cells (the so called linked T cell mechanisms) (2, 3). Further advantageously, DOM has a number of weak CD8 epitopes which are unable to compete with cancer epitopes by the process of immune-dominance, which further provides benefits for inclusion into a DNA vaccine according to the invention, which is intended to induce potent T cell responses against cancer antigens.

In one embodiment, a reference to DOM herein may alternatively be replaced by another immunogenic fragment of tetanus toxin. In particular, the reference to DOM herein may be substituted by p30 or p2 epitopes of tetanus toxin, or other tetanus toxin CD4 helper epitopes alone or in combination.

DOM may be present as the helper motif with any cancer vaccine described herein. It may be described as a helper epitope, since it includes an epitope which my help to induce a strong immune response. Data shown here supports this (FIG. 11A).

Various assemblies of DNA vaccines are shown in FIG. 7.

DOM, MAGED4B and FJX1 Combined

In one embodiment, the nucleic acid encodes DOM with MAGED4B and/or FJX1, or variants thereof. In another embodiment, the nucleic acid encodes DOM with MAGED4B and FJX1, or variants thereof.

In one embodiment DOM, MAGED4B and FJX1 are encoded as single fusion protein. In another embodiment DOM and one of MAGED4B or FJX1 are encoded as single fusion protein.

DOM may be encoded N-terminal to MAGED4B and/or FJX1.

Various assemblies of DNA vaccines are shown in FIG. 7. Any suitable assembly may be used, including a single transcription unit such as MAGED4B-2A peptide-FJX1.

Other Elements

It will be understood that the following section applies to whichever cancer vaccine is of use, including a single antigen or both antigens. In one embodiment, linker residues may be provided between one or more, or all, of the antigens of DOM, MAGED4B and FJX1. The linker residues may comprise random amino acid sequences, or amino-acids that have been selected to be non-immunogenic based on epitope prediction computer programs or experiments in animal models. For example, a linker may not be considered if it is predicted or known to be an epitope (i.e. in order to avoid an immune response to epitopes, e.g. artificial epitopes, not found in nature). The linker may be flexible. The linker may comprise or consist of K, G, P or S amino acid residues, or combinations thereof. In one embodiment, the linker may comprise or consist of G and/or P amino acid residues. The linker residues may be between 1 and 10 amino acids in length. In another embodiment, the linker residues may be between 2 and 8 residues in length. In another embodiment, the linker residues may be between 1 and 7 residues in length.

The MAGED4B and FJX1 fusion protein may comprise a linker in between the MAGED4B and FJX1 sequences. The linker between MAGED4B and FJX1 may comprise or consist of between about 1 and about 10 amino acids. In another embodiment, the linker between MAGED4B and FJX1 may comprise or consist of between about 1 and about 6 amino acids. In another embodiment, the linker between MAGED4B and FJX1 may comprise or consist of between about 1 and about 5 amino acids. In another embodiment, the linker between MAGED4B and FJX1 may comprise or consist of between about 2 and about 6 amino acids. In another embodiment, the linker between MAGED4B and FJX1 may comprise or consist of between about 2 and about 5 amino acids. In another embodiment, the linker between MAGED4B and FJX1 may comprise or consist of between about 3 and about 5 amino acids. In another embodiment, the linker between MAGED4B and FJX1 may comprise or consist of between about 4 and about 6 amino acids. In another embodiment, the linker between MAGED4B and FJX1 may comprise or consist of about 5 amino acids.

The linker between MAGED4B and FJX1 may comprise or consist of 3-5 amino acids selected from G, S, T, and A. The linker between MAGED4B and FJX1 may comprise or consist of G and/or S residues. In one embodiment, the linker between MAGED4B and FJX1 may comprise or consist of alternating G and/or S residues. In one embodiment, the linker between MAGED4B and FJX1 may comprise or consist of GSGSG (SEQ ID NO: 6/Linker 2). Alternative linkers may comprise or consist of GGGGG (SEQ ID NO: 10) or SSSSS (SEQ ID NO: 11). Glycine and serine amino-acids are flexible are when included in the linker they allow protein flexibility for efficient expression.

The advantage of such linker is that they are not significantly immunogenic, which will minimise false epitopes (we have used MHC I prediction algorithms to predicts the absence of junctional peptides). The linkers are flexible will not significantly affect the structure of the antigens to allow efficient translation and the proteasomal processing for presentation by MHC.

In an embodiment encoding a DOM with MAGED4B and/or FJX1 fusion protein, the fusion protein may comprise a linker in between the sequence of DOM and the sequence of MAGED4B and/or FJX1. The linker between DOM and MAGED4B and/or FJX1 sequences may comprise or consist of between about 1 and about 10 amino acids. In another embodiment, the linker between DOM and MAGED4B and/or FJX1 sequences may comprise or consist of between about 1 and about 8 amino acids. In another embodiment, the linker between DOM and MAGED4B and/or FJX1 sequences may comprise or consist of between about 2 and about 8 amino acids. In another embodiment, the linker between DOM and MAGED4B and/or FJX1 sequences may comprise or consist of between about 4 and about 8 amino acids. In another embodiment, the linker between DOM and MAGED4B and/or FJX1 sequences may comprise or consist of between about 5 and about 8 amino acids. In another embodiment, the linker between DOM and MAGED4B and/or FJX1 sequences may comprise or consist of between about 6 and about 8 amino acids. In another embodiment, the linker between DOM and MAGED4B and/or FJX1 sequences may comprise or consist of about 7 amino acids. In another embodiment, the linker between DOM and MAGED4B and/or FJX1 sequences may comprise or consist of about 8 amino acids. In another embodiment, the linker between DOM and MAGED4B and/or FJX1 sequences may comprise or consist of about 9 amino acids. In another embodiment, the linker between DOM and MAGED4B and/or FJX1 sequences may comprise or consist of about 10 amino acids.

In one embodiment, the linker between DOM and MAGED4B and/or FJX1 may comprise or consist of AAAGPGP (SEQ ID NO: 5/Linker 1). The linker between DOM and MAGED4B and/or FJX1 may comprise or consist of 3-10 amino acids selected from G, S, T, and A. Alternatively, the linker between DOM and MAGED4B and/or FJX1 may comprise or consist of 3-5 amino acids selected from G, S, T, and A. In one embodiment, the linker between DOM and MAGED4B and/or FJX1 may comprise or consist of alternating G and/or S residues. In one embodiment, the linker between DOM and MAGED4B and/or FJX1 may comprise or consist of GSGSG (SEQ ID NO: 6/Linker 2). Alternative linkers may comprise or consist of GGGGG (SEQ ID NO: 10) or SSSSS (SEQ ID NO: 11).

Advantageously, linker AAAGPGP (SEQ ID NO: 5/Linker 1) minimises the occurrence of false epitopes and inserts a restriction enzyme Not I site to aid cloning. In particular, MHC I prediction algorithms have been utilised to predict the absence of junctional peptides. Furthermore, the linkers are flexible and will not significantly affect the structure of the antigens to allow efficient translation and the proteasomal processing for presentation by MHC.

The nucleic acid may further encode a leader sequence, such as a signal peptide for enhancing the efficacy of secretion. The leader sequence may comprise or consist of an IgH signal peptide, such as a mus IgH signal peptide, or an orthologue thereof. The leader sequence may comprise or consist of the sequence MGWSCIIFFLVATATGVHS (SEQ ID NO: 1), or a functional variant thereof. The leader sequence may be N terminal to the DOM sequence, and forms part of a fusion peptide therewith.

The nucleic acid may comprise one or more promoters. The promoter may comprise a eukaryote promoter, and the nucleic acid may optionally further comprise a prokaryote promoter, such as T7. In one embodiment, the promoter is a dual eukaryote/prokaryote promoter. The promoter may be a strong promoter. In one embodiment, the promoter is a viral promoter. The promoter may be selected from any of the group comprising simian virus 40 early promoter (SV40), cytomegalovirus immediate-early promoter (CMV), T7, human Ubiquitin C promoter (UBC), human elongation factor 1a promoter (EF1A), mouse phosphoglycerate kinase 1 promoter (PGK), and chicken 3-Actin promoter coupled with CMV early enhancer (CAGG). In one embodiment, the promoter comprises CMV. In one embodiment, the promoter comprises CMV/T7 dual promoter, for example in accordance with SEQ ID NO: 9. In one embodiment, the promoter comprises CMV/T7 dual promoter comprising or consisting of SEQ ID NO: 9, or a functional variant thereof. The variant of SEQ ID NO: 9 may have at least 80%, 85%, 90%, 95%, 98% or 99% identity to SEQ ID NO: 9.

The promoter may be encoded N-terminal to the antigenic protein(s) to be expressed (e.g. DOM, MAGED4B, and/or FJX1). It will be understood that this means that the promoter is upstream of the coding sequence. The promoter needs simply to be operably linked to the coding sequence.

In an embodiment wherein MAGED4B and FJX1 are expressed as separate polypeptides, the nucleic may comprise a promoter for each polypeptide. A single promoter may be used for one or more, or all of the antigens to be expressed.

The nucleic acid may encode a polyA transcription termination sequence. In one embodiment the polyA transcription termination sequence is a mammalian terminator comprising the sequence motif AAUAAA which promotes both polyadenylation and termination. The mammalian terminator may be any one of SV40, hGH, BGH, and rbGlob. In one embodiment the polyA transcription termination sequence is a bovine growth hormone (BGH) polyA transcription termination sequence. A polyadenylation signal can be downstream of the coding sequence(s) of the cancer antigens. The polyadenylation signal can be a LTR polyadenylation signal, polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, CA).

In one embodiment, the nucleic acid is DNA encoding:

a single fusion polypeptide comprising DOM antigen, full length MAGED4B antigen, and full length FJX1 antigen, and with linker residues encoded between each antigen;

a N-terminal CMV/T7 promoter; and a C-terminal PolyA sequence.

In another embodiment, the nucleic acid is DNA encoding:

a single fusion peptide comprising DOM antigen, and one of full length MAGED4B antigen or full length FJX1 antigen as, and with linker residues encoded between each antigen;

a N-terminal CMV/T7 promoter; and a C-terminal PolyA sequence.

Ideally, the CMV/T7 promoter may be replaced with a CMV promoter.

The nucleic acid may be a DNA encoding:

a single fusion polypeptide comprising a helper motif and a MAGED4B antigen;

an operably linked promoter; and a PolyA signal sequence.

The nucleic acid may be a DNA encoding:

a single fusion polypeptide comprising DOM antigen and a MAGED4B antigen;

an operably linked promoter; and a PolyA signal sequence.

The nucleic acid may comprise sequences encoding SEQ ID NOs: 2-4 described herein, or variants thereof. In another embodiment, the nucleic acid may comprise sequences encoding SEQ ID NOs: 1-4 described herein, or variants thereof. In another embodiment, the nucleic acid may comprise sequences encoding SEQ ID NOs: 2-6 described herein, or variants thereof. In another embodiment, the nucleic acid may comprise sequences encoding SEQ ID NOs: 1-6 described herein, or variants thereof.

The nucleic acid encoding MAGED4B and/or FJX1 may be provided in an appropriate backbone vector for delivery and expression in vivo. In one embodiment, the backbone vector comprises pcDNA3.0 vector.

Any suitable nucleic acid construct may be used for the vaccine. For a DNA vaccine, the DNA may be in the form of a plasmid, minicircle, single stranded circle, or closed linear DNA. A closed linear DNA may be preferred as it is possible to include no bacterial sequences and it is a minimal vector designed for uses such as DNA vaccines.

In one embodiment, the nucleic acid may comprise or consist of any one of the vectors selected from pDOM MAGED4B-FJX1; pDOM MAGED4B, and pDOM FJX1 as described herein.

In one embodiment, the nucleic acid may comprise or consist of any one of the constructs selected from DB MAGED4B-FJX1; DBMAGED4B, and DB FJX1. These may further include DOM. Various architectures have been tested in relation to these closed linear DNA structures; these are depicted in FIG. 18.

In one embodiment, the nucleic acid may comprise or consist of the sequence of SEQ ID NO: 12. In another embodiment, the nucleic acid may comprise or consist of the sequence of SEQ ID NO: 13. In another embodiment, the nucleic acid may comprise or consist of the sequence of SEQ ID NO: 14.

In one embodiment, the nucleic acid may comprise or consist of the sequence of SEQ ID NO: 16. In another embodiment, the nucleic acid may comprise or consist of the sequence of SEQ ID NO: 17. In another embodiment, the nucleic acid may comprise or consist of the sequence of SEQ ID NO: 18. In one embodiment, the nucleic acid may comprise or consist of the sequence of SEQ ID NO: 19. In another embodiment, the nucleic acid may comprise or consist of the sequence of SEQ ID NO: 20. In another embodiment, the nucleic acid may comprise or consist of the sequence of SEQ ID NO: 21. In another embodiment, the nucleic acid may comprise or consist of the sequence of SEQ ID NO: 22. In another embodiment, the nucleic acid may comprise or consist of the sequence of SEQ ID NO: 23.

The nucleic acid may comprise or consist of DNA. The nucleic acid may comprise or consist of RNA, such as mRNA or self-replicating RNA. Artificial nucleic acids are also envisioned, as discussed herein.

The nucleic acid may be linear or in a circular form, for example in a plasmid. The nucleic acid may comprise the sequence of a mammalian expression vector, such as pcDNA3.0 vector, or an equivalent thereof. The skilled person will recognise that any appropriate mammalian expression vector may be used to insert the nucleic acid according to the invention herein. It may be preferred that the vector is a closed linear DNA.

The cancer vaccine may comprise a composition. For example, the cancer vaccine may be provided in the form of the nucleic acid in a pharmaceutically acceptable carrier. The MAGED4B and/or FJX1 antigens may be encoded on separate nucleic acids, such as vectors, in the same composition.

Further Definitions

As used herein, "coding sequence or "encoding" may mean the nucleic acids (RNA or DNA molecule) that comprise a nucleotide sequence which encodes a protein or a fragment thereof. The coding sequence can further include initiation and termination signals operably linked to regulatory elements including a promoter and polyadenylation signal capable of directing expression in the cells of an individual or mammal to which the nucleic acid is administered.

As used herein "fragment" or "immunological fragment" with respect to proteins may mean a protein or a polypeptide portion thereof, capable of eliciting an immune response in a mammal that cross reacts with the antigen disclosed herein. The fragments can be polypeptide fragments selected from at least one of the various amino acids sequences described herein. Fragments of proteins can comprise at least 10%, at least 20%, at least 30%, at least 40%, at least 50%, at least 60%, at least 70%, at least 80%, at least 90% or at least 95% of a protein.

As used herein, "identity" in the context of nucleic acid or protein/polypeptide sequences means that the sequence of one has a specified percentage of residues that are the same over a specified region to the reference sequence. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. Optionally, where a sequence is referenced herein, sequences which preferably have at least 50% identity, 55%, 60%, 65%, 70%, 75%, 80% sequence identity, 85%, 90%, 93%, 95%, 97%, 98% or 99% sequence identity are also encompassed.

As used herein, nucleic acids can be single stranded or double stranded, or can contain sections of both double stranded and single stranded sequence. The nucleic acid can be DNA (including cDNA), RNA, or a hybrid thereof, where the nucleic acid can contain combinations of deoxyribo- and ribo-nucleotides, and combinations of bases including natural bases (uracil, adenine, thymine, cytosine, guanine) and unnatural bases (such as inosine, xanthine hypoxanthine, isocytosine and isoguanine). The nucleic acid may be composed of any nucleotides. These nucleotides may be natural, modified or artificial. The nucleotides may be polymerised to form RNA, DNA, locked nucleic acid (LNA), peptide nucleic acid (PNA), morpholino nucleic acid, glycol nucleic acid (GNA), threose nucleic acid (TNA), hybrids and mixtures thereof and any other artificial (xeno) nucleic acids. It may be preferred that the polynucleotide is DNA or a modified version thereof (i.e. with modifications in the backbone, sugar residue or nucleobase). ModRNA is considered to be appropriate nucleic acid with which to form the vaccine.

The nucleic acid may be in any appropriate format and include any additional sequences or elements that may be required. The nucleic acid may be a plasmid (double stranded circular), a minicircle, a closed linear DNA, a single stranded circular DNA, or any other nucleic acid construct suitable for delivering the vaccine to a cell. The nucleic acid may be an RNA, such as an mRNA (messenger RNA), self-replicating RNA, or non-replicating mRNA, such as that suitable to transfect dendritic cells in vitro.

As used herein, “operably linked” may mean that expression of a coding sequence is under the control of a promoter with which it is spatially connected. A promoter can be positioned 5' (upstream) or 3' (downstream) of a coding sequence under its control.

As used herein “promoter” as used herein means a synthetic or naturally-derived sequence which is capable of conferring, activating or enhancing expression of a coding sequence in a cell. A promoter can be derived from sources including viral, bacterial, fungal, plants, insects, and animals. A promoter can regulate the expression of a gene component constitutively or differentially with respect to cell, the tissue or organ in which expression occurs, or in response to external stimuli such as inducing agents. Examples of suitable promoters include lac operator-promoter, SV40 late promoter, SV40 early promoter, RSV-LTR promoter, CMV promoter, or SV40 promoters (e.g. pcDNA3.1, pVAX1, pVIVO2, pCl, pCMV and pSV2).

The terms “signal peptide” and “leader sequence” are used interchangeably herein and refer to an amino acid sequence that can be linked at the N terminus of a protein described here. Signal peptides/leader sequences typically direct localisation of a protein. Signal peptides/leader sequences used herein preferably facilitate secretion of the protein from the cell in which it is produced.

As used herein “immune response” as used herein means the activation of the immune system, e.g., that of a mammal, in response to the introduction of antigen. The immune response can be in the form of a cellular or humoral response, or both. It is preferred that the immune response that is elicited is a CD4+ and CD8+ T cell response.

“Treatment” or “treating” as used herein can mean protecting an animal (including a human) from a disease through means of preventing, suppressing, repressing, or completely eliminating the disease. Preventing the disease involves administering a vaccine of the present invention to an animal (such as a human) prior to onset of the disease. Suppressing the disease involves administering a vaccine of the present invention to an animal (human) after induction of the disease but before clinical appearance. Repressing the disease involves administering a vaccine of the present invention to an animal (human) after appearance of clinical symptoms.

The cancer may be any cancer, including but not limited to head and neck cancer, oral cancer, oropharyngeal cancer, lung cancer, breast cancer, oesophageal cancer, nasopharyngeal cancer stomach cancer, liver cancer, colon cancer, kidney cancer, cholangiocarcinoma, cutaneous melanoma, rectal cancer, thyroid cancer, bladder urothelial carcinoma, renal cancer, and stomach adenocarcinoma.

The cancer vaccine may be used to prevent malignant or cancer cells from developing. In some instances, cellular changes that precede cancer development can be detected, and the cancer vaccine administered or used to prevent the development of cancer. Thus, the cancer vaccine may be used to treat pre-malignant cells. Further the cells may progress through several phenotypes before a cancer phenotype is acquired. Therefore the prevention of cancer may involve the treatment of pre-cancerous but invasive cell types. For example, in cancers of the mouth cells may pass through several phenotypes, including but not limited to oral premalignant lesions (OPML): leukoplakia, erythroplakia, lichen planus, and oral epithelial dysplasia. Further exemplarily, some lung cancers may pass through several phenotypes, including but not limited to squamous metaplasia, atypical adenomatous hyperplasia, and/or squamous carcinoma in situ (CIS).

The cancer vaccine can prevent tumour growth. The cancer vaccine can reduce tumour growth. The vaccine can prevent metastasis of tumour cells. The cancer vaccine can reduce immune evasion of a tumour cell. The cancer vaccine can be targeted to treat the cancer antigen of the vaccine induces or eliciting an immune response that is directed to or reactive against the cancer or tumour expressing the antigen. The induced or elicited cellular immune response can include induction or secretion of interferon-gamma (IFN-γ), tumour necrosis factor alpha (TNF-α) and/or formation of cytolytic granules containing perforin/granzymes. In other embodiments, the induced or elicited immune response can reduce or inhibit one or more immune suppression factors that promote growth of the tumour or cancer expressing the antigen, for example, but not limited to, factors that down regulate MHC presentation, factors that up regulate antigen-specific regulatory T cells (Tregs), PD-L1, FasL, cytokines such as IL-10 and TFG-β, tumour associated macrophages, cancer associated fibroblasts, soluble factors produced by immune suppressor cells, CTLA-4, PD-1, MDSCs, MCP-1, and an immune checkpoint molecule.

The vaccine can increase a cellular immune response in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to a cellular immune response in a subject not administered the vaccine.

The vaccine can increase interferon gamma (IFN-γ) levels in a subject administered the vaccine by about 50-fold to about 6000-fold, about 50-fold to about 5500-fold, about 50-fold to about 5000-fold, about 50-fold to about 4500-fold, about 100-fold to about 6000-fold, about 150-fold to about 6000-fold, about 200-fold to about 6000-fold, about 250-fold to about 6000-fold, or about 300-fold to about 6000-fold as compared to IFN-γ levels in a subject not administered the vaccine.

The cancer vaccine can be a DNA. A DNA vaccine can further comprise elements or reagents that inhibit it from integrating into the chromosome.

The cancer vaccine can be an RNA of the one or more cancer antigens.

The vaccine of the present invention can have features required of effective vaccines such as being safe so that the vaccine itself does not cause any detriment to normal cells, illness or death; being protective against illness; inducing protective T cell responses; and providing ease of administration, few side effects, biological stability, and low cost per dose, particularly where a closed linear DNA is used.

The cancer vaccine can further comprise one or more inhibitors of one or more immune checkpoint molecules (i.e., an immune checkpoint inhibitor or "checkpoint inhibitor"). The immune checkpoint inhibitor is any nucleic acid or protein that prevents the suppression of any component in the immune system such as MHC class presentation, T cell presentation and/or differentiation, B cell presentation and/or differentiation, any cytokine, chemokine or signalling for immune cell proliferation and/or differentiation. as the cancer vaccine may be combined further with antibodies to checkpoint inhibitors such as CTLA-4, PD-1 and PDL-1 to increase the stimulation of the cellular and immune responses. Using anti-PD-1 or anti-PDL-1 antibodies prevents PD-1 or PDL-1 from suppressing T cell and responses.

Combination Therapy

The cancer vaccine may be used as a vaccine in combination with another therapeutically or prophylactically active ingredient. The cancer vaccine may be used as a vaccine in combination with an adjuvant.

The therapeutically or prophylactically active agent may be any anti-cancer agent.

Suitable anti-cancer agents include chemotherapeutics, including but not limited to alkylating agents, mustard gas derivatives (mechlorethamine, cyclophosphamide, chlorambucil, melphalan, and ifosfamide), ethylenimines, alkylsulfonates, hydrazines and triazines, nitrosureas, metal salts (such as carboplatin, cisplatin, and oxaliplatin), plant alkaloids, *vinca* alkaloids, taxanes, podophyllotoxins, camptothecan analogues, antitumor antibiotics, anthracyclines, chromomycin, mitomycin, bleomycin, antimetabolites, folic acid antagonist, pyrimidine antagonist, purine antagonist, adenosine deaminase inhibitor, and topoisomerase (I and II) inhibitors.

Suitable anti-cancer agents include immunotherapeutics, including but not limited to immune checkpoint inhibitors, T cell transfer therapy, adoptive cell therapy, adoptive immunotherapy, or immune cell therapy, antibody therapy, vaccines, or immune system modulators. Further contemplated are immune therapies targeting T cell checkpoint or agonist pathways, adoptive cell therapy (ACT) using T cells engineered to express chimeric antigen receptors (CAR T cells), T cell receptor (TCR) or in vitro expanded T cells.

Suitable anti-cancer agents may include radiotherapy or radiomimetics, targeted therapy, surgery or laser therapy.

Suitable anti-cancer agents include targeted therapies. Such therapies depend on the cancer being treated, and may involve an analysis of what genes the cancer cells are expressing or entail a review of what genetic mutations underlie the mutagenesis. Several targeted therapies are described herein, and include cytostatic and cytotoxic agents that target the tumour cells, agents that target angiogenesis (such as angiogenesis inhibitors lenvatinib and sorafenib), agents that target markers that the cancer cells are specifically expressing (i.e. Herceptin that target HER2 positive cells), therapies targeting macrophages, therapies targeting T cell checkpoint or agonist pathways and the like.

Additionally or alternatively, the cancer vaccine according to the invention may be used alone or in combination with a checkpoint inhibitor for prevention or treatment of cancer. The checkpoint inhibitor may comprise an anti-PD1 binding molecule. He binding molecule comprise an anti-PD1 antibody, or fragment thereof. In another embodiment, the checkpoint inhibitor may comprise an anti-CTLA4 binding molecule.

Advantageously, the preclinical data herein demonstrates the DNA vaccines targeting MAGED4B/FJX1 and having a significant potential to suppress the growth of tumour expressing these antigens can be further enhanced by combination with a checkpoint inhibitor, such as an anti-PD1 or anti-CTLA4 binding molecule.

The anti-PD1 binding molecule may comprise an antibody or antibody variant, such as an antibody fragment, or an antibody mimetic. The antibody or variant thereof may be monoclonal. In one embodiment, the antibody or variant thereof may comprise or consist of Nivolumab, or an antibody or variant thereof that competes for binding with Nivolumab. In one embodiment, the antibody or variant thereof may comprise the six heavy and light chain CDRs of Nivolumab. In an alternative embodiment, the antibody or variant thereof may comprise the variable heavy and light chain sequences of Nivolumab.

The anti-CTLA4 binding molecule may comprise an antibody or antibody variant, such as an antibody fragment, or an antibody mimetic. The antibody or variant thereof may be monoclonal. In one embodiment, the antibody or variant thereof may comprise or consist of Ipilimumab, or an antibody or variant thereof that competes for binding with Ipilimumab. In one embodiment, the antibody or variant thereof may comprise the six heavy and light chain CDRs of Ipilimumab. In an alternative embodiment, the antibody or variant thereof may comprise the variable heavy and light chain sequences of Ipilimumab.

In one embodiment, the checkpoint inhibitor, such as anti-PD1 or anti-CTLA4 binding molecules, may be provided by the provision/administration of nucleic acid encoding the checkpoint inhibitor for expression in vivo. The checkpoint inhibitor may be encoded on a plasmid. The checkpoint inhibitor may comprise a DNA-encoded monoclonal antibody (DMAb), for example as described in Perales-Puchalt et al. (Oncotarget. 2019 Jan. 1; 10(1):13-16. doi: 10.18632/oncotarget.26535), which is herein incorporated by reference.

DNA-encoded monoclonal antibodies (DMAbs) can help to overcome difficulties in production, stability, the requirement of frequent high doses for antibody administration and long intravenous administration are recurring issues. Synthetically designed DMAbs can simplify design and implementation of MAb-based therapies. DMAbs delivered through plasmid DNA injection and electroporation have been used in preclinical models for the treatment or prophylaxis of infectious diseases, cancer and cardiovascular disease. Perales-Puchalt et al. (Oncotarget. 2019 Jan. 1; 10(1):13-16. doi: 10.18632/oncotarget.26535) and Duperret E K et al. (Cancer Res. 2018; 78:6363-70), both of which are incorporated herein by reference, reported that immune checkpoint blockers can be optimised and delivered in vivo advancing further DMAb technology by optimisation, expression and in vivo functional characterisation of anti-CTLA4 and anti-PD1 antibodies.

The use may be in a combined formulation. In another embodiment, the use may be concurrent or sequential administration (e.g. formulated separately, but administered together). In one embodiment, the vaccine according to the invention may be administered prior to the checkpoint inhibitor.

According to another aspect of the invention there is provided a fusion peptide encoded by the nucleic acid of the cancer vaccine described herein.

According to another aspect of the invention there is provided a composition comprising the cancer vaccine according to the invention.

The composition may be immunogenic, for example in a mammal, such as a human. The composition may comprise a pharmaceutically acceptable carrier. The composition may be a pharmaceutical composition comprising a pharmaceutically acceptable carrier. The composition may be for use in the prophylaxis or treatment of cancer.

According to another aspect of the invention, there is provided a kit for the treatment or prevention of cancer, the kit comprising

- a cancer vaccine according to the invention herein; and
- a checkpoint inhibitor agent, such as an anti-PD1 binding molecule.

According to another aspect of the invention, there is provided a kit for the treatment or prevention of cancer, the kit comprising

- a first cancer vaccine according to the invention herein, wherein the nucleic acid encodes MAGED4B;
- a second cancer vaccine according to the invention herein, wherein the nucleic acid encodes FJX1; and optionally
- a checkpoint inhibitor agent, such as an anti-PD1 binding molecule.

Accordingly, there may be provided a kit for the treatment or prevention of cancer, the kit comprising

- a cancer vaccine comprising a sequence encoding a MAGED4B antigen or variant thereof; and
- a checkpoint inhibitor agent, such as an anti-PD1 binding molecule.

Accordingly, there may be provided a kit for the treatment or prevention of cancer, the kit comprising

- a first cancer vaccine wherein the nucleic acid encodes MAGED4B or a variant thereof and a
- a checkpoint inhibitor agent, such as an anti-PD1 binding molecule. The cancer vaccine can further comprise one or more inhibitors of one or more immune checkpoint molecules (i.e., an immune checkpoint inhibitor). The immune checkpoint inhibitor may be any nucleic acid or protein that prevents the suppression of any component in the immune system such as MHC class presentation, T cell presentation and/or differentiation, any cytokine, chemokine or signalling for immune cell proliferation and/or differentiation.

The immune checkpoint inhibitor can be one or more nucleic acid sequences encoding an antibody, a variant thereof, a fragment thereof, or a combination thereof. In other embodiments, the immune check point inhibitor can be an antibody, a variant thereof, a fragment thereof, or a combination thereof.

The immune check point molecule can be a nucleic acid sequence, an amino acid sequence, a small molecule, or a combination thereof.

PD-1 and PD-L1

The immune checkpoint molecule may be programmed cell death protein 1 (PD-1), programmed cell death ligand 1 (PD-L1), a fragment thereof, a variant thereof, or a combination thereof. PD-1 is a cell surface protein encoded by the PDCD1 gene. PD-1 is a member of the immunoglobulin superfamily and is expressed on T cells and pro-B cells, and thus, contributes to the fate and/or differentiation of these cells. In particular, PD-1 is a type 1 membrane protein of the CD28/CTLA-4 family of T cell regulators and negatively regulates T cell receptor (TCR) signals, thereby negatively regulating immune responses. PD-1 can negatively regulated CD8+ T cell responses, and thus inhibit CD8-mediated cytotoxicity and enhance tumour growth.

PD-1 has two ligands, PD-L1 and PD-L2, which are members of the B7 family. PD-L1 is upregulated on macrophages and dendritic cells (DCs) in response to LPS and GM-CSF treatment and on T cells upon TCR receptor signalling. PD-L1 is expressed by several tumour cell lines.

Anti-Immune Checkpoint Molecule Antibody

The immune checkpoint inhibitor can be an antibody. The antibody can bind or react with the immune checkpoint molecule. Accordingly, the antibody may be considered an anti-immune checkpoint molecule antibody or an immune checkpoint molecule antibody. The antibody can be encoded by a nucleic acid sequence contained in the cancer vaccine, or can be supplied as an antibody.

The antibody can be a polyclonal or monoclonal antibody. The antibody can be a chimeric antibody, a single chain antibody, an affinity matured antibody, a human antibody, a humanised antibody, or a fully human antibody.

Cancer Vaccine Constructs

The cancer vaccine can comprise nucleic acid constructs that encode cancer antigens. The nucleic acid constructs can include or contain one or more heterologous nucleic acid sequences. The construct can be present in the cell as a functioning extrachromosomal molecule. The construct is preferably a closed linear DNA molecule.

Closed linear DNA is generally understood to be double-stranded DNA covalently closed at each end. The double stranded section of the DNA is therefore complementary. When denatured, closed linear DNA may form a single stranded circle. The DNA may be closed at each end by any suitable structure, including a cruciform, a hairpin or a hairpin loop, depending on preference. The end of the closed linear DNA may be composed of a non-complementary sequence, thus forcing the DNA into a single stranded configuration at the cruciform, hairpin or hairpin loop. Alternatively, the sequence can be complementary. It may be preferred that the end is formed by a portion of a target sequence for a protelomerase enzyme. A protelomerase target sequence is any DNA sequence whose presence in a DNA template allows for the enzymatic activity of protelomerase, which cuts a double stranded section of DNA and re-ligates them, leaving covalently closed ends. In general, a protelomerase target sequence comprises any perfect palindromic sequence i.e. any double-stranded DNA sequence having two-fold rotational symmetry, or a perfect inverted repeat. The closed linear DNA may have a portion of a protelomerase target sequence at one or both ends. This portion is effectively a single strand of the whole double stranded recognition site. The protelomerase target sequence can have the same cognate protelomerase at each end, or require a different protelomerase for each end. Closed linear DNA constructed via the action of various protelomerase enzymes have been previously disclosed in WO2010/086626, WO2012/017210 and WO2016/132129, all of which are incorporated by reference. Closed linear DNA constructed using in vitro DNA amplification followed by cleavage with a protelomerase enzyme has the advantage that the closed linear DNA is produced in an in vitro, cell-free environment, and can be scaled up for commercial production. These closed linear DNA vectors are known as Doggybone DNA or dbDNA™. It is preferred that the closed linear DNA vectors are made using the prior methods of the applicants, in an in vitro, cell-free manner based upon polymerase based amplification of a DNA template with at least one protelomerase target sequence, and processing of the amplified DNA with a protelomerase to produce closed linear DNA.

Closed linear DNA can be constructed by a conversion of a plasmid with the requisite protelomerase target sequences into a closed linear DNA vector, although this is not an efficient method of production.

Other closed linear DNA vectors have been constructed by various in vitro strategies including the capping of PCR products, and the "minimalistic immunogenic defined gene expression (MIDGE)" vectors. MIDGE is generated by the digestion of both prokaryotic and eukaryotic backbones after isolation of plasmid from bacterial cells, followed by ligation of the required DNA sequence into hairpin sequences for end-refilling.

DNA "ministrings", which are produced in an in vivo manner in cell culture, based upon the action of protelomerase, are also closed linear DNA vectors that would be suitable for use in the invention.

Other forms of closed linear DNA that may be suitable include those closed at the ends with cruciform structures, which can again be manufactured in cell culture.

It may be preferred that the closed linear DNA is manufactured in a cell-free system, since this ensures purity of product, in the alternative, stringent purification of closed linear DNA made by cellular methods will be required by the regulatory authorities.

The nucleic acid constructs can comprise regulatory elements for gene expression of the coding sequences of the nucleic acid. The regulatory elements can be a promoter, an enhancer, a stop codon, or a polyadenylation signal.

The cancer vaccine as described herein can be capable of expressing the cancer antigens in the cell of an animal in a quantity effective to elicit an immune response in the animal. The cancer vaccine can be useful for transfecting cells with nucleic acid encoding the cancer antigens, wherein expression of the above described antigens takes place. Closed linear DNA is shown to be an effective construct for DNA vaccines.

Methods of Preparing the Vaccine

Closed linear DNA molecules can be formulated or manufactured using a combination of known devices and techniques, but preferably they are manufactured using a cell-free synthetic method as described in WO2010/086626, WO2012/017210 and WO2016/132129.

Standard recombinant technologies can be used to prepare the DNA constructs.

Other Aspects

According to another aspect of the present invention, there is provided the cancer vaccine or composition according to the invention herein, for use as a medicament.

According to another aspect of the present invention, there is provided the cancer vaccine or composition according to the invention herein, for use for treating or preventing cancer in a subject.

According to another aspect of the present invention, there is provided a method of treating or preventing cancer in a subject, the method comprising the administration of the cancer vaccine or composition according to the invention herein.

The cancer to be treated or prevented may be oral and/or oropharyngeal cancer. The oral and/or oropharyngeal cancer may be HPV negative or positive oral and/or oropharyngeal cancer. In one embodiment, the cancer is oral cancer. In another embodiment, the cancer is oropharyngeal cancer. In one embodiment the cancer is a squamous cell cancer. In another embodiment, the cancer to be treated may be lung cancer or nasopharyngeal cancer.

The cancer may be characterised by cancer cells expressing or overexpressing MAGED4B and/or FJX1.

The cancer may be characterised by tumour associated cells expressing or overexpressing MAGED4B.

Expression of cancer antigens can be determined by routine methods such as interrogating biopsies or samples with relevant antibodies, and/or probing the RNA sequences present in the cell.

The cancer may additionally or alternatively be characterised by being associated with CAF overexpressing MAGED4B. Such cells may be protecting the cancer cells from the immune system and from other anti-cancer agents.

The expression of the cancer antigen on cancer and cancer associated cells may be determined in comparison with normal cells from the same tissue or organ. Expression or overexpression can therefore be a comparative level of expression relative to normal cells.

In one embodiment, the subject is tested for the presence of MAGED4B and/or FJX1 antigens in their cancerous tissue or cells prior to the treatment or prevention. In another embodiment, the subject is tested for the level of MAGED4B and/or FJX1 antigens in their cancerous tissue or cells prior to the treatment or prevention. The subject may be selected for the treatment or prevention if they have MAGED4B and/or FJX1 antigens in their cancerous tissue or cells, or have overexpression thereof relative to equivalent non-cancerous tissue or cells. The cells around the tumour may also be tested for cancer antigen expression, notably MAGED4B expression.

The skilled person will be familiar with vaccine administration routes and doses. For example the administration may be sub-cutaneous, intra-muscular, or intravenous. A typical dose may be about 4-8 mg per patient/subject administered one or more times. For example the dose may be administered multiple times until the therapeutic effect is observed. In one embodiment, in vivo electroporation is used to enhance delivery into cells, either in vivo or ex vivo.

The subject may be mammalian. In one embodiment, the subject is human. In another embodiment, the subject may be a domestic or livestock animal.

According to another aspect of the invention, there is provided a polypeptide comprising a MAGED4B protein or variant or truncated version thereof. The polypeptide may be presented as a fusion with a helper motif. The polypeptide may be presented as a fusion with DOM. Exemplary polypeptide sequences are described here as SEQ ID No. 32, 35, 36 and 37. The MAGED4B sequence may be fused with FJX1 as encoded by SEQ ID No. 12 (with DOM in this instance).

Cancer Vaccine Compositions

The vaccine can be in the form of a composition, optionally pharmaceutical composition. The pharmaceutical compositions can comprise about 5 nanograms to about 10 mg of the vaccine. In some embodiments, pharmaceutical compositions according to the present invention comprise about 25 nanogram to about 5 mg of DNA of the vaccine. In some embodiments, the pharmaceutical compositions contain about 50 nanograms to about 1 mg of DNA of the vaccine.

The composition can further comprise other additives for formulation purposes, which may vary according to the mode of administration. In cases where compositions are injectable, they are sterile, pyrogen free and particulate free. Suitable formulations may include sodium chloride, dextrose, mannitol, sorbitol and lactose. In some cases, isotonic solutions such as phosphate buffered saline are preferred. Stabilisers may include gelatine and albumin.

The vaccine can further comprise an acceptable excipient. The acceptable excipient can be functional molecules as vehicles, adjuvants, carriers, or diluents.

Vaccination

The cancer vaccines disclosed herein are provided for use in methods for treating or prevent cancer. The vaccines described herein can be for use in a method of administration or vaccination, to induce a therapeutic and/or prophylactic immune response. The vaccination process can generate in the animal an immune response against one or more of the cancer antigens. The administration of the vaccine can be the transfection of the one or more cancer antigens as a nucleic acid molecule that is expressed in the cell and thus, delivered to the surface of the cell upon which the immune system recognises and induces an immune response.

The vaccine can be administered to an animal, preferably a mammal in order to elicit an immune response. The mammal can be human, non-human primate (particularly chimpanzee and monkey), cow, pig, sheep, goat, deer, llama, alpaca, dog, cat, guinea pigs, rabbits, mice, rats, and preferably human, dog or cat.

The vaccine dose can be between 1 μg to 10 mg active component/kg body weight/time and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, 10, or more doses.

The vaccine may be administered using a "prime boost" strategy. A prime-boost immunisation strategy can be defined as a regimen of immunisation with the same vaccine during the prime and booster doses. There may be one or more booster doses. The treatment strategy used in the Examples in some instances used a prime boost strategy.

The cancer vaccine can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. The vaccine can be administered by traditional syringes, needleless injection devices, "microprojectile bombardment gone guns", or other physical methods such as tattooing, electroporation ("EP"), "hydrodynamic method", or ultrasound.

The cancer vaccine is a nucleic acid. It may be delivered using any appropriate nucleic acid delivery method used to transfect cells. Naked nucleic acid may be used, particularly where the nucleic acid is in a minimal form (such as a minicircle or a closed linear DNA). However, the nucleic acid may also be "packaged" for administration, for example using different materials. These materials include lipids, linear and branched polymers, and peptides/proteins with either natural or synthetic sources. The complexing products of lipids/nucleic acids lead to lipoplexes with representative lamellar or hexagonal structures. The polymers and nucleic acids may complex into polyplexes with polymer chains tangling together without any ordered internal structure. Peptides/proteins interact with nucleic acids to form either disordered polyplexes or ordered artificial viruses with filamentous or spherical morphologies, depending on the primary structure of the peptide/protein. Alternatively, the nucleic acid may be packaged in a viral coat, such as a in a virus like particle (VLP) or indeed packaged into any suitable viral vector such as a lentivirus, a retrovirus, and adeno-associated virus (AAV) adenovirus, Modified vaccinia Ankara (MVA) or oncolytic Maraba MG1 rhadovirus.

The cancer vaccine may be used on cells ex vivo. Thus, suitable cells can be obtained, which are either autologous or allogenic, transfected in vitro, and then these cells can be supplied to a patient in need thereof. Suitable cells for ex vivo transfection include any type of antigen presenting cells including natural killer cells or dendritic cells, autologous or allogeneic tumour cells (usually irradiated). Autologous cells may be transiently transfected with the cancer vaccine in an mRNA or DNA format. The cancer antigen may be codon optimised and contain a helper motif resulting in both MHC-1 and MHC-II presentation of cancer antigen peptides to both CD8+ and CD4+ T cells in the patients. As a result, a strong, tumour-specific immune response after reintroduction into the patient may be achieved.

Thus the present application extends to the use of the cancer vaccine to transfect cells in vitro or ex vivo, prior to the use of those cells for the treatment or prevention of cancer in a patient. Such cells may no longer include the cancer vaccine when administered, since the transfection can be transient.

The data shows that the combination of the cancer vaccine and an immune checkpoint inhibitor induces the immune system more efficiently than a vaccine comprising the cancer antigen alone, and in fact these two work synergistically. This more efficient immune response provides increased efficacy in the treatment of cancer.

Definitions

A Checkpoint inhibitor therapy is a form of cancer immunotherapy. A checkpoint inhibitor targets immune checkpoints, key regulators of the immune system that stimulate or inhibit its actions, which tumours can use to protect themselves from attacks by the immune system. Checkpoint therapy can block inhibitory checkpoints, restoring immune system function.

The term "immunogenic", when applied to the protein or composition of the present invention means capable of eliciting an immune response in a human or animal body. The immune response may be protective.

The term "protective" means prevention of a cancer, a reduced risk of cancer infection, transmission and/or progression, reduced severity of cancer, a cure of a cancer, an alleviation of symptoms, or a reduction in severity of a cancer or cancer symptoms.

The term "treatment", means a cure of cancer, an alleviation of symptoms, or a reduction in severity of a cancer or cancer symptoms.

The term "prevention" in the context of oral cancer means the prevention of transformation from oral dysplasia to oral cancer.

By "antibody" we include substantially intact antibody molecules, as well as chimeric antibodies, human antibodies, humanised antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same. In particular, the term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes (e.g., IgG, IgE, IgM, IgD and IgA) and their isotypic subclasses; fragments which comprise an antigen binding domain such as Fab, scFv, Fv, dAb, Fd; and diabodies. Antibodies may be polyclonal or monoclonal. A monoclonal antibody may be referred to as a "mAb".

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, incorporated herein by reference. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023, incorporated herein by reference. A humanised antibody may be a modified antibody having the variable regions of a non-human, e.g., murine, antibody and the constant region of a human antibody. Methods for making humanised antibodies are described in, for example, U.S. Pat. No. 5,225,539, incorporated herein by reference.

The antibodies of the present disclosure may be intact or engineered For example, the antibody may be fully or partially glycosylated and/or selected for increased or diminished binding to human effector systems such as complement, FcR-bearing effectors, such as macrophages, or to extend or reduce half-life. These modifications can be made to improve effectiveness and potentially also reduce toxic side effects.

It has been shown that fragments of a whole antibody can perform the function of binding antigens. Examples of binding molecules for use in the invention are (i) the Fab fragment consisting of VL, VH, CL and CHI domains; (ii) the Fd fragment consisting of the VH and CHI domains; (iii) the Fv fragment consisting of the VL and VH domains of a single antibody; (iv) the dAb fragment which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen binding site; (viii) bispecific single chain Fv dimers (PCT/US92/09965, incorporated herein by reference) and; (ix) "diabodies", multivalent or multispecific fragments constructed by gene fusion (WO94/13804, incorporated herein by reference).

The determination of percent identity between two sequences can be accomplished using a mathematical algorithm known to those of skill in the art. An example of a mathematical algorithm for comparing two sequences is the algorithm of Karlin and Altschul (Proc Natl Acad Sci USA. 1990 March; 87(6):2264-8), modified as in Karlin and Altschul (Proc Natl Acad Sci USA. 1993 Jun. 15; 90(12): 5873-7). The NBLAST and XBLAST programs of Altschul et al. have incorporated such an algorithm, and may be used under standard parameters.

The skilled person will understand that optional features of one embodiment or aspect of the invention may be applicable, where appropriate, to other embodiments or aspects of the invention.

References to any publications herein shall be taken as incorporation by reference for the purposed of US patent prosecution only.

BRIEF DESCRIPTION OF THE DRAWINGS

Embodiments of the invention will now be described in more detail, by way of example only, with reference to the accompanying drawings.

FIG. 2. Both MAGED4B and FJX1 antigens are strongly expressed in HPV negative squamous cell carcinoma (SCC), non-malignant oral dysplasia and nasopharyngeal carcinoma (NPC). MAGED4B (Novus-Bio:NBP1-89594) was stained at 1:200 dilution. FJX1 (Novus-Bio:NBP1-59470) was stained at 1:100 dilution. Staining was performed on a DAKO autostainer. Testis serves as a positive control with strong expression. Oral fibroepithelial polyp (FEP) serves as negative control, indicating low levels of expression in non-dysplastic oral tissue. This data confirms that the target cancer antigens are expressed as proteins.

FIG. 4 (A and B). CD8 T cell specific for both target antigens MAGED4B and FJX1. FIG. 4A. D4B specific CD8 T cells were detected in tumour infiltrating lymphocytes (TILs; expanded with 60001 U/ml recombinant human IL-2) in HLA-A2+ HNSCC patient HN337 using D4B$^{501-509}$/HLA-A2 tetramer staining and flow cytometry. $10^6$ expanded TILs were strained with anti-CD3 (FITC:OKT3), CD4 (APC:OKT4), CD8 (APC-Cy7) (BioLegend), DAPI (live/dead stain) (Miltenyi) and MAGED4B$^{501-509}$ tetramer (PE). Flow cytometry performed on a FACSCanto, using UltraComp eBeads (Invitrogen) for compensation. Analysis was performed using FlowJo. The gating was on live/dead lymphocytes, then CD8 plus tetramer. Tetramer positive CD8 cells are indicated in the gates. FIG. 4B. IFNγ CD8 T cells in expanded TILs from HLA-A2 negative, HLA-A1 positive HN337 tumour sample. Expanded with anti-CD3 (clone OKT3) TILs were stimulated with control (peptide pool MAGED4B HLA-A2 peptides), MAGED4B peptide pool consisting of 15mer peptides with 11aa overlap for the entire sequence of the antigen (183 peptides pooled), FJX1 peptide pool (predicted by NetMHC 4.0, iedb.org) to bind HLA-A1 only (3 of 15 mer peptides derived from the FJX1 aa sequence: ARFADGTRACVRYGI; DLVQWTDLILFDYLT; WTDLILFDYLTANFD epitopes are in bold) for 8 h and intracellular IFNγ staining was performed followed by flow cytometry. The antibody panel for flow was anti-CD3 (FITC:OKT3), CD8 (PerCp-Cy5.5: RPA-T8), anti-CD56 (PE: HCD56), IFNγ (APC 4S.B3) (all from BioLegend) and Zombi Aqua (live/dead stain) (Miltenyi) was applied after blocking Fc receptors using HuMan TrueStain (Biolegend). Gates show specific populations of IFNγ CD8 positive T cells after restimulation with the reagent indicated at the top of the plot. The data in these figures again demonstrates that in patients with confirmed HNSCC that there exists a pool of T cells that are available for expansion by vaccination and these cells can be also found in the tumour. Further, this is encouraging data which suggests that the presence of such T cells alone is not causing any pathology in these individuals, although they are not fully functional otherwise the individuals would be controlling their tumour using such cells.

FIG. 5A shows Tetramer+ 0.0%; FIG. 5B shows M-Tetramer+ 1.8% and FIG. 5C shows F-Tetramer+ 0.2%. Expanded TILs were stained with anti-CD3 (FITC; SK7), CD4 (PerCP-Cy5.5; SK3), CD8 (BV510; RPA-T8) (BD Biosciences), FVS780 (viability stain) (BD Biosciences) and MAGED4B$^{501-509}$ tetramer (PE). Flow cytometry performed on a BD LSRFortessa, using BD CompBead for compensation. Analysis was performed using FACS DIVA software. The gating was on live/dead lymphocytes, then CD8 plus tetramer. Tetramer positive CD8 cells are indicated in the gates. This data demonstrates that antigen-specific T cells have been identified in the tumours. This further suggests that there is a pool of cells available for expansion in addition to de novo activation and expansion from the vaccine.

FIG. 9A depicts the treatment strategy. Individual group of mice (6-10) were challenged with the B16 tumour expressing both MAGED4B and FJX1 and then were treated combined DNA vaccines (DV; p.Dom-MAGED4B and p.Dom FJX1; 100 μg/mouse in 100 μl of saline injected intra-muscularly 50 μg into each leg) anti-PD-1 antibody (200 μg per injection given i.p. in 0.5 mL) or combination of DV and anti-PD1 as indicated in the diagram. The control group was given control IgG+pDOM (vector backbone). Tumour size was measured every 2-3 days and the tumours sizes for each group are depicted in FIG. 9B (mean+s.e.m) FIG. 9C. ELISpot assay demonstrated the MAGED4B specific immune responses in a specific fashion in DV and DV+a-PD1 groups but not in a-PD1 or control groups: splenocytes isolated from vaccinated animals are able to secrete IFN-γ upon re-stimulation with MAGED4B peptide library overlapping the entire antigen sequence (183 peptides 15mer 11 aa overlap pooled together). FIG. 9D as in FIG. 9C but FJX1 peptide library overlapping the entire antigen was used. This data shows clear impact on tumour progression of the monotherapy (vaccine alone) and the synergistic effect of the combination therapy (vaccine plus anti-PD1). In particular, FIGS. 9C and 9D show that vaccination expands antigen-specific T cells in tumour bearing mice—these mice have been exposed to the antigens on the tumour but have failed to mount a good immune response. This supports the assertion that the vaccine can improve the immune response and effectively "expose" the tumour to the immune system.

FIG. 10A depicts the treatment strategy tumour volume reduction and mechanisms of actions. Individual group of mice (8-12) were challenged with the tumour expressing both MAGED4B and FJX1 and then were treated with DNA vaccines (DV; p.Dom-MAGED4B and p.Dom-FJX1; 100 μg/mouse in 100 μl of saline injected intra-muscularly 50 μg into each leg) as indicated in the diagram. The control group was given pDOM vector backbone. Tumour size was measured every 2-3 days and the tumours sizes for each group are depicted in FIG. 10A (mean+s.e.m). FIG. 10(B) is cell photographs. The staining of the tumour in the right hand panel demonstrates T cell infiltration following vaccination with DNA vaccines, the left hand panel shows poorly infiltrated pDOM control tumours (Hematoxylin & eosin stain, original magnification: ×10 objective). FIG. 10C depicts the results of flow cytometry analysis, demonstrating increase in CD4+ and CD8+ immune cells in the tumour harvested from the vaccinated animals compared to control animals. Significantly, checkpoint protein PD1 is found to be markedly elevated in both CD4+ and CD8+ immune cells harvested from vaccinated animals. This study has used a higher dose of tumour cells to accelerate the progression of the cancer, and thus is a particularly aggressive tumour model. This again shows that vaccination expands the T cells in tumour bearing mice, in which the mice have failed to raise a good immune response to the tumours despite being exposed to them. This supports the assertion that the vaccine can improve the immune response and effectively "expose" the tumour to the immune system.

FIG. 11A shows the data for with and without DOM. The Dom sequence is shown to be critical for induction of T cells and therefore improved the response for MAGED4B. FIG. 11B shows the data for with and without a leader sequence. A leader sequence that directs the expression of the encoded construct to endoplasmic reticulum for secretion is also essential for induction of T cell immunity. Individual peptides were generated by JPT, Germany, to 90% purity. For ELISpot IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassberg, Germany). This data shows that generally FJX1 responses are improved by the inclusion of a leader sequence.

FIG. 13. Assembly of alternative MAGED4-B and FJX1 targeting DNA vaccines to target cancer. Diagram of vaccine constructs of pDOM (control), pMAGED4B/FJX1, pMAGED4B/FJX1-MITD, pPVXCP-MAGED4B/FJX1 and pMIP3α-MAGED4B/FJX1. Alternative gene fusion partners includes MITD, PVXCP, and MIP3α. MITD (165 bp) encodes MHC I (HLA-A2) trafficking signals. PVXCP (732 bp) encodes potato virus X coat protein. MIP3α (252 bp) encodes macrophage inflammatory protein 3 alpha. MITD, PVXCP and MIP3α gene were optimised with human codon usage and ordered from GeneArt (Invitrogen). The genes (with or without fusion partner) were inserted between CMV/T7 dual promoter and BGH Poly (A) site. The leader sequence encoding mouse IgH signal peptide (MGWSCIIFFLVATATGVHS) was inserted at the N terminus of the construct to enhance the efficacy of secretion.

Fusion partners and the gene of interest (MAGED4B or FJX1) were linked using a seven amino acid linker 1 (AAAGPGP). With the exemption of MITD, all other fusion partners were fused at the upstream of gene of interest. MITD were added at the downstream of gene of interest. The genes for MAGED4-B, FJX1 or their fusions of interest were inserted into pcDNA3 vector at NotI, XhoI and XbaI restriction enzyme sites to generate the DNA vaccines.

Figures 14, 15:
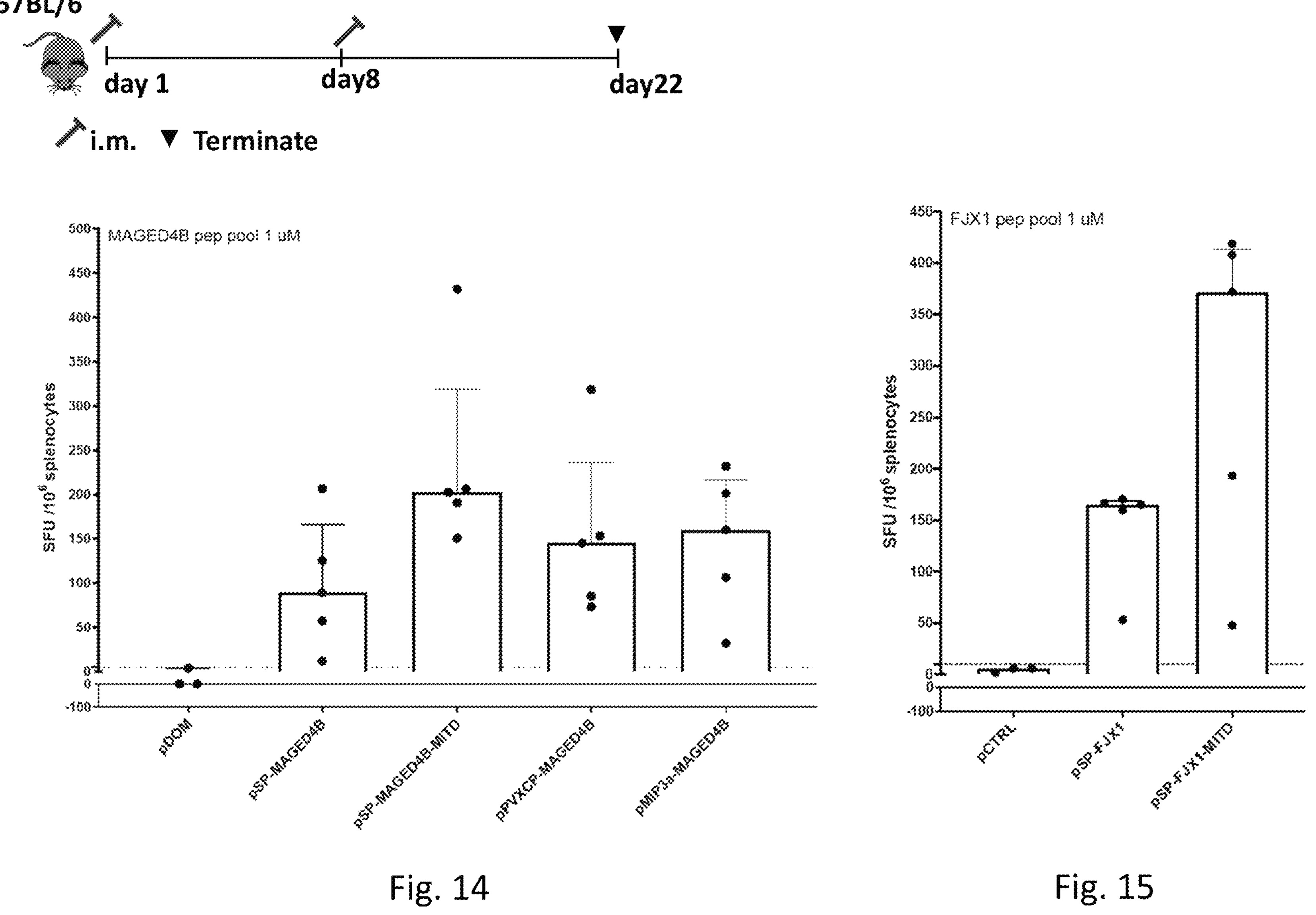

FIG. 14 MAGED4B specific T cell responses were induced by DNA vaccines on C57BL/6 mice. The treatment strategy is depicted. Non-tumour bearing C57BL/6 mice were vaccinated 50 μg pDOM vaccine (as a negative control, 3 mice), 50 μg pSP-MAGED4B (5 mice), 50 μg pSP-MAGED4B-MITD (5 mice), 50 μg pPVXCP-MAGED4B (5 mice), and 50 μg pMIP3a-MAGED4B (5 mice) on day 1 and day 8. Lymphocytes isolated from mouse spleens were plated to ELISpot plates on day 22 and overlapping peptides pool for MAGED4B was used to detect responding specific T cells. The overlapping peptide pools (OPP) consisted of 15 mer peptides with 11aa overlap for the entire sequence (183 individual peptides were pooled for MAGED4B). IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassburg, Germany). The graph shows the responses to MAGED4B OPP in each group respectively. The values were the responses minus the number of spots without stimulus. Cut off set as 2x background (Irr OPPs, shown as red-dotted line). P values were calculated by Mann-Whitney test. (Irr=irrelevant). This data shows that MAGED4B responses can be generated from full length protein, and that the response can be improved by the fusion with various helper motifs.

FIG. 15 FJX1 specific T cell responses were induced by DNA vaccines on C57BL/6 mice. Non-tumour bearing C57BL/6 mice were vaccinated 50 μg pDOM vaccine (as a negative control, 3 mice), 50 μg pSP-FJX1 (5 mice), and 50 μg pSP-FJX1-MITD (5 mice). The vaccinated were administered i.m. (intra-muscularly) on day 1. Lymphocytes isolated from mouse spleens were plated to ELISpot plates on day 14 and overlapping peptides pool for FJX1 was used to detect responding specific T cells. The overlapping peptide pools consisted of 15 mer peptides with 11aa overlap for the entire sequence (107 individual peptides were pooled for FJX1). IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassburg, Germany). The graph shows the responses to FJX1 OPP in each group respectively. pSP-FJX1-MITD induced the strongest response among all the groups. Median+Interquatile and responses in individual mice are shown. The results were normalised by subtracting the number of spots without stimulus. Cut off set as 2x background (Irr OPPs, shown as red-dotted line). P values were calculated by Mann-Whitney test. Only one experiment was represented, since lab shutdown over the pandemic restricted repeating these experiments.

Figure 16:
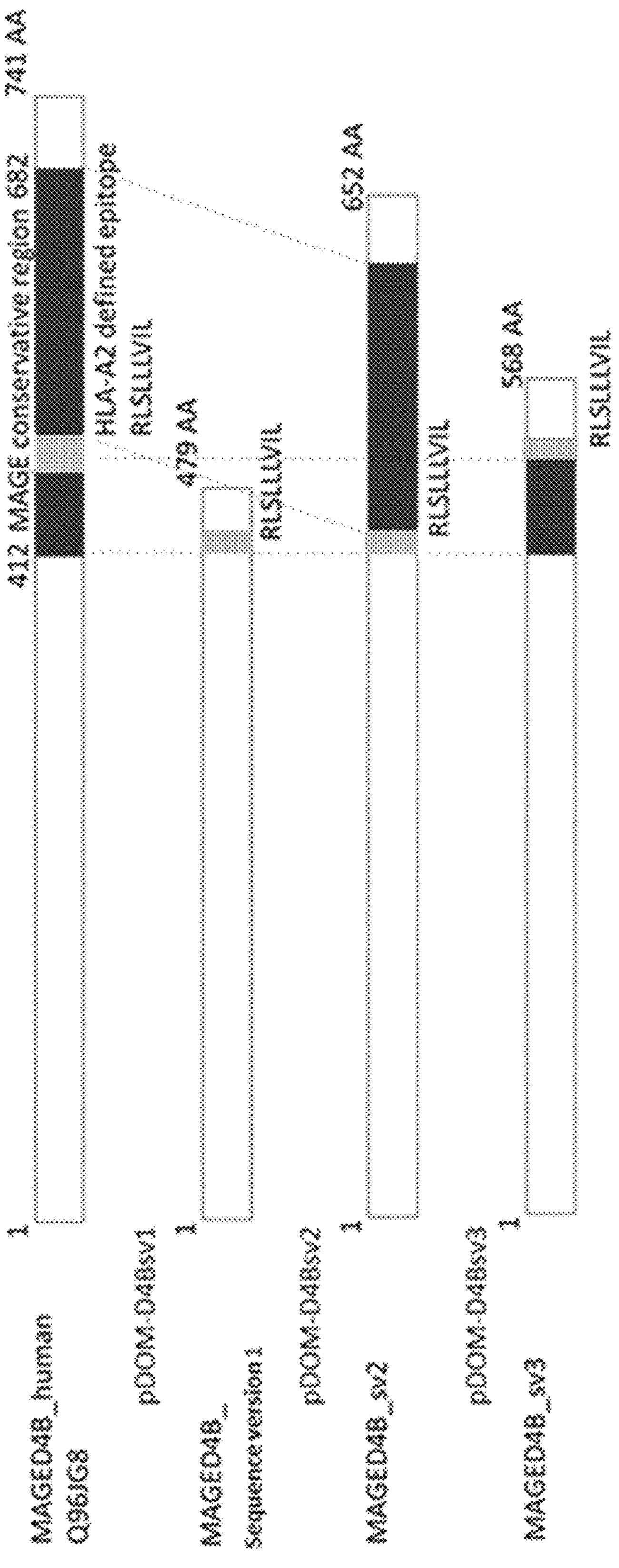

FIG. 16. Amino acid sequence maps of the whole MAGED4B amino acids sequence and three truncated fragments. As a member of melanoma-associated antigen family, MAGED4B contains a MAGE common homology domain MAGED4B 412-682(SEQ ID No. 3). The defined HLA-A2 epitope RLSLLLVIL (MAGED4B501-509) sits inside the homology domain. Three truncated MAGED4B sequences were designed as following: 1) MAGED4B sequence version (v) 1 doesn't contains homology domain but contains RLSLLLVIL; 2) MAGED4B.sv2 retains second half of homology domain (MAGED4B 510-682) including RLSLLLVIL; 3) MAGED4B.sv3 retains first half of homology domain (MAGED4B 412-500) including RLSLLLVIL. These are all, therefore, immunogenic fragments of MAGED4B suitable for use in the vaccine described here.

Figure 17:
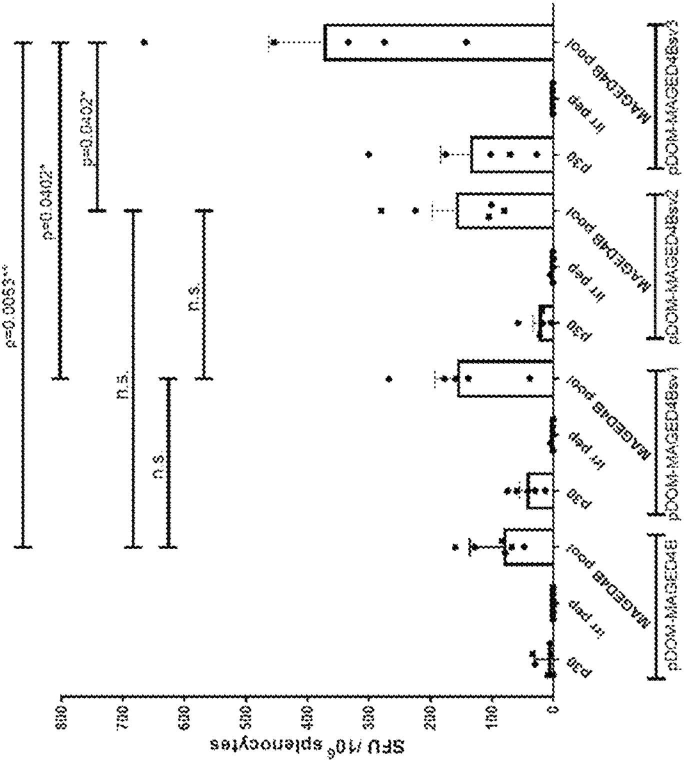
Figure 17:
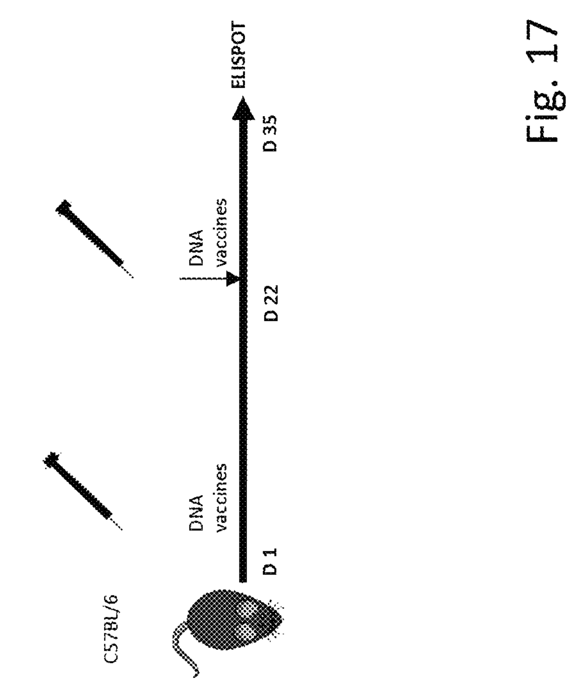

FIG. 17. Fragments of MAGED4B as detailed in FIG. 16 are shown to be immunogenic. The treatment strategy is shown: four groups of 5 non-tumour bearing C57BL/6 mice were vaccinated with 50 μg of p.Dom-MAGED4B (full length), p.Dom-MAGED4Bsv1, p.Dom-MAGED4Bsv2, p.Dom-MAGED4Bsv3 individually on day 1 following by a booster injection of the same DNA vaccine on d 22. Their immunogenicity was evaluated by IFNγ ELISpot. Lymphocytes isolated from mouse spleens were plated to ELISpot plates on d 35 and overlapping peptides pool for MAGED4B was used to detect responding specific T cells. The overlapping peptide pools consisted of 15 mer peptides with 11aa overlap for the entire sequence (183 individual peptides were pooled for MAGED4B). P30 peptide an MHCII peptide from tetanus DOM was used as a control for vaccination. p.Dom-MAGED4Bsv3 induced significantly stronger specific T cell response than p.Dom-MAGED4B (full length), p.Dom-MAGED4Bsv1, and p.Dom-MAGED4Bsv2. Neither p.Dom-MAGED4Bsv1 or p.Dom-MAGED4Bsv2 performed better than p.Dom-MAGED4B. P values were calculated with one-way ANOVA analysis by Graphpad prism 8.0. For ELISpot IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassburg, Germany). Thus, the MAGE homology domain can be removed in whole or in part without affecting the activity of the vaccine.

Figure 18:
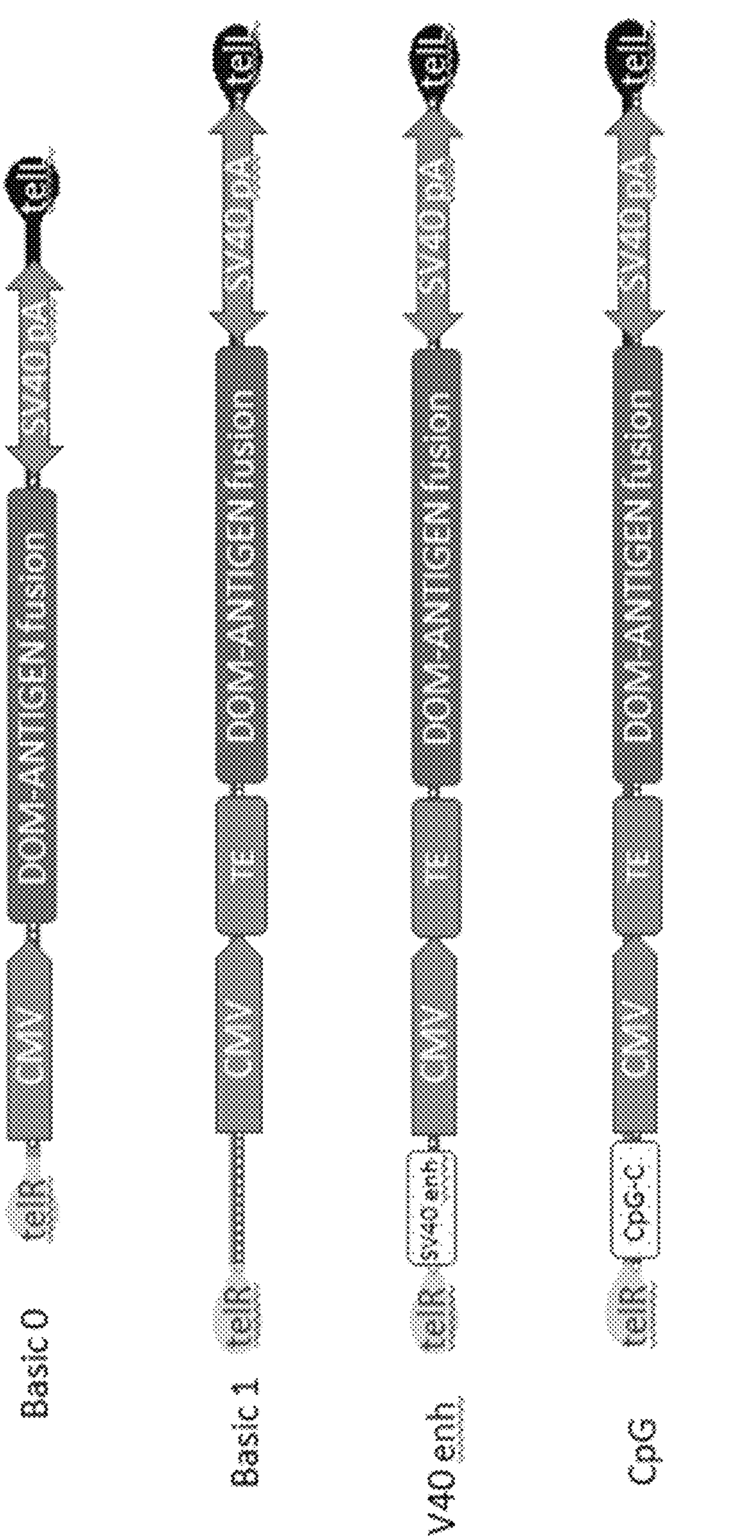

FIG. 18. Vector maps of the closed linear DNA (dbDNA™) used in vaccination experiments. Shown are the sequences at the closed ends of the dbDNA (TelR or TelL from the protelomerase target sequence TelRL)—these are portions of the target sequence that together make a whole sequence. Four construct architectures are shown: Basic 0 (minimal construct architecture—CMV promoter, Dom and antigen fusion, SV40 poly A signal sequence) upon which all other constructs are based. Added to other constructs are: Basic 1 (plus TE—Triple enhancer); SV40 enh (plus TE and SV40 enhancer sequence); CpG (plus TE and a section of sequence with CpG motifs). These are used in the experimental vaccination work described herein.

Figure 19:
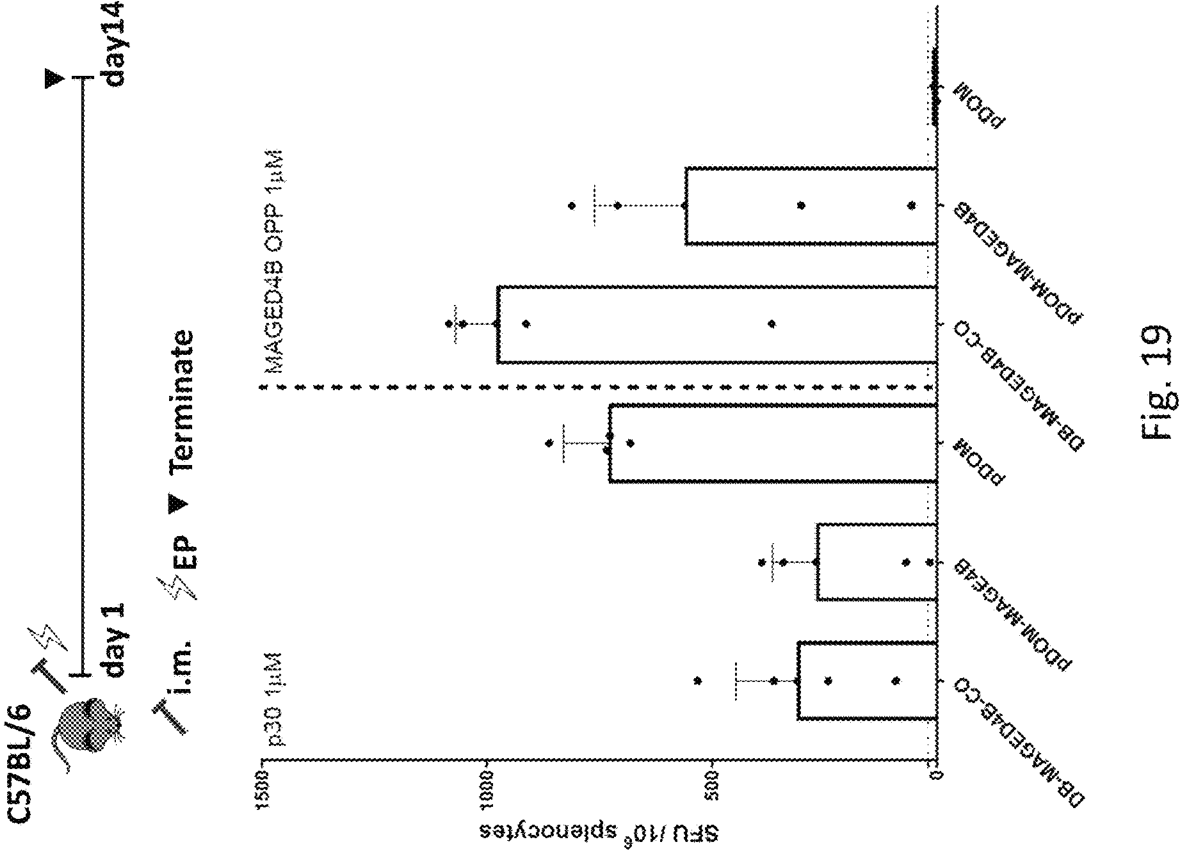

FIG. 19. MAGED4B specific T cell responses were induced by doggy bone (DB) and plasmid DNA vaccines in C57BL/6 mice. Non-tumour bearing C57BL/6 mice were vaccinated 50 μg pDOM plasmid vaccine (as a negative control, 3 mice), 25 μg DB-MAGED4B-CO (5 mice), and 25 μg pDOM-MAGED4B plasmid (5 mice). The vaccinated were administered i.m. with EP at day 1. Electroporation (EP) was carried out on mice anaesthetised by isofluorane, using intramuscular TriGrid Delivery System (TDS-IM) from Ichor EP device. Lymphocytes isolated from mouse spleens were plated to ELISpot plates on day 14 and overlapping peptides pool for MAGED4B was used to detect responding specific T cells. The overlapping peptide pools consisted of 15 mer peptides with 11aa overlap for the entire sequence (183 individual peptides were pooled for MAGED4B, 107 individual peptides were pooled for FJX1). P30 peptide an MHCII peptide from tetanus DOM was used as a control to valid vaccination. FJX1 OPP served as Irr peptide control in this experiment. IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassburg, Germany). The graph shows the responses to p30 peptide and MAGED4B OPP in each group respectively. Median+Interquatile and responses in individual mice are shown. The values were the responses minus the number of spots without stimulus. Cut off set as 2x background (Irr OPPs, shown as red-dotted line). P values were calculated by Mann-Whitney test.

Figures 20A, 20B:
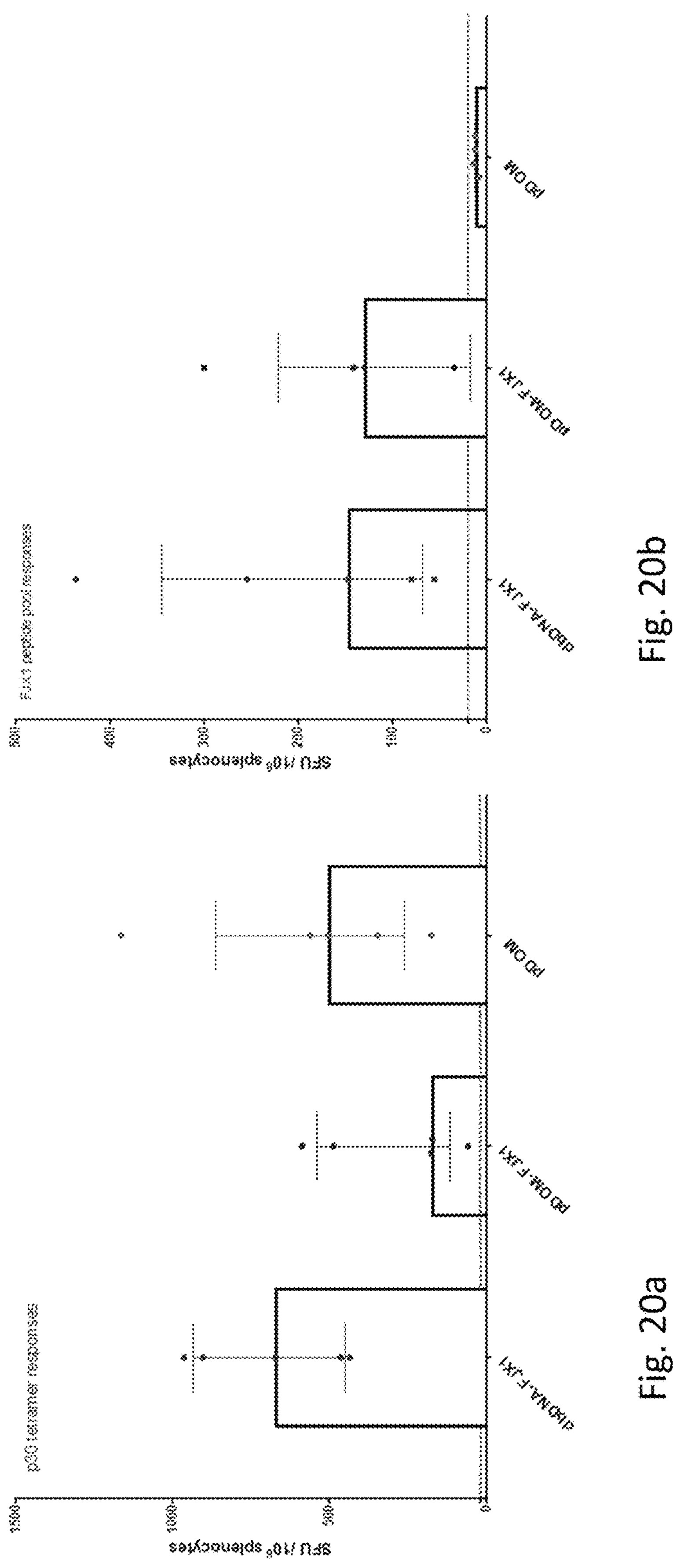

FIG. 20. FJX1 specific T cell responses were induced by doggy bone (DB) and plasmid DNA vaccines. Non-tumour bearing C57BL/6 mice were vaccinated 50 μg pDOM plasmid vaccine (as a negative control, 3 mice), 25 μg DB-DOM-FJX1 CO (5 mice), and 25 μg pDom-FJX1 plasmid (5 mice). The vaccines were administered i.m. with EP on day 1. EP was carried out on mice anaesthetised by isofluorane, using intramuscular TriGrid Delivery System (TDS-IM Ichor Medical System). Lymphocytes isolated from mouse spleens were plated to ELISpot plates on day 14 and overlapping peptides pool for FJX1 was used to detect responding specific T cells. The overlapping peptide pools (OPP) consisted of 15 mer peptides with 11aa overlap for the entire sequence (183 individual peptides were pooled for MAGED4B, 107 individual peptides were pooled for FJX1). P30 peptide an MHCII peptide from tetanus DOM was used as a control to valid vaccination. MAGED4B OPP served as Irr peptide control in this experiment. IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassburg, Germany). The graph shows the responses to p30 peptide (FIG. 20*a*) and FJX1OPP (FIG. 20*b*) in each group respectively. Median+Interquatile and responses in individual mice are shown. The values were the responses minus the number of spots without stimulus. Cut off set as 2x background (Irr OPPs, shown as red-dotted line). P values were calculated by Mann-Whitney test.

Figure 21:
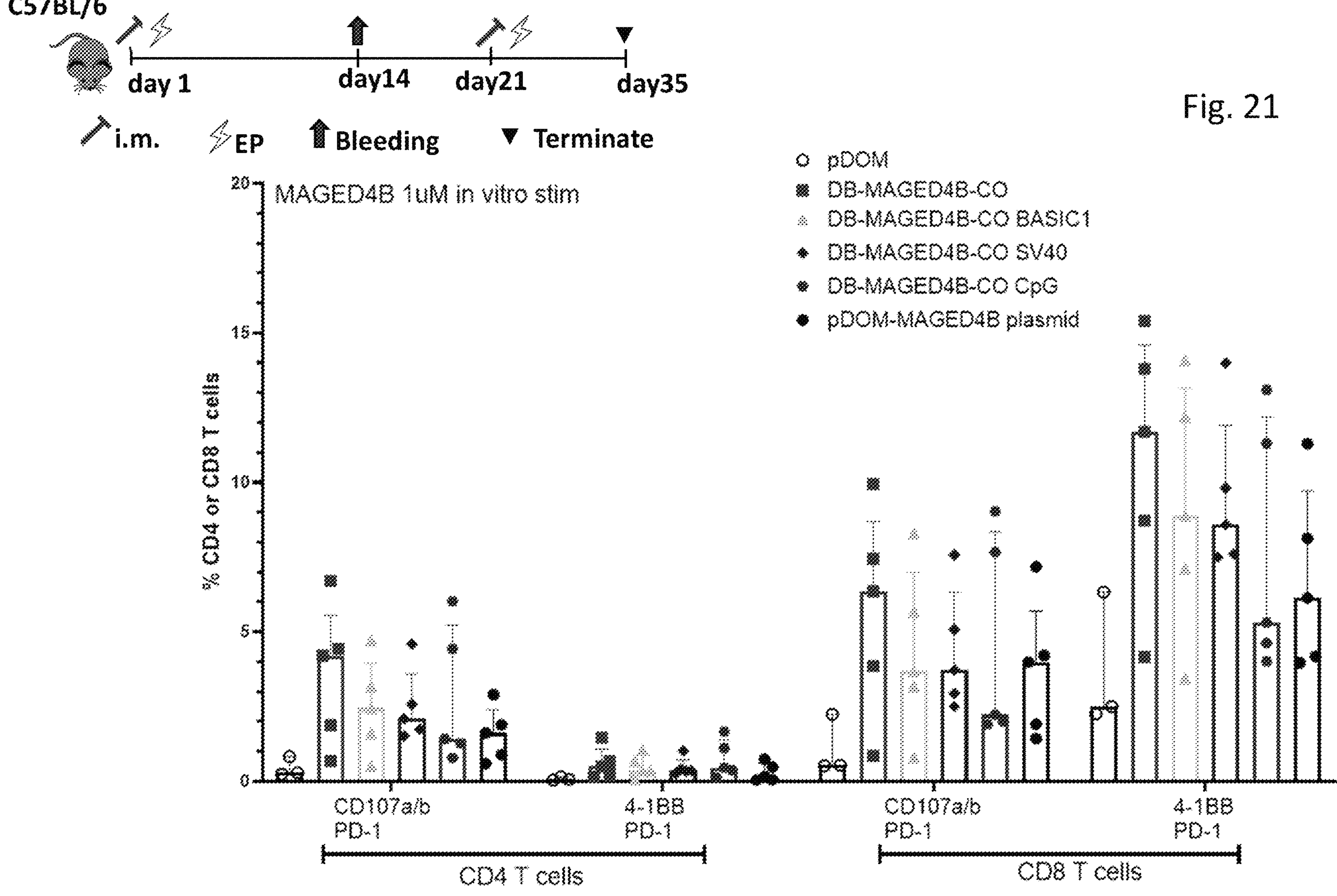

FIG. 21. dbDNA DOM-MAGED4B and pDOM-MAGED4B DNA vaccines induce specific CD4 and CD8 T cell responses. The treatment strategy is depicted. Non-tumour bearing C57BL/6 mice were vaccinated with 50 μg pDOM plasmid vaccine (as a negative control, 3 mice), 10 μg DB-MAGED4B-CO (5 mice), 10 μg DB-MAGED4B-CO basic 1 (5 mice), 10 μg DB-MAGED4B-CO SV40 (5 mice), 10 μg DB-MAGED4B-CO CpG (5 mice), and 10 μg pDOM-MAGED4B plasmid (5 mice). The vaccines were administered i.m. with EP at day 1 and day 21. EP was carried out on mice anaesthetised by isofluorane, using intramuscular TriGrid Delivery System (TDS-IM; Ichor Medical System). FACS was performed following in vitro stimulation 50 μl blood samples taken on day 12, bleeds were treated using red blood lysis buffer (RBC lysis buffer, Biolegend) first. White blood cells were stimulated with 1 μM MAGED4B overlapping peptide pool (OPP; in 96-well plate, added 1 μl of anti-CD107a-FITC and anti-CD107b-FITC (both from Biolegend) and incubated at 37° C. 5% CO2 overnight. The following day the cells were wash and stained with anti-CD3-PE, anti-CD4-PEcy7, anti-CD8-APCcy7, anti-CD137 (4-1BB)-APC, anti-PD1-PerCPcy5 (all from Biolegend), and live/dead-violet (Invitrogen). The OPP consisted of 15 mer peptides with 11aa overlap for the entire sequence (183 individual peptides were pooled for MAGED4B). Flow cytometry was performed on a FACSCanto II. Analysis was performed using FlowJo software. The responses were evaluated using FACS. CD107a/b+PD-1+ double positive T cells and 4-1BB+PD-1+ double positive T cells indicate cytotoxic and activated population specific to MAGED4B OPP respectively. The responses to MAGED4B OPP from groups vaccinated with pDOM, DB-MAGED4B-CO, DB-MAGED4B-CO basic 1, DB-MAGED4B-CO SV40, DB-MAGED4B-CO CpG and pDOM-MAGED4B plasmid respectively were summarised in this column graph. Median+Interquatile and individual mice responses are shown. P values were calculated by Kruskal-Wallis test. This data shows that the MAGED4B antigen can be delivered in different architectures and still induce antigen-experiences CD4 and CD8 T cells. CO is a codon optimised sequence.

Figure 22:
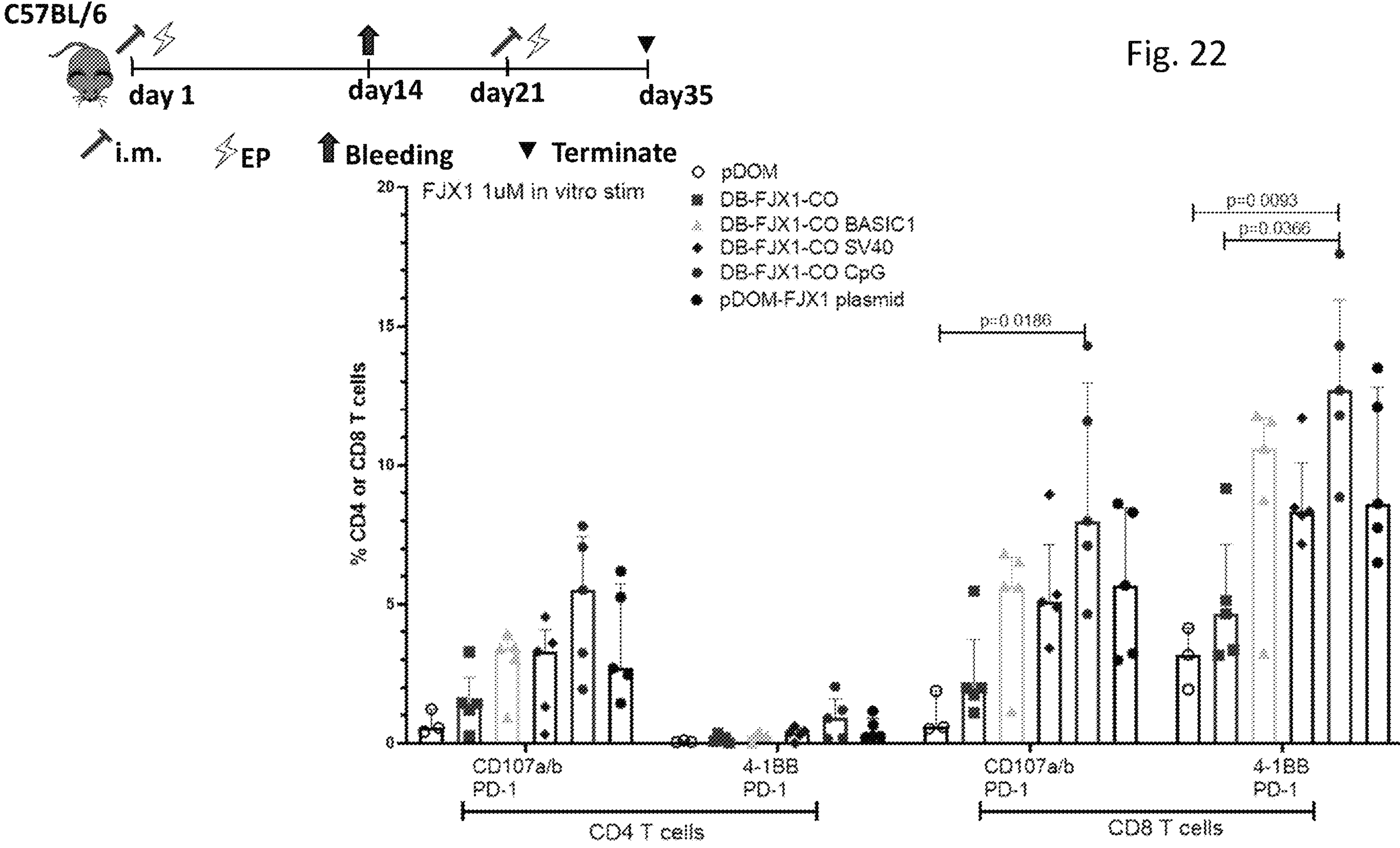

FIG. 22. Doggybone DOM-FJX1 and pDOM-FJX1 DNA vaccine induces specific CD4 and CD8 T cell responses. The treatment strategy is depicted. Non-tumour bearing C57BL/6 mice were vaccinated with 50 μg pDOM plasmid vaccine (as a negative control, 3 mice), 10 μg DB-FJX1-CO (5 mice), 10 μg DB-FJX1-CO basic 1 (5 mice), 10 μg DB-FJX1-CO SV40 (5 mice), 10 μg DB-FJX1-CO CpG (5 mice), and 10 μg pDOM-FJX1 plasmid (5 mice). The vaccines were administered i.m. with EP at day 1 and day 21. EP was carried out on mice anaesthetised by isofluorane, using intramuscular TriGrid Delivery System (TDS-IM; Ichor Medical System). FACS was performed following In vitro stimulation 50 μl bleed blood samples taken on day 12, (50 μl bleeds were used which were treated using red blood lysis buffer (RBC lysis buffer, Biolegend) first. White blood cells were stimulated with 1 μM FJX1 overlapping peptide pool (OPP; in 96-well plate, whilst added 1 μl of anti-CD107a-FITC and anti-CD107b-FITC (both from Biolegend) and incubated at 37° C. 5% CO2 overnight. The following day the cells were wash and stained with anti-CD3-PE, anti-CD4-PEcy7, anti-CD8-APCcy7, anti-CD137 (4-1BB)-APC, anti-PD1-PerCPcy5 (all from Biolegend), and live/dead-violet (Invitrogen). The overlapping peptide pools consisted of 15 mer peptides with 11aa overlap for the entire sequence (107 individual peptides were pooled for FJX1). Flow cytometry was performed on a FACSCanto II. Analysis was performed using FlowJo software. The responses were evaluated using FACS. CD107a/b+PD-1+ double positive T cells and 4-1BB+PD-1+ double positive T cells indicate cytotoxic and activated population specific FJX 1 OPP respectively. T cell responses to FJX1 OPP from groups vaccinated with pDOM, DB-FJX1-CO, DB-FJX1-CO basic 1, DB-FJX1-CO SV40, DB-FJX1-CO CpG, and pDOM-FJX1 plasmid respectively were summarised in this column graph. Median+Interquatile and individual mice responses are shown. P values were calculated by Kruskal-Wallis test. This data shows that the FJX1 antigen can be delivered in different architectures and still induce antigen-experiences CD4 and CD8 T cells. CO is a codon optimised sequence.

Figure 23:
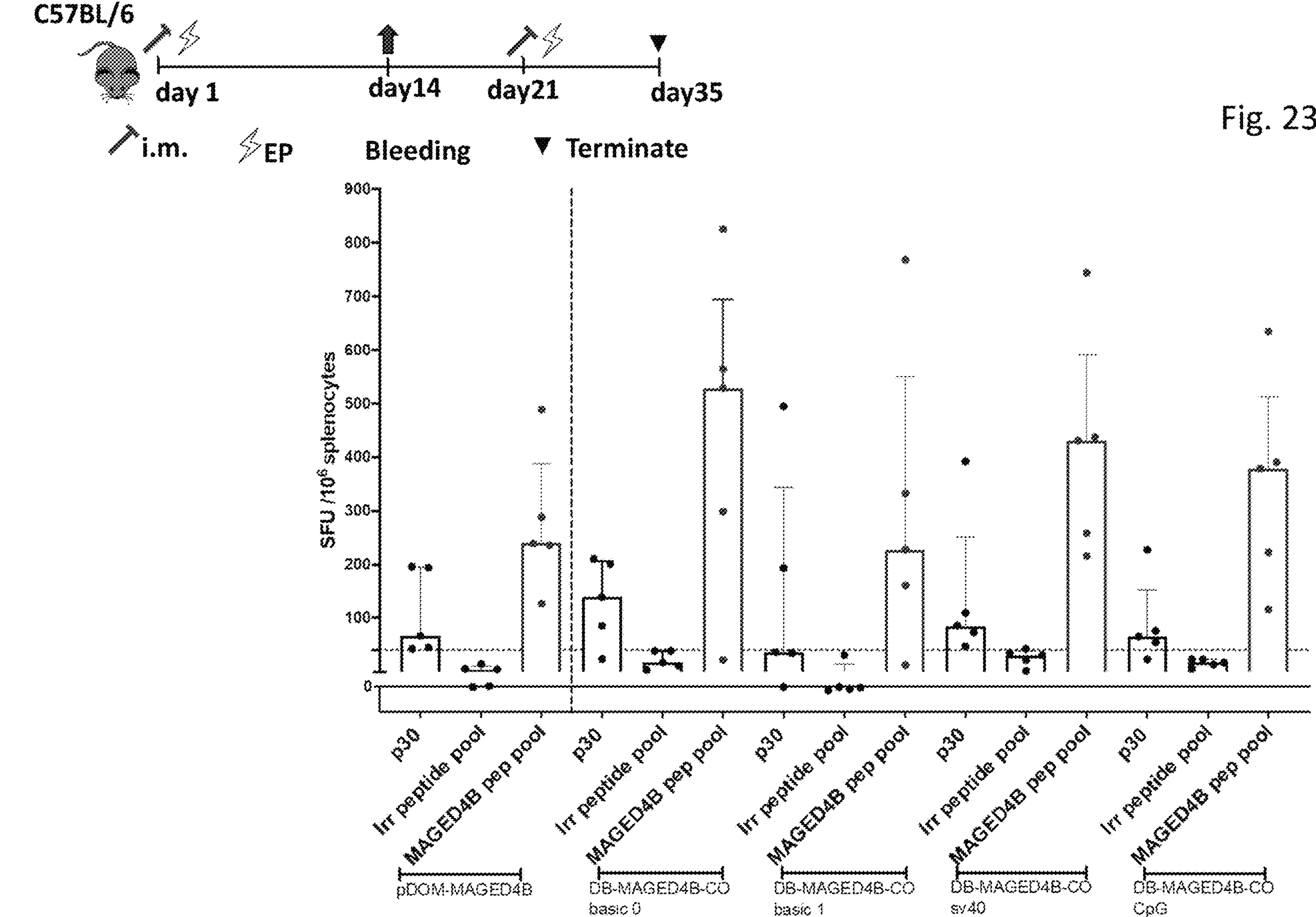

FIG. 23. Doggybone DOM-MAGED4B and pDOM-MAGED4B DNA vaccines induce specific CD4 and CD8 T cell responses. The treatment strategy is depicted. Non-tumour bearing C57BL/6 mice were vaccinated 50 μg pDOM plasmid vaccine (as a negative control, 3 mice), 10 μg DB-MAGED4B-CO (5 mice), 10 μg DB-MAGED4B-CO basic 1 (5 mice), 10 μg DB-MAGED4B-CO SV40 (5 mice), 10 μg DB-MAGED4B-CO CpG (5 mice), and 10 μg pDOM-MAGED4B plasmid (5 mice). The vaccines were administered i.m. with EP at day 1 and day 21. EP was carried out on mice anaesthetised by isofluorane, using intramuscular TriGrid Delivery System (TDS-IM; Ichor Medical System). On d 35 lymphocytes were isolated from mouse spleens and were plated to ELISpot plates and overlapping peptides pool (OPP) for MAGED4B was used to stimulate responding specific T cells. The OPP consisted of 15 mer peptides with 11aa overlap for the entire sequence (183 individual peptides were pooled for MAGED4B). P30 peptide an MHCII peptide from tetanus DOM sequence was used to assess induction of CD4 responses against Dom helper sequence. IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassburg, Germany). The graph shows the responses to p30 peptides, Irr OPP (FJX1 OPP), and MAGED4B OPP. DB-MAGED4B-CO basic 0 induced the strongest response among all the groups. Median+Interquatile and responses in individual mice are shown. Cut off set as 2x background (Irr OPPs), shown as a dotted line. The values were the responses minus the number of spots without stimulus. The number of spots/$10^6$ cells is shown. P values were calculated by Mann-Whitney test. This data shows that the MAGED4B antigen can be delivered in different architectures and still induce antigen-experiences CD4 and CD8 T cells. CO is a codon optimised sequence.

Figure 24:
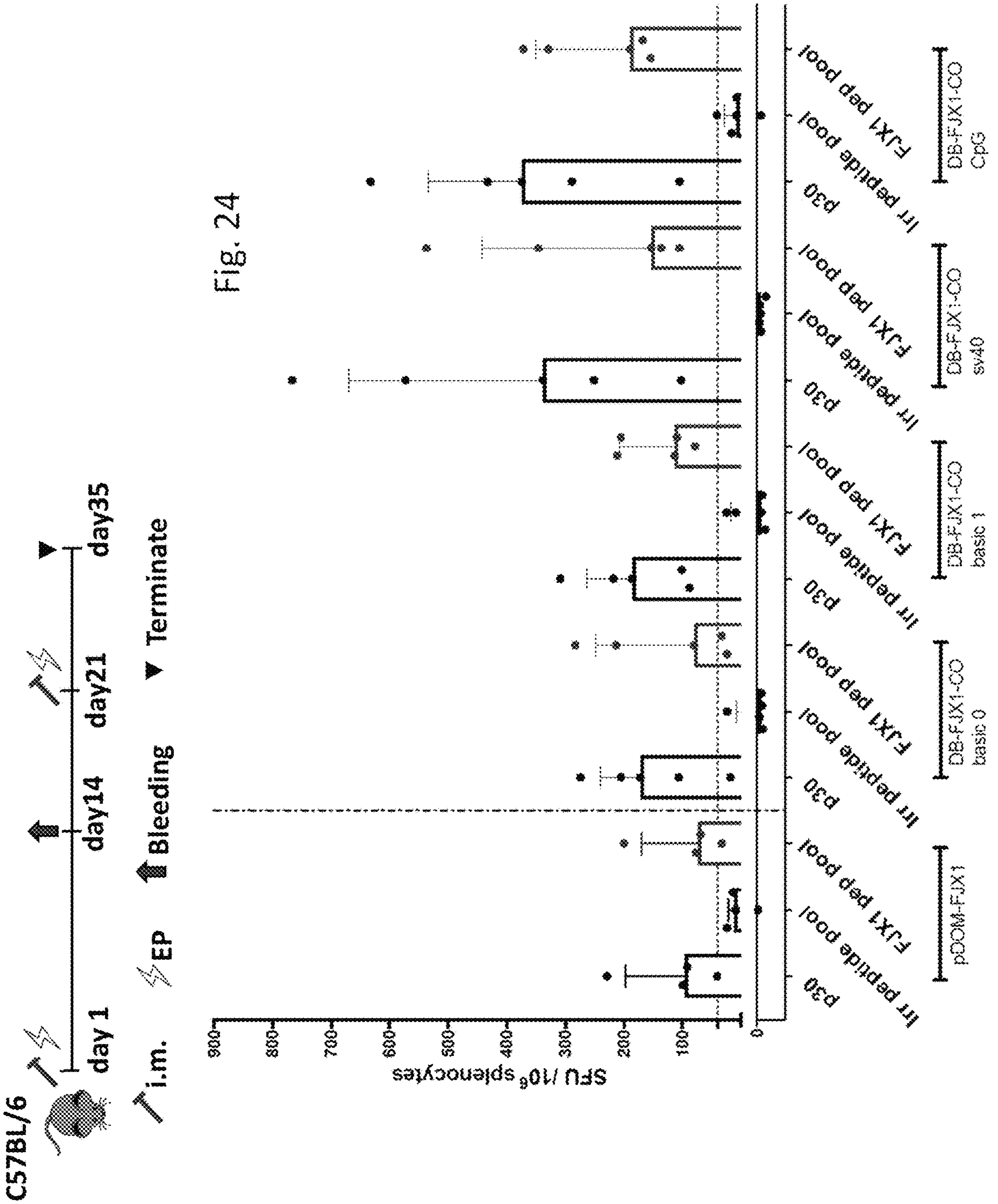

FIG. 24. dbDNA (DB) DOM-FJX1 and plasmid (p) DOM-FJX1 DNA vaccines induce specific CD4 and CD8 T cell responses. The treatment strategy is depicted. Non-tumour bearing C57BL/6 mice were vaccinated 50 μg pDOM plasmid vaccine (as a negative control, 3 mice), 10 μg DB-FJX1-CO (5 mice), 10 μg DB-FJX1-CO basic 1 (5 mice), 10 μg DB-FJX1-CO SV40 (5 mice), 10 μg DB-FJX1-CO CpG (5 mice), and 10 μg pDOM-FJX1 plasmid (5 mice). The vaccines were administered i.m. with EP at day 1 and day 21. EP was carried out on mice anaesthetised by isofluorane, using intramuscular TriGrid Delivery System (TDS-IM; Ichor Medical System). Lymphocytes isolated from mouse spleens were plated to ELISpot plates on d 35 and overlapping peptides pool for FJX1 was used to detect responding specific T cells. The overlapping peptide pools (OPP) consisted of 15 mer peptides with 11aa overlap for the entire sequence (107 individual peptides were pooled for FJX1). P30 peptide an MHCII peptide from tetanus DOM sequence was used to assess induction of CD4 responses against Dom helper sequence. IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassburg, Germany). The graph shows the responses to p30 peptides, Irr OPP (MAGED4B OPP), and FJX1 OPP. All groups performed with similarities. Median+ Interquatile and responses in individual mice are shown. Cut off set as 2x background (Irr OPPs), shown as a dotted line. Cut off set as 2x background (Irr OPPs), shown as a dotted line. The values were the responses minus the number of spots without stimulus. The number of spots/$10^6$ cells is shown. P values were calculated by Mann-Whitney test. This data shows that FJX1 can be delivered by multiple architectures can induce antigen-specific CD4 and CD8 T cells.

Figure 25:
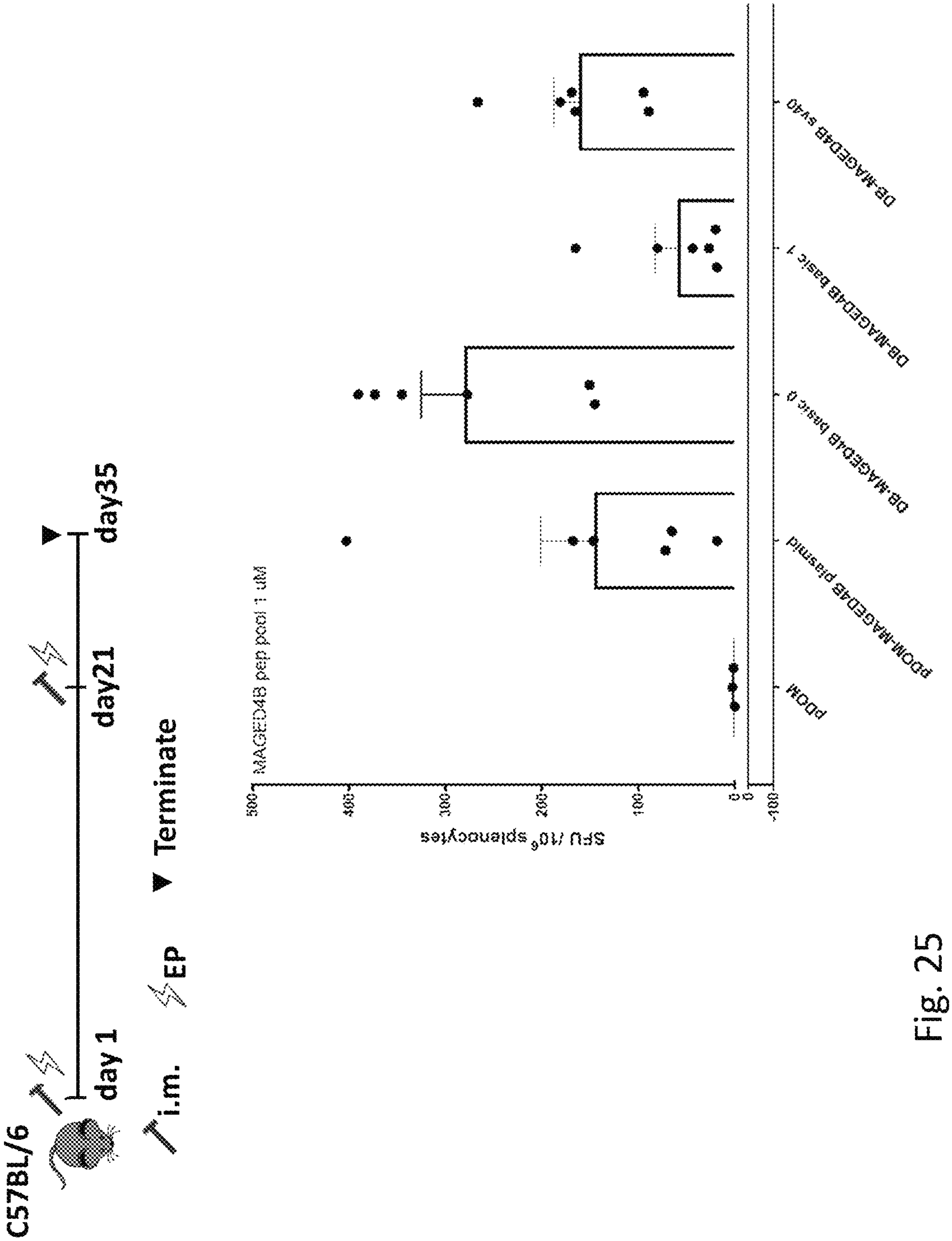

FIG. 25. dbDNA (DB) DOM-MAGED4B and plasmid (p) DOM-MAGED4B DNA vaccines induce specific T cell responses. The treatment strategy is depicted. Non-tumour bearing C57BL/6 mice were vaccinated 50 μg pDOM plasmid vaccine (as a negative control, 3 mice), 25 μg DB-MAGED4B-CO (6 mice), 25 μg DB-MAGED4B-CO basic 1 (6 mice), 25 μg DB-MAGED4B-CO SV40 (6 mice), and 25 μg pDOM-MAGED4B plasmid (6 mice). The vaccines were administered i.m. with EP at day 1 and day 21. EP was carried out on mice anaesthetised by isofluorane, using intramuscular TriGrid Delivery System (TDS-IM; Ichor Medical System). On day 35 lymphocytes were isolated from mouse spleens and were plated to ELISpot plates and overlapping peptides pool (OPP) for MAGED4B was used to stimulate responding specific T cells. The OPP consisted of 15 mer peptides with 11aa overlap for the entire sequence (183 individual peptides were pooled for MAGED4B). IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassburg, Germany). Response to MAGED4B OPP is shown. Median+Interquatile and individual mice are shown. The values were the responses minus the number of spots without stimulus. P values were calculated by Mann-Whitney test.

Figure 26:
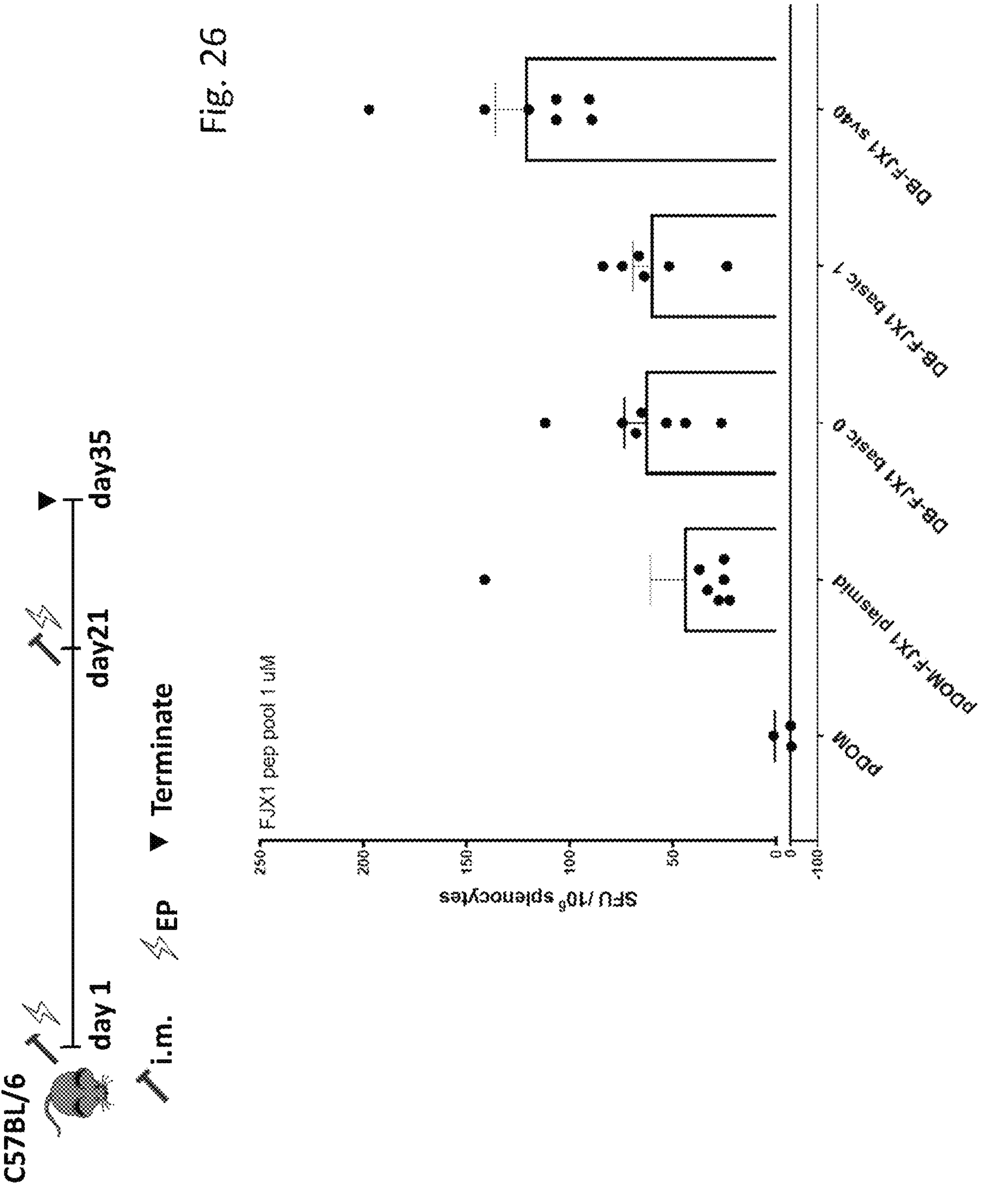

FIG. 26. dbDNA (DB) DOM-FJX1 and plasmid (p) DOM-FJX1 DNA vaccines induce specific CD4 and CD8 T cell responses. The treatment strategy is depicted. Non-tumour bearing C57BL/6 mice were vaccinated 50 μg pDOM plasmid vaccine (as a negative control, 3 mice), 10 μg DB-FJX1-CO (5 mice), 10 μg DB-FJX1-CO basic 1 (5 mice), 10 μg DB-FJX1-CO sv40 (5 mice), 10 μg DB-FJX1-CO CpG (5 mice), and 10 μg pDOM-FJX1 plasmid (5 mice) on day 1 and d 21. EP was carried out on mice anaesthetised by isofluorane, using intramuscular TriGrid Delivery System (TDS-IM; Ichor Medical System). Lymphocytes isolated from mouse spleens were plated to ELISpot plates on d 35 and overlapping peptides pool for FJX1 was used to detect responding specific T cells. The overlapping peptide pools consisted of 15 mer peptides with 11aa overlap for the entire sequence (107 individual peptides were pooled for FJX1). IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassburg, Germany). The values were the responses minus the number of spots without stimulus. The graph shows the responses to FJX1 OPP. Median+Interquatile and responses in individual mice shown.

Figure 27:
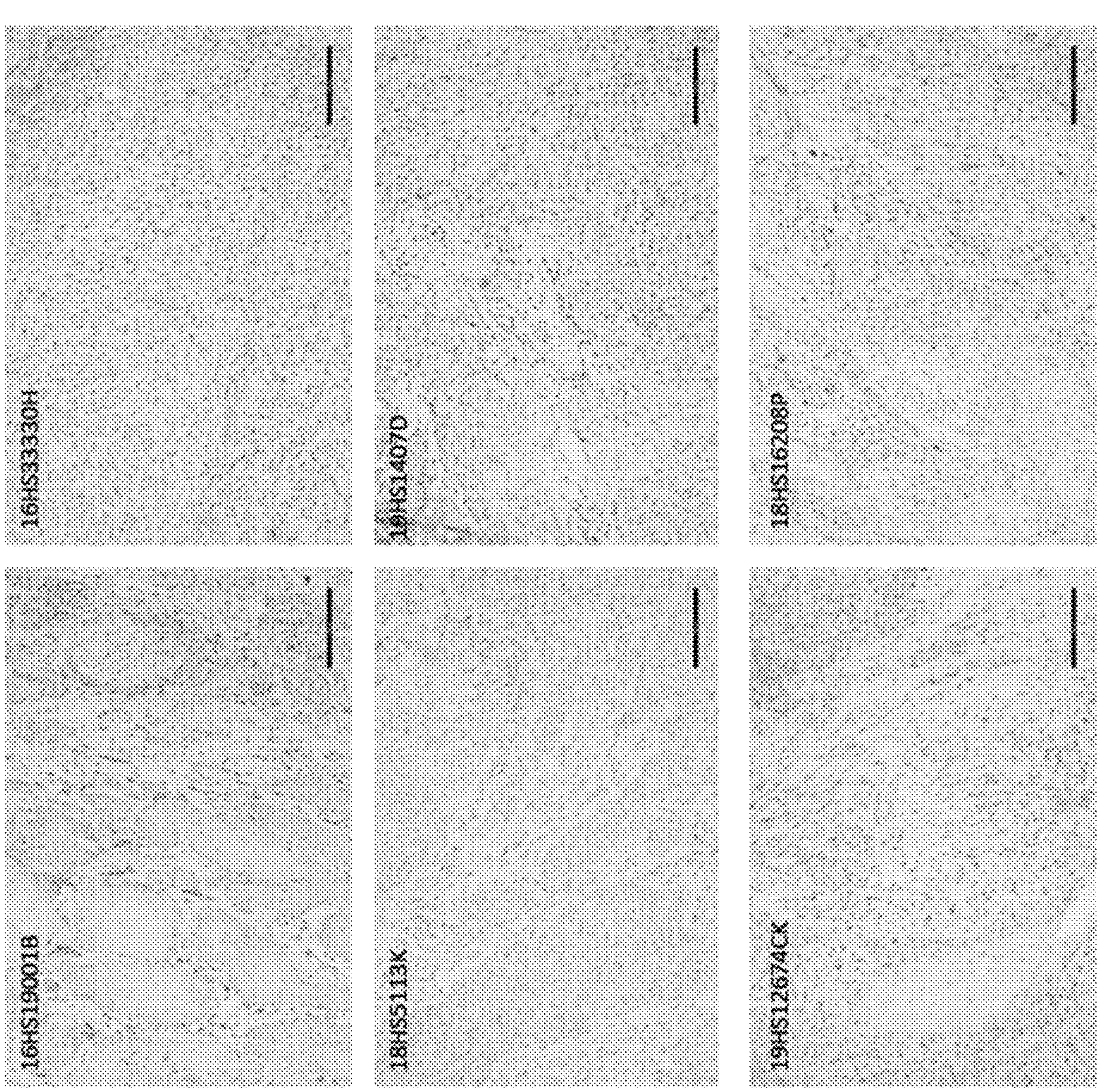

FIG. 27. Cancer Associated Fibroblasts (CAF) express MAGED4B. Immunohistochemical analysis of HNSCC cases, demonstrating MAGED4B expression in cancer cells and cancer associated fibroblast, the latter demonstrating strong expression. Anti-MAGED4B monoclonal antibody (Santa Cruz, G12; sc-393059) was used on HNSCC tissues at 1:50 dilution. Staining was performed on a DAKO autostainer (K4065). Six individual HNSCC cases which were available in Pathology lab in Southampton General hospital (Southampton, UK) are presented.

Figures 28A, 28B:
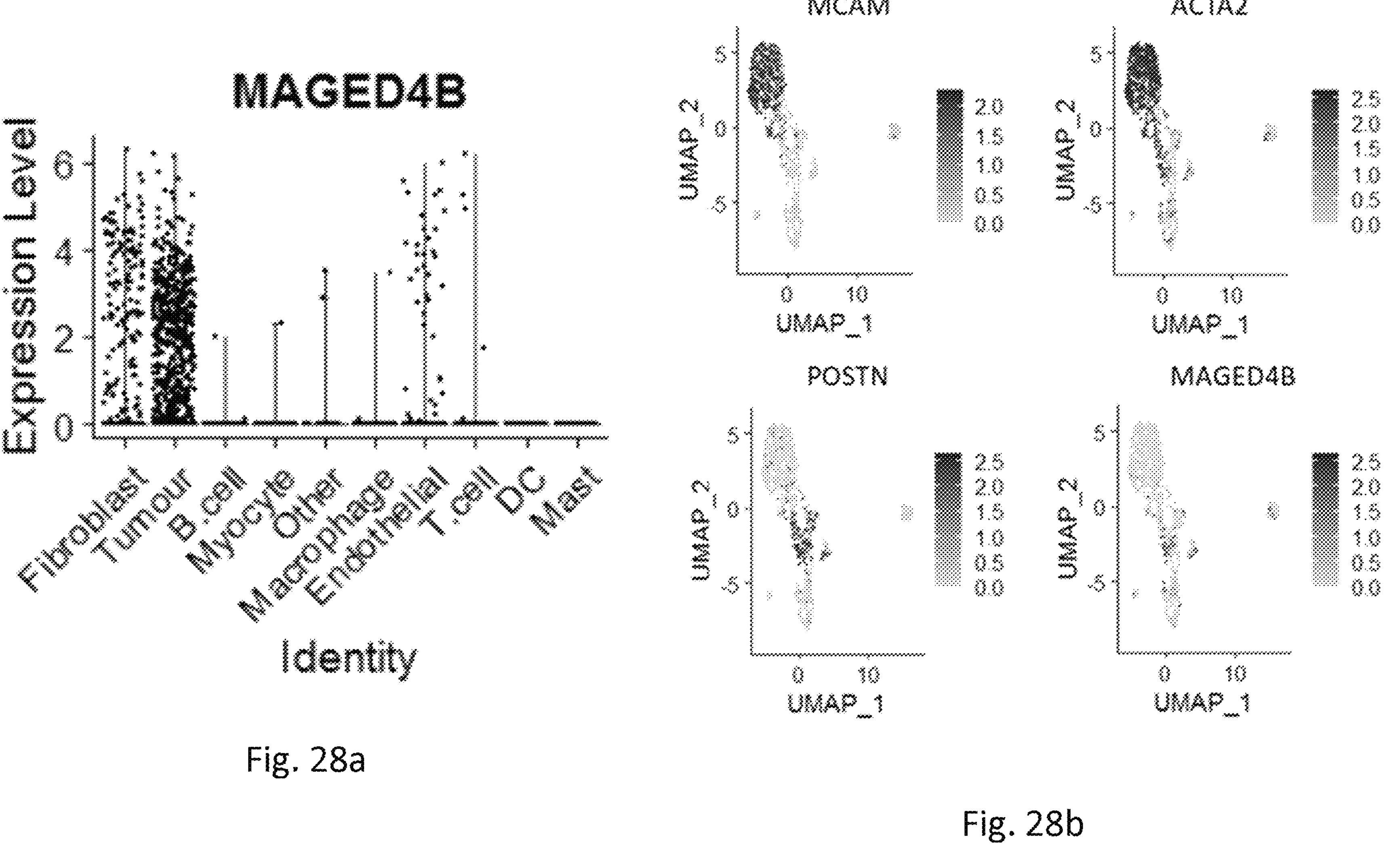

FIG. 28 (A and B) Cancer Associated Fibroblasts (CAF) express MAGED4B. FIG. 28A: Publicly available single-cell RNA-sequencing (scRNA-seq) data, generated from Smart-Seq analysis of HNSCC patient samples was used to assess MAGED4B expression across different cell-types. Cell lineages were identified as described by Puram et al *Cell* 2017 Dec. 14; 171(7):1611-1624. FIG. 28B: Fibroblast subpopulations were identified by unsupervised hierarchical clustering as implemented in the Seurat R package (v3.2) (Butler A et al, Nat Biotechnol. 2018 June; 36(5):411-420).

Fibroblast subpopulation markers MCAM, ACTA2 and POSTIN were identified using a Wilcox-test and compared with those previously identified for lung cancer fibroblast subpopulations to annotate different subpopulations (CJ Hanley et al, bioRxiv 2020.06.08.134270).

Figure 29:
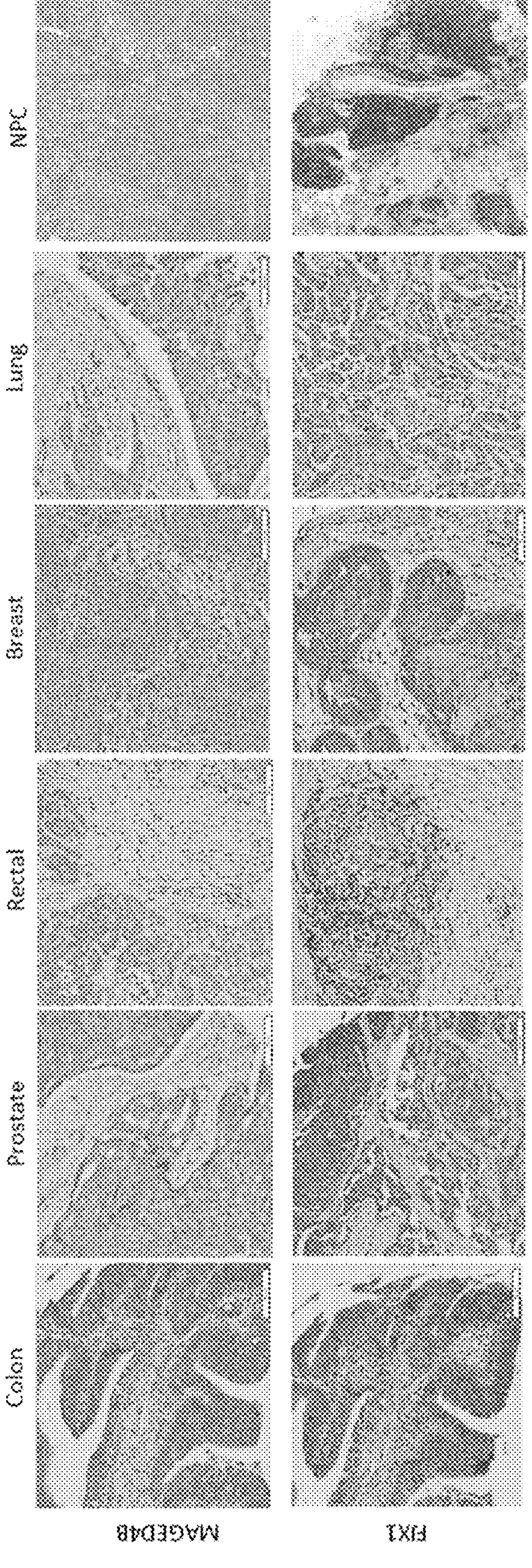

FIG. 29 Both MAGED4B and FJX1 antigens are strongly expressed in colon, prostate, rectal, breast, lung and naso-pharyngeal carcinoma. Expression levels of the target proteins were detected by immunohistochemistry (IHC) using anti-MAGED4B (1:100; Sigma Aldrich, Cat. #HPA003554) and anti-FJX1 (1:200; Sigma Aldrich, Cat. #HPA059220) antibodies, and processed using Dakocytomation Envision+ Dual Link System HRP (DAB+) kit (Dako, Cat. #K4065) as described previously.

SEQUENCES

Sequences, or encoded sequences, of the potential DNA vaccine components are described below. The DNA vaccine of the invention may comprise any one of the nucleic acid sequences provided below, or variants thereof. Alternatively, or additionally, the DNA vaccine of the invention may comprise nucleic acid encoding any one of the amino acid sequences provided below, or variants thereof.

Figure 7:
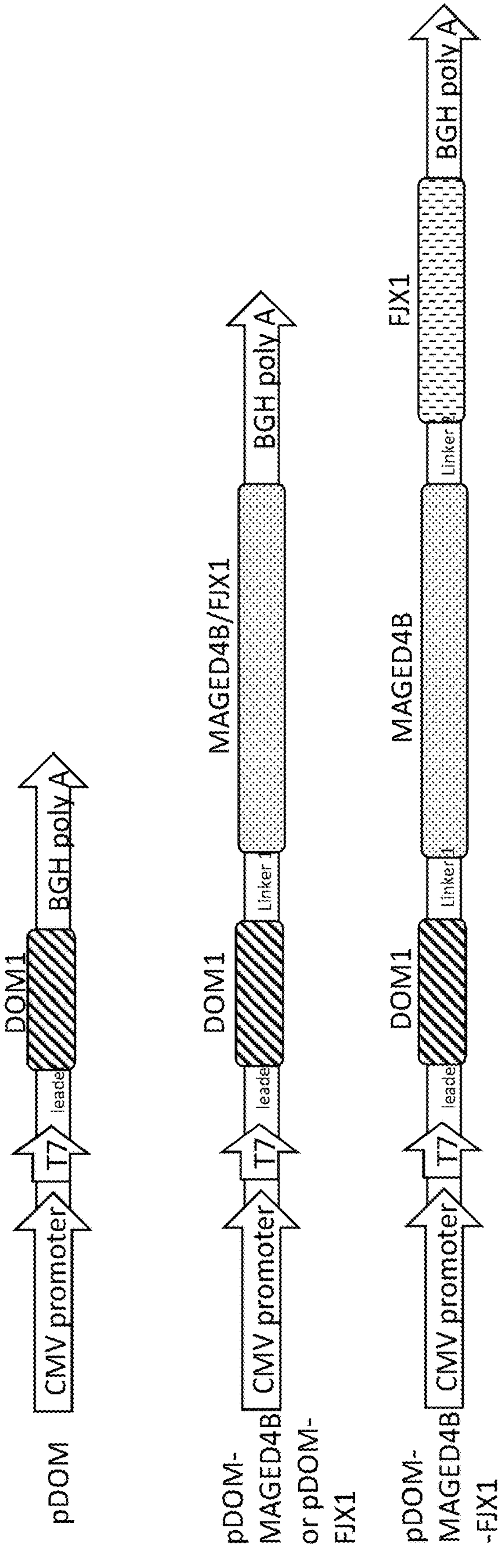
FIG. 7. Assembly of MAGED4B and FJX1 targeting DNA vaccines to target head and neck cancer. Diagram of vaccine constructs of pDOM (control), vaccines delivering single antigen pDOM-MAGED4B and pDOM-FJX1, and both antigens simultaneously pDOM-MAGED4B-FJX1 vaccines. DOM fragment of tetanus toxin gene and the gene of interest (MAGED4B or FJX1) were linked using a seven amino acid linker 1 (AAAGPGP). The fused gene was inserted between CMV/T7 dual promoter and BGH Poly (A) site. The leader sequence encoding mus IgH signal peptide (MGWSCIIFFLVATATGVHS) was inserted at the N terminus of the construct to enhance the efficacy of secretion. If the gene of interest was encoding the fused MAGED4B and FJX1 antigen, a five amino acids linker 2(GSGSG) was applied to link those two genes. DOM1 was inserted into pcDNA3.0 vector using NotI and HindIII restriction sites to generate pDOM vector. The genes for MAGED4-B, FJX1 or their fusions of interest were inserted into pDOM vector at NotI and XhoI restriction enzyme sites to generate the DNA vaccines. As used herein, p in terms of the vector relates to a plasmid vector or construct.

Amino acid sequences of the genes in the DNA vaccine assembled as in FIG. 7:

```
Leader sequence (SEQ ID NO: 1)
MGWSCIIFFLVATATGVHS

DOM (SEQ ID NO: 2)
KNLDCWVDNEEDIDVILKKSTILNLKINNIDDIIDISGFNSSVITYPDAQLVPGINGKAIHLVNNESSEVIVHKAMDIEYNDMFNNFTVSFWLRVPK

VSASHLEQYGTNEYSIISSMKKHSLSIGSGWSVSLKGNNLIWTLKDSAGEVRQITFRDLPDKFNAYLANKWVFITITNDRLSSANLYINGVLMGS

AEITGLGAIREDNNITLKLDRCNNNNQYVSIDKRIFCKALNPKEIEKLYTSYLSITFLRDFWGN

MAGED4B (SEQ ID NO: 3)
MAEGSFSVQSESYSVEDMDEGSDEVGEEEMVEGNDYEEFGAFGGYGTLTSFDIHILRAFGSLGPGLRILSNEPWELENPVLAQTLVEALQLDP

ETLANETAARAANVARAAASNRAARAAAAAARTAFSQVVASHRVATPQVSGEDTQPTTYAAEAQGPTPEPPLASPQTSQMLVTSKMAAPE

APATSAQSQTGSPAQEAATEGPSSACAFSQAPCAREVDANRPSTAFLGQNDVFDFTQPAGVSGMAFPRPKRPAPAQEAATEGPSAASGVP

QTGPGREVAATRPKTTKSGKALAKTRWVEPQNVVAAAAAKAKMATSIPEPEGAAAATAQHSAEPWARMGGKRTKKSKHLDDEYESSEEER

ETPAVPPTWRASQPSLTVRAQLAPRPPMAPRSQIPSRHVLCLPPRNVTLLQERANKLVKYLMIKDYKKIPIKRADMLKDVIREYDEHFPEIIERA

TYTLEKKFGIHLKEIDKEEHLYILVCTRDSSARLLGKTKDTPRLSLLLVILGVIFMNGNRASEAVLWEALRKMGLRPGVRHPFLGDLRKLITDDFVK

QKYLEYKKIPNSNPPEYEFLWGLRARHETSKMRVLRFIAQNQNRDPREWKAHFLEAVDDAFKTMDVDMAEEHARAQMRAQMNIGDEALI

GRWSWDDIQVELLTWDEDGDFGDAWARIPFAFWARYHQYILNSNRANRRATWRAGVSSGTNGGASTSVLDGPSTSSTIRTRNAARAGASF

FSWIQHR

FJX1 (SEQ ID NO: 4)
MGRRMRGAAATAGLWLLALGSLLALWGGLLPPRTELPASRPPEDRLPRRPARSGGPAPAPRFPLPPPLAWDARGGSLKTFRALLTLAAGAD

GPPRQSRSEPRWHVSARQPREPEESAAVHGGVFWFFSRGLEEQVPPGFSEAQAAAWLEAARGARMVALERGGCGRSSNRLARFADGTRACVR

YGINPEQIQGEALSYYLARLLGLQRHVPPLALARVEARGAQWAQVQEELRAAHWTEGSVVSLTRWLPNLTDVVVPAPWRSEDGRLRPLRDA

GGELANLSQAELVDLVQWWTDLILFDYLTANFDRLVSNLFSLQWDPRVMQRATSNLHRGPGGALVFLDNEAGLVHGYRVAGMWDKYNEPLL

QSVCVFRERTARRVLELHRGQDAAARLLRLYRRHEPRFPELAALADPHAQLLQRRLDFLAKHILHCKAKYGRRSGT

Linker 1 (SEQ ID NO: 5)
AAAGPGP

Linker 2 (SEQ ID NO: 6)
GSSGSG

MAGEDRB Nucleotide Sequence (SEQ ID NO: 7):
>NG_029896.1:5001-12446 Homo sapiens MAGE family member D4B (MAGED4B), RefSeqGene on chromosome X
GCATGCGCAGGCTACCCAGCCGCGGGGGGTGCACGGAGAAAGGGGCGGGGTGGTCCGGGCTGCTGTGCT

GGCAGCAGTAGGCGAGGGCGCGGCTGCGGGGTTCCTGGTGCTGAGGACGGACGCCATTGGAGTTCCCGAG

AAGGTAAGGATCCAGCCCCAGACAGGACCGGGAGAGGGCGAGTGGAACCCGACACGCTGCGCCCTCCCTC

CGCCTCCGGATCTGAACAAAGCCCAAGCACTCAGAACCGGAACCCCATTAGACCCAAGGTCTAGATAGGA

GCCCCCATCACCATCAGACCCAGGCGCCCCGATCTGAGCCCTACTGAAACCGGAGCCCAGGATCCTCACC

CCTTTAGCAGACCCGTGTGCTCCGAGCTGAGCTCCCTTGGACCTGAGGCCCCACCCCCACCCCAACCACT

CCTAGATTACTCGAACCGAGCTGACCGCTTGCCCCCTTCCTGGAGTGCCCAGTCCTCGCGTTTGAGATCT

GCAGCGCTCCGATTGGAGCCTCACCTAGGTCTGAGGCCCCCACTCCATCCGCCTCTAGTGCTCGAGTCTG
```

-continued

AGCCCCACCTAGGCCCCCCCGCCCGGACCTAGCCAAAGGTCCCTGGGGTTCTGTTTCGCAGAGCTTGCGGC

TTGCCACTGTCCCTGTTGTCTGAGCTCTCCCATCTGCTCCCCCTTCATCCCGGTCCCCTTCTCTGGCCCG

TAAATCCAAACCCTTTGTTTCTCTCTTCCCCAATGCATTCCCTTTGGGACTCTTCGGACCCCAGCCCTCC

AGAACACCCCCTCGTCAAATCTAGCCGCTGGGATGGCGAGCCTGCCCATCCTAAACTCCGCTTTCAGTGC

GGCGCCTCCTGCGACCTCCTCTGTCCCTTTCCTTGGGCTCTGTCCCTGACCAGGTCTACCCCATCAGAAA

GCCAAACCGTCTCCCCCCCGCTCCTCCTCCCCCCCCCCGCCCCCTACTGCCTAATATTGCCTAGTAACCT

GATGATTGTCGCCCCTCACCTCCCGGGAGATCCCGCCTCCCATTGGATCCCGCCCCCCTCCCCCTGCAGCT

GCTTCACCCTCCCTCTCAGGCTGAGCTCTCATCTCCCTGGGACCCGCAGCATGGCTGAGGGAAGCTTCAG

CGTGCAATCGGAAAGCTACAGTGTTGAAGACATGGATGAGGGTAGCGACGAAGTCGGGGAGGAAGAGATG

GTTGAAGGCAACGACTATGAAGAATTCGGTGCGTTTGGTGGCTATGGCACCCTCACCAGCTTTGACATCC

ATATCCTCAGAGCCTTCGGAAGCTTGGGTCCAGGCCTTCGCATCTTATCGGTGAGGCCCCTTCCTGGACA

CCTGCTGGCCTGGGCCTTTCCCCTGTGAATGGGGGAGGGAGGAGGGGGGAGCCAGGAGGGTTGTGTGGGA

AAGGACTGCCCAGCTTCCCAAGCCTTCCCTCCCCTGCTCGGAAGAAGAAGATTTGGGAAGGTCTTGGGGT

GTTCAGGGCTGACTGCTGGGAAGAGGCTGGCCAGCACAGGGAAGCTAACACAAGTATGTCGTCGAGTGGC

CTGCCTTCCCCAACCCCTCTCTCTGGCCTTGCAGAATGAGCCCTGGGAACTGGAAAACCCTGTGCTGGCC

CAGACCCTGGTGGAGGCATTGCAGCTGGATCCGGAAACACTTGCCAATGAGACGGCCGCCCGTGCTGCCA

ACGTAGCCCGCGCCGCCGCCTCCAACCGTGCGGCTCGGGCCGCTGCCGCCGCTGCCCGTACCGCCTTCAG

TCAGGTGGTCGCTAGCCACCGGGTGGCCACGCCGCAGGTCTCAGGAGAGGATACCCAGCCCACGACCTAC

GCCGCCGAGGCTCAGGGGCCCACCCCTGAGCCACCCCTTGCTTCTCCGCAGACCTCCCAGATGTTAGTCA

CCAGTAAGATGGCTGCCCCCGAGGCTCCGGCAACCTCCGCACAGTCCCAGACAGGCTCCCCGGCCCAGGA

GGCTGCTACTGAGGGCCCTAGTAGGCGCCTGTGCTTTCTCTCAGGCTCCGTGTGCCAGGGAGGTGGACGCC

AACCGGCCCAGCACAGCCTTCCTGGGCCAGAATGATGTCTTCGATTTCACTCAGCCGGCAGGTGTCAGTG

GCATGGCCTTCCCGCGCCCCAAGAGACCTGCCCCAGCCCAAGAGGCTGCCACAGAGGGCCCCAGTGCTGC

CTCTGGTGTGCCCCAGACGGGACCTGGCAGGGAGGTGGCAGCCACCCGGCCCAAGACCACCAAGTCGGGG

AAGGCGCTGGCCAAGACTCGGTGGGTGGAGCCTCAGAATGTTGTGGCAGCAGCTGCTGCCAAGGCCAAGA

TGGCCACGAGCATCCCTGAGCCGGAGGGTGCAGCTGCTGCCACTGCTCAGCACAGTGCTGAGCCCTGGGC

CAGGATGGGAGGCAAGAGGACCAAGAAGGTGAGATCCCCCTGCCCCCTGCCACCTCCACACCCCCTTGCT

CCTGTCCTTTCCTTCTCCTCCCTTTCCTGCTCCTCTCCTCCCTCTCCTCTCCCCCTTCTTCCTCTCTTCT

CCTCTTTCCCCCTCCTTCTCTCCTCACCTCCCCTCTCCTCCCCTCCTCTCCTCTCAGCTAGTCCATGTTTC

TCCAACACAAGTTTGCTGAGCATGTTTTCACTCCACGTAGTCCCTACCCTCAGGACTGGTGGGAGAAGAG

GCTGGCTCAGTGCCTGGCACTTAGTAAGCACGCAGCACATGCCAGCCGCTGCTGGTACTGCTCTCATTTC

CAAGAGCCTGCTACGGGTGAGGTGCGTGCCGGGTGCTTTGGCACGGGGAGCCTGGTAGCCCTGGGTCTCT

CCTCTCTCAAATGATACAGTCCAAGCACCTGGATGATGAGTATGAGAGCAGCGAGGAGGAGAGAGAGACT

CCCGCGGTCCCACCCACCTGGAGAGCATCACAGCCCTCATTGACGGTGCGGGCTCAGTTGGCCCCTCGGC

CCCCGATGGCCCCGAGGTCCCAGATACCCTCAAGGCACGTACTGTGCCTGCCCCCCCGCAACGTGACCCT

TCTGCAGGAGAGGGTAAGAAGCCCACCCTCCCCCATCTCCTTCCTCTCCTCCCTTGTGGGCCACGTCTCT

GCTGTCACCCATGCCTTGACCTCCCCGCATGTTCCTCCTTCTCCAGGCAAATAAGTTGGTGAAATACCTG

ATGATTAAGGACTACAAGAAGATCCCCATCAAGCGCGCAGGTAGGCAGCCTGTGCCCCTTCACCATCCC

CTAGTCTGTGGGCATCCCTTTGCTTGCGTGCCACGGCTGGTCCCTCCATAGCCACAGGACGGGGTCCTGG

CTGCGTCACCCTCGGCAGAGCTGACCAAGGGGCTACAGCTCTATGACCCCCTGCTCAGCCCAGGTGCTTTC

-continued

TCCAACTCTTCCCCCTCCTGCAGACATGCTGAAGGATGTCATCAGAGAATATGATGAACATTTCCCTGAG

ATCATTGAACGAGCAACGTACACCCTGGAAAAGGTGGGTGCAGGATGGGAGCAGCTCTGTGGGGGAAGAG

CGGGCATGGGGGTGCGGTGACCCTGCAGCCCCTCAAGGCCCAGTCTCTGGAGCCATCTCTCACCTCTCCG

ACTCTGAGCTTCCACTGCACTGGCAGTTTGACTCGTGCTTCCTGCCCTCGGCTTCTCTCTCTCATGCTCT

CTGAGTGTCTCGCCGTCTGGCCAGGTGGGTCTCATCGCCTCTGCCAGCGTCAGCTCCCACAGCGAAGGTC

TTCCGTGTGCTGTCTTCTTCTGCCCTCGCTCACGAGTTTGGATTCCTTGCTGAGGAGCAGTTCTAACCCG

GAATCACTGTCTGCCGGCAGGATGCCCAGCATGGGGTTTGGATCTCACACTCTGTTTTCTCCCCCACGTA

GAAGTTTGGGATCCACCTGAAGGAGATCGACAAGGAAGAACACCTGTATATTCTTGTCTGCACACGGGAC

TCCTCAGCTCGCCTCCTTGGAAAGTAAGAAAGGGAAAGCGGGTCGTGGCCTTCCTCGGTGGTGTCCCTTC

CCTGCCCACACCCCTTCAGTGAAGCAGGAAGACGGGGCTTGAGTGCGGCGCACCGCTCCCACACACAGCG

AGGGCTGCCTGGTGACTGCTGGATGAAAGGAATGATAGCCTGGGGTGAGGCCTTGCTGCCATCAGTTCTC

CCCAAGCTGCTGCCGGGCTTTATCCCCAAAGCTTCGGAGGAAAGTGCCTCTTCCTCCTGCCTGCCTGGCC

TGGGCCTGGCAGAGCTGGCCTAGGGGAGAGCTGCCTCTTCAGTGTAGGTGCTGATGTGGAAGGGGCAGGA

AAGGTCTGGAGCCATCTCTGGGCACACGTTTGCCATTTGCAGAGCTTCGGCTCCCTGCCTCGCCCTGTCC

TCTGCAGAACCCTGTCAGGGAAGTGTTAGTACCCATGTTTTATAGAGGAGGCGATTAAGTCTCAGGCGGA

GGTGCGAATGGTCTGTCAGCAGCTAGTGAACTGTGCCTGTCCTGGGAAGAGTTCCCCTCAAGCTGGGAAA

CCTGAGAGAGGCTAGTTGGGAGAGCCTGGTGGTGTCTCTCAGGCAAATAGCTGCTAAACAGGATTTCTCT

TTCCACACCTTTAGAACCAAGGACACTCCCAGGCTGAGTCTCCTCTTGGTGATTCTGGGCGTCATCTTCA

TGAATGGCAACCGTGCCAGCGAGGGTGAGTGGCTGGACCTGCAACTGGGGGGCTGCCCATAGTCTCATCT

TCTGGGTGCCAAACTCTCGTACCTCCTCTCCCCTCGCAGCTGTCCTCTGGGAGGCACTACGCAAGATGGG

ACTGCGCCCTGGGTATGATTGGCCTCTCCAGCTCCTCCCCTCGGTGCTATCCTCTGGCCAAAGAGGTCCT

GGGATTGCAATAGCCTGGTGGTCTGGCGCAAGGGCGTGGGGTGCCCTGGGCTCGGTAGAGAGCAAAGGAT

CTCACCAGGGCGGATGGGGAAGCGGTGCTGGACGCTGCTCAGCCCTCTCTCTGCTCTGTGGCCCCAGATG

ACATCTAAGAGAGACAGTCAGAGTCAGGGATTCCATCAAATCCTACCTGGGGCGTCCCTGACCAACAGT

CCTCTGGCCTCTGCTGCATGCCCAGGCCTCCACAGCGACTCCCCGGGGGCTGGGAAGTCATAGTCATGCT

AGGGAGGGCCCCTGCCACCGTCTCTGCTCATGGATTCCTTTCCTTGCCCTCAGGGTGAGGCACCCATTCC

TCGGCGATCTGAGGAAGCTCATCACAGATGACTTTGTGAAGCAGAAGTAAGTATCACCTGAGCTAACTGC

GGCTCTCACTCGAGCATCCTTTGTGTGCTGGTCTGGCTGAGAAAGCAGTTCCCTATCCCAAATCTTCAAC

TGGAGGGATGGGTGCCTCTGACCTGGGAGTGAGTGGCAGTGGGGGGTATGCGAGTGTGTGGGGAGCCGAA

GGCCAGGGCGGTCTTGGGAAAAGGGAGCTCACGTCACCTGAGAACACGGTGTGGGGTGTGAAAACGGCCG

CCATCACCTTGAGCACCTGCCCTGTAGACTGACACAAGAGTTCCCCCCTGGTTTACACCTAAGGAACCCGG

AGCTCAGAGAGGAGACGCCTCTGAGCATGGCTCCCAGCTGGTAAGGGCCTCAGCCCAACTCTCCTGATTT

TCAGGCCAGGGGCCACCCTCTCCCCGTCCCTGGAGGACTTGCCAACGCACAGGCGCGCATGCACACCAAC

AAAGGGTCAGGACTTGAGGAGGATGCCTGGAGCACGCTTCTCCTGGCTGACTGTTTCTTCCTCTCCAGTC

GTTTCCTCTGGTGGGCCTCTCCAGGGCTCCGCCGGGGTGTGGCCAAGACCCTCGAGGTGGGGTGTGCTCA

GAGCAGGGGGCCTGAAGAATGGCTCCTCTGTTTACAACACACCCAACAGGAAGCTGGGGTCATCGTGATG

AGGGGCACAAACTTGTGGCCTCCCTACAGACAAATGCCCTACATGTGGACCCCCTGCACCTCCGCATGGC

TTCCGGGGAGGACCAATGGCAAAAGGCTTTGAAGGCCTCACTTTTGCAGGCAGAAGTCCTGGGAGTGGGT

TTGGGAATGAGTGAAGGGCTGGAGGGGCAGGACAGTCCTCTTCCAGGAGCTGAGCTGCGGCATCGGGTTG

AGGAGGGGCCCCCTGGAACCCATCCGTTCAGCAACAGGTCTGCTTGGCTAGCAGCAAAGTTTACTTTCCT

CTCATGCCAAGGTACCTGGAATACAAGAAGATCCCCAACAGCAACCCACCTGAGTATGAATTCCTCTGGG

-continued

GCCTGCGAGCCCGCCATGAGACCAGCAAGATGAGGGTCCTGAGATTCATCGCCCAGGTAAGGGAGCGCCT

CTGTTGGGTGCCCGGCACCGGGGGTGGTGCTCTCCACACCTTGCTTGTTTCTTGGTCGAGGCCTCCTTCC

CATTACCCCGTATTCCAGTGAGGGTACCAAACACTCACAGAGGCACCTGAGCACCCTACACAAGGTCACA

GATGGGGCAAAATCCCAGGTCTGGCACAGGAGAGTAGGAGCCCCCAATCCCTGTGGTCCTGATTTTTGCC

ATCATTGCACAAAGCACACGGGAGGGGGTGAGGCGGGCCGCGGGTGCTCAGCCAGTGTGGGGTAGCTCTG

TGTCTATGCCTGCCCTTTTCCTCCTCAGAATCAGAACCGAGACCCCGGGAATGGAAGGCTCATTTCTTG

GAGGCTGTGGATGATGCTTTCAAGACAATGGATGTGGATATGGCCGAGGAACATGCCAGGGCCCAGATGA

GGGCCCAGATGAATATCGGGGATGAAGCGCTGATTGGACGGTGGAGCTGGGATGACATACAAGTCGAGCT

CCTGACCTGGGATGAGGACGGAGATTTTGGCGATGCCTGGGCCAGGATCCCCTTTGCTTTCTGGGCCAGA

TACCATCAGTACATTCTGAATAGCAACCGTGCCAACAGGAGGGCCACGTGGAGAGCTGGCGTCAGCAGTG

GCACCAATGGAGGGGCCAGCACCAGCGTCCTAGATGGCCCCAGCACCAGCTCCACCATCCGGACCAGAAA

TGCTGCCAGAGCTGGCGCCAGCTTCTTCTCCTGGATCCAGTAAGAGTTTCGGTAGAGAAATGAGACTCTG

CAGGAGGGCTGCGGAGGGGGGTGAGATGTCAGAGGGAGGGCCAGGGTGGGGGCGCTGGGGGCAACGGCAA

CAGCATGGACGGACACTTATTTTGTTACGTACACCCCTCCCTGGTTCGCGTGTGTCCACGGATGTTGTCA

CTTTGGTTTCTTGTGCTTTTATAGGCACCGTTGACGAACTGCAGCGATCTTACTGGCCAAGCCAGAGCGC

CTCCTCTCAGATTCCTTCTCGACACAGCACCCTAGGCGGCTTCTTCCTGTCAGTCGGAGGTGGCATGCAA

GATGAAGCTCTCTTTGCTCTTCCTGCTTTCATTTTGTGCTTTTCCTTGTGTTTTCATGTTTTGGGTATCA

GTGTTACATTAAAGTTGCAAAATTAA

FJX1 Nucleotide Sequence (SEQ ID NO: 8):
>NC_000011.10:35618460-35620865 Homo sapiens chromosome 11, GRCh38.p13 Primary Assembly
AGTTCCCAGCGCCGGGCGGAGCGCCGGACAGAGCCCCGCAGCGCCCCGCGGCCGCGATGGGGCCGAAGCG

CCCGAAGCCCCGGAGCCCACAAACTGCCGGGCCCGCCTCGCCGCCGGGACCCGGGTGCCTGGGCTCGGCT

TGAAGCGGCGGCGGCGCACCGGCACAGCCGCGGGAGCATGGGCAGGAGGATGCGGGGCGCCGCCGCCACC

GCGGGGCTCTGGCTGCTGGCGCTGGGCTCGCTGCTGGCGCTGTGGGGAGGGCTCCTGCCGCCGCGGACCG

AGCTGCCCGCCTCCCGGCCGCCCGAAGACCGACTCCCACGGCGCCCGGCCCGGAGCGGCGGCCCCGCGCC

CGCGCCTCGCTTCCCTCTGCCCCCGCCCCTGGCGTGGGACGCCCGCGGCGGCTCCCTGAAAACTTTCCGG

GCGCTGCTCACCCTGGCGGCCGGCGCGGACGGCCCGCCCCGGCAGTCCCGGAGCGAGCCCAGGTGGCACG

TGTCAGCCAGGCAGCCCCGGCCGGAGGAGAGCGCCGCGGTGCACGGGGGCGTCTTCTGGAGCCGCGGCCT

GGAGGAGCAGGTGCCCCCGGGCTTTTCGGAGGCCCAGGCGGCGGCGTGGCTGGAGGCGGCTCGCGGCGCC

CGGATGGTGGCCCTGGAGCGCGGGGGTTGCGGGCGCAGCTCCAACCGACTGGCCCGTTTTGCCGACGGCA

CCCGCGCCTGCGTGCGCTACGGCATCAACCCGGAGCAGATTCAGGGCGAGGCCCTGTCTTACTATCTGGC

GCGCCTGCTGGGCCTCCAGCGCCACGTGCCGCCGCTGGCACTGGCTCGGGTGGAGGCTCGGGGCGCGCAG

TGGGCGCAGGTGCAGGAGGAGCTGCGCGCTGCGCACTGGACCGAGGGCAGCGTGGTGAGCCTGACACGCT

GGCTGCCCAACCTCACGGACGTGGTGGTGCCCGCGCCCTGGCGCRCGGAGGACGGCCGTCTGCGCCCCCT

CCGGGATGCCGGGGGTGAGCTGGCCAACCTCAGCCAGGCGGAGCTGGTGGACCTAGTACAATGGACCGAC

TTAATCCTTTTCGACTACCTGACGGCCAACTTCGACCGGCTCGTAAGCAACCTCTTCAGCCTGCAGTGGG

ACCCGCGCGTCATGCAGCGTGCCACCAGCAACCTGCACCGCGGTCCGGGCGGGGCGCTGGTCTTTCTGGA

CAATGAGGCGGGCTTGGTGCACGGCTACCGGGTAGCAGGCATGTGGGACAAGTATAACGAGCCGCTGTTG

CAGTCAGTGTGCGTGTTCCGCGAGCGGACCGCGCGGCGCGTCCTGGAGCTGCACCGCGGACAGGACGCCG

CGGCCCGGCTGCTGCGCCTCTACCGGCGCCACGAGCCTCGCTTCCCCGAGCTGGCCGCCCTTGCAGACCC

CCACGCTCAGCTGCTACAGCGCCGCCTCGACTTCCTCGCCAAGCACATTTTGCACTGTAAGGCCAAGTAC

-continued

GGCCGCCGGTCTGGGACTTAGTGTCACCGGGAGGAAAAGAGAGAGATCTGGGGCTGGGGTATGGATGATG

GGGGGAAGGGCGGTCGCCTCTGCCACTGTCAGGGACCAGCCGGCCAACGCCCACCCGCAAAGGTGTCTAA

AAACTTCAGCTTTTCACCCACCTGCCCCTTTCTTTCAATCCCACGCTGTTTCCTTTCAAAGTTCTGGGAG

GACGAACTCACCGAGGCGAGAAGTGTAACATTCTCTCCACCCAGCTTATAAAAGGATTCTTTACTGTGCC

AGCACGGGGATTGGATCCGAAGAAACTGGCTACTGGGGTTTGGCCCCCGAGTGGCCGTCCCTGTGGGAGA

TGCACCCCATTCTTGGGCCCCCCCTCATTCCCTTTCCGAAAAAGGAAAACTTGCGTTTGAGCCGTTGAGC

TAATTCTGCAATTTTCTACCAAACAGAGCGCTGGTGGCCCCGGAGCAGGGCTGTGACATTGGCTGGTGGA

GCCCCCTTCCTGTGTTCTCCCTTTGTTCCAGCGCCGCGATGGTGAGATCACTGTTCCAAGCAGGGGGACG

GCTCGCGATAGGACAAAGAGAGCAGGACCTCCAGACTCTGGGGAGCCCTGCAGACCTTGACAATTTGCCT

GACTCATTCCTGACCTCTTGTCATTTTGGCCTGAAGGCTACAAATTCAGGGTCAGCTGTATGCACTAAGT

CAAATAATGAATTTCTTCCTCCCTCTCGCAACCGACCAAAATTTTGACAACGATGATGTTCACCAGAAGG

AAAAAAAAAAATCAGTTTTATGCACTTTATTTTGTTTTGATTTTCATTTTTTATTAAGAAAAAATTTTAT

TTTACAGAATTTACCTTCTCTGTATATATGTGCATAAAGTGTGGTGTAAATATACTAAACAAACTTATAT

TTCAATAAAAGGGAGTTTAAAATTTA

CMV/T7 Dual promoter sequence (SEQ ID NO: 9):
ACATTGATTATTGACTAGTTATTAATAGTAATCAATTACGGGGTCATTAGTTCATAGCCCATATATGGAGTTCCGCGTTACATAACTTACG GTAAATGGCCCGCCTGGCTGACCGCCCAACGACCCCCGCCCATTGACGTCAATAATGACGTATGTTCCCATAGTAACGCCAATAGGGAC TTTCCATTGACGTCAATGGGTGGAGTATTTACGGTAAACTGCCCACTTGGCAGTACATCAAGTGTATCATATGCCAAGTACGCCCCCTAT TGACGTCAATGACGGTAAATGGCCCGCCTGGCATTATGCCCAGTACATGACCTTATGGGACTTTCCTACTTGGCAGTACATCTACGTATT AGTCATCGCTATTACCATGGTGATGCGGTTTTGGCAGTACATCAATGGGCGTGGATAGCGGTTTGACTCACGGGGATTTCCAAGTCTCC ACCCCATTGACGTCAATGGGAGTTTGTTTTGGCACCAAAATCAACGGGACTTTCCAAAATGTCGTAACAACTCCGCCCCATTGACGCAAA TGGGCGGTAGGCGTGTACGGTGGGAGGTCTATATAAGCAGAGCTCTCTGGCTAACTAGAGAACCCACTGCTTACTGGCTTATCGAAATT

AATACGACTCACTATAGG

SEQ ID NO: 10
GGGGG

SEQ ID NO: 11
SSSSS pDOM.MAGED4B-FJX1 (SEQ ID NO: 12)
GACGGATCGGGAGATCTCCCGATCCCCTATGGTGCACTCTCAGTACAATCTGCTCTGATGCCGCATAGTTAAGCCAGTATCTGCTCCCTG

CTTGTGTGTTGGAGGTCGCTGAGTAGTGCGCGAGCAAAATTTAAGCTACAACAAGGCAAGGCTTGACCGACAATTGCATGAAGAATCT

GCTTAGGGTTAGGCGTTTTGCGCTGCTTCGCGATGTACGGGCCAGATATACGCGTTGACATTGATTATTGACTAGTTATTAATAGTAATC

AATTACGGGGTCATTAGTTCATAGCCCATATATGGAGTTCCGCGTTACATAACTTACGGTAAATGGCCCGCCTGGCTGACCGCCCAACGA

CCCCCGCCCATTGACGTCAATAATGACGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTCAATGACGGTAAATGGCCCGCCTGGCA

TTATGCCCAGTACATGACCTTATGGGACTTTCCTACTTGGCAGTACATCTACGTATTAGTCATCGCTATTACCATGGTGATGCGGTTTTGG

CAGTACATCAATGGGCGTGGATAGCGGTTTGACTCACGGGGATTTCCAAGTCTCCACCCCATTGACGTCAATGGGAGTTTGTTTTGGCA

CCAAAATCAACGGGACTTTCCAAAATGTCGTAACAACTCCGCCCCATTGACGCAAATGGGCGGTAGGCGTGTACGGTGGGAGGTCTATA

TAAGCAGAGCTCTCTGGCTAACTAGAGAACCCACTGCTTACTGGCTTATCGAAATTAATACGACTCACTATAGGGAGACCCAAGCTTGCC

GCCACCATGGGTTGGAGCTGTATCATCTTCTTTCTGGTAGCAACAGCTACAGGTGTGCACTCCAAAAACCTTGATTGTTGGGTCGACAAC

GAAGAAGACATCGATGTTATCCTGAAAAAGTCTACCATTCTGAACTTGGACATCAACAACGATATTATCTCCGACATCTCTGGTTTCAACT

CCTCTGTTATCACATATCCAGATGCTCAATTGGTGCCGGGCATCAACGGCAAAGCTATCCACCTGGTTAACAACGAATCTTCTGAAGTTA

TCGTGCACAAGGCCATGGACATCGAATACAACGACATGTTCAACAACTTCACCGTTAGCTTCTGGCTGCGCGTTCCGAAAGTTTCTGCTT

CCCACCTGGAACAGTACGGCACTAACGAGTACTCCATCATCAGCTCTATGAAGAAACACTCCCTGTCCATCGGCTCTGGTTGGTCTGTTT

-continued

CCCTGAAGGGTAACAACCTGATCTGGACTCTGAAAGACTCCGCGGGCGAAGTTCGTCAGATCACTTTCCGCGACCTGCCGGACAAGTTC

AACGCGTACCTGGCTAACAAATGGGTTTTCATCACTATCACTAACGATCGTCTGTCTTCTGCTAACCTGTACATCAACGGCGTTCTGATGG

GCTCCGCTGAAATCACTGGTCTGGGCGCTATCCGTGAGGACAACAACATCACTCTTAAGCTGGACCGTTGCAACAACAACAACCAGTAC

GTATCCATCGACAAGTTCCGTATCTTCTGCAAAGCACTGAACCCGAAAGAGATCGAAAAACTGTATACCAGCTACCTGTCTATCACCTTC

CTGCGTGACTTCTGGGGTAACGCGGCCGCTGGACCCGGACCTATGGCTGAGGGAAGCTTCAGCGTGCAATCGGAAAGCTACAGTGTTG

AAGACATGGATGAGGGTAGCGACGAAGTCGGGGAGGAAGAGATGGTTGAAGGCAACGACTATGAAGAATTCGGTGCGTTTGGTGGC

TATGGCACCCTCACCAGCTTTGACATCCATATCCTCAGAGCCTTCGGAAGCTTGGGTCCAGGCCTTCGCATCTTATCGAATGAGCCCTGG

GAACTGGAAAACCCTGTGCTGGCCCAGACCCTGGTGGAGGCATTGCAGCTGGATCCGGAAACACTTGCCAATGAGACGGCCGCCCGTG

CTGCCAACGTAGCCCGCGCCGCCGCCTCCAACCGTGCGGCTCGGGCCGCTGCCGCCGCTGCCCGTACCGCCTTCAGTCAGGTGGTCGCT

AGCCACCGGGTGGCCACGCCGCAGGTCTCAGGAGAGGATACCCAGCCCACGACCTACGCCGCCGAGGCTCAGGGGCCCACCCCTGAGC

CACCCCTTGCTTCTCCGCAGACCTCCCAGATGTTAGTCACCAGTAAGATGGCTGCCCCCGAGGCTCCGGCAACCTCCGCACAGTCCCAGA

CAGGCTCCCCGGCCCAGGAGGCTGCTACTGAGGGCCCTAGTAGCGCCTGTGCTTTCTCTCAGGCTCCGTGTGCCAGGGAGGTGGACGC

CAACCGGCCCAGCACAGCCTTCCTGGGCCAGAATGATGTCTTCGATTTCACTCAGCCGGCAGGTGTCAGTGGCATGGCCTTCCCGCGCC

CCAAGAGACCTGCCCCAGCCCAAGAGGCTGCCACAGAGGGCCCCAGTGCTGCCTCTGGTGTGCCCCAGACGGGACCTGGCAGGGAGG

TGGCAGCCACCCGGCCCAAGACCACCAAGTCGGGGAAGGCGCTGGCCAAGACTCGGTGGGTGGAGCCTCAGAATGTTGTGGCAGCAG

CTGCTGCCAAGGCCAAGATGGCCACGAGCATCCCTGAGCCGGAGGGTGCAGCTGCTGCCACTGCTCAGCACAGTGCTGAGCCCTGGGC

CAGGATGGGAGGCAAGAGGACCAAGAAGTCCAAGCACCTGGATGATGAGTATGAGAGCAGCGAGGAGGAGAGAGAGACTCCCGCGG

TCCCACCCACCTGGAGAGCATCACAGCCCTCATTGACGGTGCGGGCTCAGTTGGCCCCTCGGCCCCCGATGGCCCCGAGGTCCCAGATA

CCCTCAAGGCACGTACTGTGCCTGCCCCCCCGCAACGTGACCCTTCTGCAGGAGAGGGCAAATAAGTTGGTGAAATACCTGATGATTAA

GGACTACAAGAAGATCCCCATCAAGCGCGCAGACATGCTGAAGGATGTCATCAGAGAATATGATGAACATTTCCCTGAGATCATTGAAC

GAGCAACGTACACCCTGGAAAAGAAGTTTGGGATCCACCTGAAGGAGATCGACAAGGAAGAACACCTGTATATTCTTGTCTGCACACG

GGACTCCTCAGCTCGCCTCCTTGGAAAAACCAAGGACACTCCCAGGCTGAGTCTCCTCTTGGTGATTCTGGGCGTCATCTTCATGAATGG

CAACCGTGCCAGCGAGGCTGTCCTCTGGGAGGCACTACGCAAGATGGGACTGCGCCCTGGGGTGAGGCACCCATTCCTCGGCGATCTG

AGGAAGCTCATCACAGATGACTTTGTGAAGCAGAAGTACCTGGAATACAAGAAGATCCCCAACAGCAACCCACCTGAGTATGAATTCCT

CTGGGGCCTGCGAGCCCGCCATGAGACCAGCAAGATGAGGGTCCTGAGATTCATCGCCCAGAATCAGAACCGAGACCCCCGGGAATG

GAAGGCTCATTTCTTGGAGGCTGTGGATGATGCTTTCAAGACAATGGATGTGGATATGGCCGAGGAACATGCCAGGGCCCAGATGAGG

GCCCAGATGAATATCGGGGATGAAGCGCTGATTGGACGGTGGAGCTGGGATGACATACAAGTCGAGCTCCTGACCTGGGATGAGGAC

GGAGATTTTGGCGATGCCTGGGCCAGGATCCCCTTTGCTTTCTGGGCCAGATACCATCAGTACATTCTGAATAGCAACCGTGCCAACAG

GAGGGCCACGTGGAGAGCTGGCGTCAGCAGTGGCACCAATGGAGGGGCCAGCACCAGCGTCCTAGATGGCCCCAGCACCAGCTCCAC

CATCCGGACCAGAAATGCTGCCAGAGCTGGCGCCAGCTTCTTCTCCTGGATCCAGCACCGTGGTTCTGGCTCTGGCATGGGCAGGAGGA

TGCGGGGCGCCGCCGCCACCGCGGGGCTCTGGCTGCTGGCGCTGGGCTCGCTGCTGGCGCTGTGGGGAGGGCTCCTGCCGCCGCGGA

CCGAGCTGCCCGCCTCCCGGCCGCCCGAAGACCGACTCCCACGGCGCCCGGCCCGGAGCGGCGGCCCCGCGCCCGCGCCTCGCTTCCCT

CTGCCCCCGCCCCTGGCGTGGGACGCCCGCGGCGGCTCCCTGAAAACTTTCCGGGCGCTGCTCACCCTGGCGGCCGGCGCGGACGGCC

CGCCCCGGCAGTCCCGGAGCGAGCCCAGGTGGCACGTGTCAGCCAGGCAGCCCCGGCCGGAGGAGAGCGCCGCGGTGCACGGGGGC

GTCTTCTGGAGCCGCGGCCTGGAGGAGCAGGTGCCCCCGGGCTTTTCGGAGGCCCAGGCGGCGGCGTGGCTGGAGGCGGCTCGCGGC

GCCCGGATGGTGGCCCTGGAGCGCGGGGGTTGCGGGCGCAGCTCCAACCGACTGGCCCGTTTTGCCGACGGCACCCGCGCCTGCGTGC

GCTACGGCATCAACCCGGAGCAGATTCAGGGCGAGGCCCTGTCTTACTATCTGGCGCGCCTGCTGGGCCTCCAGCGCCACGTGCCGCCG

CTGGCACTGGCTCGGGTGGAGGCTCGGGGCGCGCAGTGGGCGCAGGTGCAGGAGGAGCTGCGCGCTGCGCACTGGACCGAGGGCAG

-continued

CGTGGTGAGCCTGACACGCTGGCTGCCCAACCTCACGGACGTGGTGGTGCCCGCGCCCTGGCGCTCGGAGGACGGCCGTCTGCGCCCC

CTCCGGGATGCCGGGGGTGAGCTGGCCAACCTCAGCCAGGCGGAGCTGGTGGACCTAGTACAATGGACCGACTTAATCCTTTTCGACT

ACCTGACGGCCAACTTCGACCGGCTCGTAAGCAACCTCTTCAGCCTGCAGTGGGACCCGCGCGTCATGCAGCGTGCCACCAGCAACCTG

CACCGCGGTCCGGGCGGGGCGCTGGTCTTTCTGGACAATGAGGCGGGCTTGGTGCACGGCTACCGGGTAGCAGGCATGTGGGACAAG

TATAACGAGCCGCTGTTGCAGTCAGTGTGCGTGTTCCGCGAGCGGACCGCGCGGCGCGTCCTGGAGCTGCACCGCGGACAGGACGCCG

CTGCTGCGCCTCTACCGGCGCCACGAGCCTCGCTTCCCCGAGCTGGCCGCCTTGCAGACCCCCACGCTCAGCTGCTACAGCGCCGCCTCGAC

CGCCGCCTCGACTTCCTCGCCAAGCACATTTTGCACTGTAAGGCCAAGTACGGCCGCCGGTCTGGGACTTAGACTCGAGGACGGGCCCG

TTTAAACCCGCTGATCAGCCTCGACTGTGCCTTCTAGTTGCCAGCCATCTGTTGTTTGCCCCTCCCCCGTGCCTTCCTTGACCCTGGAAGG

TGCCACTCCCACTGTCCTTTCCTAATAAAATGAGGAAATTGCATCGCATTGTCTGAGTAGGTGTCATTCTATTCTGGGGGGTGGGGTGGG

GCAGGACAGCAAGGGGGAGGATTGGGAAGACAATAGCAGGCATGCTGGGGATGCGGTGGGCTCTATGGCTTCTGAGGCGGAAAGAA

CCAGCTGGGGCTCTAGGGGGTATCCCCACGCGCCCTGTAGCGGCGCATTAAGCGCGGCGGGTGTGGTGGTTACGCGCAGCGTGACCG

CTACACTTGCCAGCGCCCTAGCGCCCGCTCCTTTCGCTTTCTTCCCTTCCTTTCTCGCCACGTTCGCCGGCTTTCCCCGTCAAGCTCTAATC

GGGGGCTCCCTTTAGGGTTCCGATTTAGTGCTTTACGGCACCTCGACCCCAAAAAACTTGATTAGGGTGATGGTTCACGTAGTGGGCCA

TCGCCCTGATAGACGGTTTTTCGCCCTTTGACGTTGGAGTCCACGTTCTTTAATAGTGGACTCTTGTTCCAAACTGGAACAACACTCAAC

CTATCTCGGTCTATTCTTTTGATTTATAAGGGATTTTGCCGATTTCGGCCTATTGGTTAAAAAATGAGCTGATTTAACAAAAATTTAACGC

GAATTAATTCTGTGGAATGTGTGTCAGTTAGGGTGTGGAAAGTCCCCAGGCTCCCCAGCAGGCAGAAGTATGCAAAGCATGCATCTCAA

TTAGTCAGCAACCAGGTGTGGAAAGTCCCCAGGCTCCCCAGCAGGCAGAAGTATGCAAAGCATGCATCTCAATTAGTCAGCAACCATAG

TCCCGCCCCTAACTCCGCCCATCCCGCCCCTAACTCCGCCCAGTTCCGCCCATTCTCCGCCCCATGGCTGACTAATTTTTTTTATTTATGCA

GAGGCCGAGGCCGCCTCTGCCTCTGAGCTATTCCAGAAGTAGTGAGGAGGCTTTTTTGGAGGCCTAGGCTTTTGCAAAAAGCTCCCGGG

AGCTTGTATATCCATTTTCGGATCTGATCAAGAGACAGGATGAGGATCGTTTCGCATGATTGAACAAGATGGATTGCACGCAGGTTCTCC

GGCCGCTTGGGTGGAGAGGCTATTCGGCTATGACTGGGCACAACAGACAATCGGCTGCTCTGATGCCGCCGTGTTCCGGCTGTCAGCG

CAGGGGCGCCCGGTTCTTTTTGTCAAGACCGACCTGTCCGGTGCCCTGAATGAACTGCAGGACGAGGCAGCGCGGCTATCGTGGCTGG

CCACGACGGGCGTTCCTTGCGCAGCTGTGCTCGACGTTGTCACTGAAGCGGGAAGGGACTGGCTGCTATTGGGCGAAGTGCCGGGGCA

GGATCTCCTGTCATCTCACCTTGCTCCTGCCGAGAAAGTATCCATCATGGCTGATGCAATGCGGCGGCTGCATACGCTTGATCCGGCTAC

CTGCCCATTCGACCACCAAGCGAAACATCGCATCGAGCGAGCACGTACTCGGATGGAAGCCGGTCTTGTCGATCAGGATGATCTGGAC

GAAGAGCATCAGGGGCTCGCGCCAGCCGAACTGTTCGCCAGGCTCAAGGCGCGCATGCCCGACGGCGAGGATCTCGTCGTGACCCATG

GCGATGCCTGCTTGCCGAATATCATGGTGGAAAATGGCCGCTTTTCTGGATTCATCGACTGTGGCCGGCTGGGTGTGGCGGACCGCTAT

CAGGACATAGCGTTGGCTACCCGTGATATTGCTGAAGAGCTTGGCGGCGAATGGGCTGACCGCTTCCTCGTGCTTTACGGTATCGCCGC

TCCCGATTCGCAGCGCATCGCCTTCTATCGCCTTCTTGACGAGTTCTTCTGAGCGGGACTCTGGGGTTCGAAATGACCGACCAAGCGACG

CCCAACCTGCCATCACGAGATTTCGATTCCACCGCCGCCTTCTATGAAAGGTTGGGCTTCGGAATCGTTTTCCGGGACGCCGGCTGGATG

ATCCTCCAGCGCGGGGATCTCATGCTGGAGTTCTTCGCCCACCCCAACTTGTTTATTGCAGCTTATAATGGTTACAAATAAAGCAATAGC

ATCACAAATTTCACAAATAAAGCATTTTTTTCACTGCATTCTAGTTGTGGTTTGTCCAAACTCATCAATGTATCTTATCATGTCTGTATACC

GTCGACCTCTAGCTAGAGCTTGGCGTAATCATGGTCATAGCTGTTTCCTGTGTAAATTGTTATCCGCTCACAATTCCACACAACATACGA

GCCGGAAGCATAAAGTGTAAAGCCTGGGGTGCCTAATGAGTGAGCTAACTCACATTAATTGCGTTGCGCTCACTGCCCGCTTTCCAGTC

GGGAAACCTGTCGTGCCAGCTGCATTAATGAATCGGCCAACGCGCGGGGAGAGGCGGTTTGCGTATTGGGCGCTCTTCCGCTTCCTCGC

TCACTGACTCGCTGCGCTCGGTCGTTCGGCTGCGGCGAGCGGTATCAGCTCACTCAAAGGCGGTAATACGGTTATCCACAGAATCAGGG

GATAACGCAGGAAAGAACATGTGAGCAAAAGGCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAACCCGACAGGACTATAAAGATACCAGGCGTTTCC

CCCTGGAAGCTCCCTCGTGCGCTCTCCTGTTCCGACCCTGCCGCTTACCGGATACCTGTCCGCCTTTCTCCCTTCGGGAAGCGTGGCGCTT

TCTCATAGCTCACGCTGTAGGTATCTCAGTTCGGTGTAGGTCGTTCGCTCCAAGCTGGGCTGTGTGCACGAACCCCCCGTTCAGCCCGAC

-continued

CGCTGCGCCTTATCCGGTAACTATCGTCTTGAGTCCAACCCGGTAAGACACGACTTATCGCCACTGGCAGCAGCCACTGGTAACAGGATT

AGCAGAGCGAGGTATGTAGGCGGTGCTACAGAGTTCTTGAAGTGGTGGCCTAACTACGGCTACACTAGAAGAACAGTATTTGGTATCT

GCGCTCTGCTGAAGCCAGTTACCTTCGGAAAAAGAGTTGGTAGCTCTTGATCCGGCAAACAAACCACCGCTGGTGCGGTTTTTTTGTTT

GCAAGCAGCAGATTACGCGCAGAAAAAAAGGATCTCAAGAAGATCCTTTGATCTTTTCTACGGGGTCTGACGCTCAGTGGAACGAAAAC

TCACGTTAAGGGATTTTGGTCATGAGATTATCAAAAAGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACCTATCTCAGCGATCTGTCTATTTCGTTCATCCATAGT

TGCCTGACTCCCCGTCGTGTAGATAACTACGATACGGGAGGGCTTACCATCTGGCCCCAGTGCTGCAATGATACCGCGAGACCCACGCT

CACCGGCTCCAGATTTATCAGCAATAAACCAGCCAGCCGGAAGGGCCGAGCGCAGAAGTGGTCCTGCAACTTTATCCGCCTCCATCCAG

TCTATTAATTGTTGCCGGGAAGCTAGAGTAAGTAGTTCGCCAGTTAATAGTTTGCGCAACGTTGTTGCCATTGCTACAGGCATCGTGGTG

TCACGCTCGTCGTTTGGTATGGCTTCATTCAGCTCCGGTTCCCAACGATCAAGGCGAGTTACATGATCCCCCATGTTGTGCAAAAAAGCG

GTTAGCTCCTTCGGTCCTCCGATCGTTGTCAGAAGTAAGTTGGCCGCAGTGTTATCACTCATGGTTATGGCAGCACTGCATAATTCTCTTA

CTGTCATGCCATCCGTAAGATGCTTTTCTGTGACTGGTGAGTACTCAACCAAGTCATTCTGAGAATAGTGTATGCGGCGACCGAGTTGCT

CTTGCCCGGCGTCAATACGGGATAATACCGCGCCACATAGCAGAACTTTAAAAGTGCTCATCATTGGAAAACGTTCTTCGGGGCGAAAA

CTCTCAAGGATCTTACCGCTGTTGAGATCCAGTTCGATGTAACCCACTCGTGCACCCAACTGATCTTCAGCATCTTTTACTTTCACCAGCGT

TTCTGGGTGAGCAAAAACAGGAAGGCAAAATGCCGCAAAAAAGGGAATAAGGGCGACACGGAATGTTGAATACTCATACTCTTCCTT

TTTCAATATTATTGAAGCATTTATCAGGGTTATTGTCTCATGAGCGGATACATATTTGAATGTATTTAGAAAAATAAACAAATAGGGGTTC

CGCGCACATTTCCCCGAAAAGTGCCACCTGACGTC

DOM1 = underlined
MAGED4B = double underlined
FJX1 = dotted underlined pDOM.MAGED4B (SEQ ID NO: 13)
GACGGATCGGGAGATCTCCCGATCCCCTATGGTGCACTCTCAGTACATCTGCTCTGATGCCGCATAGTTAAGCCAGTATCTGCTCCCTG CTTGTGTGTTGGAGGTCGCTGAGTAGTGCGCGAGCAAAATTTAAGCTACAACAAGGCAAGGCTTGACCGACAATTGCATGAAGAATCT GCTTAGGGTTAGGCGTTTTGCGCTGCTTCGCGATGTACGGGCCAGATATACGCGTTGACATTGATTATTGACTAGTTATTAATAGTAATC AATTACGGGGTCATTAGTTCATAGCCCATATATGGAGTTCCGCGTTACATAACTTACGGTAAATGGCCCGCCTGGCTGACCGCCCAACGA CCCCCGCCCATTGACGTCAATAATGACGTATGTTCCCATAGTAACGCCAATAGGGACTTTCCATTGACGTCAATGGGTGGAGATTTACG GTAAACTGCCCACTTGGCAGTACATCAAGTGTATCATATGCCAAGTACGCCCCCTATTGACGTCAATGACGGTAAATGGCCCGCCTGGCA TTATGCCCAGTACATGACCTTATGGGACTTTCCTACTTGGCAGTACATCTACGTATTAGTCATCGCTATTACCATGGTGATGCGGTTTTGG CAGTACATCAATGGGCGTGGATAGCGGTTTGACTCACGGGGATTTCCAAGTCTCCACCCCATTGACGTCAATGGGAGTTTGTTTTGGCA CCAAAATCAACGGGACTTTCCAAAATGTCGTAACAACTCCGCCCCATTGACGCAAATGGGCGGTAGGCGTGTACGGTGGGAGGTCTATA TAAGCAGAGCTCTCTGGCTAACTAGAGAACCCACTGCTTACTGGCTTATCGAAATTAATACGACTCACTATAGGGAGACCCAAGCTTGCC GCCACCATGGGTTGGAGCTGTATCATCTTCTTTCTGGTAGCAACAGCTACAGGTGTGCACTCCAAAAACCTTGATTGTTGGGTCGACAAC GAAGAAGACATCGATGTTATCCTGAAAAAGTCTACCATTCTGAACTTGGACATCAACAACGATATTATCTCCGACATCTCTGGTTTCAACT CCTCTGTTATCACATATCCAGATGCTCAATTGGTGCCGGGCATCAACGGCAAAGCTATCCACCTGGTTAACAACGAATCTTCTGAAGTTA TCGTGCACAAGGCCATGGACATCGAATACAACGACATGTTCAACAACTTCACCGTTAGCTTCTGGCTGCGCGTTCCCGAAAGTTTCTGCTT CCCACCTGGAACAGTACGGCACTAACGAGTACTCCATCATCAGCTCTATGAAGAAACACTCCCTGTCCATCGGCTCTGGTTGGTCTGTTT CCCTGAAGGGTAACAACCTGATCTGGACTCTGAAAGACTCCGCGGGCGAAGTTCGTCAGATCACTTTCCGCGACCTGCCGGACAAGTTC AACGCGTACCTGGCTAACAAATGGGTTTTCATCACTATCACTAACGATCGTCTGTCTTCTGCTAACCTGTACATCAACGGCGTTCTGATGG GCTCCGCTGAAATCACTGGTCTGGGCGCTATCCGTGAGGACAACAACATCACTCTTAAGCTGGACCGTTGCAACAACAACAACCAGTAC GTATCCATCGACAAGTTCCGTATCTTCTGCAAAGCACTGAACCCGAAAGAGATCGAAAAACTGTATACCAGCTACCTGTCTATCACCTTC CTGCGTGACTTCTGGGGTAACGCGGCCGCTGGACCCGGACCTATGGCTGAGGGAAGCTTCAGCGTGCAATCGGAAAGCTACAGTGTTG -continued AAGACATGGATGAGGGTAGCGACGAAGTCGGGGAGGAAGAGATGGTTGAAGGCAACGACTATGAAGAATTCGGTGCGTTTGGTGGC TATGGCACCCTCACCAGCTTTGACATCCATATCCTCAGAGCCTTCGGAAGCTTGGGTCCAGGCCTTCGCATCTTATCGAATGAGCCCTGG GAACTGGAAAACCCTGTGCTGGCCCAGACCCTGGTGGAGGCATTGCAGCTGGATCCGGAAACACTTGCCAATGAGACGGCCGCCCGTG CTGCCAACGTAGCCCGCGCCGCCGCCTCCAACCGTGCGGCTCGGGCCGCTGCCGCCGCTGCCCGTACCGCCTTCAGTCAGGTGGTCGCT AGCCACCGGGTGGCCACGCCGCAGGTCTCAGGAGAGGATACCCAGCCCACGACCTACGCCGCCGAGGCTCAGGGGCCCACCCCTGAGC CACCCCTTGCTTCTCCGCAGACCTCCCAGATGTTAGTCACCAGTAAGATGGCTGCCCCCGAGGCTCCGGCAACCTCCGCACAGTCCCAGA CAGGCTCCCCGGCCCAGGAGGCTGCTACTGAGGGCCCTAGTAGCGCCTGTGCTTTCTCTCAGGCTCCGTGTGCCAGGGAGGTGGACGC CAACCGGCCCAGCACAGCCTTCCTGGGCCAGAATGATGTCTTCGATTTCACTCAGCCGGCAGGTGTCAGTGGCATGGCCTTCCCGCGCC CCAAGAGACCTGCCCCAGCCCAAGAGGCTGCCACAGAGGGCCCCAGTGCTGCCTCTGGTGTGCCCCAGACGGGACCTGGCAGGGAGG TGGCAGCCACCCGGCCCAAGACCACCAAGTCGGGGAAGGCGCTGGCCAAGACTCGGTGGGTGGAGCCTCAGAATGTTGTGGCAGCAG CTGCTGCCAAGGCCAAGATGGCCACGAGCATCCCTGAGCCGGAGGGTGCAGCTGCTGCCACTGCTCAGCACAGTGCTGAGCCCTGGGC CAGGATGGGAGGCAAGAGGACCAAGAAGTCCAAGCACCTGGATGATGAGTATGAGAGCAGCGAGGAGGAGAGAGAGACTCCCGCGG TCCCACCCACCTGGAGAGCATCACAGCCCTCATTGACGGTGCGGGCTCAGTTGGCCCCTCGGCCCCCGATGGCCCCGAGGTCCCAGATA CCCTCAAGGCACGTACTGTGCCTGCCCCCCCGCAACGTGACCCTTCTGCAGGAGAGGGCAAATAAGTTGGTGAAATACCTGATGATTAA GGACTACAAGAAGATCCCCATCAAGCGCGCAGACATGCTGAAGGATGTCATCAGAGAATATGATGAACATTTCCCTGAGATCATTGAAC GAGCAACGTACACCCTGGAAAAGAAGTTTGGGATCCACCTGAAGGAGATCGACAAGGAAGAACACCTGTATATTCTTGTCTGCACACG GGACTCCTCAGCTCGCCTCCTTGGAAAAACCAAGGACACTCCCAGGCTGAGTCTCCTCTTGGTGATTCTGGGCGTCATCTTCATGAATGG CAACCGTGCCAGCGAGGCTGTCCTCTGGGAGGCACTACGCAAGATGGGACTGCGCCCTGGGGTGAGGCACCCATTCCTCGGCGATCTG AGGAAGCTCATCACAGATGACTTTGTGAAGCAGAAGTACCTGGAATACAAGAAGATCCCCAACAGCAACCCACCTGAGTATGAATTCCT CTGGGGCCTGCGAGCCCGCCATGAGACCAGCAAGATTGAGGGTCCTGAGATTCATCGCCCAGAATCAGAACCGAGACCCCCGGGAATG GAAGGCTCATTTCTTGGAGGCTGTGGATGATGCTTTCAAGACAATGGATGTGGATATGGCCGAGGAACATGCCAGGGCCCAGATGAGG GCCCAGATGAATATCGGGGATGAAGCGCTGATTGGACGGTGGAGCTGGGATGACATACAAGTCGAGCTCCTGACCTGGGATGAGGAC GGAGATTTTGGCGATGCCTGGGCCAGGATCCCCTTTGCTTTCTGGGCCAGATACCATCAGTACATTCTGAATAGCAACCGTGCCAACAG GAGGGCCACGTGGAGAGCTGGCGTCAGCAGTGGCACCAATGGAGGGGCCAGCACCAGCGTCCTAGATGGCCCCAGCACCAGCTCCAC CATCCGGACCAGAAATGCTGCCAGAGCTGGCGCCAGCTTCTTCTCCTGGATCCAGCACCGTTGAACTCGAGGACGGGCCCGTTTAAACC CGCTGATCAGCCTCGACTGTGCCTTCTAGTTGCCAGCCATCTGTTGTTTGCCCCTCCCCCGTGCCTTCCTTGACCCTGGAAGGTGCCACTC CCACTGTCCTTTCCTAATAAAATGAGGAAATTGCATCGCATTGCTGAGTAGGTGCATTCTATTCTGGGGGGTGGGGTGGGGCAGGAC AGCAAGGGGGAGGATTGGGAAGACAATAGCAGGCATGCTGGGGATGCGGTGGGCTCTATGGCTTCTGAGGCGGAAAGAACCAGCTG GGGCTCTAGGGGGTATCCCCACGCGCCCTGTAGCGGCGCATTAAGCGCGGCGGGTGTGGTGGTTACGCGCAGCGTGACCGCTACACTT GCCAGCGCCCTAGCGCCCGCTCCTTTCGCTTTCTTCCCTTCCTTTCTCGCCACGTTCGCCGGCTTTCCCCGTCAAGCTCTAAATCGGGGGCT CCCTTTAGGGTTCCGATTTAGTGCTTTACGGCACCTCGACCCCAAAAAACTTGATTAGGGTGATGGTTCACGTAGTGGGCCATCGCCCTG ATAGACGGTTTTTCGCCCTTTGACGTTGGAGTCCACGTTCTTTAATAGTGGACTCTTGTTCCAAACTGGAACAACACTCAACCCTATCTCG GTCTATTCTTTTGATTTATAAGGGATTTTGCCGATTTCGGCCTATTGGTTAAAAAATGAGCTGATTTAACAAAAATTTAACGCGAATTAAT TCTGTGGAATGTGTGTCAGTTAGGGTGTGGAAAGTCCCCAGGCTCCCCAGCAGGCAGAAGTATGCAAAGCATGCATCTCAATTAGTCAG CAACCAGGTGTGGAAAGTCCCCAGGCTCCCCGCAGGCAGAAGTATGCAAAGCATGCATCTCAATTAGTCAGCAACCATAGTTCCCGCCC CTAACTCCGCCCATCCCGCCCCTAACTCCGCCCAGTTCCGCCCATTCTCCGCCCCATGGCTGACTAATTTTTTTTATTTATGCAGAGGCCGA GGCCGCCTCTGCCTCTGAGCTATTCCAGAAGTAGTGAGGAGGCTTTTTTGGAGGCCTAGGCTTTTGCAAAAAGCTCCCGGGAGCTTGTA TATCCATTTTCGGATCTGATCAAGAGACAGGATGAGGATCGTTTCGCATGATTGAACAAGATGGATTGCACGCAGGTTCTCCGGCCGCT TGGGTGGAGAGGCTATTCGGCTATGACTGGGCACAACAGACAATCGGCTGCTCTGATGCCGCCGTGTTCCGGCTGTCAGCGCAGGGGC GCCCGGTTCTTTTTGTCAAGACCGACCTGTCCGGTGCCCTGAATGAACTGCAGGACGAGGCAGCGCGGCTATCGTGGCTGGCCACGACG GGCGTTCCTTGCGCAGCTGTGCTCGACGTTGTCACTGAAGCGGGAAGGGACTGGCTGCTATTGGGCGAAGTGCCGGGGCAGGATCTCC -continued TGTCATCTCACCTTGCTCCTGCCGAGAAAGTATCCATCATGGCTGATGCAATGCGGCGGCTGCATACGCTTGATCCGGCTACCTGCCCAT TCGACCACCAAGCGAAACATCGCATCGAGCGAGCACGTACTCGGATGGAAGCCGGTCTTGTCGATCAGGATGATCTGGACGAAGAGCA TCAGGGGCTCGCGCCAGCCGAACTGTTCGCCAGGCTCAAGGCGCGCATGCCCGACGGCGAGGATCTCGTCGTGACCCATGGCGATGCC TGCTTGCCGAATATCATGGTGGAAAATGGCCGCTTTTCTGGATTCATCGACTGTGGCCGGCTGGGTGTGGCGGACCGCTATCAGGACAT AGCGTTGGCTACCCGTGATATTGCTGAAGAGCTTGGCGGCGAATGGGCTGACCGCTTCCTCGTGCTTTACGGTATCGCCGCTCCCGATTC GCAGCGCATCGCCTTCTATCGCCTTCTTGACGAGTTCTTCTGAGCGGGACTCTGGGGTTCGAAATGACCGACCAAGCGACGCCCAACCT GCCATCACGAGATTTCGATTCCACCGCCGCCTTCTATGAAAGGTTGGGCTTCGGAATCGTTTTCCGGGACGCCGGCTGGATGATCCTCCA GCGCGGGGATCTCATGCTGGAGTTCTTCGCCCACCCCAACTTGTTTATTGCAGCTTATAATGGTTACAAATAAAGCAATAGCATCACAAA TTTCACAAATAAAGCATTTTTTTCACTGCATTCTAGTTGTGGTTTGTCCAAACTCATCAATGTATCTTATCATGTCTGTATACCGTCGACCTC TAGCTAGAGCTTGGCGTAATCATGGTCATAGCTGTTTCCTGTGTGAAATTGTTATCCGCTCACAATTCCACACAACATACGAGCCGGAAG CATAAAGTGTAAAGCCTGGGGTGCCTAATGAGTGAGCTAACTCACATTAATTGCGTTGCGCTCACTGCCCGCTTTCCAGTCGGGAAACCT GTCGTGCCAGCTGCATTAATGAATCGGCCAACGCGCGGGGAGAGGCGGTTTGCGTATTGGGCGCTCTTCCGCTTCCTCGCTCACTGACT CGCTGCGCTCGGTCGTTCGGCTGCGGCGAGCGGTATCAGCTCACTCAAAGGCGGTAATACGGTTATCCACAGAATCAGGGGATAACGC AGGAAAGAACATGTGAGCAAAAGGCCAGCAAAAGGCCAGGAACCGTAAAAAGGCCGCGTTGCTGGCGTTTTTCCATAGGCTCCGCCCC CCTGACGAGCATCACAAAAATCGACGCTCAAGTCAGAGGTGGCGAAACCCGACAGGACTATAAAGATACCAGGCGTTTCCCCCTGGAA GCTCCCTCGTGCGCTCTCCTGTTCCGACCCTGCCGCTTACCGGATACCTGTCCGCCTTTCTCCCTTCGGGAAGCGTGGCGCTTTCTCATAG CTCACGCTGTAGGTATCTCAGTTCGGTGTAGGTCGTTCGCTCCAAGCTGGGCTGTGTGCACGAACCCCCCGTTCAGCCCGACCGCTGCGC CTTATCCGGTAACTATCGTCTTGAGTCCAACCCGGTAAGACACGACTTATCGCCACTGGCAGCAGCCACTGGTAACAGGATTAGCAGAG CGAGGTATGTAGGCGGTGCTACAGAGTTCTTGAAGTGGTGGCCTAACTACGGCTACACTAGAAGAACAGTATTTGGTATCTGCGCTCTG CTGAAGCCAGTTACCTTCGGAAAAAGAGTTGGTAGCTCTTGATCCGGCAAACAAACCACCGCTGGTAGCGGTTTTTTTGTTTGCAAGCA GCAGATTACGCGCAGAAAAAAAGGATCTCAAGAAGATCCTTTGATCTTTTCTACGGGGTCTGACGCTCAGTGGAACGAAAACTCACGTT AAGGGATTTTGGTCATGAGATTATCAAAAAGGATCTTCACCTAGATCCTTTTAAATTAAAAATGAAGTTTTAAATCAATCTAAAGTATATA TGAGTAAACTTGGTCTGACAGTTACCAATGCTTAATCAGTGAGGCACCTATCTCAGCGATCTGTCTATTTCGTTCATCCATAGTTGCCTGA CTCCCCGTCGTGTAGATAACTACGATACGGGAGGGCTTACCATCTGGCCCCAGTGCTGCAATGATACCGCGAGACCCACGCTCACCGGC TCCAGATTTATCAGCAATAAACCAGCCAGCCGGAAGGGCCGAGCGCAGAAGTGGTCCTGCAACTTTATCCGCCTCCATCCAGTCTATTAA TTGTTGCCGGGAAGCTAGAGTAAGTAGTTCGCCAGTTAATAGTTTGCGCAACGTTGTTGCCATTGCTACAGGCATCGTGGTGTCACGCTC GTCGTTTGGTATGGCTTCATTCAGCTCCGGTTCCCAACGATCAAGGCGAGTTACATGATCCCCCATGTTGTGCAAAAAAGCGGTTAGCTC CTTCGGTCCTCCGATCGTTGTCAGAAGTAAGTTGGCCGCAGTGTTATCACTCATGGTTATGGCAGCACTGCATAATTCTCTTACTGTCATG CCATCCGTAAGATGCTTTTCTGTGACTGGTGAGTACTCAACCAAGTCATTCTGAGAATAGTGTATGCGGCGACCGAGTTGCTCTTGCCCG GCGTCAATACGGGATAATACCGCGCCACATAGCAGAACTTTAAAAGTGCTCATCATTGGAAAACGTTCTTCGGGGCGAAAACTCTCAAG GATCTTACCGCTGTTGAGATCCAGTTCGATGTAACCCACTCGTGCACCCAACTGATCTTGCAGCATCTTTTACTTTCACCAGCGTTTCTGGG TGAGCAAAAACAGGAAGGCAAAATGCCGCAAAAAAGGGAATAAGGGCGACACGGAAATGTTGAATACTCATACTCTTCCTTTTTCAATA TTATTGAAGCATTTATCAGGGTTATTGTCTCATGAGCGGATACATATTTGAATGTATTTAGAAAAATAAACAAATAGGGGTTCCGCGCAC

ATTTCCCCGAAAAGTGCCACCTGACGTC

DOM1 = underlined; MAGED4B = double underlined pDOM.FJX1 (SEQ ID NO: 14)
GACGGATCGGGAGATCTCCCGATCCCCTATGGTGCACTCTCAGTACAATCTGCTCTGATGCCGCATAGTTAAGCCAGTATCTGCTCCCTG CTTGTGTGTTGGAGGTCGCTGAGTAGTGCGCGAGCAAAATTTAAGCTACAACAAGGCAAGGCTTGACCGACAATTGCATGAAGAATCT GCTTAGGGTTAGGCGTTTTGCGCTGCTTCGCGATGTACGGGCCAGATATACGCGTTGACATTGATTATTGACTAGTTATTAATAGTAATC AATTACGGGGTCATTAGTTCATAGCCCATATATGGAGTTCCGCGTTACATAACTTACGGTAAATGGCCCGCCTGGCTGACCGCCCAACGA CCCCCGCCCATTGACGTCAATAATGACGTATGTTCCCATAGTAACGCCAATAGGGACTTTCCATTGACGTCAATGGGTGGAGTATTTACG -continued GTAAACTGCCCACTTGGCAGTACATCAAGTGTATCATATGCCAAGTACGCCCCCTATTGACGTCAATGACGGTAAATGGCCCGCCTGGCA TTATGCCCAGTACATGACCTTATGGGACTTTCCTACTTGGCAGTACATCTACGTATTAGTCATCGCTATTACCATGGTGATGCGGTTTTGG CAGTACATCAATGGGCGTGGATAGCGGTTTGACTCACGGGGATTTCCAAGTCTCCACCCCATTGACGTCAATGGGAGTTTGTTTTGGCA CCAAAATCAACGGGACTTTCCAAAATGTCGTAACAACTCCGCCCCATTGACGCAAATGGGCGGTAGGCGTGACGGTGGGAGGTCTATA TAAGCAGAGCTCTCTGGCTAACTAGAGAACCCACTGCTTACTGGCTTATCGAAATTAATACGACTCACTATAGGGAGACCCAAGCTTGCC GCCACCATGGGTTGGAGCTGTATCATCTTCTTTCTGGTAGCAACAGCTACAGGTGTGCACTCCAAAAACCTTGATTGTTGGGTCGACAAC GAAGAAGACATCGATGTTATCCTGAAAAAGTCTACCATTCTGAACTTGGACATCAACAACGATATTATCTCCGACATCTCTGGTTTCAACT CCTCTGTTATCACATATCCAGATGCTCAATTGGTGCCGGGCATCAACGGCAAAGCTATCCACCTGGTTAACAACGAATCTTCTGAAGTTA TCGTGCACAAGGCCATGGACATCGAATACAACGACATGTTCAACAACTTCACCGTTAGCTTCTGGCTGCGCGTTCCGAAAGTTTCTGCTT CCCACCTGGAACAGTACGGCACTAACGAGTACTCCATCATCAGCTCTATGAAGAAACACTCCCTGTCCATCGGCTCTGGTTGGTCTGTTT CCCTGAAGGGTAACAACCTGATCTGGACTCTGAAAGACTCCGCGGGCGAAGTTCGTCAGATCACTTTCCGCGACCTGCCGGACAAGTTC AACGCGTACCTGGCTAACAAATGGGTTTTCATCACTATCACTAACGATCGTCTGTCTTCTGCTAACCTGTACATCAACGGCGTTCTGATGG GCTCCGCTGAAATCACTGGTCTGGGCGCTATCCGTGAGGACAACAACATCACTCTTAAGCTGGACCGTTGCAACAACAACAACCAGTAC GTATCCATCGACAAGTTCCGTATCTTCTGCAAAGCACTGAACCCGAAAGAGATCGAAAAACTGTATACCAGCTACCTGTCTATCACCTTC CTGCGTGACTTCTGGGGTAACGCGGCCGCTGGACCCGGACCTATGGGCAGGAGGATGCGGGGCGCCGCCGCCACCGCGGGGCTCTGG CTGCTGGCGCTGGGCTCGCTGCTGGCGCTGTGGGGAGGGCTCCTGCCGCCGCGGACCGAGCTGCCCGCCTCCCGGCCGCCCGAAGACC GACTCCCACGGCGCCCGGCCCGGAGCGGCGGCCCCGCGCCCGCGCCTCGCTTCCCTCTGCCCCCGCCCCTGGCGTGGGACGCCCGCGG CGGCTCCCTGAAAACTTTCCGGGCGCTGCTCACCCTGGCGGCCGGCGCGGACGGCCCGCCCCGGCAGTCCCGGAGCGAGCCCAGGTGG CACGTGTCAGCCAGGCAGCCCCGGCCGGAGGAGAGCGCCGCGGTGCACGGGGGCGTCTTCTGGAGCCGCGGCCTGGAGGAGCAGGT CGGGGGTTGCGGGCGCAGCTCCAACCGACTGGCCGTTTTGCCGACGGCACCCGCGCCTGCGTGCGCTACGGCATCAACCCGGCGCAGATT GCGGGCGCAGCTCCAACCGACTGGCCCGTTTTGCCGACGGCACCCGCGCCTGCGTGCGCTACGGCATCAACCCGGAGCAGATTCAGGG CGAGGCCCTGTCTTACTATCTGGCGCGCCTGCTGGGCCTCCAGCGCCACGTGCCGCCGCTGGCACTGGCTCGGGTGGAGGCTCGGGGC GCGCAGTGGGCGCAGGTGCAGGAGGAGCTGCGCGCTGCGCACTGGACCGAGGGCAGCGTGGTGAGCCTGACACGCTGGCTGCCCAA CCTCACGGACGTGGTGGTGCCCGCGCCCTGGCGCTCGGAGGACGGCCGTCTGCGCCCCCTCCGGGATGCCGGGGGTGAGCTGGCCAA CCTCAGCCAGGCGGAGCTGGTGGACCTAGTACAATGGACCGACTTAATCCTTTTCGACTACCTGACGGCCAACTTCGACCGGCTCGTAA GCAACCTCTTCAGCCTGCAGTGGGACCCGCGCGTCATGCAGCGTGCCACCAGCAACCTGCACCGCGGTCCGGGCGGGGCGCTGGTCTTT CTGGACAATGAGGCGGGCTTGGTGCACGGCTACCGGGTAGCAGGCATGTGGGACAAGTATAACGAGCCGCTGTTGCAGTCAGTGTGC GTGTTCCGCGAGCGGACCGCGCGGCGCGTCCTGGAGCTGCACCGCGGACAGGACGCCGCGGCCCGGCTGCTGCGCCTCTACCGGCGC CACGAGCCTCGCTTCCCCGAGCTGGCCGCCCTTGCAGACCCCCACGCTCAGCTGCTACAGCGCCGCCTCGACTTCCTCGCCAAGCACATT TTGCACTGTAAGGCCAAGTACGGCCGCCGGTCTGGGACTTAGaCTCGAGGACGGGCCCGTTTAAACCCGCTGATCAGCCTCGACTGTGC CTTCTAGTTGCCAGCCATCTGTTGTTTGCCCCTCCCCCGTGCCTTCCTTGACCCTGGAAGGTGCCACTCCCACTGTCCTTTCCTAATAAAAT GAGGAAATTGCATCGCATTGTCTGAGTAGGTGTCATTCTATTCTGGGGGGTGGGGTGGGGCAGGACAGCAAGGGGGAGGATTGGGAA GACAATAGCAGGCATGCTGGGGATGCGGTGGGCTCTATGGCTTCTGAGGCGGAAAGAACCAGCTGGGGCTCTAGGGGGTATCCCCAC GCGCCCTGTAGCGGCGCATTAAGCGCGGCGGGTGTGGTGGTTACGCGCAGCGTGACCGCTACACTTGCCAGCGCCCTAGCGCCCGCTC CTTTCGCTTTCTTCCCTTCCTTTCTCGCCACGTTCGCCGGCTTTCCCCGTCAAGCTCTAAATCGGGGGCTCCCTTTAGGGTTCCGATTTAGT GCTTTACGGCACCTCGACCCCAAAAAACTTGATTAGGGTGATGGTTCACGTAGTGGGCCATCGCCCTGATAGACGGTTTTTCGCCCTTTG ACGTTGGAGTCCACGTTCTTTAATAGTGGACTCTTGTTCCAAACTGGAACAACACTCAACCCTATCTCGGTCTATTCTTTTGATTTATAAG GGATTTTGCCGATTTCGGCCTATTGGTTAAAAAATGAGCTGATTTAACAAAAATTTAACGCGAATTAATTCTGTGGAATGTGTGTCAGTT -continued AGGGTGTGGAAAGTCCCCAGGCTCCCCAGCAGGCAGAAGTATGCAAAGCATGCATCTCAATTAGTCAGCAACCAGGTGTGGAAAGTCC CCAGGCTCCCCAGCAGGCAGAAGTATGCAAAGCATGCATCTCAATTAGTCAGCAACCATAGTCCCGCCCCTAACTCCGCCCATCCCGCCC CTAACTCCGCCCAGTTCCGCCCATTCTCCGCCCCATGGCTGACTAATTTTTTTTATTTATGCAGAGGCCGAGGCCGCCTCTGCCTCTGAGC TATTCCAGAAGTAGTGAGGAGGCTTTTTTGGAGGCCTAGGCTTTTGCAAAAAGCTCCCGGGAGCTTGTATATCCATTTTCGGATCTGATC AAGAGACAGGATGAGGATCGTTTCGCATGATTGAACAAGATGGATTGCACGCAGGTTCTCCGGCCGCTTGGGTGGAGAGGCTATTCGG CTATGACTGGGCACAACAGACAATCGGCTGCTCTGATGCCGCCGTGTTCCGGCTGTCAGCGCAGGGGCGCCCGGTTCTTTTTGTCAAGA CCGACCTGTCCGGTGCCCTGAATGAACTGCAGGACGAGGCAGCGCGGCTATCGTGGCTGGCCACGACGGGCGTTCCTTGCGCAGCTGT GCTCGACGTTGTCACTGAAGCGGGAAGGGACTGGCTGCTATTGGGCGAAGTGCCGGGGCAGGATCTCCTGTCATCTCACCTTGCTCCTG CCGAGAAAGTATCCATCATGGCTGATGCAATGCGGCGGCTGCATACGCTTGATCCGGCTACCTGCCCATTCGACCACCAAGCGAAACAT CGCATCGAGCGAGCACGTACTCGGATGGAAGCCGGTCTTGTCGATCAGGATGATCTGGACGAAGAGCATCAGGGGCTCGCGCCAGCC GAACTGTTCGCCAGGCTCAAGGCGCGCATGCCCGACGGCGAGGATCTCGTCTGACCCATGGCGATGCCTGCTTGCCGAATATCATGGT GGAAAATGGCCGCTTTTCTGGATTCATCGACTGTGGCCGGCTGGGTGTGGCGGACCGCTATCAGGACATAGCGTTGGCTACCCGTGATA TTGCTGAAGAGCTTGGCGGCGAATGGGCTGACCGCTTCCTCGTGCTTTACGGTATCGCCGCTCCCGATTCGCAGCGCATCGCCTTCTATC GCCTTCTTGACGAGTTCTTCTGAGCGGGACTCTGGGGTTCGAAATGACCGACCAAGCGACGCCCAACCTGCCATCACGAGATTTCGATTC CACCGCCGCCTTCTATGAAAGGTTGGGCTTCGGAATCGTTTTCCGGGACGCCGGCTGGATGATCCTCCAGCGCGGGGATCTCATGCTGG AGTTCTTCGCCCACCCCAACTTGTTTATTGCAGCTTATAATGGTTACAAATAAAGCAATAGCATCACAAATTTCACAAATAAAGCATTTTT TCACTGCATTCTAGTTGTGGTTTGTCCAAACTCATCAATGTATCTTATCATGTCTGTATACCGTCGACCTCTAGCTAGAGCTTGGCGTAATC ATGGTCATAGCTGTTTCCTGTGTGAAATTGTTATCCGCTCACAATTCCACACAACATACGAGCCGGAAGCATAAAGTGTAAAGCCTGGG GTGCCTAATGAGTGAGCTAACTCACATTAATTGCGTTGCGCTCACTGCCCGCTTTCCAGTCGGGAAACCTGTCGTGCCAGCTGCATTAAT GAATCGGCCAACGCGCGGGGAGAGGCGGTTTGCGTATTGGGCGCTCTTCCGCTTCCTCGCTCACTGACTCGCTGCGCTCGGTCGTTCGG CTGCGGCGAGCGGTATCAGCTCACTCAAAGGCGGTAATACGGTTATCCACAGAATCAGGGGATAACGCAGGAAAGAACATGTGAGCAA AAGGCCAGCAAAAGGCCAGGAACCGTAAAAAGGCCGCGTTGCTGGCGTTTTTCCATAGGCTCCGCCCCCCTGACGAGCATCACAAAAAT CGACGCTCAAGTCAGAGGTGGCGAAACCCGACAGGACTATAAAGATACCAGGCGTTTCCCCCTGGAAGCTCCCTCGTGCGCTCTCCTGT TCCGACCCTGCCGCTTACCGGATACCTGTCCGCCTTTCTCCCTTCGGGAAGCGTGGCGCTTTCTCATAGCTCACGCTGTAGGTATCTCAGT TCGGTGTAGGTCGTTCGCTCCAAGCTGGGCTGTGTGCACGAACCCCCCGTTCAGCCCGACCGCTGCGCCTTATCCGGTAACTATCGTCTT GAGTCCAACCCGGTAAGACACGACTTATCGCCACTGGCAGCAGCCACTGGTAACAGGATTAGCAGAGCGAGGTATGTAGGCGGTGCTA CAGAGTTCTTGAAGTGGTGGCCTAACTACGGCTACACTAGAAGAACAGTATTTGGTATCTGCGCTCTGCTGAAGCCAGTTACCTTCGGA AAAAGAGTTGGTAGCTCTTGATCCGGCAAACAAACCACCGCTGGTAGCGGTTTTTTTGTTTGCAAGCAGCAGATTACGCGCAGAAAAAA AGGATCTCAAGAAGATCCTTTGATCTTTTCTACGGGGTCTGACGCTCAGTGGAACGAAAACTCACGTTAAGGGATTTTGGTCATGAGATT ATCAAAAAGGATCTTCACCTAGATCCTTTTAAATTAAAAATGAAGTTTTAAATCAATCTAAAGTATATATGAGTAAACTTGGTCTGACAGT TACCAATGCTTAATCAGTGAGGCACCTATCTCAGCGATCTGTCTATTTCGTTCATCCATAGTTGCCTGACTCCCCGTCGTGTAGATAACTA CGATACGGGAGGGCTTACCATCTGGCCCCAGTGCTGCAATGATACCGCGAGACCCACGCTCACCGGCTCCAGATTTATCAGCAATAAAC CAGCCAGCCGGAAGGGCCGAGCGCAGAAGTGGTCCTGCAACTTTATCCGCCTCCATCCAGTCTATTAATTGTTGCCGGGAAGCTAGAGT AAGTAGTTCGCCAGTTAATAGTTTGCGCAACGTTGTTGCCATTGCTACAGGCATCGTGGTGTCACGCTCGTCGTTTGGTATGGCTTCATT CAGCTCCGGTTCCCAACGATCAAGGCGAGTTACATGATCCCCCATGTTGTGCAAAAAAGCGGTTAGCTCCTTCGGTCCTCCGATCGTTGT CAGAAGTAAGTTGGCCGCAGTGTTATCACTCATGGTTATGGCAGCACTGCATAATTCTTACTGTCATGCCATCCGTAAGATGCTTTTCT GTGACTGGTGAGTACTCAACCAAGTCATTCTGAGAATAGTGTATGCGGCGACCGAGTTGCTCTTGCCCGGCGTCAATACGGGATAATAC CGCGCCACATAGCAGAACTTTAAAAGTGCTCATCATTGGAAAACGTTCTTCGGGGCGAAAACTCTCAAGGATCTTACCGCTGTTGAGATC CAGTTCGATGTAACCCACTCGTGCACCCAACTGATCTTCAGCATCTTTTACTTTCACCAGCGTTTCTGGGTGAGCAAAAACAGGAAGGCA -continued AAATGCCGCAAAAAAGGGAATAAGGGCGACACGGAAATGTTGAATACTCATACTCTTCCTTTTTCAATATTATTGAAGCATTTATCAGGG TTATTGTCTCATGAGCGGATACATATTTGAATGTATTTAGAAAAATAAACAAATAGGGGTTCCGCGCACATTTCCCCGAAAAGTGCCACC

TGACGTC

DOM1 = underlined; FJX1 = dotted underlined

CMV promoter (SEQ ID NO: 15)
TAGTAATCAATTACGGGGTCATTAGTTCATAGCCCATATATGGAGTTCCGCGTTACATAACTTACGGTAAATGGCCCGCCTGGCTGACCG CCCAACGACCCCCGCCCATTGACGTCAATAATGACGTATGTTCCCATAGTAACGCCAATAGGGACTTTCCATTGACGTCAATGGGTGGAG TATTTACGGTAAACTGCCCACTTGGCAGTACATCAAGTGTATCATATGCCAAGTACGCCCCCTATTGACGTCAATGACGGTAAATGGCCC GCCTGGCATTATGCCCAGTACATGACCTTATGGGACTTTCCTACTTGGCAGTACATCTACGTATTAGTCATCGCTATTACCATGGTGATGC GGTTTTGGCAGTACATCAATGGGCGTGGATAGCGGTTTGACTCACGGGGATTTCCAAGTCTCCACCCCATTGACGTCAATGGGAGTTTG TTTTGGCACCAAAATCAACGGGACTTTCCAAAATGTCGTAACAACTCCGCCCCATTGACGCAAATGGGCGGTAGGCGTGTACGGTGGGA

GGTCTATATAAGCAGAGCTGGTTTAGTGAACCGTCAG

MAGED4B DNA wild type (SEQ ID NO: 16)
ATGGCTGAGGGAAGCTTCAGCGTGCAATCGGAAAGCTACAGTGTTGAAGACATGGATGAGGGTAGCGACGAAGTCGGGGAGGAAGA GATGGTTGAAGGCAACGACTATGAAGAATTCGGTGCGTTTGGTGGCTATGGCACCCTCACCAGCTTTGACATCCATATCCTCAGAGCCTT CGGAAGCTTGGGTCCAGGCCTTCGCATCTTATCGAATGAGCCCTGGGAACTGGAAAACCCTGTGCTGGCCCAGACCCTGGTGGAGGCA TTGCAGCTGGATCCGGAAACACTTGCCAATGAGACGGCCGCCCGTGCTGCCAACGTAGCCCGCGCCGCCGCCTCCAACCGTGCGGCTCG GGCCGCTGCCGCCGCTGCCCGTACCGCCTTCAGTCAGGTGGTCGCTAGCCACCGGGTGGCCACGCCGCAGGTCTCAGGAGAGGATACC CAGCCCACGACCTACGCCGCCGAGGCTCAGGGGCCCACCCCTGAGCCACCCCTTGCTTCTCCGCAGACCTCCCAGATGTTAGTCACCAGT AAGATGGCTGCCCCCGAGGCTCCGGCAACCTCCGCACAGTCCCAGACAGGCTCCCCGGCCCAGGAGGCTGCTACTGAGGGCCCTAGTA GCGCCTGTGCTTTCTCTCAGGCTCCGTGTGCCAGGGAGGTGGACGCCAACCGGCCCAGCACAGCCTTCCTGGGCCAGAATGATGTCTTC GATTTCACTCAGCCGGCAGGTGTCAGTGGCATGGCCTTCCCGCGCCCCAAGAGACCTGCCCCAGCCCAAGAGGCTGCCACAGAGGGCC CCAGTGCTGCCTCTGGTGTGCCCCAGACGGGACCTGGCAGGGAGGTGGCAGCCACCCGGCCCAAGACCACCAAGTCGGGGAAGGCGC TGGCCAAGACTCGGTGGGTGGAGCCTCAGAATGTTGTGGCAGCAGCTGCTGCCAAGGCCAAGATGGCCACGAGCATCCCTGAGCCGG AGGGTGCAGCTGCTGCCACTGCTCAGCACAGTGCTGAGCCCTGGGCCAGGATGGGAGGCAAGAGGACCAAGAAGTCCAAGCACCTGG ATGATGAGTATGAGAGCAGCGAGGAGGAGAGAGAGACTCCCGCGGTCCCACCCACCTGGAGAGCATCACAGCCCTCATTGACGGTGC GGGCTCAGTTGGCCCCTCGGCCCCCGATGGCCCCGAGGTCCCAGATACCCTCAAGGCACGTACTGTGCCTGCCCCCCCGCAACGTGACC CTTCTGCAGGAGAGGGCAAATAAGTTGGTGAAATACCTGATGATTAAGGACTACAAGAAGATCCCCATCAAGCGCGCAGACATGCTGA AGGATGTCATCAGAGAATATGATGAACATTTCCCTGAGATCATTGAACGAGCAACGTACACCCTGGAAAAGAAGTTTGGGATCCACCTG AAGGAGATCGACAAGGAAGAACACCTGTATATTCTTGTCTGCACACGGGACTCCTCAGCTCGCCTCCTTGGAAAAACCAAGGACACTCC CAGGCTGAGTCTCCTCTTGGTGATTCTGGGCGTCATCTTCATGAATGGCAACCGTGCCAGCGAGGCTGTCCTCTGGGAGGCACTACGCA AGATGGGACTGCGCCCTGGGGTGAGGCACCCATTCCTCGGCGATCTGAGGAAGCTCATCACAGATGACTTTGTGAAGCAGAAGTACCT GGAATACAAGAAGATCCCCAACAGCAACCCACCTGAGTATGAATTCCTCTGGGGCCTGCGAGCCCCGCCATGAGACCAGCAAGATGAGG GTCCTGAGATTCATCGCCCAGAATCAGAACCGAGACCCCCGGGAATGGAAGGCTCATTTCTTGGAGGCTGTGGATGATGCTTTCAAGAC AATGGATGTGGATATGGCCGAGGAACATGCCAGGGCCCAGATGAGGGCCCAGATGAATATCGGGGATGAAGCGCTGATTGGACGGTG GAGCTGGGATGACATACAAGTCGAGCTCCTGACCTGGGATGAGGACGGAGATTTTGGCGATGCCTGGGCCAGGATCCCCTTTGCTTTCT GGGCCAGATACCATCAGTACATTCTGAATAGCAACCGTGCCAACAGGAGGGCCACGTGGAGAGCTGGCGTCAGCAGTGGCACCAATG GAGGGGCCAGCACCAGCGTCCTAGATGGCCCCAGCACCAGCTCCACCATCCGGACCAGAAATGCTGCCAGAGCTGGCGCCAGCTTCTTC

TCCTGGATCCAGCACCGTTGA

MAGED4B DNA codon optimised (SEQ ID NO: 17)
ATGGCCGAGGGATCTTTTTTCTGTGCAGAGCGAAAGCTACAGCGTCGAGGACATGGACGAGGGTTCTGATGAAGTTGGCGAAGAAGAA ATGGTGGAAGGAAATGACTACGAGGAGTTCGGCGCCTTCGGCGGCTACGGCACCCTGACATCCTTCGACATCCACATCCTAAGAGCCT -continued CGGCTCTCTGGGCCCTGGTCTTCGGATCCTGTCTAATGAGCCTTGGGAGCTGGAAAACCCCGTGCTGGCTCAAACCCTGGTGGAAGCAC TCCAGCTGGATCCTGAAACCCTGGCCAACGAGACAGCTGCGCGTGCTGCCAATGTGGCCAGAGCTGCTGCAAGCAACAGAGCTGCTCG CGCCGCCGCTGCTGCCGCCCGGACAGCCTTTAGCCAGGTGGTGGCCAGCCACAGAGTGGCCACTCCTCAGGTTAGCGGCGAGGATACA CAGCCTACCACCTACGCCGCCGAAGCCCAGGGCCCCACCCCTGAACCCCCTCTGGCCTCCCCTCAGACCTCCCAGATGCTGGTGACAAGC AAAATGGCCGCACCTGAGGCCCCTGCCACATCAGCCCAAAGCCAGACAGGCAGCCCTGCTCAGGAGGCCGCTACTGAGGGCCCTAGCT CAGCTTGTGCCTTCAGCCAGGCCCCGTGCGCCAGAGAGGTGGACGCCAACAGACTTAGCACCGCCTTCCTGGGCCAGAACGACGTCTTT GATTTCACCCAGCCAGCCGGAGTGTCCGGCATGGCCTTTCCTAGACCCAAGAGACCTGCCCCTGCCCAGGAGGCCGCCACCGAGGGCCC TAGCGCCGCCAGCGGAGTTCCACAGACCGGCCCCGGCAGAGAAGTGGCCGCCACGAGACCTAAGACCACAAAGAGCGGCAAAGCCCT GGCTAAGACAAGATGGGTCGAACCGCAAAACGTGGTGGCCGCCGCTGCCGCCAAGGCCAAAATGGCTACAAGTATCCCTGAGCCTGAG GGCGCTGCCGCGGCCACCGCCCAGCACAGCGCCGAGCCCTGGGCCCGGATGGGCGGAAAGAGAACCAAAAAAAGCAAGCACCTCGAT GATGAGTACGAGAGCTCTGAGGAAGAGCGGGAAACACCTGCCGTGCCCCCCACCTGGAGAGCCAGCCAGCCTAGCCTGACCGTGCGG GCCCAGCTGGCCCCTCGCCCACCTATGGCCCCTAGAAGCCAGATCCCTAGCAGACACGTGCTGTGCCTGCCTCCCCGGAACGTGACCCT GCTGCAGGAGAGAGCCAACAAGCTGGTGAAGTACCTGATGATCAAGGACTATAAGAAGATCCCCATCAAGCGGGCCGACATGCTGAA GGATGTGATTAGAGAGTACGACGAGCACTTCCCCGAGATCATCGAGCGGGCCACGTACACCCTGGAAAAGAAATTCGGCATCCACCTG AAAGAGATCGACAAGGAAGAACACCTGTACATCCTGGTGTGCACCAGAGACAGCAGCGCTCGGCTGCTGGGAAAAACCAAGGACACC CCTCGGCTGAGCCTGCTGCTCGTGATCCTGGGCGTGATTTTCATGAACGGCAACAGAGCTTCTGAGGCAGTGCTGTGGGAAGCCCTCAG AAAGATGGGCCTGAGACCCGGAGTCAGACATCCTTTCCTGGGCGACCTGAGAAAGCTGATCACCGACGACTTCGTGAAGCAGAAGTAC CTGGAATACAAGAAGATCCCTAATAGCAATCCTCCAGAGTACGAGTTCCTGTGGGGCCTGCGGGCCCGCCACGAGACATCCAAGATA GAGTGCTGAGGTTCATCGCCCAGAACCAGAACCGCGACCCCAGAGAGTGGAAGGCCCACTTCCTGGAAGCCGTGGATGACGCTTTTAA GACAATGGATGTGGACATGGCCGAGGAACACGCCCGAGCTCAGATGCGGGCCCAAATGAACATCGGCGACGAGGCCCTGATCGGCAG ATGGTCCTGGGACGATATCCAGGTGGAACTGCTGACCTGGGATGAGGACGGCGATTTCGGCGACGCCTGGGCCCGAATCCCATTCGCC TTCTGGGCTAGATACCACCAGTACATCCTGAACAGCAACAGAGCTAACCGTAGAGCCACCTGGCGGGCCGGCGTGTCCAGCGGCACAA ACGGCGGCGCCTCTACAAGCGTGCTGGACGGCCCAAGCACAAGCAGCACCATCAGAACCAGAAACGCCGCTAGAGCCGGCGCCAGCTT

CTTCAGCTGGATCCAGCATAGATGA

DOM-MAGED4B DNA sequence (SEQ ID NO: 18)
ATGGGTTGGAGCTGTATCATCTTCTTTCTGGTAGCAACAGCTACAGGTGTGCACTCCAAAAACCTTGATTGTTGGGTCGACAACGAAGA AGACATCGATGTTATCCTGAAAAAGTCTACCATTCTGAACTTGGACATCAACAACGATATTATCTCCGACATCTCTGGTTTCAACTCCTCT GTTATCACATATCCAGATGCTCAATTGGTGCCGGGCATCAACGGCAAAGCTATCCACCTGGTTAACAACGAATCTTCTGAAGTTATCGTG CACAAGGCCATGGACATCGAATACAACGACATGTTCAACAACTTCACCGTTAGCTTCTGGCTGCGCGTTCCGAAAGTTTCTGCTTCCCAC CTGGAACAGTACGGCACTAACGAGTACTCCATCATCAGCTCTATGAAGAAACACTCCCTGTCCATCGGCTCTGGTTGGTCTGTTTCCCTG AAGGGTAACAACCTGATCTGGACTCTGAAAGACTCCGCGGGCGAAGTTCGTCAGATCACTTTCCGCGACCTGCCGGACAAGTTCAACGC GTACCTGGCTAACAAATGGGTTTTCATCACTATCACTAACGATCGTCTGTCTTCTGCTAACCTGTACATCAACGGCGTTCTGATGGGCTCC GCTGAAATCACTGGTCTGGGCGCTATCCGTGAGGACAACAACATCACTCTTAAGCTGGACCGTTGCAACAACAACAACCAGTACGTATC CATCGACAAGTTCCGTATCTTCTGCAAAGCACTGAACCCGAAAGAGATCGAAAACTGTATACCAGCTACCTGTCTATCACCTTCCTGCG TGACTTCTGGGGTAACGCGGCCGCTGGACCCGGACCTATGGCTGAGGGAAGCTTCAGCGTGCAATCGGAAAGCTACAGTGTTGAAGAC ATGGATGAGGGTAGCGACGAAGTCGGGGAGGAAGAGATGGTTGAAGGCAACGACTATGAAGAATTCGGTGCGTTTGGTGGCTATGGC ACCCTCACCAGCTTTGACATCCATATCCTCAGAGCCTTCGGAAGCTTGGGTCCAGGCCTTCGCATCTTATCGAATGAGCCCTGGGAACTG GAAAACCCTGTGCTGGCCCAGACCCTGGTGGAGGCATTGCAGCTGGATCCGGAAACACTTGCCAATGAGACGGCCGCCCGTGCTGCCA ACGTAGCCCGCGCCGCCGCCTCCAAACCGTGCGGCTCGGGCCGCTGCCGCCGCTGCCCGTACCGCCTTCAGTCAGGTGGTCGTAGCCAC CGGGTGGCCACGCCGCAGGTCTCAGGAGAGGATACCCAGCCCACGACCTACGCCGCCGAGGCTCAGGGGCCCACCCCTGAGCCACCCC TTGCTTCTCCGCAGACCTCCCAGATGTTAGTCACCAGTAAGATGGCTGCCCCCGAGGCTCCGGCAACCTCCGCACAGTCCCAGACAGGCT -continued CCCCGGCCCAGGAGGCTGCTACTGAGGCCCTAGTAGCGCCTGTGCTTTCTCTCAGGCTCCGTGTGCCAGGGAGGTGGACGCCAACCG GCCCAGCACAGCCTTCCTGGGCCAGAATGATGTCTTCGATTTCACTCAGCCGGCAGGTGTCAGTGGCATGGCCTTCCCGCGCCCCAAGA GACCTGCCCCAGCCCAAGAGGCTGCCACAGAGGGCCCCAGTGCTGCCTCTGGTGTGCCCCAGACGGGACCTGGCAGGGAGGTGGCAG CCACCCGGCCCAAGACCACCAAGTCGGGGAAGGCGCTGGCCAAGACTCGGTGGGTGGAGCCTCAGAATGTTGTGGCAGCAGCTGCTG CCAAGGCCAAGATGGCCACGAGCATCCCTGAGCCGGAGGGTGCAGCTGCTGCCACTGCTCAGCACAGTGCTGAGCCCTGGGCCAGGAT GGGAGGCAAGAGGACCAAGAAGTCCAAGCACCTGGATGATGAGTATGAGAGCAGCGAGGAGGAGAGAGAGACTCCCGCGGTCCCAC CCACCTGGAGAGCATCACAGCCCTCATTGACGGTGCGGGCTCAGTTGGCCCCTCGGCCCCCGATGGCCCCGAGGTCCCAGATACCCTCA AGGCACGTACTGTGCCTGCCCCCCCGCAACGTGACCCTTCTGCAGGAGAGGGCAAATAAGTTGGTGAAATACCTGATGATTAAGGACTA CAAGAAGATCCCCATCAAGCGCGCAGACATGCTGAAGGATGTCATCAGAGAATATGATGAACATTTCCCTGAGATCATTGAACGAGCAA CGTACACCCTGGAAAAGAAGTTTGGGATCCACCTGAAGGAGATCGACAAGGAAGAACACCTGTATATTCTTGTCTGCACACGGGACTCC TCAGCTCGCCTCCTTGGAAAAACCAAGGACACTCCCAGGCTGAGTCTCCTCTTGGTGATTCTGGGCGTCATCTTCATGAATGGCAACCGT GCCAGCGAGGCTGTCCTCTGGGAGGCACTACGCAAGATGGGACTGCGCCCTGGGGTGAGGCACCCATTCCTCGGCGATCTGAGGAAGC TCATCACAGATGACTTTGTGAAGCAGAAGTACCTGGAATACAAGAAGATCCCCAACAGCAACCCACCTGAGTATGAATTCCTCTGGGGC CTGCGAGCCCGCCATGAGACCAGCAAGATGAGGGTCCTGAGATTCATCGCCCAGAATCAGAACCGAGACCCCCGGGAATGGAAGGCTC ATTTCTTGGAGGCTGTGGATGATGCTTTCAAGACAATGGATGTGGATATGGCCGAGGAACATGCCAGGGCCCAGATGAGGGCCCAGAT GAATATCGGGGATGAAGCGCTGATTGGACGGTGGAGCTGGGATGACATACAAGTCGAGCTCCTGACCTGGGATGAGGACGGAGATTT TGGCGATGCCTGGGCCAGGATCCCCTTTGCTTTCTGGGCCAGATACCATCAGTACATTCTGAATAGCAACCGTGCCAACAGGAGGGCCA CGTGGAGAGCTGGCGTCAGCAGTGGCACCAATGGAGGGGCCAGCACCAGCGTCCTAGATGGCCCCAGCACCAGCTCCACCATCCGGAC

CAGAAATGCTGCCAGAGCTGGCGCCAGCTTCTTCTCCTGGATCCAGCACCGTTGA

DOM-MAGED4B Codon optimised DNA sequence (SEQ ID NO: 19)
ATGGGTTGGAGCTGTATCATCTTCTTTCTGGTAGCAACAGCTACAGGTGTGCACTCCAAAAACCTTGATTGTTGGGTCGACAACGAAGA AGACATCGATGTTATCCTGAAAAAGTCTACCATTCTGAACTTGGACATCAACAACGATATTATCTCCGACATCTCTGGTTTCAACTCCTCT GTTATCACATATCCAGATGCTCAATTGGTGCCGGGCATCAACGGCAAAGCTATCCACCTGGTTAACAACGAATCTTCTGAAGTTATCGTG CACAAGGCCATGGACATCGAATACAACGACATGTTCAACAACTTCACCGTTAGCTTCTGGCTGCGCGTTCCGAAAGTTTCTGCTTCCCAC CTGGAACAGTACGGCACTAACGAGTACTCCATCATCAGCTCTATGAAGAAACACTCCCTGTCCATCGGCTCTGGTTGGTCTGTTTCCCTG AAGGGTAACAACCTGATCTGGACTCTGAAAGACTCCGCGGGCGAAGTTCGTCAGATCACTTTCCGCGACCTGCCGGACAAGTTCAACGC GTACCTGGCTAACAAATGGGTTTTCATCACTATCACTAACGATCGTCTGTCTTCTGCTAACCTGTACATCAACGGCGTTCTGATGGGCTCC GCTGAAATCACTGGTCTGGGCGCTATCCGTGAGGACAACAACATCACTCTTAAGCTGGACCGTTGCAACAACAACAACCAGTACGTATC CATCGACAAGTTCCGTATCTTCTGCAAAGCACTGAACCCGAAAGAGATCGAAAAACTGTATACCAGCTACCTGTCTATCACCTTCCTGCG TGACTTCTGGGGTAACGCGGCCGCTGGACCCGGACCTATGGCCGAGGGATCTTTTTCTGTGCAGAGCGAAAGCTACAGCGTCGAGGAC ATGGACGAGGGTTCTGATGAAGTTGGCGAAGAAGAAATGGTGGAAGGAAATGACTACGAGGAGTTCGGCGCCTTCGGCGGCTACGGC ACCCTGACATCCTTCGACATCCACATCCTAAGAGCCTTCGGCTCTCTGGGCCCTGGTCTTCGGATCCTGTCTAATGAGCCTTGGGAGCTG GAAAACCCCGTGCTGGCTCAAACCCTGGTGGAAGCACTCCAGCTGGATCCTGAAACCCTGGCCAACGAGACAGCTGCGCGTGCTGCCA ATGTGGCCAGAGCTGCTGCAAGCAACAGAGCTGCTCGCGCCGCCGCTGCTGCCGCCCGGACAGCCTTTAGCCAGGTGGTGGCCAGCCA CAGAGTGGCCACTCCTCAGGTTAGCGGCGAGGATACACAGCCTACCACCTACGCCGCCGAAGCCCAGGGCCCCACCCCTGAACCCCCTC TGGCCTCCCCTCAGACCTCCCAGATGCTGGTGACAAGCAAAATGGCCGCACCTGAGGCCCCTGCCACATCAGCCCAAAGCCAGACAGGC AGCCCTGCTCAGGAGGCCGCTACTGAGGGCCCTAGCTCAGCTTGTGCCTTCAGCCAGGCCCCGTGCGCCAGAGAGGTGGACGCCAACA GACCTAGCACCGCCTTCCTGGGCCAGAACGACGTCTTTGATTTCACCCAGCCAGCCGGAGTGTCCGGCATGGCCTTTCCTAGACCCAAGA GACCTGCCCCTGCCCAGGAGGCCGCCACCGAGGGCCCTAGCGCCGCCAGCGGAGTTCCACAGACCGGCCCCGGCAGAGAAGTGGCCG CCACGAGACCTAAGACCACAAAGAGCGGCAAAGCCCTGGCTAAGACAAGATGGGTCGAACCGCAAAACGTGGTGGCCGCCGCTGCCG CCAAGGCCAAAATGGCTACAAGTATCCCTGAGCCTGAGGGCGCTGCCGCGGCCACCGCCCAGCACAGCGCCGAGCCCTGGGCCCGGAT -continued GGGCGGAAAGAGAACCAAAAAAAGCAAGCACCTCGATGATGAGTACGAGAGCTCTGAGGAAGAGCGGGAAACACCTGCCGTGCCCCC CACCTGGAGAGCCAGCCAGCCTAGCCTGACCGTGCGGGCCCAGCTGGCCCCTCGCCCACCTATGGCCCCTAGAAGCCAGATCCCTAGCA GACACGTGCTGTGCCTGCCTCCCCGGAACGTGACCCTGCTGCAGGAGAGAGCCAACAAGCTGGTGAAGTACCTGATGATCAAGGACTA TAAGAAGATCCCCATCAAGCGGGCCGACATGCTGAAGGATGTGATTAGAGAGTACGACGAGCACTTCCCCGAGATCATCGAGCGGGCC ACGTACACCCTGGAAAAGAAATTCGGCATCCACCTGAAAGAGATCGACAAGGAAGAACACCTGTACATCCTGGTGTGCACCAGAGACA GCAGCGCTCGGCTGCTGGGAAAAACCAAGGACACCCCTCGGCTGAGCCTGCTGCTCGTGATCCTGGGCGTGATTTTCATGAACGGCAAC AGAGCTTCTGAGGCAGTGCTGTGGGAAGCCCTCAGAAAGATGGGCCTGAGACCCGGAGTCAGACATCCTTTCCTGGGCGACCTGAGAA AGCTGATCACCGACGACTTCGTGAAGCAGAAGTACCTGGAATACAAGAAGATCCCTAATAGCAATCCTCCAGAGTACGAGTTCCTGTGG GGCCTGCGGGCCCGCCACGAGACATCCAAGATGAGAGTGCTGAGGTTCATCGCCCAGAACCAGAACCGCGACCCCAGAGAGTGGAAG GCCCACTTCCTGGAAGCCGTGGATGACGCTTTTAAGACAATGGATGTGGACATGGCCGAGGAACACGCCCGAGCTCAGATGCGGGCCC AAATGAACATCGGCGACGAGGCCCTGATCGGCAGATGGTCCTGGGACGATATCCAGGTGGAACTGCTGACCTGGGATGAGGACGGCG ATTTCGGCGACGCCTGGGCCCGAATCCCATTCGCCTTCTGGGCTAGATACCACCAGTACATCCTGAACAGCAACAGAGCTAACCGTAGA GCCACCTGGCGGGCCGGCGTGTCCAGCGGCACAAACGGCGGCGCCTCTACAAGCGTGCTGGACGGCCCAAGCACAAGCAGCACCATC

AGAACCAGAAACGCCGCTAGAGCCGGCGCCAGCTTCTTCAGCTGGATCCAGCATAGATGA

FJX1 wild type DNA sequence (SEQ ID NO: 20)
ATGGGCAGGAGGATGCGGGGCGCCGCCGCCACCGCGGGGCTCTGGCTGCTGGCGCTGGGCTCGCTGCTGGCGCTGTGGGGAGGGCT CCTGCCGCCGCGGACCGAGCTGCCCGCCTCCCGGCCGCCCGAAGACCGACTCCCACGGCGCCCGGCCCGGAGCGGCGGCCCCGCGCCC GCGCCTCGCTTCCCTCTGCCCCCGCCCCTGGCGTGGGACGCCCGCGGCGGCTCCCTGAAAACTTTCCGGGCGCTGCTCACCCTGGCGGC CGGCGCGGACGGCCCGCCCCGGCAGTCCCGGAGCGAGCCCAGGTGGCACGTGTCAGCCAGGCAGCCCCGGCCGGAGGAGAGCGCCG CGGTGCACGGGGGCGTCTTCTGGAGCCGCGGCCTGGAGGAGCAGGTGCCCCCGGGCTTTTCGGAGGCCCAGGCGGCGGCGTGGCTGG AGGCGGCTCGCGGCGCCCGGATGGTGGCCCTGGAGCGCGGGGGTTGCGGGCGAGCTCCAACCGACTGGCCCGTTTTGCCGACGGCA CCCGCGCCTGCGTGCGCTACGGCATCAACCCGGAGCAGATTCAGGGCGAGGCCCTGTCTTACTATCTGGCGCGCCTGCTGGGCCTCCAG CGCCACGTGCCGCCGCTGGCACTGGCTCGGGTGGAGGCTCGGGGCGCGCAGTGGGCGCAGGTGCAGGAGGAGCTGCGCGCTGCGCA CTGGACCGAGGGCAGCGTGGTGAGCCTGACACGCTGGCTGCCCAACCTCACGGACGTGGTGGTGCCCGCGCCCTGGCGCTCGGAGGA CGGCCGTCTGCGCCCCCTCCGGGATGCCGGGGGTGAGCTGGCCAACCTCAGCCAGGCGGAGCTGGTGGACCTAGTACAATGGACCGAC TTAATCCTTTTCGACTACCTGACGGCCAACTTCGACCGGCTCGTAAGCAACCTCTTCAGCCTGCAGTGGGACCCGCGCGTCATGCAGCGT GCCACCAGCAACCTGCACCGCGGTCCGGGCGGGGCGCTGGTCTTTCTGGACAATGAGGCGGGCTTGGTGCACGGCTACCGGGTAGCA GGCATGTGGGACAAGTATAACGAGCCGCTGTTGCAGTCAGTGTGCGTGTTCCGCGAGCGGACCGCGCGGCGCGTCCTGGAGCTGCACC GCGGACAGGACGCCGCGGCCCGGCTGCTGCGCCTCTACCGGCGCCACGAGCCTCGCTTCCCCGAGCTGGCCGCCCTTGCAGACCCCCAC GCTCAGCTGCTACAGCGCCGCCTCGACTTCCTCGCCAAGCACATTTTGCACTGTAAGGCCAAGTACGGCCGCCGGTCTGGGACTTAG FJX1 Codon optimised DNA sequence (SEQ ID NO: 21)
ATGGGCAGAAGAATGAGAGGCGCCGCTGCCACCGCCGGACTCTGGCTACTGGCTCTGGGCAGCCTGCTGGCTCTGTGGGGCGGCCTGC TGCCTCCACGAACAGAGCTGCCCGCTAGCAGACCTCCAGAAGATAGACTGCCTCGGCGGCCTGCCAGAAGCGGCGGACCTGCACCAGC CCCTAGATTCCCCCTGCCTCCTCCTCTTGCCTGGGATGCCAGAGGCGGAAGCCTGAAGACCTTCAGAGCCCTGCTCACCCTGGCAGCTGG AGCCGACGGCCCTCCTAGACAGAGCAGATCAGAGCCTCGGTGGCACGTGTCCGCCCGGCAGCCTCGGCCCGAGGAAAGCGCCGCCGT GCACGGCGGCGTGTTCTGGTCCAGAGGCCTGGAAGAACAGGTGCCTCCCGGCTTCTCAGAGGCCCAGGCCGCTGCCTGGCTGGAAGCT GCTAGAGGCGCCAGAATGGTGGCCCTCGAGCGGGGCGGTTGTGGCAGAAGCAGCAATAGACTGGCTCGGTTCGCCGATGGCACCAGA GCCTGCGTGCGGTACGGCATCAACCCCGAGCAGATCCAGGGCGAGGCCCTCAGCTACTACCTGGCCAGACTGCTGGGACTGCAAAGAC ACGTGCCACCTCTGGCCCTCGCCAGGGTGGAAGCCAGAGGGGCCCAGTGGGCCCAAGTGCAGGAGGAACTGAGAGCCGCCCACTGGA CCGAGGGCAGCGTGGTCAGCCTGACCAGATGGCTGCCCAACCTGACCGACGTGGTGGTTCCTGCCCTTGGCGGTCTGAAGATGGAAG ACTGAGACCCCTGCGCGATGCCGGCGGCGAGCTGGCCAATCTGAGCCAGGCCGAGCTGGTCGACCTGGTGCAGTGGACAGACCTGATG -continued CTGTTTGATTACCTGACCGCCAACTTCGACCGGCTGGTGTCCAACCTGTTCAGCCTGCAGTGGGACCCTAGAGTGATGCAGCGGGCCAC AAGCAACCTCCACCGGGGTCCTGGCGGCGCCCTCGTGTTTCTGGACAACGAGGCCGGACTGGTTCATGGCTACAGAGTGGCCGGCATG TGGGACAAGTACAACGAGCCCCTGCTTCAAAGCGTGTGCGTGTTCCGCGAGAGAACCGCCAGAAGAGTGCTGGAACTGCACAGAGGA CAGGACGCCGCCGCCAGACTGCTGCGGCTGTACCGGCGGCACGAGCCTAGATTCCCTGAACTGGCCGCTCTGGCCGACCCCCACGCCCA GCTGCTGCAGAGAAGGCTCGACTTCCTGGCTAAGCACATCCTGCACTGCAAGGCCAAGTACGGCAGACGGAGCGGAACATGA DOM-FJX1 DNA sequence (SEQ ID NO: 22)
ATGGGTTGGAGCTGTATCATCTTCTTTCTGGTAGCAACAGCTACAGGTGTGCACTCCAAAAACCTTGATTGTTGGGTCGACAACGAAGA AGACATCGATGTTATCCTGAAAAAGTCTACCATTCTGAACTTGGACATCAACAACGATATTATCTCCGACATCTCTGGTTTCAACTCCTCT GTTATCACATATCCAGATGCTCAATTGGTGCCGGGCATCAACGGCAAAGCTATCCACCTGGTTAACAACGAATCTTCTGAAGTTATCGTG CACAAGGCCATGGACATCGAATACAACGACATGTTCAACAACTTCACCGTTAGCTTCTGGCTGCGCGTTCCGAAAGTTTCTGCTTCCCAC CTGGAACAGTACGGCACTAACGAGTACTCCATCATCAGCTCTATGAAGAAACACTCCCTGTCCATCGGCTCTGGTTGGTCTGTTTCCCTG AAGGGTAACAACCTGATCTGGACTCTGAAAGACTCCGCGGGCGAAGTTCGTCAGATCACTTTCCGCGACCTGCCGGACAAGTTCAACGC GTACCTGGCTAACAAATGGGTTTTCATCACTATCACTAACGATCGTCTGTCTTCTGCTAACCTGTACATCAACGGCGTTCTGATGGGCTCC GCTGAAATCACTGGTCTGGGCGCTATCCGTGAGGACAACAACATCACTCTTAAGCTGGACCGTTGCAACAACAACAACCAGTACGTATC CATCGACAAGTTCCGTATCTTCTGCAAAGCACTGAACCCGAAAGAGATCGAAAACTGTATACCAGCTACCTGTCTATCACCTTCCTGCG TGACTTCTGGGGTAACGCGGCCGCTGGACCCGGACCTATGGGCAGGAGGATGCGGGGCGCCGCCGCCACCGCGGGGCTCTGGCTGCT GGCGCTGGGCTCGCTGCTGGCGCTGTGGGGAGGGCTCCTGCCGCCGCGGACCGAGCTGCCCGCCTCCCGGCCGCCCGAAGACCGACTC CCACGGCGCCCGGCCCGGAGCGGCGGCCCCGCGCCCGCGCCTCGCTTCCCTCTGCCCCCGCCCCTGGCGTGGGACGCCCGCGGCGGCT CCCTGAAAACTTTCCGGGCGCTGCTCACCCTGGCGGCCGGCGCGGACGGCCCGCCCCGGCAGTCCCGGAGCGAGCCCAGGTGGCACGT GTCAGCCAGGCAGCCCCCGGCCGGAGGAGAGCGCCGCGGTGCACGGGGGCGTCTTCTGGAGCCGCGGCCTGGAGGAGCAGGTGCCCC CGGGCTTTTCGGAGGCCCAGGCGGCGGCGTGGCTGGAGGCGGCTCGCGGCGCCCGGATGGTGGCCCTGGAGCGCGGGGGTTGCGGG CGCAGCTCCAACCGACTGGCCCGTTTTGCCGACGGCACCCGCGCCTGCGTGCGCTACGGCATCAACCCGGAGCAGATTCAGGGCGAGG CCCTGTCTTACTATCTGGCGCGCCTGCTGGGCCTCCAGCGCCACGTGCCGCCGCTGGCACTGGCTCGGGTGGAGGCTCGGGGCGCGCA GTGGGCGCAGGTGCAGGAGGAGCTGCGCGCTGCGCACTGGACCGAGGGCAGCGTGGTGAGCCTGACACGCTGGCTGCCCAACCTCAC GGACGTGGTGGTGCCCGCGCCCTGGCGCTCGGAGGACGGCCGTCTGCGCCCCCTCCGGGATGCCGGGGGTGAGCTGGCCAACCTCAG CCAGGCGGAGCTGGTGGACCTAGTACAATGGACCGACTTAATCCTTTTCGACTACCTGACGGCCAACTTCGACCGGCTCGTAAGCAACC TCTTCAGCCTGCAGTGGGACCCGCGCGTCATGCAGCGTGCCACCAGCAACCTGCACCGCGGTCCGGGCGGGGCGCTGGTCTTTCTGGA CAATGAGGCGGGCTTGGTGCACGGCTACCGGGTAGCAGGCATGTGGGACAAGTATAACGAGCCGCTGTTGCAGTCAGTGTGCGTGTTC CGCGAGCGGACCGCGCGGCGCGTCCTGGAGCTGCACCGCGGACAGGACGCCGCGGCCCGGCTGCTGCGCCTCTACCGGCGCCACGAG CCTCGCTTCCCCGAGCTGGCCGCCCTTGCAGACCCCCACGCTCAGCTGCTACAGCGCCGCCTCGACTTCCTCGCCAAGCACATTTTGCACT

GTAAGGCCAAGTACGGCCGCCGGTCTGGGACTTAG

DOM-FJX1 Codon optimised DNA sequence (SEQ ID NO: 23)
ATGGGTTGGAGCTGTATCATCTTCTTTCTGGTAGCAACAGCTACAGGTGTGCACTCCAAAAACCTTGATTGTTGGGTCGACAACGAAGA AGACATCGATGTTATCCTGAAAAAGTCTACCATTCTGAACTTGGACATCAACAACGATATTATCTCCGACATCTCTGGTTTCAACTCCTCT GTTATCACATATCCAGATGCTCAATTGGTGCCGGGCATCAACGGCAAAGCTATCCACCTGGTTAACAACGAATCTTCTGAAGTTATCGTG CACAAGGCCATGGACATCGAATACAACGACATGTTCAACAACTTCACCGTTAGCTTCTGGCTGCGCGTTCCGAAAGTTTCTGCTTCCCAC CTGGAACAGTACGGCACTAACGAGTACTCCATCATCAGCTCTATGAAGAAACACTCCCTGTCCATCGGCTCTGGTTGGTCTGTTTCCCTG AAGGGTAACAACCTGATCTGGACTCTGAAAGACTCCGCGGGCGAAGTTCGTCAGATCACTTTCCGCGACCTGCCGGACAAGTTCAACGC GTACCTGGCTAACAAATGGGTTTTCATCACTATCACTAACGATCGTCTGTCTTCTGCTAACCTGTACATCAACGGCGTTCTGATGGGCTCC GCTGAAATCACTGGTCTGGGCGCTATCCGTGAGGACAACAACATCACTCTTAAGCTGGACCGTTGCAACAACAACAACCAGTACGTATC CATCGACAAGTTCCGTATCTTCTGCAAAGCACTGAACCCGAAAGAGATCGAAAACTGTATACCAGCTACCTGTCTATCACCTTCCTGCG TGACTTCTGGGGTAACGCGGCCGCTGGACCCGGACCTATGGGCAGAAGAATGAGAGGCGCCGCTGCCACCGCCGGACTCTGGCTACTG -continued GCTCTGGGCAGCCTGCTGGCTCTGTGGGGCGGCCTGCTGCCTCCACGAACAGAGCTGCCCGCTAGCAGACCTCCAGAAGATAGACTGC CTCGGCGGCCTGCCAGAAGCGGCGGACCTGCACCAGCCCCTAGATTCCCCTGCCTCCTCCTCTTGCCTGGGATGCCAGAGGCGGAAGC CTGAAGACCTTCAGAGCCCTGCTCACCCTGGCAGCTGGAGCCGACGGCCCTCCTAGACAGAGCAGATCAGAGCCTCGGTGGCACGTGT CCGCCCGGCAGCCTCGGCCCGAGGAAAGCGCCGCCGTGCACGGCGGCGTGTTCTGGTCCAGAGGCCTGGAAGAACAGGTGCCTCCCG GCTTCTCAGAGGCCCAGGCCGCTGCCTGGCTGGAAGCTGCTAGAGGCGCCAGAATGGTGGCCCTCGAGCGGGGCGGTTGTGGCAGAA GCAGCAATAGACTGGCTCGGTTCGCCGATGGCACCAGAGCCTGCGTGCGGTACGGCATCAACCCCGAGCAGATCCAGGGCGAGGCCCT CAGCTACTACCTGGCCAGACTGCTGGGACTGCAAAGACACGTGCCACCTCTGGCCCTCGCCAGGGTGGAAGCCAGAGGGGCCCAGTGG GCCCAAGTGCAGGAGGAACTGAGAGCCGCCCACTGGACCGAGGGCAGCGTGGTCAGCCTGACCAGATGGCTGCCCAACCTGACCGAC GTGGTGGTTCCTGCCCTTGGCGGTCTGAAGATGGAAGACTGAGACCCTGCGCGATGCCGGCGGCGAGCTGGCCAATCTGAGCCAGG CCGAGCTGGTCGACCTGGTGCAGTGGACAGACCTGATCCTGTTTGATTACCTGACCGCCAACTTCGACCGGCTGGTGTCCAACCTGTTCA GCCTGCAGTGGGACCCTAGAGTGATGCAGCGGGCCACAAGCAACCTCCACCGGGGTCCTGGCGGCGCCCTCGTGTTTCTGGACAACGA GGCCGGACTGGTTCATGGCTACAGAGTGGCCGGCATGTGGGACAAGTACAACGAGCCCCTGCTTCAAAGCGTGTGCGTGTTCCGCGAG AGAACCGCCAGAAGAGTGCTGGAACTGCACAGAGGACAGGACGCCGCCGCCAGACTGCTGCGGCTGTACCGGCGGCACGAGCCTAGA TTCCCTGAACTGGCCGCTCTGGCCGACCCCCACGCCCAGCTGCTGCAGAGAAGGCTCGACTTCCTGGCTAAGCACATCCTGCACTGCAA

GGCCAAGTACGGCAGACGGAGCGGAACATGA

MAGED4B truncations

MAGED4B sv1 (SEQ ID NO: 24)
ATGGCTGAGGGAAGCTTCAGCGTGCAATCGGAAAGCTACAGTGTTGAAGACATGGATGAGGGTAGCGACGAAGTCGGGGAGGAAGA

GATGGTTGAAGGCAACGACTATGAAGAATTCGGTGCGTTTGGTGGCTATGGCACCCTCACCAGCTTTGACATCCATATCCTCAGAGCTT

CGGAAGCTTGGGTCCAGGCCTTCGCATCTTATCGAATGAGCCCTGGGAACTGGAAAACCCTGTGCTGGCCCAGACCCTGGTGGAGGCA

TTGCAGCTGGATCCGGAAACACTTGCCAATGAGACGGCCGCCCGTGCTGCCAACGTAGCCCGCGCCGCCGCCTCCAACCGTGCGGCTCG

GGCCGCTGCCGCCGCTGCCCGTACCGCCTTCAGTCAGGTGGTCGCTAGCCACCGGGTGGCCACGCCGCAGGTCTCAGGAGAGGATACC

CAGCCCACGACCTACGCCGCCGAGGCTCAGGGGCCCACCCCTGAGCCACCCCTTGCTTCTCCGCAGACCTCCCAGATGTTAGTCACCAGT

AAGATGGCTGCCCCCGAGGCTCCGGCAACCTCCGCACAGTCCCAGACAGGCTCCCCGGCCCAGGAGGCTGCTACTGAGGGCCCTAGTA

GCGCCTGTGCTTTCTCTCAGGCTCCGTGTGCCAGGGAGGTGGACGCCAACCGGCCCAGCACAGCCTTCCTGGGCCAGAATGATGTCTTC

GATTTCACTCAGCCGGCAGGTGTCAGTGGCATGGCCTTCCCGCGCCCCAAGAGACCTGCCCCAGCCCAAGAGGCTGCCACAGAGGGCC

CCAGTGCTGCCTCTGGTGTGCCCCAGACGGGACCTGGCAGGGAGGTGGCAGCCACCCGGCCCAAGACCACCAAGTCGGGGAAGGCGC

TGGCCAAGACTCGGTGGGTGGAGCCTCAGAATGTTGTGGCAGCAGCTGCTGCCAAGGCCAAGATGGCCACGAGCATCCCTGAGCCGG

AGGGTGCAGCTGCTGCCACTGCTCAGCACAGTGCTGAGCCCTGGGCCAGGATGGGAGGCAAGAGGACCAAGAAGTCCAAGCACCTGG

ATGATGAGTATGAGAGCAGCGAGGAGGAGAGAGAGACTCCCGCGGTCCCACCCACCTGGAGAGCATCACAGCCCTCATTGACGGTGC

GGGCTCAGTTGGCCCCTCGGCCCCCGATGGCCCCGAGGTCCCAGATACCCTCAAGGCACGTACTGTGCCTGCCCCCCCGCAACGTGACC

AGACTGTCTCTGCTGCTGGTCATCCTGTACATTCTGAATAGCAACCGTGCCAACAGGAGGGCCACGTGGAGAGCTGGCGTCAGCAGTG

GCACCAATGGAGGGGCCAGCACCAGCGTCCTAGATGGCCCCAGCACCAGCTCCACCATCCGGACCAGAAATGCTGCCAGAGCTGGCGC

CAGCTTCTTCTCCTGGATCCAGCACCGT

MAGED4B sv2 (SEQ ID NO: 25)
ATGGCTGAGGGAAGCTTCAGCGTGCAATCGGAAAGCTACAGTGTTGAAGACATGGATGAGGGTAGCGACGAAGTCGGGGAGGAAGA

GATGGTTGAAGGCAACGACTATGAAGAATTCGGTGCGTTTGGTGGCTATGGCACCCTCACCAGCTTTGACATCCATATCCTCAGAGCCTT

CGGAAGCTTGGGTCCAGGCCTTCGCATCTTATCGAATGAGCCCTGGGAACTGGAAAACCCTGTGCTGGCCCAGACCCTGGTGGAGGCA

TTGCAGCTGGATCCGGAAACACTTGCCAATGAGACGGCCGCCCGTGCTGCCAACGTAGCCCGCGCCGCCGCCTCCAACCGTGCGGCTCG

GGCCGCTGCCGCCGCTGCCCGTACCGCCTTCAGTCAGGTGGTCGCTAGCCACCGGGTGGCCACGCCGCAGGTCTCAGGAGAGGATACC

CAGCCCACGACCTACGCCGCCGAGGCTCAGGGGCCCACCCCTGAGCCACCCCTTGCTTCTCCGCAGACCTCCCAGATGTTAGTCACCAGT

-continued

AAGATGGCTGCCCCCGAGGCTCCGGCAACCTCCGCACAGTCCCAGACAGGCTCCCCGGCCCAGGAGGCTGCTACTGAGGGCCCTAGTA

GCGCCTGTGCTTTCTCTCAGGCTCCGTGTGCCAGGGAGGTGGACGCCAACCGGCCCAGCACAGCCTTCCTGGGCCAGAATGATGTCTTC

GATTTCACTCAGCCGGCAGGTGTCAGTGGCATGGCCTTCCCGCGCCCCAAGAGACCTGCCCCAGCCCAAGAGGCTGCCACAGAGGGCC

CCAGTGCTGCCTCTGGTGTGCCCCAGACGGGACCTGGCAGGGAGGTGGCAGCCACCCGGCCCAAGACCACCAAGTCGGGGAAGGCGC

TGGCCAAGACTCGGTGGGTGGAGCCTCAGAATGTTGTGGCAGCAGCTGCTGCCAAGGCCAAGATGGCCACGAGCATCCCTGAGCCGG

AGGGTGCAGCTGCTGCCACTGCTCAGCACAGTGCTGAGCCCTGGGCCAGGATGGGAGGCAAGAGGACCAAGAAGTCCAAGCACCTGG

ATGATGAGTATGAGAGCAGCGAGGAGGAGAGAGAGACTCCCGCGGTCCCACCCACCTGGAGAGCATCACAGCCCTCATTGACGGTGC

GGGCTCAGTTGGCCCCTCGGCCCCCGATGGCCCCGAGGTCCCAGATACCCTCAAGGCACGTACTGTGCCTGCCCCCCCGCAACGTGACC

AGGCTGAGTCTCCTCTTGGTGATTCTGGGCGTCATCTTCATGAATGGCAACCGTGCCAGCGAGGCTGTCCTCTGGGAGGCACTACGCAA

GATGGGACTGCGCCCTGGGGTGAGGCACCCATTCCTCGGCGATCTGAGGAAGCTCATCACAGATGACTTTGTGAAGCAGAAGTACCTG

GAATACAAGAAGATCCCCAACAGCAACCCACCTGAGTATGAATTCCTCTGGGGCCTGCGAGCCCGCCATGAGACCAGCAAGATGAGGG

TCCTGAGATTCATCGCCCAGAATCAGAACCGAGACCCCCGGGAATGGAAGGCTCATTTCTTGGAGGCTGTGGATGATGCTTTCAAGACA

ATGGATGTGGATATGGCCGAGGAACATGCCAGGGCCCAGATGAGGGCCCAGATGAATATCGGGATGAAGCGCTGATTGGACGGTGG

AGCTGGGATGACATACAAGTCGAGCTCCTGACCTGGGATGAGGACGGAGATTTTGGCGATGCCTGGGCCAGGATCCCCTTTGCTTTCTG

GGCCAGATACCATCAGTACATTCTGAATAGCAACCGTGCCAACAGGAGGGCCACGTGGAGAGCTGGCGTCAGCAGTGGCACCAATGGA

GGGGCCAGCACCAGCGTCCTAGATGGCCCCAGCACCAGCTCCACCATCCGGACCAGAAATGCTGCCAGAGCTGGCGCCAGCTTCTTCTC

CTGGATCCAGCACCGT

MAGED4B sv3 (SEQ ID NO: 26)
ATGGCTGAGGGAAGCTTCAGCGTGCAATCGGAAAGCTACAGTGTTGAAGACATGGATGAGGGTAGCGACGAAGTCGGGGAGGAAGA

GATGGTTGAAGGCAACGACTATGAAGAATTCGGTGCGTTTGGTGGCTATGGCACCCTCACCAGCTTTGACATCCATATCCTCAGAGCCTT

CGGAAGCTTGGGTCCAGGCCTTCGCATCTTATCGAATGAGCCCTGGGAACTGGAAAACCCTGTGCTGGCCCAGACCCTGGTGGAGGCA

TTGCAGCTGGATCCGGAAACACTTGCCAATGAGACGGCCGCCCGTGCTGCCAACGTAGCCCGCGCCGCCGCCTCCAAACCGTGCGGCTCG

GGCCGCTGCCGCCGCTGCCCGTACCGCCTTCAGTCAGGTGGTCGCTAGCCACCGGGTGGCCACGCCGCAGGTCTCAGGAGAGGATACC

CAGCCCACGACCTACGCCGCCGAGGCTCAGGGGCCCACCCCCTGAGCCACCCCTTGCTTCTCCGCAGACCTCCCAGATGTTAGTCACCAGT

AAGATGGCTGCCCCCGAGGCTCCGGCAACCTCCGCACAGTCCCAGACAGGCTCCCCGGCCCAGGAGGCTGCTACTGAGGGCCCTAGTA

GCGCCTGTGCTTTCTCTCAGGCTCCGTGTGCCAGGGAGGTGGACGCCAACCGGCCCAGCACAGCCTTCCTGGGCCAGAATGATGTCTTC

GATTTCACTCAGCCGGCAGGTGTCAGTGGCATGGCCTTCCCGCGCCCCAAGAGACCTGCCCCAGCCCAAGAGGCTGCCACAGAGGGCC

CCAGTGCTGCCTCTGGTGTGCCCCAGACGGGACCTGGCAGGGAGGTGGCAGCCACCCGGCCCAAGACCACCAAGTCGGGGAAGGCG

TGGCCAAGACTCGGTGGGTGGAGCCTCAGAATGTTGTGGCAGCAGCTGCTGCCAAGGCCAAGATGGCCACGAGCATCCCTGAGCCGG

AGGGTGCAGCTGCTGCCACTGCTCAGCACAGTGCTGAGCCCTGGGCCAGGATGGGAGGCAAGAGGACCAAGAAGTCCAAGCACCTGG

ATGATGAGTATGAGAGCAGCGAGGAGGAGAGAGAGACTCCCGCGGTCCCACCCACCTGGAGAGCATCACAGCCCTCATTGACGGTGC

GGGCTCAGTTGGCCCCTCGGCCCCCGATGGCCCCGAGGTCCCAGATACCCTCAAGGCACGTACTGTGCCTGCCCCCCCGCAACGTGACC

CTTCTGCAGGAGAGGGCAAATAAGTTGGTGAAATACCTGATGATTAAGGACTACAAGAAGATCCCCATCAAGCGCGCAGACATGCTGA

AGGATGTCATCAGAGAATATGATGAACATTTCCCTGAGATCATTGAACGAGCAACGTACACCCTGGAAAAGAAGTTTGGGATCCACCTG

AAGGAGATCGACAAGGAAGAACACCTGTATATTCTTGTCTGCACACGGGACTCCTCAGCTCGCCTCCTTGGAAAAACCAAGGACACTCC

CAGGCTGAGTCTCCTCTTGGTGATTCTGTACATTCTGAATAGCAACCGTGCCAACAGGAGGGCCACGTGGAGAGCTGGCGTCAGCAGTG

GCACCAATGGAGGGGCCAGCACCAGCGTCCTAGATGGCCCCAGCACCAGCTCCACCATCCGGACCAGAAATGCTGCCAGAGCTGGCGC

CAGCTTCTTCTCCTGGATCCAGCACCGT

-continued

Leader/signal peptide
mIGH SP (SEQ ID NO: 27)
ATGGGTTGGAGCTGTATCATCTTCTTTCTGGTAGCAACAGCTACAGGTGTGCACTCC Alternative fusions-Helper Motifs
PVXCP (SEQ ID NO: 28)
ATGAGCGCCCCTGCCTCTACAACACAGCCTATCGGCAGCACCACCTCCACCACCACAAAAACAGCTGGCGCTACCCCTGCCACAGCCTCT GGCCTGTTTACAATCCCTGACGGCGACTTCTTCAGCACCGCCAGAGCTATCGTGGCCTCTAACGCCGTGGCCACAAACGAGGACCTGAG CAAGATCGAGGCCATCTGGAAGGACATGAAGGTGCCCACCGACACAATGGCCCAGGCTGCTTGGGATCTCGTCAGACACTGTGCCGAT GTGGGCAGCTCTGCCCAGACAGAGATGATCGACACAGGCCCCTACAGCAACGGCATCAGCAGAGCTAGACTGGCCGCTGCCATCAAAG AAGTGTGCACCCTGAGACAGTTCTGCATGAAGTACGCCCCTGTCGTGTGGAACTGGATGCTGACCAACAACAGCCCTCCTGCCAACTGG CAGGCTCAGGGCTTTAAGCCAGAGCACAAGTTCGCCGCCTTCGATTTCTTCAACGGCGTGACAAACCCTGCCGCCATCATGCCTAAAGA GGGCCTGATCAGACCTCCTAGCGAGGCCGAGATGAACGCCGCTCAGACTGCTGCCTTCGTGAAGATCACCAAGGCCAGGGCTCAGAGC AACGACTTCGCCTCTCTTGATGCCGCCGTGACCAGAGGCAGAATCACCGGAACCACAACAGCCGAGGCTGTCGTGACATTGCCTCCTCC

A

MIP3a (SEQ ID NO: 29)
ATGTGCTGTACCAAGTCTCTGCTGCTGGCCGCTCTGATGTCTGTGCTGCTGCTGCATCTGTGTGGCGAGTCTGAGGCCGCCAGCAACTTC

GACTGTTGTCTGGGCTACACCGACAGAATCCTGCATCCTAAGTTCATCGTGGGCTTCACCAGACAGCTGGCCAACGAGGGCTGTGACAT

CAACGCCATCATCTTCCACACCAAGAAGAAGCTGAGCGTCTGCGCTAACCCCAAGCAGACCTGGGTCAAGTACATCGTGCGGCTGCTGA

GCAAGAAAGTGAAGAACATG

MITD: HLA-A2 MITD (SEQ ID NO: 30)
ATCGTGGGAATTGTGGCTGGACTGGCCCTGTTTGGCGCCGTGATTACAGGTGCTGTGGTGGCCGCTGTTATGTGGCGGAGAAAGAGCA

GCGACAGAAAAGGCGGCAGCTACTCTCAGGCCGCCAGCTCTGATTCTGCCCAGGGCTCTGATGTGTCCCTGACAGCT

MAGED4B protein (SEQ ID NO: 31)
MAEGSFSVQSESYSVEDMDEGSDEVGEEEMVEGNDYEEFGAFGGYGTLTSFDIHILRAFGSLGPGLRILSNEPWELENPVLAQTLVEALQLDP ETLANETAARAANVARAAASNRAARAAAAAAARTAFSQVVASHRVATPQVSGEDTQPTTYAAEAQGPTPEPPLASPQTSQMLVTSKMAAPE APATSAQSQTGSPAQEAATEGPSSACAFSQAPCAREVDANRPSTAFLGQNDVFDFTQPAGVSGMAFPRPKRPAPAQEAATEGPSAASGVP QTGPGREVAATRPKTTKSGKALAKTRWVEPQNVVAAAAAKAKMATSIPEPEGAAAATAQHSAEPWARMGGKRTKKSKHLDDEYESSEEER ETPAVPPTWRASQPSLTVRAQLAPRPPMAPRSQIPSRHVLCLPPRNVTLLQERANKLVKYLMIKDYKKIPIKRADMLKDVIREYDEHFPEIIERA TYTLEKKFGIHLKEIDKEEHLYILVCTRDSSARLLGKTKDTPRLSLLLVILGVIFMNGNRASEAVLWEALRKMGLRPGVRHPFLGDLRKLITDDFVK QKYLEYKKIPNSNPPEYEFLWGLRARHETSKMRVLRFIAQNQNRDPREWKAHFLEAVDDAFKTMDVDMAEEHARAQMRAQMNIGDEALI GRWSWDDIQVELLTWDEDGDFGDAWARIPFAFWARYHQYILNSNRANRRATWRAGVSSGTNGGASTSVLDGPSTSSTIRTRNAARAGASF

FSWIQHR

DOM-MAGED4B protein (SEQ ID NO: 32)
MGWSCIIFFLVATATGVHSKNLDCWVDNEEDIDVILKKSTILNLDINNDIISDISGFNSSVITYPDAQLVPGINGKAIHLVNNESSEVIVHKAMDIE YNDMFNNFTVSFWLRVPKVSASHLEQYGTNEYSIISSMKKHSLSIGSGWSVSLKGNNLIWTLKDSAGEVRQITFRDLPDFNAYLANKWVFITI TNDRLSSANLYINGVLMGSAEITGLGAIREDNNITLKLDRCNNNNQYVSIDKFRIFCKALNPKEIEKLYTSYLSITFLRDFWGNAAAGPGPMAEG SFSVQSESYSVEDMDEGSDEVGEEEMVEGNDYEEFGAFGGYGTLTSFDIHILRAFGSLGPGLRILSNEPWELENPVLAQTLVEALQLDPETLAN ETAARAANVARAAASNRAARAAAAAAARTAFSQVVASHRVATPQVSGEDTQPTTYAAEAQGPTPEPPLASPQTSQMLVTSKMAAPEAPATS AQSQTGSPAQEAATEGPSSACAFSQAPCAREVDANRPSTAFLGQNDVFDFTQPAGVSGMAFPRPKRPAPAQEAATEGPSAASGVPQTGPG REVAATRPKTTKSGKALAKTRWVEPQNVVAAAAAKAKMATSIPEPEGAAAATAQHSAEPWARMGGKRTKKSKHLDDEYESSEEERETPAVP PTWRASQPSLTVRAQLAPRPPMAPRSQIPSRHVLVLPPRNVTLLQERANKLVKYLMIKDYKKIPIKRADMLKDVIREYDEHFPEIIERATYTLEKK FGIHLKEIDKEEHLYILVCTRDSSARLLGKTKDTPRLSLLLVILGVIFMNGNRASEAVLWEALRKMGLRPGVRHPFLGDLRKLITDDFVKQKYLEYK KIPNSNPPEYEFLWGLRARHETSKMRVLRFIAQNQNRDPREWKAHFLEAVDDAFKTMDVDMAEEHARAQMRAQMNIGDEALIGRWSWD DIQVELLTWDEDGDFGDAWWARIPFAFWARYHQYILNSNRANRRATWRAGVSSGTVGGASTSVLDGPSTSSTIRTRNAARAGASFFSWIQHR -continued FJX1 protein sequence (SEQ ID NO: 33)
MGRRMRGAAATAGLWLLALGSLLALWGGLLPPRTELPASRPPEDRLPRRPARSGGPAPAPRFPLPPPLAWDARGGSLKTFRALLTLAAGAD GPPRQSRSEPRWHVSARQPRPEESAAVHGGVFWSRGLEEQVPPGFSEAQAAAWLEAARGARMVALERGGCGRSSNRLARFADGTRACVR YGINPEQIQGEALSYYLARLLGLQRHVPPLALARVEARGAQWAQVQEELRAAHWTEGSVVSLTRWLPNLTDVVVPAPWRSEDGRLRPLRDA GGELANLSQAELVDLVQWTDLILFDYLTANFDRLVSNLFSLQWDPRVMQRATSNLHRGPGGALVFLDNEAGLVHGYRVAGMWDKYNELL

QSVCVFRERTARRVLELHRGQDAAARLLRLYRRHEPRFPELAALADPHAQLLQRRLDFLAKHILHCKAKYGRRSGT

DOM-FJX1 protein sequence (SEQ ID NO: 34)
MGWSCIIFFLVATATGVHSKNLDCWVDNEEDIDVILKKSTILNLDINNDIISDISGFNSSVITYPDAQLVPGINGKAIHLVNNESSEVIVHKAMDIE YNDMFNNFTVSFWLRVPKVSASHLEQYGTNEYSIISSMKKHSLSIGSGWSVSLKGNNLIWTLKDSAGEVRQITFRDLPDKFNAYLANKWVFITI TNDRLSSANLYINGVLMGSAEITGLGAIREDNNITLKLDRCNNNNQYVSIDKFRIFCKALNPKEIEKLYTSYLSITFLRDFWGNAAAGPGPMGRR MRGAAATAGLWLLALGSLLALWGGLLPPRTELPASRPPEDRLPRRPARSGGPAPAPRFPLPPPLSWDARGGSLKTFRALLTLAAGADGPPRQ SRSEPRWHVSARQPRPEESAAVHGGVFWSRGLEEQVPPGFSEAQAAAWLEAARGARMVALERGGCGRSSNRLARFADGTRACVRYGINPE QIQGEALSYYLARLLGLQRHVPPLALARVEARGAQWAQVQEELRAAHWTEGSVVSLTRWLPNLTDVVVPAPWRSEDGRLRPLRDAGGELA NLSQAELVDLVQWTDLILFDYLTANFDRLVSNLFSLQWDPRVMQRATSNLHRGPGGALVFLDNEAGLVHGYRVAGMWDKNEPLLQSVCV

FRERTARRVLELHRGQDAAARLLRLYRRHEPRFPELAALADPHAQLLQRRLDFLAKHILHCKAKYGRRSGT

Leader sequence underlined.

MAGED4B truncations

MAGED4B sv1 (SEQ ID NO: 35)
MAEGSFSVQSESYSVEDMDEGSDEVGEEEMVEGNDYEEFGAFGGYGTLTSFDIHILRAFGSLGPGLRILSNEPWELENPVLAQTLVEALQLDP

ETLANETAARAANVARAAASNRAARAAAAAARTAFSQVVASHRVATPQVSGEDTQPTTYAAEAQGPTPEPPLASPQTSQMLVTSKMAAPE

APATSAQSQTGSPAQEAATEGPSSACAFSQAPCAREVDANRPSTAFLGQNDVFDFTQPAGVSGMAFPRPKRPAPAQEAATEGPSAASGVP

QTGPGREVAATRPKTTKSGKALAKTRWVEPQNVVAAAAAKAKMATSIPEPEGAAAATAQHSAEPWARMGGKRTKKSKHLKKEYESSEEER

ETPAVPPTWRASQPSLTVRAQLAPRPPMAPRSQIPSRHVLVLPPRNVTRLSLLLVILYILNSNRANRRATWRAGVSSGTNGGASTSVLDGPSTS

STIRTRNAARAGASFFSWIQHR

MAGED4B sv2 (SEQ ID NO: 36)
MAEGSFSVQSESYSVEDMDEGSDEVGEEEMVEGNDYEEFGAFGGYGTLTSFDIHILRAFGSLGPGLRILSNEPWELENPVLAQTLVEALQLDP

ETLANETAARAANVARAAASNRAARAAAAAARTAFSQVVASHRVATPQVSGEDTQPTTYAAEAQGPTPEPPLASPQTSQMLVTSKMAAPE

APATSAQSQTGSPAQEAATEGPSSACAFQAPCAREVDANRPSTAFLGQNDVFDFTQPAGVSGMAFPRPKRPAPAQEAATEGPSAASGVP

QTGPGREVAARTRPKTTKSGKALAKTRWVEPQNVVAAAAAKAKMATSIPEPEGAAAATAQHSAEPWARMGGKRTKKSKHLDDEYESSEEER

ETPAVPPTWRASQPSLTVRAQLAPRPPMAPRSQIPSRHVLCLPPRNVTRLSLLLVILGVIFMNGNRASEVLWEALRKMGLRPGVRHPFLGDL

RKLITDDFVKQKYLEEYKKIPNSNPPEYEFLWGLRARHETSKMRVLRFIAQNQNRDPREWKAHFLEAVDDAFKTMDVDMAEEHARAQMRAQ

MNIGDEALIGRWSWDDIQVELLTWDEDGDFGDAWARIPFAFWARYHQYILNSNRANRRATWRAGVSSGTNGGASTSVLDGPSTSSTIRTR

NAARAGASFFSWIQHR

MAGED4 sv3 (SEQ ID NO: 37)
MAEGSFSVQSESYSVEDMDEGSDEVGEEEMVEGNDYEEFGAFGGYGTLTSFDIHILRAFGSLGPGLRILSNEPWELENPVLAQTLVEALQLDP

ETLANETAARAANVARAAASNRAARAAAAAARTAFSQVVASHRVATPQVSGEDTQPTTYAAEAQGPTPEPPLASPQTSQMLVTSKMAAPE

APATSAQSQTGSPAQEAATEGPSSACAFSQAPCAREVDANRPSTAFLGQNDVFDFTQPAGVSGMAFPRPKRPAPAQEAATEGPSAASGVP

QTGPGREVAATRPKTTKSGKALAKTRWVEPQNVVAAAAAKAKMATSIPEPEGAAAATAQHSAEPWARMGGKRTKKSKHLDDEYESSEEER

ETPAVPPTWRASQPSLTVRAQLAPRPPMAPRSQIPSRGVLCLPPRNVTLLQERANKLVKYLMIKDYKKIPIKRADMLKDVIREYDEHFPEIIERA

TYTLEKKFGIHLKEIDKEEHLYILVCTRDSSARLLGKTKDTPRLSLLLVILYILNSNRANRRATWRAGVSSGTNGGASTSVLDGPSTSSTIRTRNAAR

AGASFFSWIQHR

-continued

```
Alternative fusions-helper motifs:
PVXCP (SEQ ID NO: 38)
MSAPASTTQPIGSTTSTTTKTAGATPATASGLFTIPDGDFFSTARAIVASNAVATNEDLSKIEAIWKDMKVPTDTMAQAAWDLVRHCADVGS

SAQTEMIDTGPYSNGISRARLAAAIKEVCTLRQFCMKYAPVVWNWMLTNNSPPANWQAQGFKPEHKFAAFDFFNGVTNPAAIMPKEGLIR

PPSEAEMNAAQTAAFVKITKARAQSNDFASLDAAVTRGRITGTTTAEAVVTLPPP

MIP3a (SEQ ID NO: 39)
MCCTKSLLLAALMSVLLLHLCGESEAASNFDCCLGYTDRILHPKFIVGFTRQLANEGCDINAIIFHTKKKLSVCANPKQTWVKYIVRLLSKKVKN

M

MITD (SEQ ID NO: 40)
IVGIVAGLALFGAVITGAVVAAVMWRRKSSDRKGGSYSQAASSDSAQGSDVSLTA

MAGED4B Human isoform 2 (SEQ ID NO: 41)
MAEGSFSVQSESYSVEDMDEGSDEVGEEEMVEGNDYEEFGAFGGYGTLTSFDIHILRAFGSLGPGLRILSNEPWELENPVLAQTLVEALQLDP

ETLANETAARAANVARAAASNRAARAAAAAARTAFSQVVASHRVATPQVSGEDTQPTTYAAEAQGPTPEPPLASPQTSQMLVTSKMAAPE

APATSAQSQTGSPAQEAATEGPSSACAFSQAPCAREVDANRPSTAFLGQNDVFDFTQPAGVSGMAFPRPKRPAPAQEAATEGPSAASGVP

QTGPGREVAATRPKTTKSGKALAKTRWVEPQNVVAAAAAKAKMATSIPEPEGAAAATAQHSAEPWARMGGKRTKKSKHLDDEYESSEEER

ETPAVPPTWRASQPSLTVRAQLAPRPPMAPRSQIPSRHVLVLPPRNVTLLQERANKLVKYLMIKDYKKIPKRADMLKDVIREYDEHFPEIIERA

TYTLEKKFGIHLKEIDKEEHLYILVCTRDSSARLLGKTKDTPRLSLLLVILGVIFMNGNRASEAVLWEALRKMGLRPGVRHPFLGDLRKLITDDFVK

QKYLEYKKIPNSNPPEYEFLWGLRARHETSKMRVLRFIAQNQNRDPREWKAHFLEAVDDAFKTMDVDMAEEHARAQMRAQMNIGDEALI

GRWSWDDIQVELLTWDEDGDFGDAWARIPFAFWARYHQYILNSNRANRRATWRAGVSSGTNGGASTSVLDGPSTSSTIRTRNAARAGASF

FSWIQ

MAGED4B Human isoform 3 (SEQ ID NO: 42)
MAEGSFSVQSESYSVEDMDEGSDEVGEEEMVEGNDYEEFGAFGGYGTLTSFDIHILRAFGSLGPGLRILSNEPWELENPVLAQTLVEALQLDP

ETLANETAARAAVNARAAASNRAARAAAAAARTAFQVVASHRVATPQVSGEDTQPTTYAAEAQGPTPEPPLASPQTSQMLVTSKMAAPE

APATSAQSQTGSPAQEAATEGPSSACAFSQAPCAREVDANRPSTAFLGQNDVFDFTQPAGVSGMAFPRPKRPAPAQEAATEGPSAASGVP

QTGPGREVAATRPKTTKSGKALAKTRWVEPQNVVAAAAAKAKMATSIPEPEGAAAATAQHSAEPWARMGGKRTKKVRSPCPLPPPHPLAP

VLSFSSLSCSSPPSPLPLLPLFSSFPSFSPHLPSPPLLSSQLVHVSPTQVC

MAGED4B Human isoform 4 (SEQ ID NO: 43)
MAEGSFSVQSESYSVEDMDEGSDEVGEEEMVEGNDYEEFGAFGGYGTLTSFDIHILRAFGSLSPGLRILSNEPWELENPVLAQTLVEALQLDP

ETLANETAARAANVARAAASNRAARAAAAAARTAFSQVVASHRVATPQVSGEDTQPTTYAAEAQGPTPEPPLASPQTSQMLVTSKMAAPE

APATSAQSQTGSPAQEAATEGPSSACAFSQAPCAREVDANRPSTAFLGQNDVFDFTQPAGVSGMAFPRPKRPAPAQEAATEGPSAASGVP

QTGPGREVAATRPKTTKSGKALAKTRWVEPQNVVAAAAAKAKMATSIPEPEGAAAATAQHSAEPWARMGGKRTKKSKHLDDEYESSEEER

ETPAVPPTWRASQPSLTVRAQLAPRPPMAPRSQIPSRHVLVLPPRNVTLLQERANKLVKYMIKDYKKIPIKRADMLKDVIREYDEHFPEIIRA

TYTLEKKFGIHLKEIDKEEHLYILVCTRDSSARLLGKTKDTPRLSLLLVILGVIFMNGNRASEAVLWEALRKMGLRPGVRHPFLGDLRKLITDDFVK

QKNPELREETPLSMAPSWYLEYKKIPNSNPPEYEFLWGLRARHETSKMRVLRFIAQNQNRDPREWKAHFLEAVDDAFKTMDVDMAEEHAR

AQMRAQMNIGDEALIGRWSWDDIQVELLTWDEDGDFGDAWARIPFAFWARYHQYILNSNRANRRATWRAGVSSGTNGGASTSVLDGPS

TSSTIRTRNAARAGASFFSWIQHR
```

The invention defines:

A. A cancer vaccine comprising nucleic acid encoding the proteins MAGED4B and/or FJX1, or variants thereof, and further encoding an immunogenic fragment of tetanus toxin.

B. The cancer vaccine according to paragraph A, wherein the MAGED4B protein comprises or consists of the sequence of SEQ ID NO: 3, or a variant thereof.

C. The cancer vaccine according to paragraph A or paragraph B, wherein the FJX1 protein comprises or consists of the sequence of SEQ ID NO: 4, or a variant thereof.

D. The cancer vaccine according to any one of the preceding paragraphs, wherein the immunogenic fragment of tetanus toxin comprises or consists of the p30 MHC II epitope of tetanus toxin.

E. The cancer vaccine according to any one of the preceding paragraphs, wherein the immunogenic fragment of tetanus toxin comprises or consists of DOM.

F. The cancer vaccine according to any one of the preceding paragraphs, wherein the MAGED4B and FJX1 antigens are encoded as a single fusion protein.

G. The cancer vaccine according to any one of the preceding paragraphs, wherein the immunogenic fragment of tetanus toxin, MAGED4B and FJX1 are encoded as single fusion protein.

H. The cancer vaccine according to any one of the preceding paragraphs, wherein linker residues are provided between one or more, or all, of the antigens of the immunogenic fragment of tetanus toxin, MAGED4B and FJX1.

I. The cancer vaccine according to any one of the preceding paragraphs, wherein the nucleic acid further encodes a signal peptide for enhancing the efficacy of secretion.

J. The cancer vaccine according to any one of the preceding paragraphs, wherein the nucleic acid further encodes one or more promoters.

K. The cancer vaccine according to any one of the preceding paragraphs, wherein the nucleic acid further encodes a polyA transcription termination sequence.

L. The cancer vaccine according to any one of the preceding paragraphs, wherein the nucleic acid comprises sequences encoding SEQ ID NOs: 2-4, or variants thereof.

M. The cancer vaccine according to any one of the preceding paragraphs, wherein the nucleic acid comprises sequences encoding SEQ ID NOs: 1-6.

N. The cancer vaccine according to any one of the preceding paragraphs, wherein the nucleic acid comprises or consists of the sequence of SEQ ID NOs: 12, 13 or 14.

O. A composition comprising the cancer vaccine according to any one of the preceding paragraphs.

P. A cancer vaccine according to any one of paragraphs A-M, or a composition according to paragraph O, for use as a medicament.

Q. A cancer vaccine according to any one of paragraphs A-M, or a composition according to paragraph 1O, for use for treating or preventing cancer in a subject.

R. A method of treating or preventing cancer in a subject, the method comprising the administration of the cancer vaccine according to any one of paragraphs A-M, or a composition according to paragraph O, to the subject.

S. The cancer vaccine or composition for use according to paragraph Q, or the method of treatment or prevention according to paragraph R, wherein the cancer to be treated or prevented is oral and/or oropharyngeal cancer.

T. The cancer vaccine or composition for use according to any one of paragraphs P, Q or S, or the method of treatment or prevention according to paragraph R or S, wherein the cancer vaccine or composition is used in combination with the administration of a checkpoint inhibitor to the subject.

U. The cancer vaccine or composition for use according to paragraph T, or the method according to paragraph T, wherein the checkpoint inhibitor comprises an anti-PD1 or anti-CTLA4 binding molecule, or nucleic acid encoding an anti-PD1 or anti-CTLA4 binding molecule.

V. A kit for the treatment or prevention of cancer, the kit comprising:

a cancer vaccine according to any one of paragraphs A-M; and a checkpoint inhibitor agent, such as an anti-PD1 or anti-CTLA4 binding molecule.

W. A kit for the treatment or prevention of cancer, the kit comprising:

a first cancer vaccine according to any one of paragraphs A-M, wherein the nucleic acid encodes MAGED4B;

a second cancer vaccine according to any one of paragraphs A-M, wherein the nucleic acid encodes FJX1; and optionally a checkpoint inhibitor agent, such as an anti-PD1 binding molecule.

The present invention has been extensively demonstrated and material and methods for the data obtained and presented in the Figures included herein are presented below, with specific information, on matters such as treatments strategies, are included in the Figures and legends. The methods and data presented here are to support the present invention and are exemplary, depicting some alternative vaccine constructs and the like.

EXAMPLES

Example 1

Figure 1:
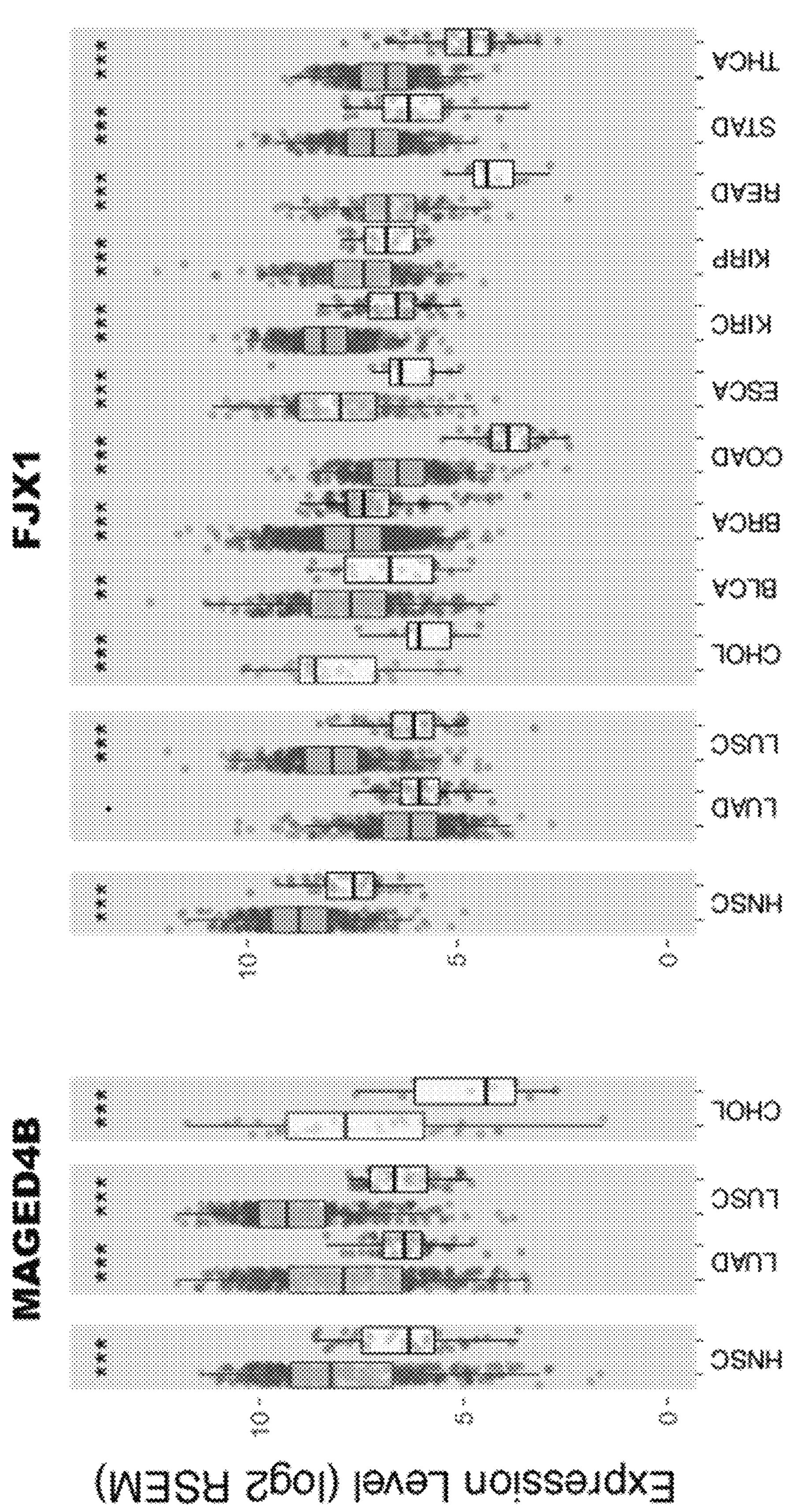
FIG. 1. Overexpression of the target antigens in head and neck squamous carcinoma (HNSC) and other types of cancer of potential interest. Both MAGED4B and FJX1 transcripts are expressed at significantly higher levels in Head and Neck tumours, than in adjacent normal tissue. Regarding other cancer types, MAGED4B expression is also significantly higher in lung adeno (LUAD), squamous (LUSC) carcinomas and Cholangiocarcinoma (CHOL), whilst FJX1 is significantly higher in many tumour types compared to their respective adjacent normal tissues. Transcriptional data is from The Cancer Genome Atlas (TCGA), processed by Li et al (2016) and publicly available online at cistrome.shinyapps.io/timer. This data demonstrates that the target cancer antigens are expressed in multiple cancers, depicting the utility of the vaccine as described here.
Figure 2:
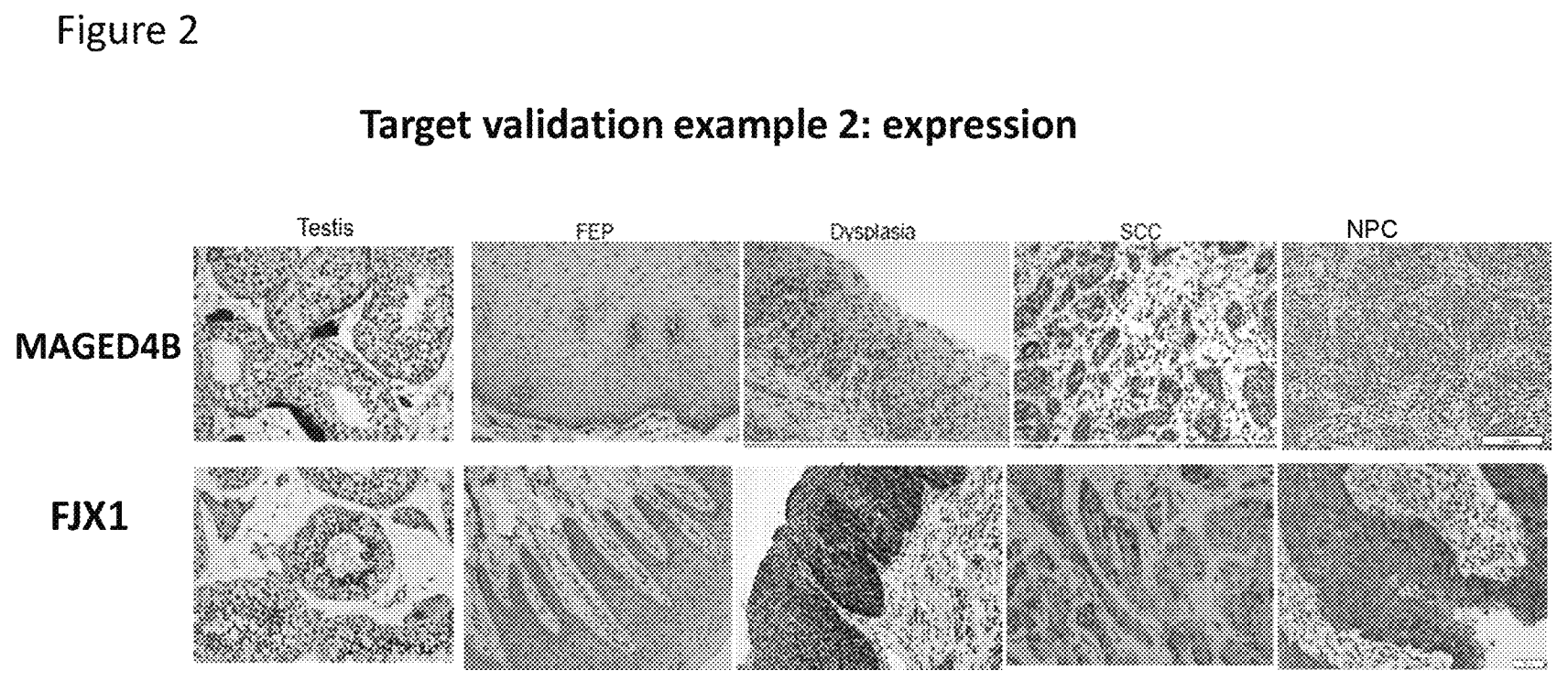
Figure 3:
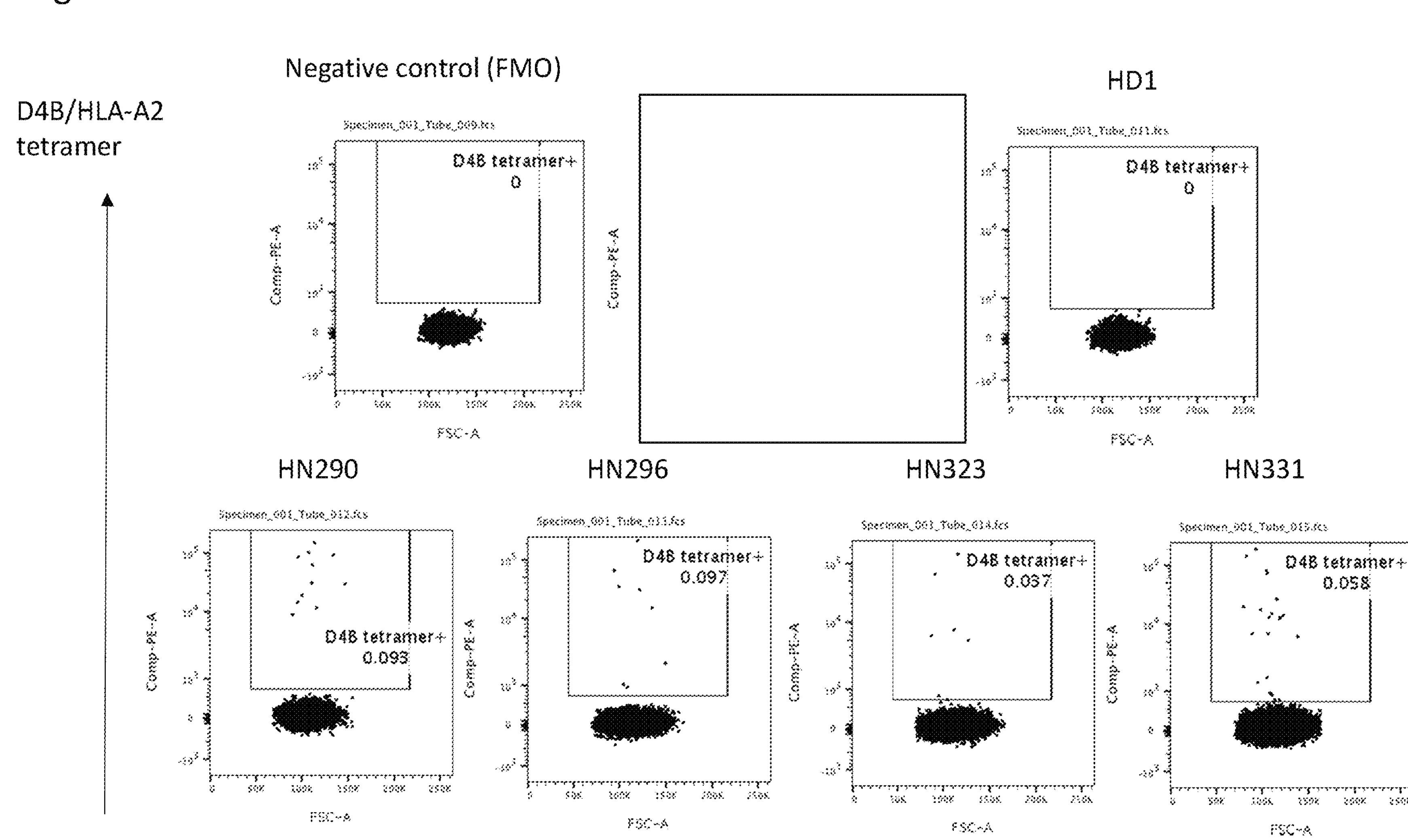
FIG. 3. MAGED4B (D4B) is immunogenic in patient with HPV negative HNSCC patients. The circulating D4B specific CD8 T cells were detected in 5/7 HLA-A2+ patients HNSC patients (4 shown here but not in HLA-A2+ heathy donor (HD1) D4B$^{50}$1-5$^{09}$/HLA-A2-PE tetramer staining in flow cytometry. Staining was performed using peripheral blood mononuclear cells (PBMC) from patients undergoing surgery in Pool, UK. $10^6$ PBMC were strained with anti-CD3 (FITC:OKT3), CD4 (APC:OKT4), CD8 (PE-Cy7: SK1) (BioLegend), DAPI (live/dead stain) (Miltenyi), and MAGED4B$^{501-509}$ tetramer (PE). Flow cytometry performed on a FACSCanto, using UltraComp eBeads (Invitrogen) for compensation. Analysis performed using FlowJo; the gating was on live/dead lymphocytes and CD8 and then tetramer. Tetramer positive CD8 cells are indicated in the gates. This data confirms that in patients with confirmed HNSCC that there exist a pool of T cells that are available for expansion by vaccination. Further, this is encouraging data which suggests that the presence of such T cells alone is not causing any pathology in these individuals, although they are not fully functional otherwise the individuals would be controlling their tumour using such cells.
Figure 5:
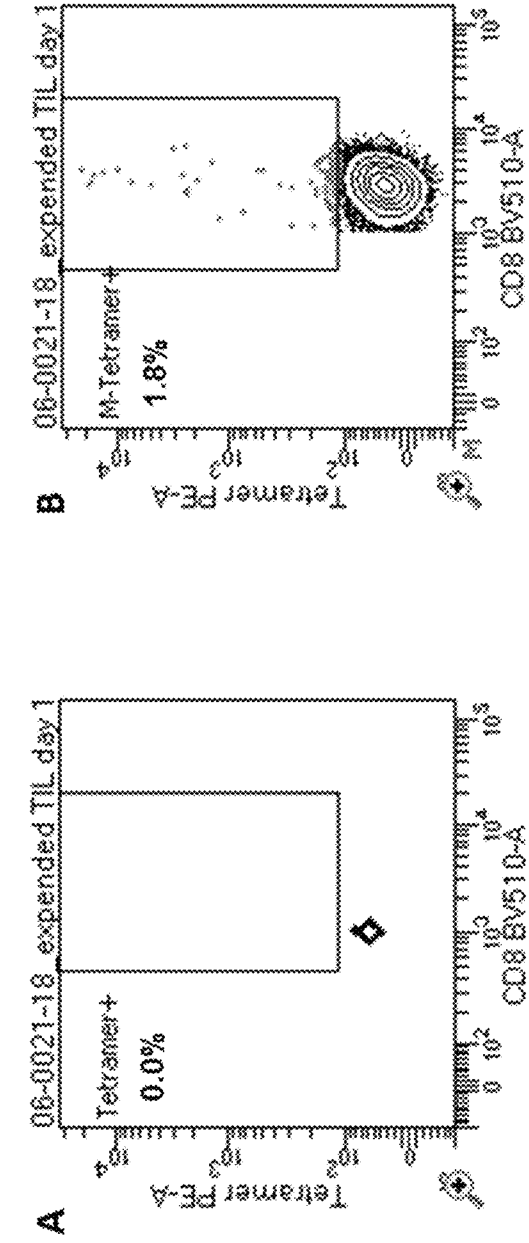
FIG. 5 (A-C). CD8 T cell specific for both target antigens MAGED4B and FJX1. MAGED4B and FJX1-specific CD8 T cells were detected in tumour infiltrating lymphocytes (TILs; expanded with 6000 IU/ml recombinant human IL-2) in HLA-A2+ Malaysian OSCC patient 06-0021-18 using MAGED4B$^{501-509}$ and FJX1$^{15-25}$ HLA-A2 tetramer staining and flow cytometry.
Figure 5:
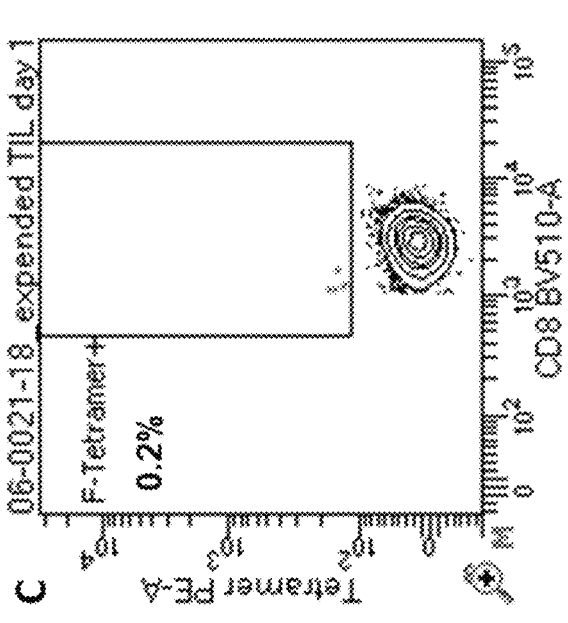
Figure 6:
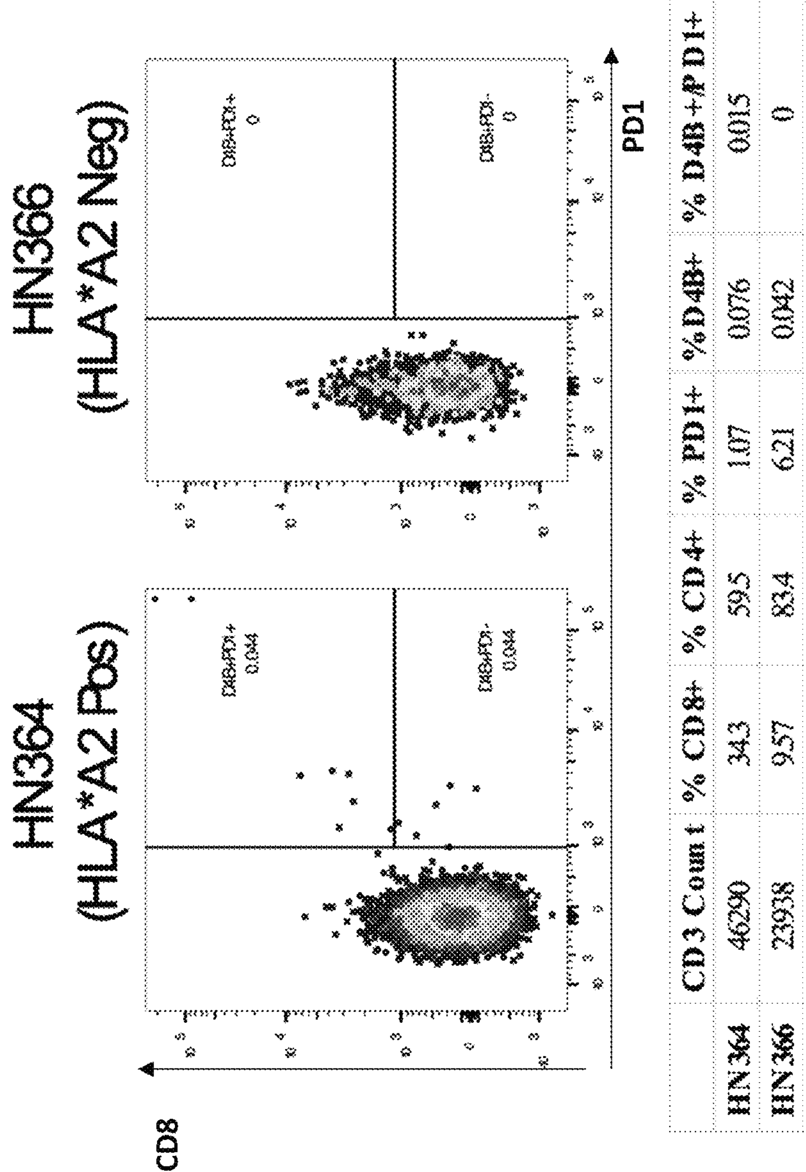
FIG. 6. T cells specific for the target antigen MAGED4B express PD1 in HNSC patients and hence can be targeted with anti-PD1. The specific T cells were detected using MAGED4B$^{501-509}$ tetramer in circulation using PBMCs. Half of the tetramer positive population were also PD1+. This subpopulation is absent in the PBMCs of a HLA*A2 negative HNSC patient (control group). The panel consisted of CD3 (FITC:OKT3), CD4 (APC:OKT4), CD8 (PE-Cy7: SK1), PD-1 (PerCP-Cy5.5:EH12.2H7), CD19 (Pacific Blue: HIB19.11,) and CD14 (Pacific Blue:HCD14) (BioLegend), Live/Dead Violet (Pacific Blue) (Invitrogen), and MAGED4B$^{501-509}$ tetramer (PE). Flow cytometry performed on a FACSCanto, using UltraComp eBeads (Invitrogen) for compensation. Analysis performed using FlowJo software. This data confirms the specificity of HLA-2 tetramer, since in the HLA-2 negative patient (HN366) it does not work. In the HLA-2 positive patient (HN364) this data confirms the antigen sensitivity of T cells.

Evaluation of Immunogenicity of DNA Vaccine Targeting MAGED4B/FJX Antigens in HPV-Ve HNSCC Target Antigens Expression and Pre-Existing T Cell Responses in Patients with HPV Independent HNSCC While there is intriguing potential for the development of patient-specific vaccines based on an individual's tumour mutanome, the costliness and technical difficulty of such an approach means that, even if successful, it is unlikely to benefit most patients. Identifying common tumour antigens that are shared between patients, to the production of generic cancer vaccines that would provide a cheap and widely available treatment for OSCC. Among the different types of TAA, cancer/testis (CT) antigens are highly promising therapeutic targets; cellular and humoral immune responses to CT antigens are frequently observed in cancer patients, and there is an association between CT antigen expression and cytolytic activity of tumour immune infiltrates. The immunogenicity and cancer-specificity of CT antigens have made them prioritised targets for cancer immunotherapy, and their therapeutic function has been tested in a variety of clinical settings. CT antigen vaccines are generally well tolerated, and there are presently a large number of ongoing cancer vaccination trials assessing their therapeutic efficacy. We selected two cancer testis antigens MAGED4B and FJX1 that are identified as frequently expressed in OSCC. We then extended these data to analyses using the CGA (Cancer Genome Atlas) data set and confirmed the expression. Overall the two antigens are expressed at 96% of OSCC cases at the RNA level. Furthermore we have confirmed the expression of both antigens at protein levels in oral dysplasia and OSCC cases (10/10 were positive; 5 for each condition) with no expression in non-malignant oral mucosa (FIG. 2). Expression data in healthy tissues at protein levels have been paralleled by study of pre-existing immunity to the antigens in patients with HPV independent HNSCC using an HLA-A2 tetramer (at present available for MAGED4B only) and overlapping peptide pools (OPP) for the entire amino acid sequence of each antigen. These were measured in both blood and the tumour using expanded tumour infiltrating lymphocytes. Circulating MAGED4B tetramer positive CD8+ T cells were observed in 4/6 HLA-A2 patients (0.04-0.1% of total CD8+ T cells) (FIG. 3) with 2/2 expanded TILs also having the tetramer positive at a similar frequency (FIG. 4 A and FIG. 5). Higher levels of MAGED4B positive CD8 T cells (5-10 times) was detected in HLA-A2 negative HLA-A1 positive TIL samples using OPP indicating reactivities beyond HLA-A2 restriction (FIG. 4B). For FJX1 so far CD8 T cell reactivity has been only evaluated in expanded TIL samples using OPP with demonstration of CD8 reactivities in HLA-A1 patients coexisting with MAGED4B CD8 T cells (FIG. 4B). The patients' data indicate a significant immunogenicity of both antigens more so pronounced for MAGED4B.

Example 2

Preclinical Data on DNA Vaccines Efficacy/Immunogenicity

Vaccine Design

In HPV+ cancers DNA vaccine encoding immunogenic viral antigens have advanced significantly with the recent results of a randomised phase 2b clinical trial in cervical neoplasia demonstrating histopathological regression of the disease. Our approach for DNA vaccination has been to deliver tumour-specific peptides or antigens in the context of immunogenic sequence of tetanus toxin domain (Dom). The vaccine design is aimed to provide linked CD4 T cell help for optimal induction of CD8+ T cells in patients with cancer, a potent strategy that breaks tolerance. Phase II clinical data suggest that DNA vaccination is able to overcome peripheral tolerance in tumour tissue with CD8 T cells response to tumour antigen (carcino-embryonic antigen; CEA) detected post-vaccine and with indication of clinical benefits. We therefore applied Dom based design to generate DNA vaccines encoding full length MAGED4B and FJX1 antigens (p.Dom-MAGED4BFL and p.Dom-FJX1FL). Here we opted for full-length antigen design to achieve a wider populational coverage and not focused on targeting individual HLA alleles (HLA-A2).

Mouse Models

For immunogenicity HLA-A2 transgenic mice HHD were used without tumour challenge. B16/F10 was transfected with human HLA-A2, MAGED4B and FJX1 constructs to mimic the expression of these antigens in HNSCCs is used in the humanised mouse model (B6.Cg-Tg (HLA-A/H2-D) 2Enge/J) transgenic for the HLA-A2. The tumour was given subcutaneously.

Immunogenicity of each vaccine has been confirmed followed a single dose of the vaccines given with electroporation in non-tumour bearing mice (FIG. 7). An overlapping peptide pool (OPP) covering the entire sequence of each antigen (MAGED4B 183 peptides; FJX1 107 peptides) was used to measure the antigen specific T cell responses.

In tumour challenge experiments mice were vaccinated when the tumours were palpable at day 3 (size). The DNA vaccines were given as a mixture twice 3 weeks apart with or without anti-PD1 (In vivo Mab antimouse PD1 (RMP1-14, BEO146 from BioXcell) with anti-PD1 serving as a comparator. The experiments were paralleled by immunogenicity measurements using OPP as above. The DNA vaccine was able to reduce/supress the tumour growth at a similar level as anti-PD1 against the control DNA vaccine (p.Dom backbone) with a remarkable synergistic affect when combined together (FIG. 9B). The data were paralleled by demonstrating of induction of MAGED4B-specific T cells and an increase in MAGED4B specific T cells upon combination with anti-PD1 (FIG. 9C). Collectively the preclinical data demonstrates the DNA vaccines targeting MAGED4-B/FJX1 have a significant potential to suppress the growth of tumour expressing these antigens and this can be further enhanced by combination with anti-PD1.

Example 3

Alternative Gene Fusion Partners—Helper Motifs—MITD, PVXCP, MIP3a

MHC Class I trafficking signal (MITD) attached to the C-terminus of target antigen has been shown to promote presentation of both MHCI and MHCII epitopes leading to polyepitope expansion of CD4 and CD8 T cells (Kreiter S, et al. J Immunol. 2008; 180(1):309-18).

PVXCP (potato virus X coat protein) is a helper sequence which has been shown to enhance induction of T cell responses to fused cancer antigen through the mechanism of linked T cell help similarly to DOM helper sequence from tetanus toxin (Savelyeva N et al Nature biotechnology. 2001; 19(8):760-4, and Stegantseva M V et al, Cancer immunology, immunotherapy: CI. 2020).

Antigens fused to chemokine MIP3α have been shown to direct to immature DCs via chemokine receptor CCR6 (Biragyn A et al. J Immunol. 2001; 167(11):6644-53). Following the receptor mediated uptake fused antigens are presented by both MHC class I and II, activating significant responses CD4+ and CD8+ T cell responses (Biragyn A et al. Blood. 2004; 104(7):1961-9, Biragyn A, et al. J Immunol. 2007; 179(2):1381-8.)

Figure 13:
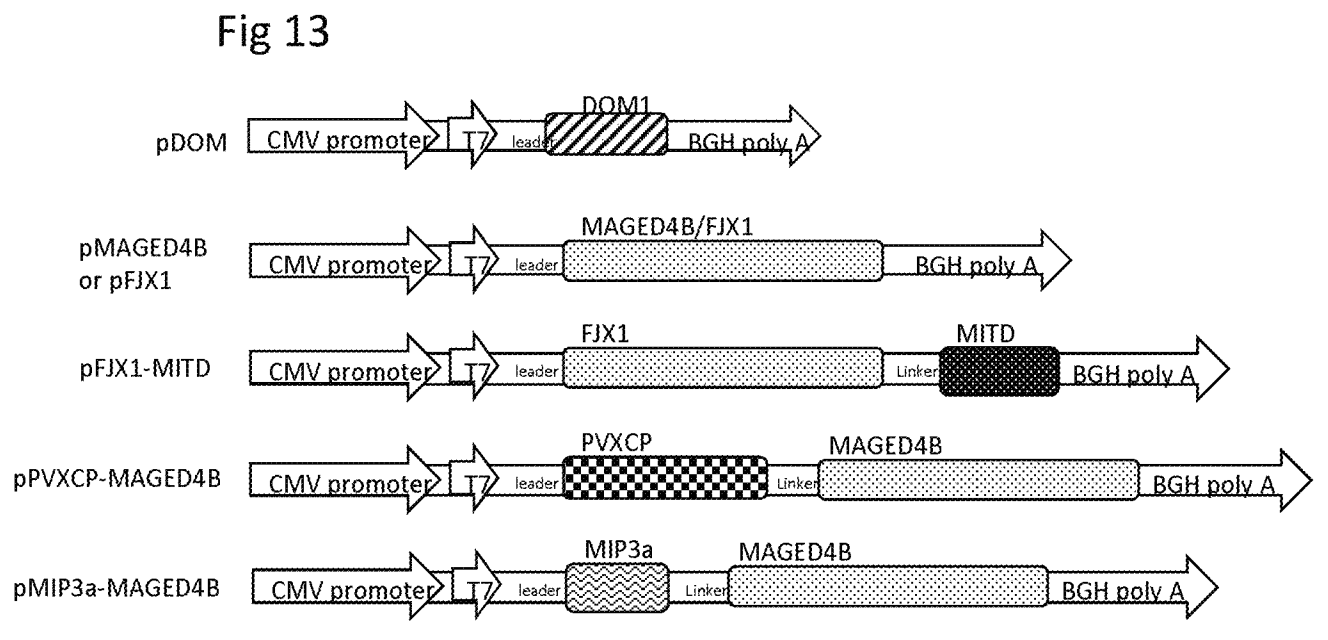

These fusions are depicted in FIG. 13 and the figure legend provides further information.

Assembly of the Fusion Constructs with Helper Motifs

MITD (165 bp) encodes the HLA-A2 trafficking signals. PVXCP (732 bp) encodes the potato virus X coat protein. MIP3α (252 bp) encodes macrophage inflammatory protein 3 alpha. MITD PVXCP and MIP3α gene were codon-optimised and synthesised by GeneArt (Invitrogen). The leader sequence encoding mouse (mus) IgH signal peptide (MGWSCIIFFLVATATGVHS) was inserted at the N terminus of each construct to enhance secretion, with the exception of MIP3α fusion constructs, which has its own signal peptide. Fusion partners and the gene of interest (MAGED4B or FJX1) were linked with a seven amino acid linker (AAAGPGP). With the exception of MITD, all other fusion partners were fused upstream of the target cancer antigens (FIG. 13). MITD sequence was added downstream of the antigenic sequence. The genes for MAGED4B, FJX1 or their fusions of interest were inserted into pcDNA3 vector at NotI, XhoI and XbaI restriction enzyme sites to generate the DNA vaccine constructs.

Figure 8:
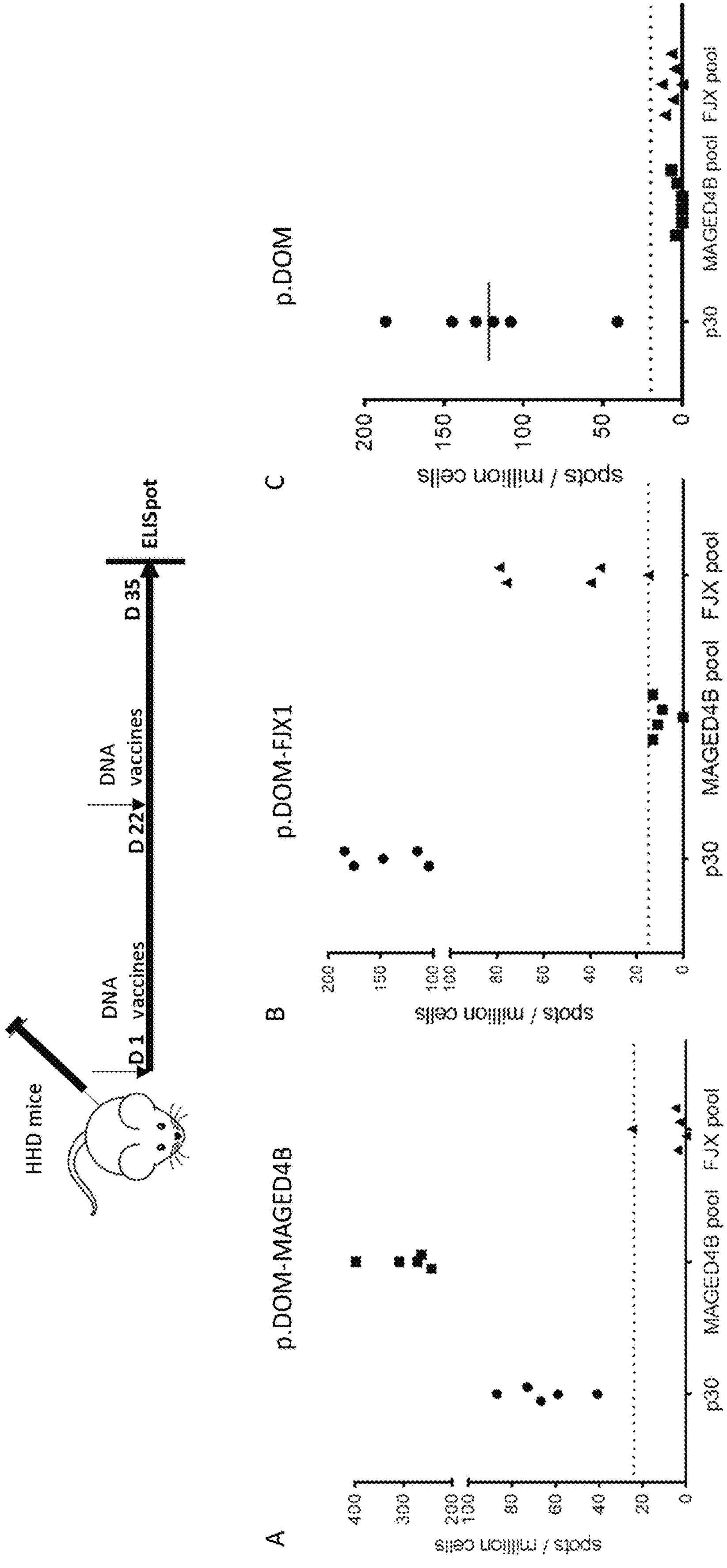
FIG. 8. Three groups of 5-6 non-tumour bearing HHD (transgenic for the human HLA-A2 allele) mice were vaccinated with 50 microgram of p.Dom-MAGED4B (A), p.Dom-FJX1 (B) or p.Dom (C) individually on day 1 following by a booster injection of the same DNA vaccine with electroporation on d 22. Their immunogenicity was evaluated by IFNγ ELISpot. Lymphocytes isolated from mouse spleens were plated to ELISpot plates on d 35 and overlapping peptides pool for each target antigen MAGED4B and FJX1 were used to detect responding specific T cells. The overlapping peptide pools consisted of 15 mer peptides with 11aa overlap for the entire sequence of each antigen (183 individual peptides were pooled for MAGED4B and 107 peptides for FJX1). P30 peptide was used as a standard for vaccination. Individual peptides were generated by JPT, Germany, to 90% purity. For ELISpot IFNγ ELISpot kit from BD Bioscience was used according to manufacturer's protocol. Spots corresponding to individual responding T cells were spots were imaged and enumerated with AID ELISpot plate reader system ELRO4 and software (AID Autoimmun Diagnostika GmbH, Strassberg, Germany). This data confirms the immunogenicity of the antigens in HAL-A2 transgenic mice.

Evaluation of Immunogenicity of Fusion Constructs Containing DOM and Different Fusion Helper Motif Partners:

Generic vaccination protocol for evaluating immunogenicity of DNA vaccines alone or in combination with electroporation was prime/boost (FIGS. 17; 21-26) (specific vaccine constructs are indicated in each figure legend):

Three groups of 5-6 non-tumour bearing HHD (transgenic for the human HLA-A2 allele) mice were vaccinated with 50 μg of p.Dom-MAGED4B, p.Dom-FJX1 or p.Dom individually on day 1 following by a booster injection of the same DNA vaccine with electroporation on d 22. Their immunogenicity was evaluated by IFN-γ ELISPOT. Lymphocytes isolated from mouse spleens were plated to ELISPOT plates on day 35 (FIG. 8). In experiments in FIG. 21-26 varying doses of dbDNA vaccines indicated in the figure legends.

Figure 11:
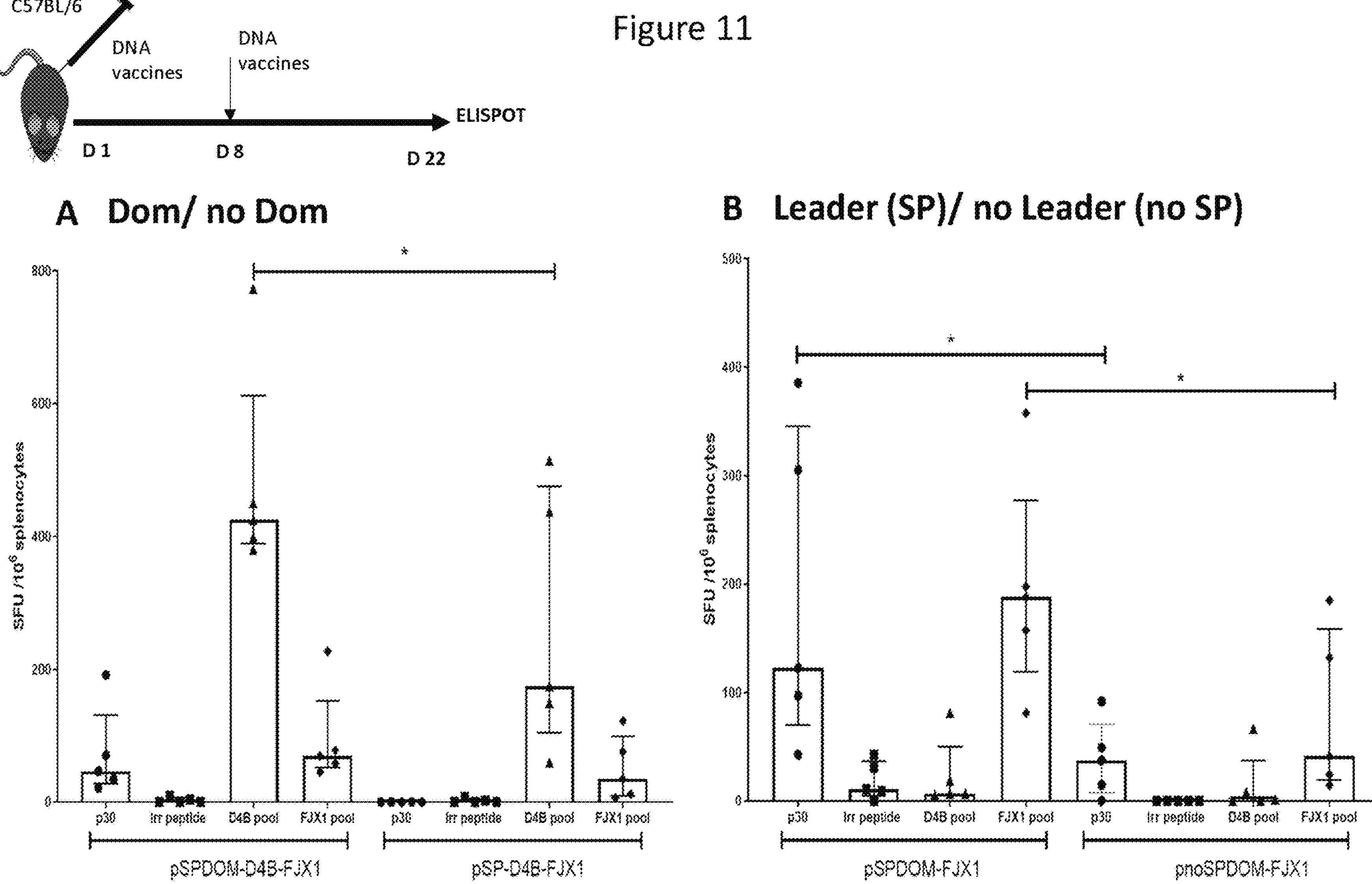
FIG. 11 (A and B). Demonstration of critical components for the design of MAGED4B and FJX1 targeting DNA vaccines. For both Figures, the treatment strategy is depicted. Four groups of 5 non-tumour bearing C57BL/6 mice were vaccinated with 50 μg of p.Dom-MAGED4B-FJX1, pSP-MAGED4B-FJX1 (no DOM), pDom-FJX1, pnoSPDOM-FJX1 (no Leader/SP) individually on day 1 following by a booster injection of the same DNA vaccine on day 8. Their immunogenicity was evaluated by IFNγ ELISpot. Lymphocytes isolated from mouse spleens were plated to ELISpot plates on d 22 and overlapping peptides pool for each target antigen MAGED4B and FJX1 were used to detect responding specific T cells. The overlapping peptide pools consisted of 15 mer peptides with 11aa overlap for the entire sequence of each antigen (183 individual peptides were pooled for MAGED4B and 107 peptides for FJX1). P30 peptide an MHCII peptide from DOM was used as a control for vaccination.
Figure 12:
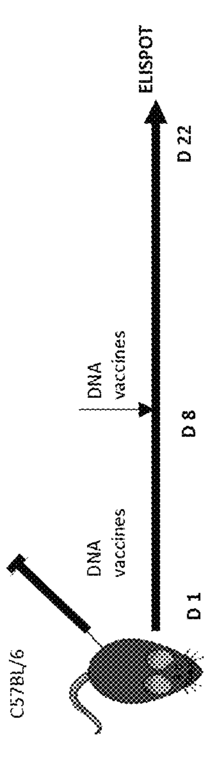
FIG. 12. DNA vaccine targeting both antigens in tandem as a fusion antigen induces comparable T cell response to DNA vaccine targeting single antigens. The treatment strategy is depicted. Three groups of 5 non-tumour bearing C57BL/6 mice were vaccinated with 50 μg of p.Dom-MAGED4B, pDom-FJX1 or p.Dom-MAGED4B-FJX1 individually on day 1 following by a booster injection of the same DNA vaccine on day 8. Their immunogenicity was evaluated by IFNγ ELISpot. Lymphocytes isolated from mouse spleens were plated to ELISpot plates on day 22 and overlapping peptides pool for each target antigen MAGED4B and FJX1 were used to detect responding specific T cells. The overlapping peptide pools consisted of 15 mer peptides with 11aa overlap for the entire sequence of each antigen (183 individual peptides were pooled for MAGED4B and 107 peptides for FJX1). P30 peptide an MHCII peptide from DOM was used as a control for vaccination. DNA vaccine targeting both antigens showed similar capability of inducing specific T cell response. P values were calculated with Mann-Whitney analysis by Graphpad prism 8.0. For ELISpot IFNγ ELISpot kit from BD Bioscience was used according to manufacturer's protocol. Spots corresponding to individual responding T cells were imaged and enumerated with AID ELISpot plate reader system ELR04 and software (AID Autoimmun Diagnostika GmbH, Strassburg, Germany).

In experiments in FIGS. 11, 12, 14 vaccinations were given at day 1 and 8 and spleens for ELISPOT were taken on day 22 (specific vaccine constructs are indicated in each figure legend).

In FIGS. 15, 19 and 20 the response was evaluated after priming only following generic (specific vaccine constructs are indicated in each figure legend) protocol: non-tumour bearing C57B/6 mice were vaccinated 50 μg pDOM plasmid vaccine (as a negative control, 3 mice), 25 μg DB-DOM-FJX1 CO (5 mice), and 25 μg pDom-FJX1 plasmid (5 mice). The vaccines were administered i.m. with EP on day 1.). In experiments in FIG. 15 mice received 50 μg of DNA vaccine. Lymphocytes isolated from mouse spleens were plated to ELISPOT plates on day 14.

Generic ELISpot Protocol as Used Herein:

IFNγ ELISpot was performed according to manufacturer's protocol; BD Biosciences). Briefly, lymphocytes were isolated from the spleens of vaccinated mice using Lymphoprep™ and plated to ELISpot plates at $2.5\times10^5$ cells per well. Overlapping peptide pools (OPP) for each target antigen MAGED4B or FJX1 were added to a final concentration of 1 μM and incubated for 40 hours at 37° C. at 5% in RPMI supplemented with 10% FCS, 20 mM L-Glutamine, 10 U/ml penicillin/streptomycin. The overlapping peptide pools for the entire sequence of each antigen consisted 15 mer peptides with 11aa overlap; 183 peptides were pooled for MAGED4B and 107 peptides for FJX1 (JPT, Germany). FJX1 OPP served as a negative control for MAGED4B targeting vaccines and vice versa. Spots forming units (SFUs) corresponding to individual responding T cells were imaged and enumerated with AID ELISpot plate reader system ELR04 and software (AID Autoimmun Diagnostika GmbH, Strassburg, Germany). The graphs were generated using PRISM graphpad package.

Example 4

Identification of MAGED4B Antigen on CAF

Immunohistochemical analysis of HNSCC cases demonstrating strong MageD4B expression in cancer associated fibroblasts as well as cancer cells. Anti-MAGED4B monoclonal antibody (Santa Cruz, G12; sc-393059) was used on HNSCC tissues at 1:50 dilution following antigen retrieval using high pH (Tris-EDTA (pH (9)) buffer. Deparaffinization, rehydration, antigen retrieval, and IHC staining were performed using a Dako PT Link Autostainer (using EnVision FLEX Target Retrieval Solution, High pH (Agilent Dako) and DAKO Auto-stainer Link48 in Cellular Pathology Department of University Hospital of Southampton NHS Trust. DAKO Envision FLEX Mouse linker was applied to sections for 15 minutes; DAKO Envision FLEX HRP (20 minutes) and DAKO Substrate Working Solution (10 minutes) and then counterstained with DAKO Envision FLEX Haematoxylin for 5 minutes. Images were captured using ZEISS Axio scanner in WISH Lab.

Six Individual HNSCC Cases are Presented (FIG. 27)

Analysis of 10 cases of HNSCC confirmed tumour cell expression of MAGED4B in 9/10 cases. Level of tumour cell expression was assessed using the H Score (the product of staining intensity (scored 0-3) and percentage of positive cells (scored 0-100); giving a maximum possible score of 300 ie 100% of tumour cells showing strong staining. Notably, (and unexpectedly), high expression of MAGED4 was also observed in CAF (7/10 cases) indicated as CAF+ in the table below. CAF staining was assessed as positive or negative. We confirmed CAF MageD4B expression by analysing scRNASeq HNSCC transcriptomic data (which also confirmed MAGED4B expression by HNSCC cells) (FIG. 28A). Single-cell RNASeq (scRNASeq) has emerged as a powerful method for quantifying the transcriptome of individual cells, and appropriate protocols are outlined in Andrews, T and Hemberg, M, Molecular Aspects of Medicine Volume 59, February 2018, Pages 114-122.

| Intensity score | 0-None Proprtion Score | 1- Low Proprtion Score | 2 - Moderate Proprtion Score | 3 - Strong Proprtion Score | Automatic H Score | |
|---|---|---|---|---|---|---|
| 17HS10920P | 30 | 10 | 10 | 50 | 180 | |
| 16HS19001B | 85 | 5 | 5 | 5 | 30 | CAF+ |
| 17HS15081C | 90 | 5 | 5 | 0 | 15 | CAF+ |
| 16HS33330H | 85 | 5 | 5 | 5 | 30 | CAF+ |
| 19HS16208P | 95 | 5 | 0 | 0 | 5 | CAF+ |
| 19HS1407D | 80 | 5 | 5 | 10 | 45 | CAF+ |
| 18HS5113K | 85 | 20 | 5 | 0 | 30 | CAF+ |
| 19HS233L | 95 | 5 | 0 | 0 | 5 | |
| 19HS7587E | 100 | 0 | 0 | 0 | 0 | |
| 19HS12674C | 85 | 5 | 10 | 0 | 25 | CAF+ |

The table shows the intensity of staining of tumour cells. CAF+ indicates strong staining for MAGED4B in CAF.

Example 5

Identification of MAGED4B Expression in Tumour and Normal Tissues

These studies were designed to evaluate MAGED4B and FJX1 expression in both tumour and normal tissue samples. Tumour biopsy samples from OSCC patients and normal tissue microarray samples were obtained and subjected to immunohistochemistry analysis. Strong expression of both antigens was evident in all samples from patients with OSCC. 5/5 samples using HPV-HNSCC and 5/5 in oral dysplastic tissues for each antigen (Southampton, UK cohort). 28 samples were evaluated for antigen expression with 28/28 samples being positive for MAGED4B and 27/28 samples positive for FJX1 (Malaysian cohort).

In addition, 5 samples from patients with lung cancer (3 LUAD, 2 LUSC) exhibited strong expression of MAGED4B.

The suitability of targeting either of these two antigens was suggested in the analysis which demonstrated no/negligible expression in healthy tissue and confirmed by low staining in the TMA samples (data not shown). Thus, the vaccine is not expected to induce an immune response to normal tissues.

This work established the expression of both antigens in multiple HPV-ve HNSCC samples from patients in Malaysia and the UK and confirmed the favourable tissue expression patterns in tissue microarray panels of major organs including non-dysplastic oral tissue.

For Southampton OSCC patient samples: samples were stained using an automated DAKO autostainer following the manufacturer's instructions.

TABLE 1

| Summary of approach (UK): | |
|---|---|
| Primary Antibody | |
| MAGED4B - NBP1-89594 (Novus Biological) | FJX1 - NBP2-32442 (Novus Biological) |

TABLE 1-continued

| Summary of approach (UK): | |
|---|---|
| Dilution Factor | |
| 1:200 | 1:100 |
| Target Retrieval | |
| Heat-Induced | Heat-Induced |
| Linker Type | |
| Rabbit IgG | Rabbit IgG |

For Malaysian cohort of OSCC patients, FFPE blocks were identified and sectioned at 4 μm on positively-charged glass slides. Briefly, wax from the sections were melted for 10 minutes at 65° C. for 10 minutes, followed by deparaffinisation by 2 washes of xylene substitute at 5 minutes each. The sections were then rehydrated in graded ethanol (100% ethanol X 2, 95% ethanol X 2, 70% ethanol X 1) and washed in distilled water for a minimum of 30 seconds. It was followed by heat-induced antigen retrieval (citrate buffer pH 6 for MAGED4B; Tris-EDTA buffer pH 9 for FJX1) for 20 minutes at 99° C. Non-specific binding was blocked by incubating sections in Dual Endogenous Enzyme Blocking Reagent from the Dako cytomation Envision+ Dual Link System HRP (DAB+) kit for 10 minutes at room temperature. Sections were then incubated with anti-MAGED4B (1:100 dilution) and anti-FJX1 antibodies (1:200 dilution) for 16 hours in 4° C. After incubation, sections were washed and incubated with peroxidase-labelled polymer (conjugated to goat anti-mouse and goat anti-rabbit) for 30 minutes at room temperature. Positive binding to respective antibodies was developed under microscope with DAB+ chromogen substrate and mounted with coverslips after counterstained by haematoxylin and dehydrated in graded ethanol.

TABLE 2

| Summary of approach, alternative antibodies (Malaysia): | |
|---|---|
| Primary Antibody | |
| MAGED4B -HPA003554 | FJX1 - HPA059220 |
| Dilution Factor | |
| 1:100 | 1:200 |
| Target Retrieval | |
| Heat-Induced | Heat-Induced |
| Linker Type | |
| Rabbit IgG | Rabbit IgG |

This work confirmed:

Strong expression of both antigens in HNSCC/OSCC patient samples from the UK and from Malaysia.

Lung cancer samples also show strong expression of MAGED4B (FJX1 not analysed), confirming the overexpression data generated using the TCGA database (detailed in TGL-100_001-R TCGA)

These data correspond broadly with the available RNAseq data showing a favourable tissue expression pattern; strong expression in tumours and low/no expression in healthy tissue.

Example 6

Preclinical Work in B16 Mouse Model

To demonstrate the impact of therapeutic vaccination with the vaccine described here on tumour progression, the B16 model expressing the antigens was employed to challenge HLA-A2 transgenic AAD mice subcutaneously. Tumours were allowed to establish for five days prior to vaccination at day 5 with the dual vaccine, tumour volume evaluation commencing once measurable at approximately day 10 post administration. Combination of the effect of vaccine treatment with anti-PD-1 was also evaluated.

Vaccine monotherapy delayed tumour growth compared with controls, with the effect further markedly enhanced upon combination with anti-PD-1. Evaluation of the tumour by immunohistochemistry revealed that in the tumours of mice vaccinated with the dual vaccine, increased T cell infiltrates were evident compared to pDOM control vaccinated mice. Flow cytometry further demonstrated that these infiltrates contained increased numbers of activated CD4+ and CD8+ T cells relative to the pDOM control. Increased expression of the T cell exhaustion marker PD-1 indicated that combining PD-1 inhibition with vaccination could be beneficial.

This work upholds our proposed mechanism of action that vaccination targeting novel antigens MAGED4B and/or FJX1 combined with PD-1 inhibition can effectively induce T cell mediated tumour attack.

Efficacy of two doses of the vaccine by intramuscular (i.m) injection was tested in the BAM model (B16 melanoma tumour genetically modified to express MAGED4B and HLA-A2) or the BAF model (B16 melanoma tumour genetically modified to express huFJX1 and HLA-A2) using the AAD mouse (HLA-A2+/Kb+). BAM cells have confirmed expression of MAGED4B and mouse FJX1 which has 95% homology to human FJX1. BAF cells have confirmed expression of huFJX1.

B16F10 melanoma cell line expressing the human HLA-A2 gene was kindly given by Professor Eric Tartour (Universite Paris Descartes, Paris). This cell line was cultured in RPMI 1640 supplemented with 10% heat inactivated-foetal bovine serum, penicillin/streptomycin (100 U/ml) and 1 mg/ml G418. B16F10/HLA-A2 was validated to endogenously express mouse FJX1 and modified to express human MAGED4B (B16F10/HLA-A2/MAGED4B, "BAM"). In parallel, B16F10/HLA-A2 was modified to express human FJX1 (B16F10/HLA-A2/FJX1, "BAF"). The expressions of HLA-A2 in these cell lines were confirmed by flow cytometry using human HLA-A2-PE (clone BB7.2)-conjugated antibody. MAGED4B and FJX1 expression levels were confirmed by western blotting using custom made anti-MAGED4B and anti-FJX1 antibodies respectively.

The immunogenicity and efficacy of DNA vaccine were tested on transgenic mice B6.Cg-Immp2lTg(HLA-A/H2-D)2Enge/J expressing chimeric HLA-A2.1/H2-Dd MHC Class I molecule (also known as the AAD mice) purchased from Jackson Laboratory, USA. AAD mice were bred in the animal laboratory for the use in subsequent experiments.

Mice were challenged with the BAM cell line ($10^6$ cells) at day 0 and then vaccinated with vaccine (50 μg of each vaccine) or 50 μg pDOM DNA vaccine control (intramuscular) in sterile saline on day 5 after palpable tumours were observed (measuring on average 25 $mm^2$). The pDOM control expressed the tetanus toxin DOM helper sequence only. Booster injections were given at day 12. The tumour growth was monitored until mice were culled to assess the tumours for T cell infiltration by immunohistochemistry and flow cytometry. Tumour volumes were evaluated using the formula: volume=½(length×width$^2$).

Figure 9:
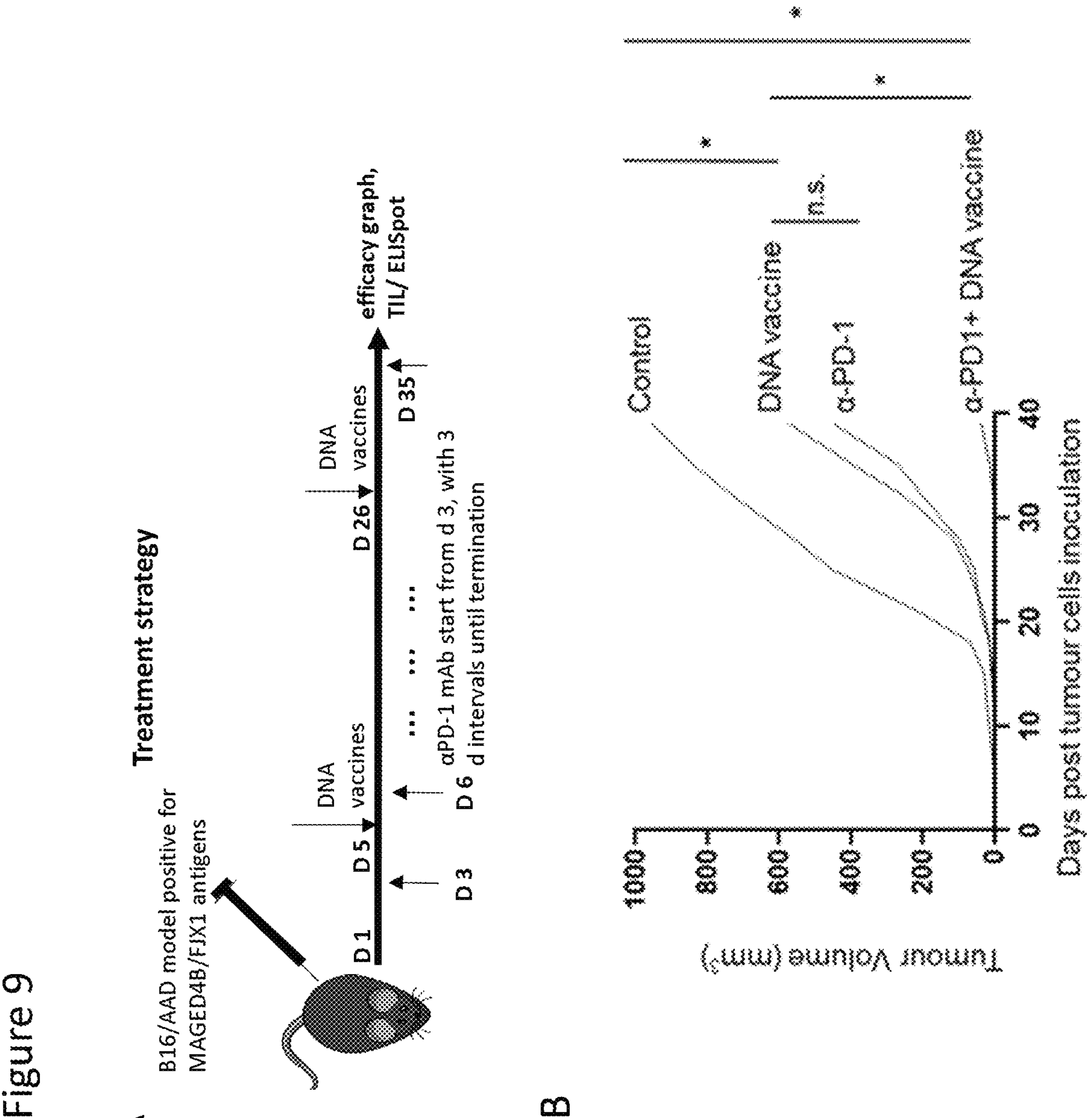
FIG. 9 (A-D). DNA vaccines are efficacious as treatment alone and in combination with anti-PD1.
Figure 9:
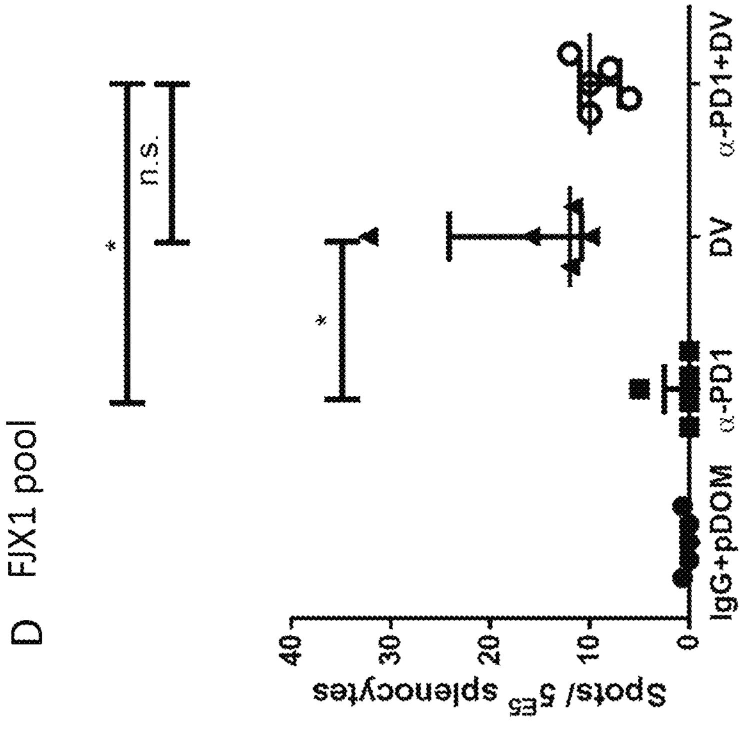
Figure 10:
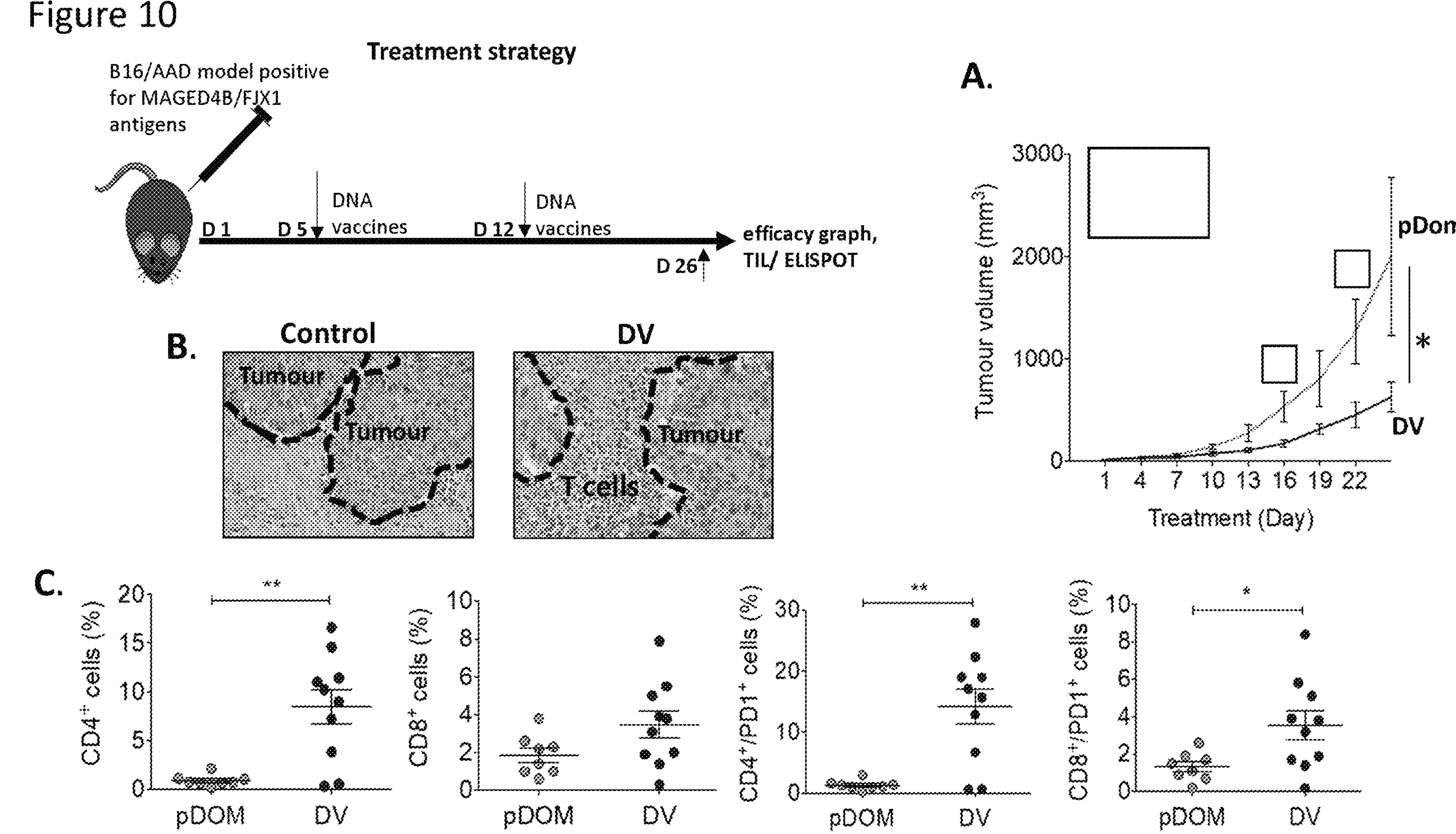
FIG. 10 (A-C). DNA vaccine is efficacious in inhibiting tumour growth.

Results for plasmid based vaccines are given on FIGS. 9 and 10.

The invention claimed is:

1. A cancer vaccine comprising a DNA encoding an immunologically active truncated version of MAGED4B protein, wherein said immunologically active truncated version of MAGED4B protein comprises between 400 and 700 amino acids of a sequence which has at least 95% sequence identity to the MAGED4B sequence as set forth in SEQ ID No: 3, wherein said immunologically active truncated version of MAGED4B comprises the removal of all or part of a MAGE homology domain corresponding to residues 412-682 of SEQ ID No. 3, and wherein the cancer vaccine further comprises a helper motif that encodes a protein, a polypeptide or an immunological fragment of a protein which stimulates an immunological response.

2. The cancer vaccine according to claim 1, wherein the nucleic acid sequence has at least 85% sequence identity to the sequence set forth in any one of SEQ ID No. 24, SEQ ID No. 25 or SEQ ID No. 26.

3. The cancer vaccine as described in claim 1, wherein said helper motif encodes an immunological fragment of a protein.

4. The cancer vaccine of claim 1, wherein the helper motif is an immunogenic fragment of tetanus toxin.

5. The cancer vaccine of claim 4, wherein the helper motif is DOM.

6. The cancer vaccine according to claim 1, wherein said vaccine further comprises a nucleic acid encoding a FJX1 protein.

7. The cancer vaccine of claim 6, wherein (a) said FJX1 protein has at least 95% identity to SEQ ID No. 4 or SEQ ID No. 33, or a truncated version thereof, and/or (b) said FJX1 protein is encoded by a nucleic acid that has at least 85% identity to SEQ ID No. 8, SEQ ID No. 20 or SEQ ID No. 21.

8. The cancer vaccine of claim 6, wherein said MAGED4B and FJX1 are encoded by the same nucleic acid and are a fusion protein.

9. The cancer vaccine of claim 8, wherein the fusion protein comprises at least one of: a linker protein between MAGED4B and FJX1, and a linker protein between MAGED4B and the immunological fragment of a protein.

10. The cancer vaccine of claim 1, wherein the nucleic acid encoding MAGED4B further encodes a signal peptide for enhancing secretion of the encoded protein.

11. The cancer vaccine of claim 1, wherein said DNA is a plasmid, a closed linear DNA, a minicircle DNA or a single stranded circular DNA.

12. The cancer vaccine of claim 1, wherein the nucleic acid further comprises a promoter operably linked to the coding sequences, and further comprises a polyadenylation signal downstream of the encoding sequences.

13. A cancer vaccine as claimed in claim 1, for use in treating cancer.

14. The cancer vaccine as for use as claimed in claim 13, wherein said vaccine is for use in combination with an anti-cancer agent.

15. A method of treating a patient in need thereof, comprising administering the cancer vaccine of claim 1 to a human or animal subject.

16. The method of claim 15, wherein said method further comprises administering an immune checkpoint inhibitor.

17. The method of claim 16, wherein said checkpoint inhibitor is an agent capable of blocking the action of PD-1, PD-L1, PD-L2 or CTLA-4.

18. The cancer vaccine, according to claim 1, wherein said cancer is any one or more of head and neck cancer, oral cancer, oropharyngeal cancer, nasopharyngeal cancer, lung cancer, breast cancer, oesophageal cancer, stomach cancer, liver cancer, colon cancer, kidney cancer, cholangiocarcinoma, cutaneous melanoma, rectal cancer, thyroid cancer, bladder urothelial carcinoma, renal cancer or stomach adenocarcinoma.

19. The cancer vaccine of claim 3, wherein the immunological fragment of a protein is a helper epitope.

20. The cancer vaccine of claim 4, wherein the immunogenic fragment of tetanus toxin is a p30 MHCII epitope of tetanus toxin.

21. The cancer vaccine of claim 1, wherein the immunologically active truncated version of MAGED4B has at least 85% sequence identity with any one of SEQ ID No. 35 to SEQ ID No. 37.

22. The cancer vaccine of claim 1, wherein the truncation comprises the removal of all of the MAGED4B common homology domain.

23. The method of claim 16, wherein said immune checkpoint inhibitor is an antibody or aptamer.

24. The cancer vaccine according to claim 1, wherein said immunologically active truncated versions of MAGED4B is selected from the group consisting of SEQ ID No. 35, SEQ ID No. 36, and SEQ ID No. 37.

25. A cancer vaccine comprising a DNA encoding an immunologically active truncated version of MAGED4B protein, wherein said immunologically active truncated version of MAGED4B protein comprises between 400 and 700 amino acids of a sequence which has at least 95% sequence identity to the MAGED4B sequence as set forth in SEQ ID No: 3, wherein said immunologically active truncated version of MAGED4B comprises the removal of all or part of a MAGE homology domain corresponding to residues 412-682 of SEQ ID No. 3, and wherein the cancer vaccine further comprises an immunogenic fragment of tetanus toxin comprising DOM, and a nucleic acid encoding a FJX1 protein which has at least 80% sequence identity to SEQ ID No. 4 or SEQ ID No. 33 or a truncated version thereof.

* * * * *